(12) United States Patent
Glezer et al.

(10) Patent No.: US 11,884,977 B2
(45) Date of Patent: Jan. 30, 2024

(54) NANOARRAYS AND METHODS OF USE THEREOF

(71) Applicant: Singular Genomics Systems, Inc., San Diego, CA (US)

(72) Inventors: Eli N. Glezer, Del Mar, CA (US); Vahid Karimkhani, Chagrin Falls, OH (US); Shahed Kay, San Diego, CA (US); Mohammad Vatankhah Varnosfaderani, San Marcos, CA (US); Daan Witters, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 18/111,422

(22) Filed: Feb. 17, 2023

(65) Prior Publication Data

US 2023/0203579 A1 Jun. 29, 2023

Related U.S. Application Data

(63) Continuation of application No. 17/817,960, filed on Aug. 5, 2022, now Pat. No. 11,629,380, which is a continuation of application No. PCT/US2022/019955, filed on Mar. 11, 2022.

(60) Provisional application No. 63/164,742, filed on Mar. 23, 2021, provisional application No. 63/160,716, filed on Mar. 12, 2021.

(51) Int. Cl.
   *C12Q 1/6874* (2018.01)
   *C12Q 1/6876* (2018.01)
   *C40B 40/06* (2006.01)

(52) U.S. Cl.
   CPC ......... *C12Q 1/6874* (2013.01); *C12Q 1/6876* (2013.01); *C40B 40/06* (2013.01)

(58) Field of Classification Search
   None
   See application file for complete search history.

(56) References Cited

U.S. PATENT DOCUMENTS

| | | |
|---|---|---|
| 4,318,846 A | 3/1982 | Khanna et al. |
| 4,882,245 A | 11/1989 | Gelorme et al. |
| 4,970,276 A | 11/1990 | Das et al. |
| 5,034,506 A | 7/1991 | Summerton et al. |
| 5,066,580 A | 11/1991 | Lee |
| 5,188,934 A | 2/1993 | Menchen et al. |
| 5,235,033 A | 8/1993 | Summerton et al. |
| 5,366,860 A | 11/1994 | Bergot et al. |
| 5,599,675 A | 2/1997 | Brenner |
| 5,688,648 A | 11/1997 | Mathies et al. |
| 5,750,341 A | 5/1998 | Macevicz |
| 5,763,594 A | 6/1998 | Hiatt et al. |
| 5,800,996 A | 9/1998 | Lee et al. |
| 5,808,045 A | 9/1998 | Hiatt et al. |
| 5,847,162 A | 12/1998 | Lee et al. |
| 5,872,244 A | 2/1999 | Hiatt et al. |
| 6,210,891 B1 | 4/2001 | Nyren et al. |
| 6,232,465 B1 | 5/2001 | Hiatt et al. |
| 6,258,568 B1 | 7/2001 | Nyren |
| 6,274,320 B1 | 8/2001 | Rothberg et al. |
| 6,897,012 B2 | 5/2005 | Hada et al. |
| 6,991,888 B2 | 1/2006 | Padmanaban et al. |
| 7,057,026 B2 | 6/2006 | Barnes et al. |
| 7,467,632 B2 | 12/2008 | Lee et al. |
| 7,541,444 B2 | 6/2009 | Milton et al. |
| 8,003,354 B2 | 8/2011 | Shen et al. |
| 8,039,817 B2 | 10/2011 | Feng et al. |
| 8,178,360 B2 | 5/2012 | Barnes et al. |
| 8,241,573 B2 | 8/2012 | Banerjee et al. |
| 10,738,072 B1 | 8/2020 | Graham et al. |
| 11,236,387 B2 | 2/2022 | Glezer et al. |
| 2006/0068378 A1 | 3/2006 | Mirkin et al. |
| 2008/0000373 A1 | 1/2008 | Petrucci-Samija et al. |
| 2010/0160478 A1 | 6/2010 | Nilsson et al. |
| 2011/0059865 A1 | 3/2011 | Smith et al. |
| 2012/0270305 A1 | 10/2012 | Reed et al. |
| 2015/0079351 A1 | 3/2015 | Atasoy et al. |
| 2016/0256846 A1 | 9/2016 | Smith et al. |
| 2017/0344866 A1 | 11/2017 | Fan et al. |
| 2018/0258472 A1 | 9/2018 | Glezer |
| 2019/0085412 A1* | 3/2019 | Fan et al. ............. C12Q 1/6888 |
| 2020/0318182 A1 | 10/2020 | Gunderson et al. |
| 2021/0040555 A1 | 2/2021 | Glezer et al. |
| 2021/0190668 A1 | 6/2021 | Kovacs et al. |

FOREIGN PATENT DOCUMENTS

| | | | |
|---|---|---|---|
| WO | WO-1989/010977 A1 | 11/1989 | |
| WO | WO-1996/007669 A1 | 3/1996 | |
| WO | WO-2004/018497 A2 | 3/1996 | |
| WO | WO-2004/018497 A3 | 3/1996 | |
| WO | WO-2017/205336 A1 | 11/2017 | |
| WO | WO-2018/148723 A1 | 8/2018 | |

(Continued)

OTHER PUBLICATIONS

You et al., "Mathematical Models for the van der Waals Force and Capillary Force between a Rough Particle and Surface," Langmuir 2013, 29:9104-9117. (Year: 2013).*

Bains, W. et al. (Dec. 7, 1988). "A novel method for nucleic acid sequence determination," *Journal of Theoretical Biology* 135(3):303-307.

Bentley, D. R. et al. (Nov. 6, 2008). "Accurate whole human genome sequencing using reversible terminator chemistry," *Nature* 456(7218): 53-59.

Brenner, S. et al. (Jun. 2000). "Gene expression analysis by massively parallel signature sequencing (MPSS) on microbead arrays," *Nature Biotechnology* 18(6): 630-634.

(Continued)

*Primary Examiner* — Kaijiang Zhang

(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are nanoarrays and methods of use thereof.

26 Claims, 12 Drawing Sheets

(56) References Cited

FOREIGN PATENT DOCUMENTS

WO     WO-2020/056044 A1     3/2020

OTHER PUBLICATIONS

Christian, A.T. et al. (Oct. 8, 2001). "Detection of DNA point mutations and mRNA expression levels by rolling circle amplification in individual cells," *PNAS* 98(25): 14238-14243.
Cohen, S.M. (Sep. 14, 2011). "Postsynthetic methods for the functionalization of metal-organic frameworks," *Chemical Reviews* 112(2): 970-1000.
Drmanac, S. et al. (Jan. 1998). "Accurate sequencing by hybridization for DNA diagnostics and individual genomics," *Nature Biotechnology* 16(1): 54-58.
Ewis, A. A. et al. (2005, e-published Jan. 9, 2014). "A history of microarrays in biomedicine," *Expert Review of Molecular Diagnostics* 5(3): 315-328.
Feeney, R. E. et al. (Apr. 1, 1982). "Chemical modification of proteins: An overview," *Advances in Chemistry Series* 182: 3-55.
Fodor, S.P. et al. (Feb. 15, 1991). "Light-directed, spatially addressable parallel chemical synthesis," *Science* 251(4995): 767-773.
Furukawa, H. et al. (Aug. 30, 2013). "The chemistry and applications of metal-organic frameworks," *Science* 341(6149): 1230444.
Gunderson, K.L. (Jan. 16, 2009). "Whole-Genome Genotyping on Bead Arrays," *DNA Microarrays for Biomedical Research: Methods in Molecular Biology* 529: 197-213. Humana Press.
Haas, K-H. et al (Dec. 1999). "Synthesis, properties and applications of inorganic-organic copolymers (ORMOCER® s)," *Current Opinion in Solid State and Materials Science* 4(6): 571-580.
Haas, K-H. et al. (Aug. 30, 1999). "Functionalized coating materials based on inorganic- organic polymers," *Thin Solid Films* 351(1-2): 198-203.
International Search report dated Jun. 24, 2022, for PCT application PCT/US2022/019955, filed Mar. 11, 2022, 3 pages.
Kato, M. et al. (Feb. 1, 1995). "Polymerization of methyl methacrylate with the carbon tetrachloride/dichlorotris-(triphenylphosphine) ruthenium (II)/methylaluminum bis (2, 6-di-tert-butylphenoxide) initiating system: possibility of living radical polymerization," *Macromolecules* 28(5): 1721-1723.
Miller, M. B. et al. (Oct. 1, 2009). "Basic concepts of microarrays and potential applications in clinical microbiology," *Clinical Microbiology Reviews* 22(4): 611-633.
Moad, G. et al. (May 3, 2005, e-published Jun. 14, 2005). "Living radical polymerization by the RAFT process," *Australian Journal of Chemistry* 58(6): 379-410.
Nilsson, M. et al. (Sep. 1994). "Padlock probes: circularizing oligonucleotides for localized DNA detection," *Science* 265(5181): 2085-2088.
Otsu, T. et al. (Feb. 16, 1982). "Role of initiator-transfer agent-terminator (iniferter) in radical polymerizations: Polymer design by organic disulfides as iniferters," *Makromolekulare Chemie, Rapid Communications* 3: 127-132.
Ronaghi, M. et al. (Nov. 1, 1996). "Real-time DNA sequencing using detection of pyrophosphate release," *Analytical Biochemistry* 242(1):84-89.
Ronaghi, M. et al. (Jul. 17, 1998). "A sequencing method based on real-time pyrophosphate," *Science* 281(5375): 363-365.
Ronaghi, M. (Jan. 2001). "Pyrosequencing sheds light on DNA sequencing," *Genome Research* 11(1): 3-11.
Shendure, J. et al. (Sep. 9, 2005, e-published Aug. 4, 2005). "Accurate multiplex polony sequencing of an evolved bacterial genome," *Science* 309(5741): 1728-1732.
Veregin, R. P. N. et al. (Sep. 1, 1993). "Free radical polymerizations for narrow polydispersity resins: electron spin resonance studies of the kinetics and mechanism," *Macromolecules* 26(20): 5316-5320.
Walt, D. R. (Jan. 21, 2000). "Bead-based fiber-optic arrays," *Science* 287(5452): 451-452.
Wang, J-S. et al. (May 1, 1995). "Controlled/ "living" radical polymerization. atom transfer radical polymerization in the presence of transition-metal complexes," *Journal of the American Chemical Society* 117(20): 5614-5615.
Written Opinion dated Jun. 24, 2022, for PCT Application No. PCT/US2022/019955, filed Mar. 11, 2022, 9 pages.
Yeole, N. "Thiocarbonylthio compounds," *Synlett* 2010(10): 1572-1573.
Zhang, D. et al. (Nov. 13, 2018) "Preparation and surface properties study of novel fluorine-containing methacrylate polymers for coating," *Materials* 11(11): 2258.

\* cited by examiner

4 µm

Particle core; diameter about 500 nm

Particle core + shell; diameter about 600 nm to about 900 nm

NANOARRAYS AND METHODS OF USE THEREOF

CROSS-REFERENCES TO RELATED APPLICATIONS

This application is a continuation U.S. patent application Ser. No. 17/817,960, filed Aug. 5, 2022, which is a continuation of PCT Application PCT/US2022/019955, filed Mar. 11, 2022, which claims the benefit of U.S. Provisional Application No. 63/160,716, filed Mar. 12, 2021; and U.S. Provisional Application No. 63/164,742, filed Mar. 23, 2021, each of which are incorporated herein by reference in their entirety and for all purposes.

BACKGROUND

Patterned arrays are an important tool in biomedical research, providing a two-dimensional platform that arranges biological samples and enables high-throughput analyses. Delivering breakthroughs in proteomics, multiplexed immunoassays, and complex genomic analyses, microarrays can be designed to host thousands, or even ten-thousands, of features that can be subjected to simultaneous reaction conditions.

Next generation sequencing (NGS) methodologies make use of simultaneously sequencing millions of fragments of nucleic acids in a single experiment. For example, sequencing-by-synthesis (SBS) is typically performed by imaging clusters of amplicons, referred to as features, having multiple identical copies of a starting molecule. In order to maximize the rate of output of sequencing information, efforts have been made to increase the ratio of nucleotides sequenced per image. Miniaturization is required for increasing the scale and density of the amplicons, that could result in lower reagent consumption and faster data acquisitions, however greater challenges arise as the feature dimensions approach submicron domains. Disclosed herein, inter alia, are solutions to these and other problems in the art.

BRIEF SUMMARY

In an aspect is provided an array, including: a solid support including a surface, the surface comprising a plurality of wells separated from each other by interstitial regions on the surface, wherein one or more wells include a particle, wherein the particle includes a plurality of bioconjugate reactive moieties, a plurality of oligonucleotide moieties, or a combination thereof; and wherein there is one particle per well.

In an aspect is provided a method of amplifying a target polynucleotide, the method including: contacting the array as described herein, including embodiments, with a plurality of oligonucleotide moieties, each oligonucleotide moiety including a bioconjugate reactive moiety that reacts and forms a bioconjugate linker that covalently links the oligonucleotide moiety to the particle, contacting the array with a sample including a target polynucleotide; and amplifying the target polynucleotide to produce an amplification product, wherein amplifying includes extension of the oligonucleotide moiety hybridized to the target polynucleotide.

In an aspect is provided a method of amplifying a target polynucleotide, the method including: contacting the array as described herein, including embodiments and wherein the particle includes a plurality of oligonucleotide moieties, with a sample including a target polynucleotide; and amplifying the target polynucleotide to produce an amplification product, wherein amplifying includes extension of the oligonucleotide moiety hybridized to the target polynucleotide.

In an aspect is provided a nucleic acid sequencing device, including: a stage configured to hold an array or solid support as described herein, including embodiments; an array or solid support as described herein, including embodiments; and a detector for obtaining sequencing data.

BRIEF DESCRIPTION OF THE DRAWINGS

FIG. 2A illustrates particles decorated with bioconjugate reactive moieties, for example, azide-reactive species. The particles are localized in wells of an array, wherein the array includes a polymer coating, for example, a silane functionalized polyethylene glycol (Si-PEG) copolymer or a silane functionalized poly(acrylamide) (Si-Pam) copolymer coating. FIG. 2B illustrates particles in wells of a similar polymer-coated array, wherein the particles include oligonucleotides linked to the bioconjugate reactive groups. The particles may include oligonucleotide moieties, or the oligonucleotide moieties may be added following deposition of the particles. The oligonucleotides may be capable of hybridizing to template nucleic acids for subsequent amplification and sequencing applications.

FIG. 6A is an image of an array substrate prepared without any polymer coating (i.e., the substrate does not contain a hydrophilic polymer) and highlights the non-specific cluster amplification in the interstitial space. FIG. 6A shows that an oligonucleotide primer may bind to the interstitial space and be amplified. FIG. 6B is an image of an array that was coated with a passivating polymer p[PEGMA-co-TESPM] prior to particle loading, which resulted in a significant reduction in non-specific clusters present in the interstitial space.

FIG. 7A an illustration of the topological differences between a comb and brush polymer. In embodiments, the solid support includes a passivating polymer coating of a brush or comb polymer. FIG. 7B shows an embodiment of an amphiphilic polymer, generated by polymerizing PEGMA and TMSPM monomers, where n is an integer from 1 to 100; n1 and n2 are integers from 1 to 1000, respectively. FIG. 7B depicts a subunit of a copolymer that includes $[PEGMA]_{n1}$ and $[TMSPM]_{n2}$, however it is understood that the copolymer may include additional repeating subunits, e.g., $[PEGMA]_{n1}$-[TMSPM]n2-$[PEGMA]_{n1}$-[TMSPM]n2 or -[TMSPM]n2-$[PEGMA]_{n1}$-[TMSPM]n2 and the like. The ratio of hydrophilic segments (e.g., PEGMA) to hydrophobic segments (e.g., TMSPM) is governed by modulating the reaction conditions (e.g., monomer concentrations, pH, and/or temperature).

FIG. 10A is an illustration of functionalized particle including a particle core (e.g., a silica core) and a particle shell (e.g., a polymer shell). The illustration depicts the polymer shell as distinct polymeric chains with exaggerated separation for clarity, however it is understood that the polymer chains form a network that coat (i.e., surround) the surface of the particle core. The thickness of the polymer layer can be controlled by varying the reaction conditions (e.g., time, temperature, and concentration of the corresponding monomers) to provide a thickness of about 50 nm to about 200 nm. FIG. 10B illustrates an individual polymeric chain covalently attached to the particle core. The polymer chain is a polyethylene glycol methacrylate (PEGMA) and glicydyl methacrylate azide (GMA azide, or GMA-Az) copolymer in a 2:1 ratio (i.e., having an ng of 3). Alternative ng copolymers were also synthesized by varying the ratio of PEGMA:GMA-Az 5:1 (ng=6) or 8:1 (ng=9), providing tunable parameters to control the density of oligonucleotide, which corresponds to density of the resulting polynucleotides.

DETAILED DESCRIPTION

Figure 1A:
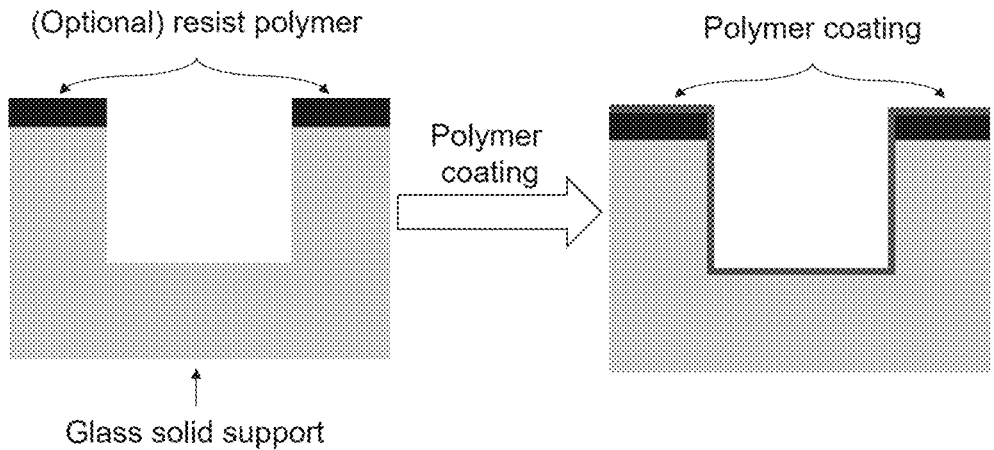
FIGS. 1A-1D. Illustrations of the different well shapes of the array. Using known nanolithographic fabrication techniques, a glass substrate may be etched such that the well is anisotropic (FIG. 1A), partially anisotropic (FIG. 1B), or isotropic (FIG. 1C). The array may include a resist polymer (e.g., a fluorinated polymer later) prior to receiving an additional polymer coating (e.g., a poloxamer or alkoxysilyl polymer). The resist may be removed prior to the addition of the additional polymer using known techniques in the art (e.g., solvent removal). In embodiments, the additional polymer coating reduces the non-specific binding of oligonucleotide moieties. Alternatively, the wells may be directly formed within the resist (e.g., a nanoimprint resist) as depicted in FIG. 1D, wherein the resist is attached to a glass solid support. In embodiments, the resist is not removed prior to loading the particles.

The aspects and embodiments described herein relate to nanoarrays and methods of making and using nanoarrays.

I. Definitions

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The terms "attached," "bind," and "bound" as used herein are used in accordance with their plain and ordinary meanings and refer to an association between atoms or molecules. The association can be direct or indirect. For example, attached molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence, only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. Another example of complementary sequences are a template sequence and an amplicon sequence polymerized by a polymerase along the template sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, one or both sequences in a pair of complementary sequences form portions of longer polynucleotides, which may or may not include additional regions of complementarity.

As used herein, the term "hybridize" or "specifically hybridize" refers to a process where two complementary nucleic acid strands anneal to each other under appropriately stringent conditions. Hybridizations are typically and preferably conducted with oligonucleotides. Non-limiting examples of nucleic acid hybridization techniques are described in, for example, Sambrook, et al., Molecular Cloning: A Laboratory Manual (2nd Edition, 1989). Those skilled in the art understand how to estimate and adjust the stringency of hybridization conditions such that sequences having at least a desired level of complementarity will stably hybridize, while those having lower complementarity will not. Hybridization reactions can be performed under conditions of different "stringency". For example, a low stringency hybridization reaction is carried out at about 40° C. in 10×SSC. A moderate stringency hybridization may be performed at about 50° C. in 6×SSC. A high stringency hybridization reaction is generally performed at about 60° C. in 1×SSC. Hybridization reactions can also be performed under "physiological conditions" which is well known to one of skill in the art (e.g., a physiological condition is the temperature, ionic strength, pH and concentration of $Mg^{2+}$ normally found in vivo). The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acids. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex, which comprises a double stranded portion of nucleic acid.

As used herein, the term "stringent condition" refers to condition(s) under which a polynucleotide probe or primer will hybridize preferentially to its target sequence, and to a lesser extent to, or not at all to, other sequences. A "stringent hybridization" and "stringent hybridization wash conditions" in the context of nucleic acid hybridization are sequence dependent, and are different under different environmental parameters.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "polynucleotide template" or "template nucleic acid" refers to any polynucleotide molecule that may be bound by a polymerase and utilized as a template for nucleic acid synthesis. As used herein, the term "polynucleotide primer" refers to any polynucleotide molecule that may hybridize to a polynucleotide template, be bound by a polymerase, and be extended in a template-directed process for nucleic acid synthesis, such as in a PCR or sequencing reaction. Polynucleotide primers attached to a core polymer within a core are referred to as "core polynucleotide primers." A primer can be of any length depending on the particular technique it will be used for. For example, PCR primers are generally between 10 and 40 nucleotides in length. The length and complexity of the nucleic acid fixed onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s).

As used herein, the term "analogue", in reference to a chemical compound, refers to a compound having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as primers attached to a polymer. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

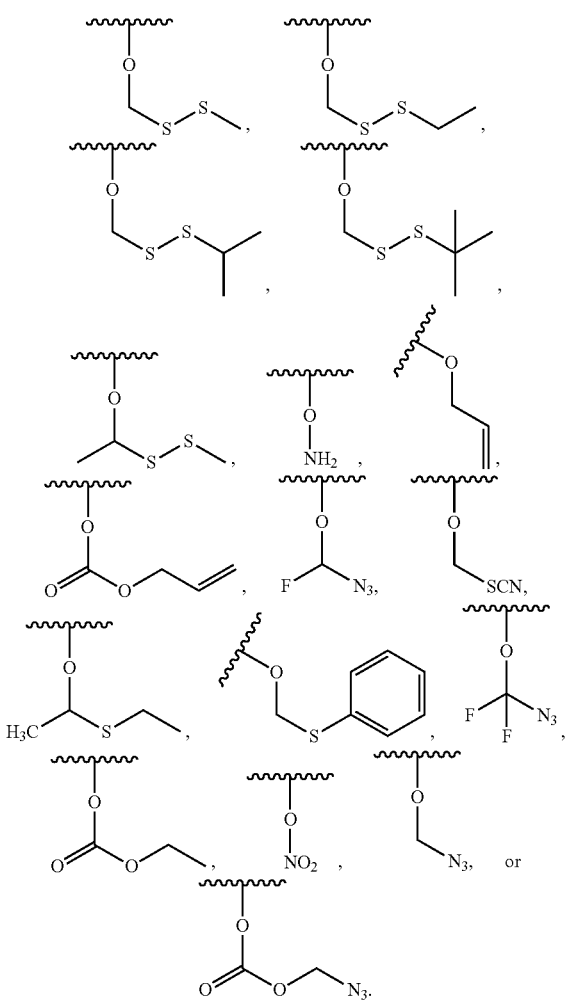

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogs include, without limitation, 7-deaza-adenine, 7-deaza-guanine, the analogs of deoxynucleotides shown herein, analogs in which a label is attached through a cleavable linker to the 5-position of cytosine or thymine or to the 7-position of deaza-adenine or deaza-guanine, and analogs in which a small chemical moiety is used to cap the —OH group at the 3'-position of deoxyribose. As used herein, the terms "blocking moiety," "reversible blocking group," "reversible terminator," and "reversible terminator moiety" are used in accordance with their plain and ordinary meanings and refer to a cleavable moiety which does not interfere with incorporation of a nucleotide comprising it by a polymerase (e.g., DNA polymerase, modified DNA polymerase), but prevents further strand extension until removed ("unblocked"). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763, 594, 5,808,045, 5,872,244 and 6,232,465 the contents of which are incorporated herein by reference in their entirety. The nucleotides may be labelled or unlabeled. They may be modified with reversible terminators useful in methods provided herein and may be 3-O-blocked reversible or 3-unblocked reversible terminators. In nucleotides with 3-O-blocked reversible terminators, the blocking group may be represented as —OR [reversible terminating (capping) group], wherein O is the oxygen atom of the 3-OH of the pentose and R is the blocking group, while the label is linked to the base, which acts as a reporter and can be cleaved. The 3-O-blocked reversible terminators are known in the art, and may be, for instance, a 3'-ONH$_2$ reversible terminator, a 3-O-allyl reversible terminator, or a 3-O-azidomethyl reversible terminator. In embodiments, the reversible terminator moiety is

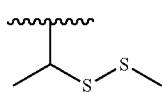 [SMILES: *C(C)SSC]

as described in U.S. Pat. No. 10,738,072, which is incorporated herein by reference for all purposes. In embodiments, the reversible terminator moiety is

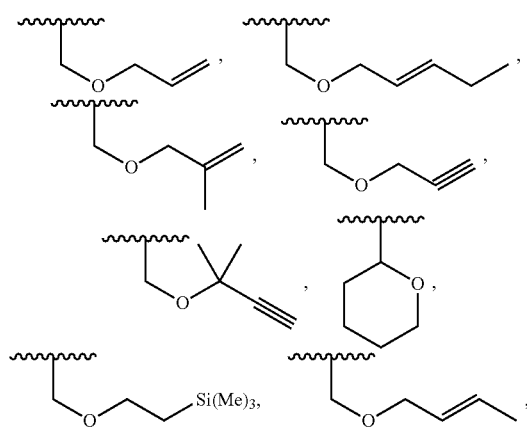

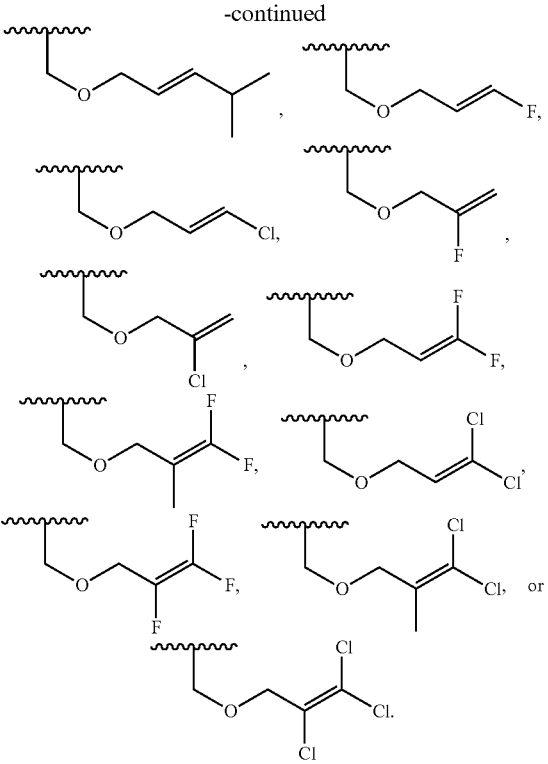

As used herein, the term "core" refers to a polymer within which polynucleotide primers are attached, and that is surrounded by a "shell polymer" to which no polynucleotide primers are attached. The presence of the polynucleotide primer within the core permits a nucleic acid amplification reaction to take place, while the shell polymer provides a physical barrier between amplification reactions in adjacent cores. The cores are "surrounded" by the shell polymer in the sense that the shell polymer completely covers each core, and no core is in direct contact with any other core. The shell layer may enclose (e.g., surround, encapsulate, envelope) a core. In embodiments, each core surrounded by the shell polymer forms a discrete particle, the outer surface of which is defined by the shell polymer. In embodiments, the shells of discrete core-shell particles suspended in a container (e.g., a well, tube, or flow cell) expands, to fill any space between adjacent particles. In such cases, the boundaries of individual particles may no longer be readily discernable, but each core remains separated from each other by the shell polymer surrounding each, which can be readily observed by, e.g., detecting products of a nucleic acid amplification reaction. The core polymer may itself surround a solid support particle, such as a glass, ceramic, metal, silica, magnetic, or paramagnetic particle (e.g., a 500 nm silica nanoparticle). Solid support particles may be composed of any appropriate material. In embodiments, the support particle is an amorphous solid. In embodiments, the support particle is a crystalline solid. For example, solid support particles may include appropriate metals and metal oxides thereof (a metal particle core), carbon (an organic particle core) silica and oxides thereof (a silica particle core) or boron and oxides thereof (a boron particle core). For example, the core/shell layers may be formed around a supporting bead (alternatively referred to as a support particle), for example, a silica, magnetic, or paramagnetic bead. The term "support particle" as used herein may refer to any particle or substance having a diameter in the micrometer range, such as a "microparticle," which typically has a diameter of approximately 1 μm and higher, or a "nanoparticle," which typically has a diameter of 1 nm to 1 μm. The core, optionally including a solid silica support particle, may be referred to herein as a nanoparticle core wherein the longest diameter is less than 1000 nanometers. Lengths and sizes of particles and their surrounding cores as described herein may be measured using Transmission Electron Microscopy (TEM). The term "silica" is used according to its plain and ordinary meaning and refers to a composition (e.g. a solid composition such as a particle) containing oxides of silicon such as Si atoms (e.g., in a tetrahedral coordination) with 4 oxygen atoms surrounding a central Si atom. A silica support particle may refer to a particle including a matrix of silicon-oxygen bonds.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers. In some embodiments, the hydrogel polymer includes 60-90% fluid, such as water, and 10-30% polymer. In certain embodiments, the water content of hydrogel is about 70-80%.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO-PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO).

The term "array" as used herein, refers to a container (e.g., a multiwell container, reaction vessel, or flow cell) including a plurality of features (e.g., wells). For example, an array may include a container with a plurality of wells. In embodiments, the array is a microplate. In embodiments, the array is a flow cell.

The term "microplate," "microtiter plate," or "multiwell plate" as used herein, refers to a substrate comprising a surface, the surface including a plurality of chambers or wells separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modern robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins, or polynucleotides in a cell.

The reaction chambers may be provided as wells, for example an array or microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments, the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples.

The terms "iniferter mediated polymerization" and the like refer, in the usual and customary sense, to polymerization employing an "iniferter" which, as known in the art, is a chemical compound that simultaneously acts as initiator, transfer agent, and terminator in controlled free radical polymerization reactions, e.g., dithiocarbamates. See, e.g., Otsu, T., & Yashida, M., *Mackromol. Chem., Rapid Commun.*, 1982, 3:127-132.

The terms "stable free radical mediated polymerization," "SRFP," and the like refer, in the usual and customary sense, to polymerization reactions wherein the coupling of the stable free radical with the polymeric radical is sufficiently reversible that the termination step is reversible, and the propagating radical concentration can be limited to levels that allow for controlled polymerization. See e.g., Veregin, R. P. N., et al., *Macromolecules* 1993, 26:5316-5320.

The terms "atom transfer radical polymerization," "ATRP" and the like refer, in the usual and customary sense, to methods of polymerization employing a transition metal catalyst, wherein the atom transfer step is the key step in the reaction responsible for uniform polymer chain growth. See e.g., Kato, M., et al., *Macromolecules* 1995, 28:1721-1723; Wang, J. & Matyjaszewski, K., *J. Am. Chem. Soc.* 1995, 117:5614-5615.

The terms "reversible addition fragmentation chain transfer polymerization," "RAFT" and the like refer, in the usual and customary sense, to methods of polymerization which use a chain transfer agent in the form of a thiocarbonylthio compound or the like to afford control over the generated molecular weight and polydispersity during a free-radical polymerization. See e.g., Yeole, N., *Synlett.* 2010(10): 1572-1573; Moad, G., et al., *Aust. J Chem.*, 2005, 58:379-410.

As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid. Discrete particles collected in a container and contacting one another will define a bulk volume containing the particles, and will typically leave some internal fraction of that bulk volume unoccupied by the particles, even when packed closely together.

In embodiments, cores and/or core-shell particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a core-shell particle) refers to the average thickness of the polymer layer.

As used herein, the term "channel" refers to a passage in or on a substrate material that directs the flow of a fluid. A channel may run along the surface of a substrate, or may run through the substrate between openings in the substrate. A channel can have a cross section that is partially or fully surrounded by substrate material (e.g., a fluid impermeable substrate material). For example, a partially surrounded cross section can be a groove, trough, furrow or gutter that inhibits lateral flow of a fluid. The transverse cross section of an open channel can be, for example, U-shaped, V-shaped, curved, angular, polygonal, or hyperbolic. A channel can have a fully surrounded cross section such as a tunnel, tube, or pipe. A fully surrounded channel can have a rounded, circular, elliptical, square, rectangular, or polygonal cross section. In particular embodiments, a channel can be located in a flow cell, for example, being embedded within the flow cell. A channel in a flow cell can include one or more windows that are transparent to light in a particular region of the wavelength spectrum. In embodiments, the channel contains one or more polymers of the disclosure. In embodiments, the channel is filled by the one or more polymers, and flow through the channel (e.g., as in a sample fluid) is directed through the polymer in the channel. In embodiments, the assay is in a channel of a flow cell.

As used herein, the term "substrate" refers to a solid support material. The substrate can be non-porous or porous. The substrate can be rigid or flexible. As used herein, the terms "solid support" and "solid surface" refers to discrete solid or semi-solid surface. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A nonporous substrate generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located within a flow cell. Solid surfaces can also be varied in their shape depending on the application in a method described herein. For example, a solid surface useful herein can be planar, or contain regions which are concave or convex. In embodiments, the geometry of the concave or convex regions (e.g., wells) of the solid surface conform to the size and shape of the particle (e.g., see FIG. 1C) to maximize the contact between as substantially circular particle. In embodiments, the wells of an array are randomly located such that nearest neighbor features have random spacing between each other. Alternatively, in embodiments the spacing between the wells can be ordered, for example, forming a regular pattern. The term solid substrate is encompassing of a substrate (e.g., a flow cell) having a surface comprising a polymer coating covalently attached thereto. In embodiments, the solid substrate is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In embodiments, a substrate comprises a surface (e.g., a surface of a flow cell, a surface of a tube, a surface of a chip), for example a metal surface (e.g., steel, gold, silver, aluminum, silicon and copper). In embodiments, a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In embodiments, a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In embodiments, a substrate comprises a magnetic bead (e.g., DYNABEADS®, hematite, AMPure XP). Magnets can be used to purify and/or capture nucleic acids bound to certain substrates (e.g., substrates comprising a metal or magnetic material). The flow cell is typically a glass slide containing small fluidic channels (e.g., a glass slide 75 mm×25 mm×1 mm having one or more channels), through which sequencing solutions (e.g., polymerases, nucleotides, and buffers) may traverse. Though typically glass, suitable flow cell materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, the material of the flow cell is selected due to the ability to conduct thermal energy. In embodiments, a flow cell includes inlet and outlet ports and a flow channel extending there between.

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "well" refers to a discrete concave feature or depression in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate may be available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells.

Figure 1B:
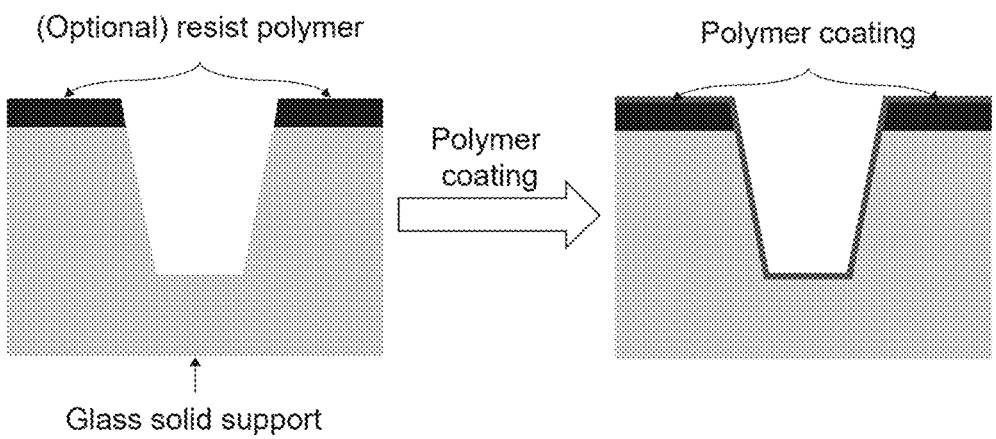
Figure 1C:
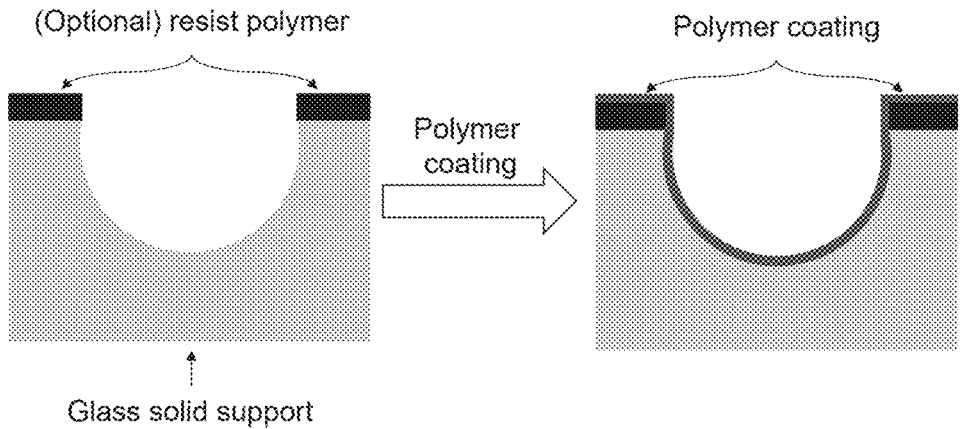

The discrete regions (i.e., features or wells) may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments, the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a passivating polymer or copolymer, as depicted in FIGS. 1A-1C). In embodiments, interstitial regions have a surface material that is the same as the surface material of the wells (e.g., both the surface of the interstitial region and the surface of well contain a polymer or copolymer).

As used herein, the term "feature" refers a point or area in a pattern that can be distinguished from other points or areas according to its relative location. An individual feature can include one or more polynucleotides. For example, a feature can include a single target nucleic acid molecule having a particular sequence or a feature can include several nucleic acid molecules having the same sequence (and/or complementary sequence, thereof). Different molecules that are at different features of a pattern can be differentiated from each other according to the locations of the features in the pattern. Non-limiting examples of features include wells in a substrate, particles (e.g., beads) in or on a substrate, polymers in or on a substrate, projections from a substrate, ridges on a substrate, or channels in a substrate.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. In embodiments, one nucleotide (e.g., a modified nucleotide) is incorporated per sequencing cycle. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes, and other substances can be removed between steps by washing. Cycles may include repeating these steps, and the sequence of each cluster is read over the multiple repetitions.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence. In embodiments, a sequencing read includes reading a barcode and not a template nucleotide sequence. Reads of length 20-40 base pairs (bp) are referred to as ultra-short. Typical sequencers produce read lengths in the range of 100-500 bp. Read length is a factor which can affect the results of biological studies. For example, longer read lengths improve the resolution of de novo genome assembly and detection of structural variants. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read includes a computationally derived string corresponding to the detected label. In some embodiments, a sequencing read may include 500, 600, 700, 800, 900, 1,000, 1,100, 1,200, 1,300, 1,400, 1,500, or more nucleotide bases.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'- and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is mono-unsaturated. In embodiments, the heterocycloalkyl is poly-unsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings. In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-S-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⤳" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

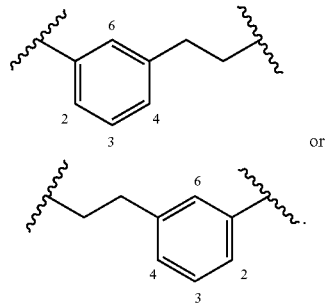

or

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$, $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$ respectively. In turn, each first substituent group (e.g., $R^{1.1}$, $R^{2.1}$, $R^{3.1}$, $R^{4.1}$, $R^{5.1}$ ... $R^{100.1}$; $R^{1A.1}$, $R^{2A.1}$, $R^{3A.1}$, $R^{4A.1}$, $R^{5A.1}$ ... $R^{100A.1}$; $R^{L1.1}$, $R^{L2.1}$, $R^{L3.1}$, $R^{L4.1}$, $R^{L5.1}$ ... $R^{L100.1}$) may be further substituted with one or more second substituent groups (e.g., $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$ ... $R^{100.2}$, $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$) may be further substituted with one or more third substituent groups (e.g., $R^{1.3}$, $R^{2.3}$, $R^{3.3}$, $R^{4.3}$, $R^{5.3}$ ... $R^{100.3}$; $R^{1A.3}$, $R^{2A.3}$, $R^{3A.3}$, $R^{4A.3}$, $R^{5A.3}$ ... $R^{100A.3}$; $R^{L1.3}$, $R^{L2.3}$, $R^{L3.3}$, $R^{L4.3}$, $R^{L5.3}$ ... $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

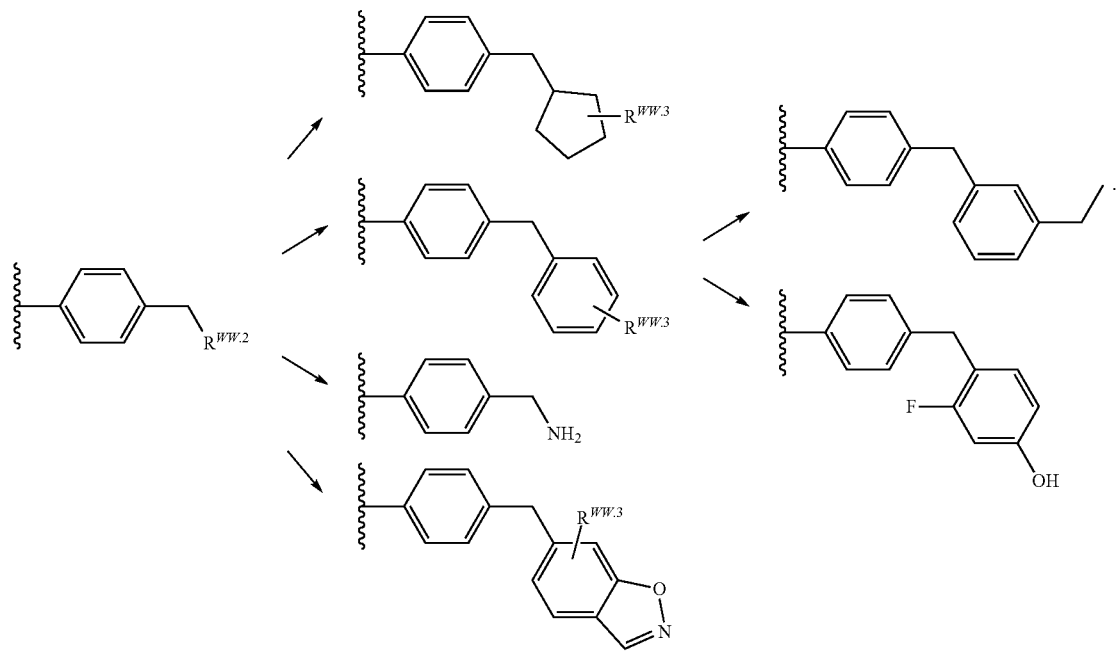

R$^{WW.1}$ is independently oxo, halogen, —CX$^{WW.1}_3$, —CHX$^{WW.1}_2$, —CH$_2$X$^{WW.1}$, —OCX$^{WW.1}_3$, —OCH$_2$X$^{WW.1}$, —OCHX$^{WW.1}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{WW.2}$-substituted or unsubstituted alkyl (e.g., C$_1$-C$_8$, C$_1$-C$_6$, C$_1$-C$_4$, or C$_1$-C$_2$), R$^{WW.2}$-substituted or unsubstituted heteroalkyl (e.g., 2 to 8 membered, 2 to 6 membered, 4 to 6 membered, 2 to 3 membered, or 4 to 5 membered), R$^{WW.2}$-substituted or unsubstituted cycloalkyl (e.g., C$_3$-C$_8$, C$_3$-C$_6$, C$_4$-C$_6$, or C$_5$-C$_6$), R$^{WW.2}$-substituted or unsubstituted heterocycloalkyl (e.g., 3 to 8 membered, 3 to 6 membered, 4 to 6 membered, 4 to 5 membered, or 5 to 6 membered), R$^{WW.2}$-substituted or unsubstituted aryl (e.g., C$_6$-C$_{12}$, C$_6$-C$_{10}$, or phenyl), or R$^{WW.2}$-substituted or unsubstituted heteroaryl (e.g., 5 to 12 membered, 5 to 10 membered, 5 to 9 membered, or 5 to 6 membered). In embodiments, R$^{WW.1}$ is independently oxo, halogen, —CX$^{WW.1}_3$, —CHX$^{WW.1}_2$, —CH$_2$X$^{WW.1}$, —OCX$^{WW.1}_3$, —OCH$_2$X$^{WW.1}$, —OCHX$^{WW.1}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{WW.1}$ is independently —F, —Cl, —Br, or —I.

R$^{WW.2}$ is independently oxo, halogen, —CX$^{WW.2}_3$, —CHX$^{WW.2}_2$, —CH$_2$X$^{WW.2}$, —OCX$^{WW.2}_3$, —OCH$_2$X$^{WW.2}$, —OCHX$^{WW.2}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{WW.3}$-substituted or unsubstituted alkyl (e.g., C$_1$-C$_8$, C$_1$-C$_6$, C$_1$-C$_4$, or C$_1$-C$_2$), R$^{WW.3}$-substituted or unsubstituted heteroalkyl (e.g., 2 to 8 membered, 2 to 6 membered, 4 to 6 membered, 2 to 3 membered, or 4 to 5 membered), R$^{WW.3}$-substituted or unsubstituted cycloalkyl (e.g., C$_3$-C$_8$, C$_3$-C$_6$, C$_4$-C$_6$, or C$_5$-C$_6$), R$^{WW.3}$-substituted or unsubstituted heterocycloalkyl (e.g., 3 to 8 membered, 3 to 6 membered, 4 to 6 membered, 4 to 5 membered, or 5 to 6 membered), R$^{WW.3}$-substituted or unsubstituted aryl (e.g., C$_6$-C$_{12}$, C$_6$-C$_{10}$, or phenyl), or R$^{WW.3}$-substituted or unsubstituted heteroaryl (e.g., 5 to 12 membered, 5 to 10 membered, 5 to 9 membered, or 5 to 6 membered). In embodiments, R$^{WW.2}$ is independently oxo, halogen, —CX$^{WW.2}_3$, —CHX$^{WW.2}_2$, —CH$_2$X$^{WW.2}$, —OCX$^{WW.2}_3$, —OCH$_2$X$^{WW.2}$, —OCHX$^{WW.2}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{WW.2}$ is independently —F, —Cl, —Br, or —I.

R$^{WW.3}$ is independently oxo, halogen, —CX$^{WW.3}_3$, —CHX$^{WW.3}_2$, —CH$_2$X$^{WW.3}$, —OCX$^{WW.3}_3$, —OCH$_2$X$^{WW.3}$, —OCHX$^{WW.3}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, —$CX^{LWW.2}_3$, —$CHX^{LWW.2}_2$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, —$CX^{LWW.2}_3$, —$CHX^{LWW.2}_2$, —$CH_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, —$CX^{LWW.3}_3$, —$CHX^{LWW.3}_2$, —$CH_2X^{LWW.3}$, —$OCX^{LWW.3}_3$, —$OCH_2X^{LWW.3}$, —$OCHX^{LWW.3}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, —$CX^{WW}_3$, —$CHX^{WW}_2$, —$CH_2X^{WW}$, —$OCX^{WW}_3$, —$OCH_2X^{WW}$, —$OCHX^{WW}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC (O)—OH, —NHOH, —N$_3$, R$^{WW.1}$-substituted or unsubstituted alkyl (e.g., C$_1$-C$_8$, C$_1$-C$_6$, C$_1$-C$_4$, or C$_1$-C$_2$), R$^{WW.1}$-substituted or unsubstituted heteroalkyl (e.g., 2 to 8 membered, 2 to 6 membered, 4 to 6 membered, 2 to 3 membered, or 4 to 5 membered), R$^{WW.1}$-substituted or unsubstituted cycloalkyl (e.g., C$_3$-C$_8$, C$_3$-C$_6$, C$_4$-C$_6$, or C$_5$-C$_6$), R$^{WW.1}$-substituted or unsubstituted heterocycloalkyl (e.g., 3 to 8 membered, 3 to 6 membered, 4 to 6 membered, 4 to 5 membered, or 5 to 6 membered), R$^{WW.1}$-substituted or unsubstituted aryl (e.g., C$_6$-C$_{12}$, C$_6$-C$_{10}$, or phenyl), or R$^{WW.1}$-substituted or unsubstituted heteroaryl (e.g., 5 to 12 membered, 5 to 10 membered, 5 to 9 membered, or 5 to 6 membered). X$^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). R$^{WW.1}$, R$^{WW.2}$ and R$^{WW.3}$ are as defined above.

In the event that any L linker group recited in a claim or chemical formula description set forth herein (i.e., an L$^{WW}$ substituent) is not explicitly defined, then that L group (L$^{WW}$ group) is herein defined as independently a bond, —O—, —NH—, —C(O)—, —C(O)NH—, —NHC(O)—, —NHC(O)NH—, —C(O)O—, —OC(O)—, —S—, —SO$_2$NH—, R$^{LWW.1}$-substituted or unsubstituted alkylene (e.g., C$_1$-C$_8$, C$_1$-C$_6$, C$_1$-C$_4$, or C$_1$-C$_2$), R$^{LWW.1}$-substituted or unsubstituted heteroalkylene (e.g., 2 to 8 membered, 2 to 6 membered, 4 to 6 membered, 2 to 3 membered, or 4 to 5 membered), R$^{LWW.1}$-substituted or unsubstituted cycloalkylene (e.g., C$_3$-C$_8$, C$_3$-C$_6$, C$_4$-C$_6$, or C$_5$-C$_6$), R$^{LWW.1}$-substituted or unsubstituted heterocycloalkylene (e.g., 3 to 8 membered, 3 to 6 membered, 4 to 6 membered, 4 to 5 membered, or 5 to 6 membered), R$^{LWW.1}$-substituted or unsubstituted arylene (e.g., C$_6$-C$_{12}$, C$_6$-C$_{10}$, or phenyl), or R$^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). R$^{LWW.1}$, as well as R$^{LWW.2}$ and R$^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The phrase "substituted with a[n]," as used herein, means the specified group may be substituted with one or more of any or all of the named substituents. For example, where a group, such as an alkyl or heteroaryl group, is "substituted with an unsubstituted C$_1$-C$_{20}$ alkyl, or unsubstituted 2 to 20 membered heteroalkyl," the group may contain one or more unsubstituted C$_1$-C$_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple R$^{13}$ substituents are present, each R$^{13}$ substituent may be distinguished as R$^{13A}$, R$^{13B}$, R$^{13C}$, R$^{13D}$, etc., wherein each of R$^{13A}$, R$^{13B}$, R$^{13C}$, R$^{13D}$, etc. is defined within the scope of the definition of R$^{13}$ and optionally differently.

Descriptions of compounds (e.g., polymers) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, —COOH, —$COOCH_3$, —N-hydroxysuccimmide, -maleimide,

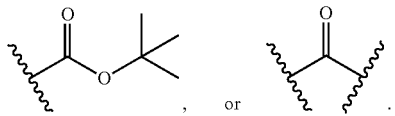, or .

In embodiments, the bioconjugate reactive group may be protected (e.g., with a protecting group). In embodiments, the bioconjugate reactive moiety is —$N_3$, -DBCO, alkynyl

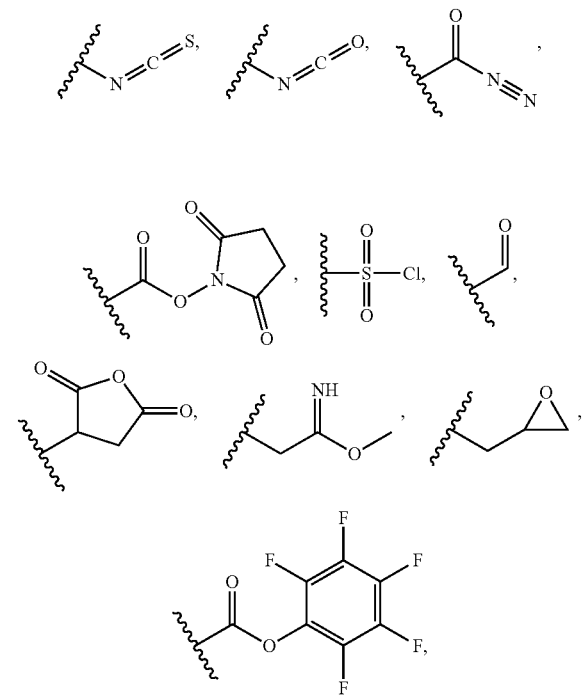

or —$NH_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
| --- | --- | --- |
| halotriazines | amines/anilines | aminotri azines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate reactive moiety" and "bioconjugate reactive group" refers to a moiety or group capable of forming a bioconjugate linker (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, a bioconjugate linker is formed by the reaction between an azide moiety and a dibenzocyclooctyne (DBCO) moiety.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The term "covalent linker" is used in accordance with its ordinary meaning and refers to a divalent moiety which connects at least two moieties to form a molecule.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "non-reactive moiety" is used in accordance with its plain ordinary meaning and refers to a moiety that does not react with a nucleophile or an electrophile (e.g., under reaction conditions wherein other moieties in the same molecule may react with a nucleophile or electrophile, under click chemistry reaction conditions such as those conditions wherein an azide may react with dibenzocyclooctyne (DBCO) or an epoxide). In embodiments, the non-reactive moiety is attached to a polymer. In embodiments, the non-reactive moiety is hydrophilic. In embodiments, the non-reactive moiety increases the water solubility of a polymer that includes the non-reactive moiety. In embodiments, the non-reactive moiety is not a bioconjugate reactive moiety. In embodiments, the non-reactive moiety is an unsubstituted alkyl. In embodiments, the non-reactive moiety is hydrogen.

"Contacting" is used in accordance with its plain ordinary meaning and refers to the process of allowing at least two distinct species (e.g., chemical compounds including biomolecules, particles, solid supports, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a particle described herein to interact with an array.

The terms "particle" and "bead" are used interchangeably and mean a small body made of a rigid or semi-rigid material. The body can have a shape characterized, for example, as a sphere, oval, microsphere, or other recognized particle shape whether having regular or irregular dimensions. A "nanoparticle," as used herein, is a particle wherein the longest diameter is less than or equal to 1000 nanometers. Nanoparticles may be composed of any appropriate material. For example, nanoparticle cores may include appropriate metals and metal oxides thereof (e.g., a metal nanoparticle core), carbon (e.g., an organic nanoparticle core) silicon and oxides thereof (e.g., a silicon nanoparticle core) or boron and oxides thereof (e.g., a boron nanoparticle core), or mixtures thereof. Nanoparticles may be composed of at least two distinct materials, one material (e.g., silica) forms the core and the other material forms the shell (e.g., copolymer) surrounding the core. In embodiments, the nanoparticle is composed of a copolymer described herein.

The term "silica nanoparticle" is used according to its plain and ordinary meaning and refers to a nanoparticle containing Si atoms (e.g., in a tetrahedral coordination) with 4 oxygen atoms surrounding a central Si atom. A person of ordinary skill in the art would recognize that the silica nanoparticle typically includes terminal oxygen atoms (e.g., the oxygens on the surface of the nanoparticle) that are hydroxyl moieties. A silica nanoparticle is a particle wherein the longest diameter is typically less than or equal to 1000 nanometers comprising a matrix of silicon-oxygen bonds. In embodiments, a nanoparticle has a shortest diameter greater than or equal to 1 nanometer (e.g., diameter from 1 to 1000 nanometers). In embodiments, the silica nanoparticle is mesoporous. In embodiments, the silica nanoparticle is nonporous.

A functionalized particle, as used herein, may refer to the post hoc conjugation (i.e. conjugation after the formation of the particle) of a moiety to a functional group on the surface of a particle. For example, a silica particle may be further functionalized to include additional atoms (e.g., nitrogen) or chemical entities (e.g., polymeric moieties or bioconjugate group). For example, when the silica nanoparticle is further functionalized with a nitrogen containing compound, one of the surface oxygen atoms surrounding the Si atom may be replaced with a nitrogen containing moiety. For example, a silica particle may be functionalized by reacting an unmodified silica nanoparticle with APTMS, APTES, or AHAMTES to generate an amine functionalized silica particle. The amine group may serve as a bioconjugate reactive moiety. In contrast to a functionalized particle, an unmodified particle refers to a particle which has not been further functionalized. Thus, for example, an unmodified particle does not include a nitrogen containing moiety (e.g., terminal amine moieties). For example, an unmodified silica nanoparticle refers to a silica nanoparticle as synthesized without post hoc functionalization. As used herein, the terms "bare particle" and "unmodified particle" are synonymous and interchangeable. In embodiments, an unmodified silica nanoparticle includes terminal oxygen atoms (e.g., the oxygens on the surface of the nanoparticle) that are hydroxyl moieties. In embodiments, the terminal oxygen atoms of the unmodified silica nanoparticle are —OH or salts thereof (e.g. —O— moieties). In contrast to a functionalized nanoparticle, an unmodified nanoparticle refers to a nanoparticle which has not been further functionalized. Thus, for example, an unmodified silica nanoparticle does not include a polymeric moiety.

Lengths and sizes of nanoparticles and functionalized particles as described herein may be measured using Transmission Electron Microscopy. For example, transmission electron microscopy measurements of the various particle samples may be drop coated (5 μL) onto 200 mesh copper EM grids, air-dried and imaged using a FEI Tecnai 12 TEM equipped with a Gatan Ultrascan 2K CCD camera at an accelerating voltage of 120 kV. The average size distributions of the particles may then be obtained from the TEM images using Image J software that were plotted using software (e.g., Origin Pro 8) to obtain the histogram size distributions of the particles. In embodiment, the length of a nanoparticle refers to the longest dimension of the particle.

As used herein, a "plurality" refers to two or more.

As used herein, "capable of hybridizing" is used in accordance with its ordinary meaning in the art and refers to two oligonucleotides that, under suitable conditions, can form a duplex (e.g., Watson-Crick pairing) which includes a double-stranded portion of nucleic acid. Such conditions, known in the art and described herein, depend upon, for example, the nature of the nucleotide sequence, temperature, and buffer conditions. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "Tm"; parameters such as salts, buffers, pH, temperature, GC % content of the polynucleotide and primers, and/or time.

Typically, hybridization is favored in lower temperatures and/or increased salt concentrations, as well as reduced concentrations of organic solvents. Some exemplary conditions suitable for hybridization include incubation of the polynucleotides to be hybridized in solutions having sodium salts, such as NaCl, sodium citrate and/or sodium phosphate. In some embodiments, hybridization or wash solutions can include about 10-75% formamide and/or about 0.01-0.7% sodium dodecyl sulfate (SDS). In some embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In some embodiments, the hybridization or washing solution can include BSA (bovine serum albumin). In some embodiments, hybridization or washing can be conducted at a temperature range of about 20-25° C., or about 25-30° C., or about 30-35° C., or about 35-40° C., or about 40-45° C., or about 45-50° C., or about 50-55° C., or higher. In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer. In some embodiments, hybridization or wash conditions can be conducted at a pH range of about 5-10, or about pH 6-9, or about pH 6.5-8, or about pH 6.5-7.

The term "alkoxysilyl" as used herein refers to silicon atom covalently bound to one or more alkoxy groups. In embodiments, the alkoxysilyl moiety has the formula —(R)$_n$—Si(—O-alkyl)$_3$ moiety, wherein n is 1, 2, or 3 and R is an unsubstituted C$_1$-C$_6$ alkyl. When used in combination with a polymerizable monomer (e.g., acrylate, methacrylate, acrylamide), it is understood the polymerizable monomer is covalently linked to the alkoxysilyl moiety. For example, alkoxysilyl methacrylate has the formula

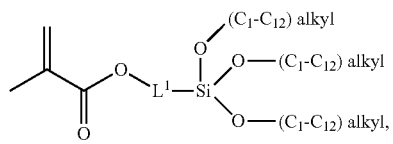

wherein L$^1$ is substituted or unsubstituted alkylene or substituted or unsubstituted heteroalkylene as described herein. In embodiments, alkoxysilyl acrylate has the formula

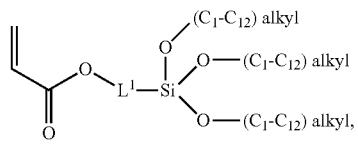

wherein L$^1$ is substituted or unsubstituted alkylene or substituted or unsubstituted heteroalkylene as described herein. In embodiments, alkoxysilyl methylacrylamide has the formula

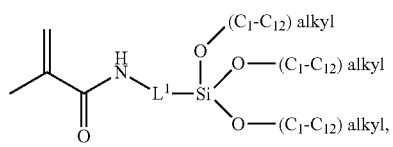

wherein L$^1$ is substituted or unsubstituted alkylene or substituted or unsubstituted heteroalkylene as described herein. In embodiments, alkoxysilyl acrylamide has the formula

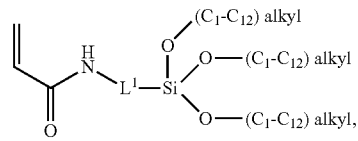

wherein L$^1$ is substituted or unsubstituted alkylene or substituted or unsubstituted heteroalkylene as described herein.

The term "alkoxy" refers to an alkyl group bonded to an oxygen atom.

The term "nucleophile" as used herein refers to a chemical group that is capable of donating electron density. All molecules or ions with a free pair of electrons or at least one pi bond can act as nucleophiles. The term "electrophile" as used herein refers to a chemical group that is capable of accepting electron density. An "electrophilic substituent", "electrophilic chemical moiety", or "electrophilic moiety" refers to an electron-poor chemical group, substituent, or moiety (monovalent chemical group), which may react with an electron-donating group, such as a nucleophile, by accepting an electron pair or electron density to form a bond.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect is provided a solid support including two or more wells, wherein each well includes one or more particles as described herein. In embodiments, each particle includes a plurality of oligonucleotide moieties covalently attached to said particle via a polymeric bioconjugate linker. In embodiments, the polymeric bioconjugate linker is formed through a reaction between a particle polymer (e.g., a polymer covalently attached to the surface of the particle) including a first bioconjugate reactive moiety and an oligonucleotide including a second bioconjugate reactive moiety. In embodiments, the average longest dimension of the particle is from about 100 nm to about 1000 nm. In embodiments, each particle includes a plurality of oligonucleotide moieties covalently attached to said particle via a bioconjugate linker, wherein the polymeric bioconjugate linker is formed through a reaction between a particle polymer (e.g., a polymer covalently attached to the surface of the particle) including a first bioconjugate reactive moiety (e.g., an azide) and an oligonucleotide including a second bioconjugate reactive moiety (e.g., DBCO).

In an aspect is provided an array (e.g., a multiwell container), including: a solid support including a surface, the surface comprising a plurality of wells separated from each other by interstitial regions on the surface, wherein one or more wells includes a particle, wherein the particle includes a plurality of bioconjugate reactive moieties, a plurality of oligonucleotide moieties (e.g., covalently bound to the particle), or a combination thereof. In embodiments, there is at least one particle per well. In embodiments, there is at most one particle per well. In embodiments, the surface is substantially free of oligonucleotides. In embodiments, the surface does not include oligonucleotide capture moieties.

In another aspect is provided an array, including: a solid support including a surface, the surface including a plurality of wells separated from each other by interstitial regions on the surface, wherein the surface comprises a polymer layer and is substantially free of oligonucleotide moieties, wherein one or more wells contains a particle, wherein the particle includes a plurality of bioconjugate reactive moieties, a plurality of oligonucleotide moieties, or a combination thereof. In embodiments, there is at least one particle per well. In embodiments, there two or more particles per well. In embodiments, there is at most one particle per well. In embodiments, the surface is substantially free of oligonucleotides. In embodiments, the surface does not include oligonucleotide capture moieties.

In an aspect is provided a solid support (e.g., a patterned glass slide or planar support) including two or more wells, wherein each well includes a particle including a plurality of bioconjugate reactive moieties, a plurality of oligonucleotide moieties, or a combination thereof, wherein the average longest dimension of the particle is from about 100 nm to about 1000 nm. In embodiments, the solid support includes a plurality of wells (e.g., a billion or more wells). In embodiments, the wells (e.g., each well) is separated by about 0.1 µm to about 5.0 µm. In embodiments, the wells (e.g., each well) is separated by about 0.2 µm to about 2.0 µm. In embodiments, the wells (e.g., each well) is separated by about 0.5 µm to about 1.5 µm. In embodiments, the wells of the solid support are all the same size. In embodiments, one or more wells are different sizes (e.g., one population of wells are 1.0 µm in diameter, and a second population are 0.5 µm in diameter). In embodiments, the solid support is a glass slide about 75 mm by about 25 mm. In embodiments, the solid support includes a resist (e.g., a photoresist or nanoimprint resist including a crosslinked polymer matrix attached to the solid support).

In an aspect is provided a solid support including two or more wells (alternatively referred to as a multiwell container or array). In embodiments, wherein each well is separated by about 0.2 µm to about 2.0 µm and each well includes at least one particle as described herein. In embodiments, the particle (e.g., a nanoparticle) includes a plurality of oligonucleotide moieties covalently attached to the particle via a bioconjugate linker, wherein the bioconjugate linker is formed via a reaction between a particle polymer including a first bioconjugate reactive moiety and an oligonucleotide including a second bioconjugate reactive moiety. In embodiments, the average longest dimension of the particle is from about 100 nm to about 1000 nm. In embodiments, the particle includes a plurality of particle polymers (e.g., a polymer or copolymer described herein). In embodiments, the particle polymer is a brush polymer. In embodiments, the plurality of particle polymers are not crosslinked (i.e., covalently bound to each other). In embodiments, the plurality of particle polymers are crosslinked.

In embodiments, density of wells on the solid support may be tuned. For example, in embodiments, the multiwell container includes a density of at least about 100 wells per $mm^2$ about 1,000 wells per $mm^2$, about 0.1 million wells per $mm^2$, about 1 million wells per $mm^2$ about 2 million wells per $mm^2$, about 5 million wells per $mm^2$, about 10 million wells per $mm^2$, about 50 million wells per $mm^2$, or more. In embodiments, the multiwell container includes no more than about 50 million wells per $mm^2$, about 10 million wells per $mm^2$, about 5 million wells per $mm^2$, about 2 million wells per $mm^2$, about 1 million wells per $mm^2$, about 0.1 million wells per $mm^2$, about 1,000 wells per $mm^2$, about 100 wells per $mm^2$, or less. In embodiments, the solid support includes about 500, 1,000, 2,500, 5,000, or about 25,000 wells per $mm^2$. In embodiments, the solid support includes about $1\times10^6$ to about $1\times10^{12}$ wells. In embodiments, the solid support includes about $1\times10^7$ to about $1\times10^{12}$ wells. In embodiments, the solid support includes about $1\times10^8$ to about $1\times10^{12}$ wells. In embodiments, the solid support includes about $1\times10^6$ to about $1\times10^9$ wells. In embodiments, the solid support includes about $1\times10^9$ to about $1\times10^{10}$ wells. In embodiments, the solid support includes about $1\times10^7$ to about $1\times10^9$ wells. In embodiments, the solid support includes about $1\times10^8$ to about $1\times10^8$ wells. In embodiments, the solid support includes about $1\times10^6$ to about $1\times10^8$ wells. In embodiments, the solid support includes about $1\times10^6$, $1\times10^7$, $1\times10^8$, $1\times10^9$, $1\times10^{10}$, $1\times10^{11}$, $1\times10^{12}$, $5\times10^{12}$, or more wells. In embodiments, the solid support includes about $1.8\times10^9$, $3.7\times10^9$, $9.4\times10^9$, $1.9\times10^{10}$, or about $9.4\times10^{10}$ wells. In embodiments, the solid support includes about $1\times10^6$ or more wells. In embodiments, the solid support includes about $1\times10^7$ or more wells. In embodiments, the solid support includes about $1\times10^8$ or more wells. In embodiments, the solid support includes about $1\times10^9$ or more wells. In embodiments, the solid support includes about $1\times10^{10}$ or more wells. In embodiments, the solid support includes about $1\times10^{11}$ or more wells. In embodiments, the solid support includes about $1\times10^{12}$ or more wells. In embodiments, the solid support is a glass slide. In embodiments, the solid support is a about 75 mm by about 25 mm. In embodiments, the solid support includes one, two, three, or four channels.

In embodiments, the solid support includes a polymer layer. In embodiments, the polymer layer includes polymerized units of alkoxysilyl methacrylate, alkoxysilyl acrylate, alkoxysilyl methacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

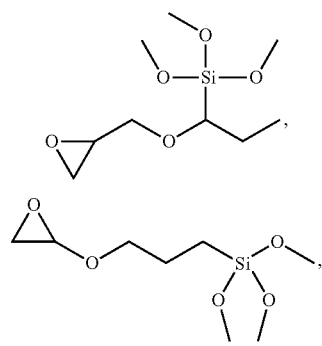

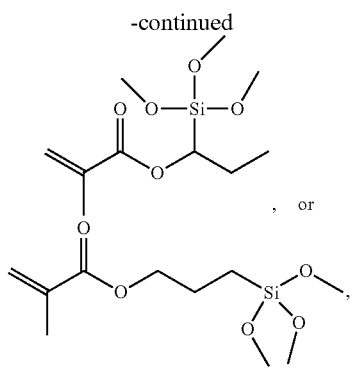

or a copolymer thereof.

In embodiments, the solid support includes a photoresist, alternatively referred to herein as a resist. A "resist" as used herein is used in accordance with its ordinary meaning in the art of lilthography and refers to a polymer matrix (e.g., a polymer network). In embodiments, the photoresist is a silsesquioxane resist, an epoxy-based polymer resist, poly (vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist. In embodiments, the photoresist is a silsesquioxane resist. In embodiments, the photoresist is an epoxy-based polymer resist. In embodiments, the photoresist is a poly(vinylpyrrolidone-vinyl acrylic acid) copolymer resist. In embodiments, the photoresist is an Off-stoichiometry thiol-enes (OSTE) resist. In embodiments, the photoresist is an amorphous fluoropolymer resist. In embodiments, the photoresist is a crystalline fluoropolymer resist. In embodiments, the photoresist is a polysiloxane resist. In embodiments, the photoresist is an organically modified ceramic polymer resist. In embodiments, the photoresist includes polymerized alkoxysilyl methacrylate polymers and metal oxides (e.g., $SiO_2$, ZrO, MgO, $Al_2O_3$, $TiO_2$ or $Ta_2O_5$). In embodiments, the photoresist includes polymerized alkoxysilyl acrylate polymers and metal oxides (e.g., $SiO_2$, ZrO, MgO, $Al_2O_3$, $TiO_2$ or $Ta_2O_5$). In embodiments, the photoresist includes metal atoms, such as Si, Zr, Mg, Al, Ti or Ta atoms.

In embodiments, the wells are separated from each other by interstitial regions including a polymer layer as described herein (e.g., an amphiphilic copolymer). In embodiments, the solid support further includes a photoresist, wherein the photoresist does not contact the bottom of the well. In embodiments, the polymer layer is substantially free of oligonucleotide moieties. In embodiments, the solid support does not include a polymer (e.g., the solid support is a patterned glass slide). In embodiments, the wells do not include a polymer (e.g., an amphiphilic polymer as described herein) prior to particle loading. In embodiments, the solid support further includes a photoresist, wherein the photoresist is in contact the bottom of the well and the interstitial space. In embodiments, the polymer layer is substantially free of oligonucleotide moieties (e.g., oligonucleotide moieties are not covalently bound to the solid support and/or the polymer layer, including the interstitial space). In embodiments, the wells include a polymer (e.g., an amphiphilic polymer and/or resist as described herein) prior to particle loading.

In embodiments, each well contains a plurality of particles (e.g., wherein the well is at least twice the diameter of the longest dimension of the particle). In embodiments, each well is referred to as a feature. In embodiments, the arrays include about 10,000,000 features/cm$^2$ to about 5,000,000,000 features/cm$^2$. In embodiments, the arrays include about 100,000,000 features/cm$^2$ to about 1,000,000,000 features/cm$^2$. In embodiments, the arrays include about 100,000 features/cm$^2$ to about 100,000,000 features/cm$^2$. In embodiments, the arrays include about or about 10,000,000 features/cm$^2$ to about 50,000,000 features/cm$^2$. In embodiments, each well includes one particle. In embodiments, each well include 10 to 100 nanoparticles (e.g., the diameter of the well is 5 mm).

In embodiments, the wells have a mean or median separation from one another of about 0.5-5 µm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm, or a number or a range between any two of these values. In embodiments, the mean or median separation is about or at least about 0.1 µm. In embodiments, the mean or median separation is about or at least about 0.2 µm. In embodiments, the mean or median separation is about or at least about 0.3 µm. In embodiments, the mean or median separation is about or at least about 0.4 µm. In embodiments, the mean or median separation is about or at least about 0.5 µm. In embodiments, the mean or median separation is about or at least about 0.6 µm. In embodiments, the mean or median separation is about or at least about 0.7 µm. In embodiments, the mean or median separation is about or at least about 0.8 µm. In embodiments, the mean or median separation is about or at least about 0.9 µm. In embodiments, the mean or median separation is about or at least about 1.0 µm. In embodiments, the mean or median separation is about or at least about 1.1 µm. In embodiments, the mean or median separation is about or at least about 1.2 µm. In embodiments, the mean or median separation is about or at least about 1.3 µm. In embodiments, the mean or median separation is about or at least about 1.4 µm. In embodiments, the mean or median separation is about or at least about 1.5 µm. In embodiments, the mean or median separation is about or at least about 1.6 µm. In embodiments, the mean or median separation is about or at least about 1.7 µm. In embodiments, the mean or median separation is about or at least about 1.8 µm. In embodiments, the mean or median separation is about or at least about 1.9 µm. In embodiments, the mean or median separation is about or at least about 2.0 µm. In embodiments, the mean or median separation is about or at least about 2.1 µm. In embodiments, the mean or median separation is about or at least about 2.2 µm. In embodiments, the mean or median separation is about or at least about 2.3 µm. In embodiments, the mean or median separation is about or at least about 2.4 µm. In embodiments, the mean or median separation is about or at least about 2.5 µm. In embodiments, the mean or median separation is about or at least about 2.6 µm. In embodiments, the mean or median separation is about or at least about 2.7 µm. In embodiments, the mean or median separation is about or at least about 2.8 µm. In embodiments, the mean or median separation is about or at least about 2.9 µm. In embodiments, the mean or median separation is about or at least about 3.0 µm. In embodiments, the mean or median separation is about or at least about 3.1 µm. In embodiments, the mean or median separation is about or at least about 3.2 µm. In embodiments, the mean or median separation is about or at least about 3.3 µm. In embodiments, the mean or median separation is about or at least about 3.4 µm. In embodiments, the mean or median separation is about or at least about 3.5 µm. In embodiments, the mean or median separation is about or at least about 3.6 µm. In embodiments, the mean or median separation is about or at least about 3.7 µm. In embodiments, the mean or median separation is about or at least about 3.8 µm. In embodiments, the mean or median separation is about or at least about 3.9 µm. In embodiments, the mean or median separation is about or at least about 4.0 µm. In embodiments, the mean or median separation is about or at least about 4.1 µm. In embodiments, the mean or median separation is about or at least about 4.2 µm. In embodiments, the mean or median separation is about or at least about 4.3 µm. In embodiments, the mean or median separation is about or at least about 4.4 µm. In embodiments, the mean or median separation is about or at least about 4.5 µm. In embodiments, the mean or median separation is about or at least about 4.6 µm. In embodiments, the mean or median separation is about or at least about 4.7 µm. In embodiments, the mean or median separation is about or at least about 4.8 µm. In embodiments, the mean or median separation is about or at least about 4.9 µm. In embodiments, the mean or median separation is about or at least about 5.0 µm. The mean or median separation may be measured center-to-center (i.e., the center of one well to the center of a second well). In embodiments of the methods provided herein, the wells have a mean or median separation (measured center-to-center) from one another of about 0.5-5 µm. The mean or median separation may be measured edge-to-edge (i.e., the edge of well to the edge of a second well). In embodiments, the wells have a mean or median separation (measured edge-to-edge) from one another of about 0.2-1.5 µm. In embodiments, the wells have a mean or median separation (measured center-to-center) from one another of about 0.7-1.5 µm.

Neighboring features of an array can be discrete one from the other in that they do not overlap. Accordingly, the features can be adjacent to each other or separated by a gap (e.g., an interstitial space). In embodiments where features are spaced apart, neighboring sites can be separated, for example, by a distance of less than 10 µm, 5 m, 1 µm, 0.9 µm, 0.8 µm, 0.7 µm, 0.6 µm, 0.5 µm, or less. The layout of features on an array can also be understood in terms of center-to-center distances between neighboring features. An array useful in the invention can have neighboring features with center-to-center spacing of less than about 10 µm, 5 µm, 1 µm, 0.9 µm, 0.8 µm, 0.7 µm, 0.6 µm, 0.5 µm, 0.4 µm, or less. In embodiments, the array has neighboring features with center-to-center spacing of less than about 10 µm. In embodiments, the array has neighboring features with center-to-center spacing of less than about 5 µm. In embodiments, the array has neighboring features with center-to-center spacing of less than about 1 µm. In embodiments, the array has neighboring features with center-to-center spacing of less than about 0.9 µm. In embodiments, the array has neighboring features with center-to-center spacing of less than about 0.8 µm. In embodiments, the array has neighboring features with center-to-center spacing of less than about 0.7 µm. In embodiments, the array has neighboring features with center-to-center spacing of less than about 0.6 µm. In embodiments, the array has neighboring features with center-to-center spacing of less than about 0.5 µm. In embodiments, the array has neighboring features with center-to-center spacing of less than about 0.4 µm. Furthermore, it will be understood that the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array.

The arrays and solid supports for some embodiments have at least one surface located within a flow cell. Flow cells provide a convenient format for housing an array of clusters produced by the methods described herein, in particular when subjected to an SBS or other detection technique that involves repeated delivery of reagents in cycles.

In some embodiments, the particle is a functionalized particle including a particle core and a particle shell, wherein said particle shell includes the plurality of bioconjugate reactive moieties, the plurality of oligonucleotide moieties, or a combination thereof, wherein each of the bioconjugate reactive moieties and each of the oligonucleotide moieties includes a linker binding the bioconjugate reactive moieties and oligonucleotide to the particle core.

Figure 10A:
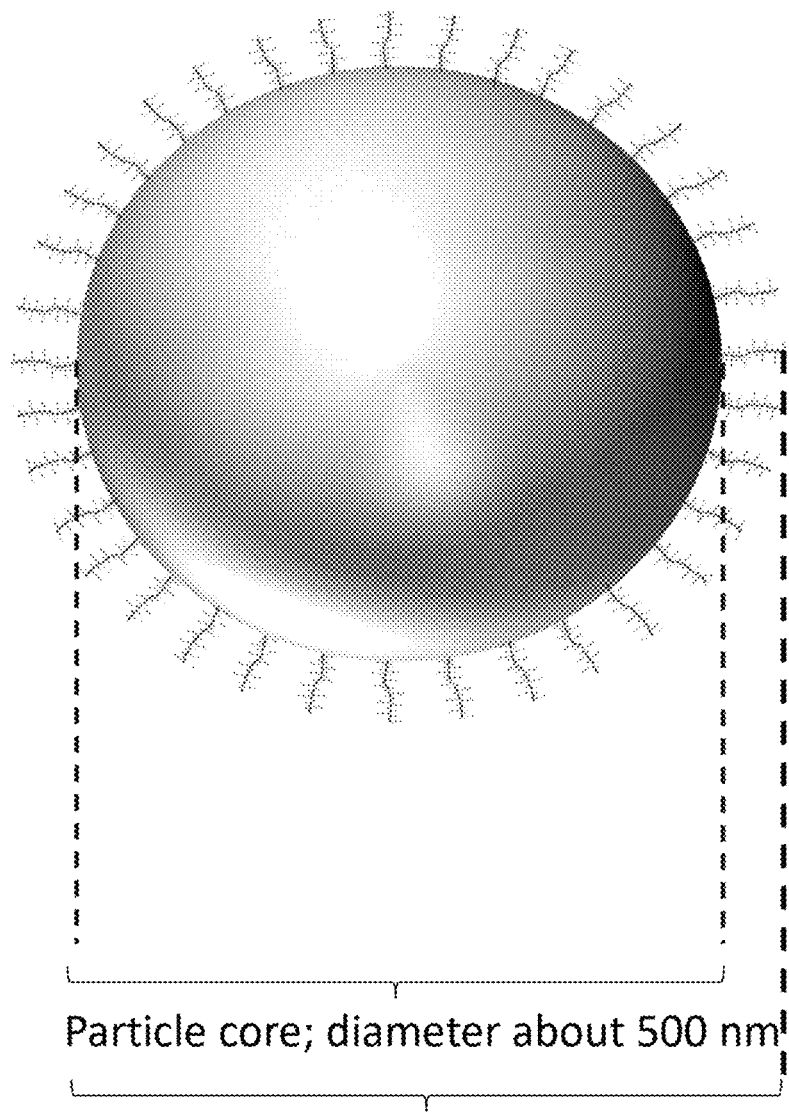
FIGS. 10A-10B.
Figure 10B:
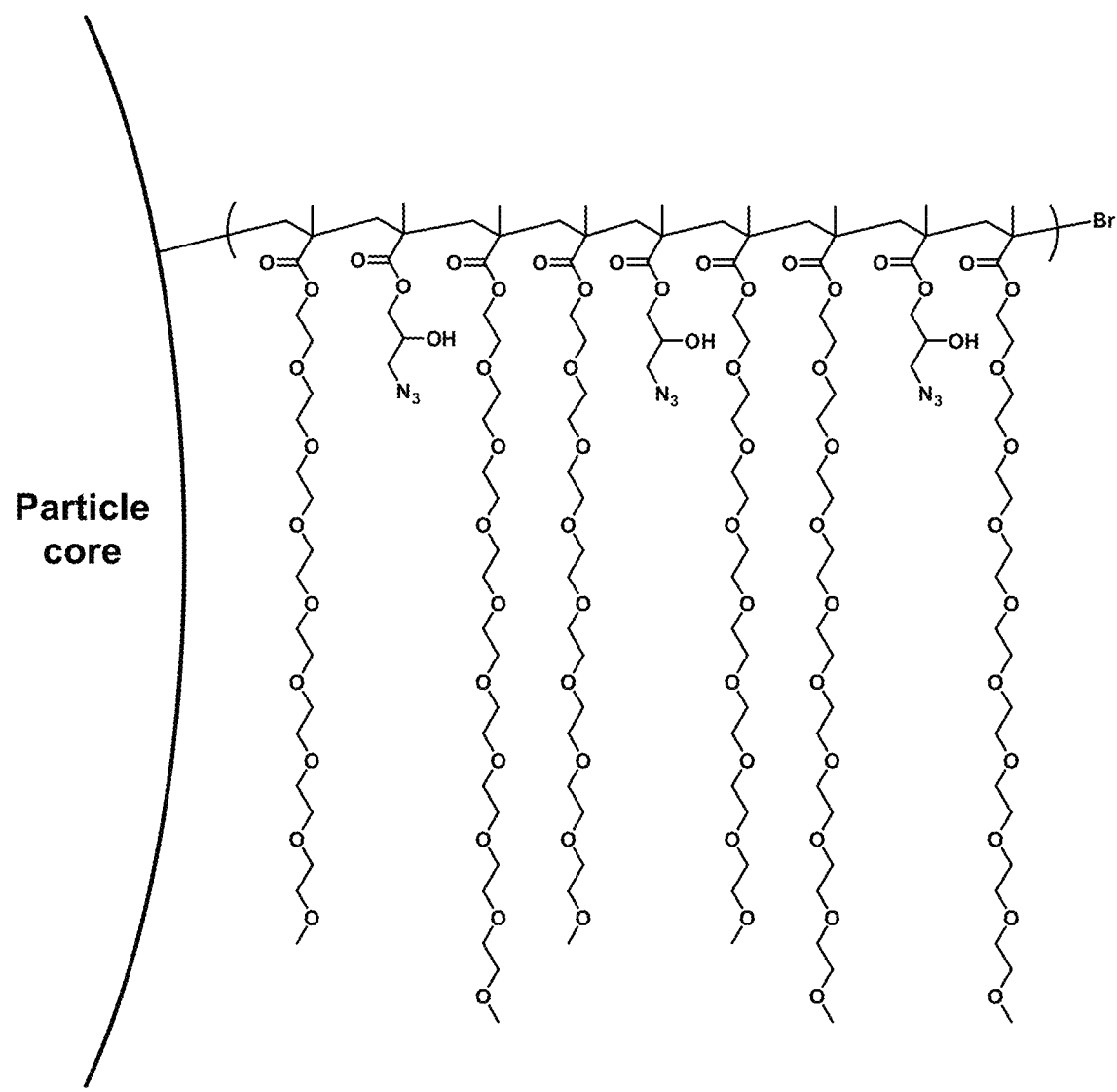
Figure 11:
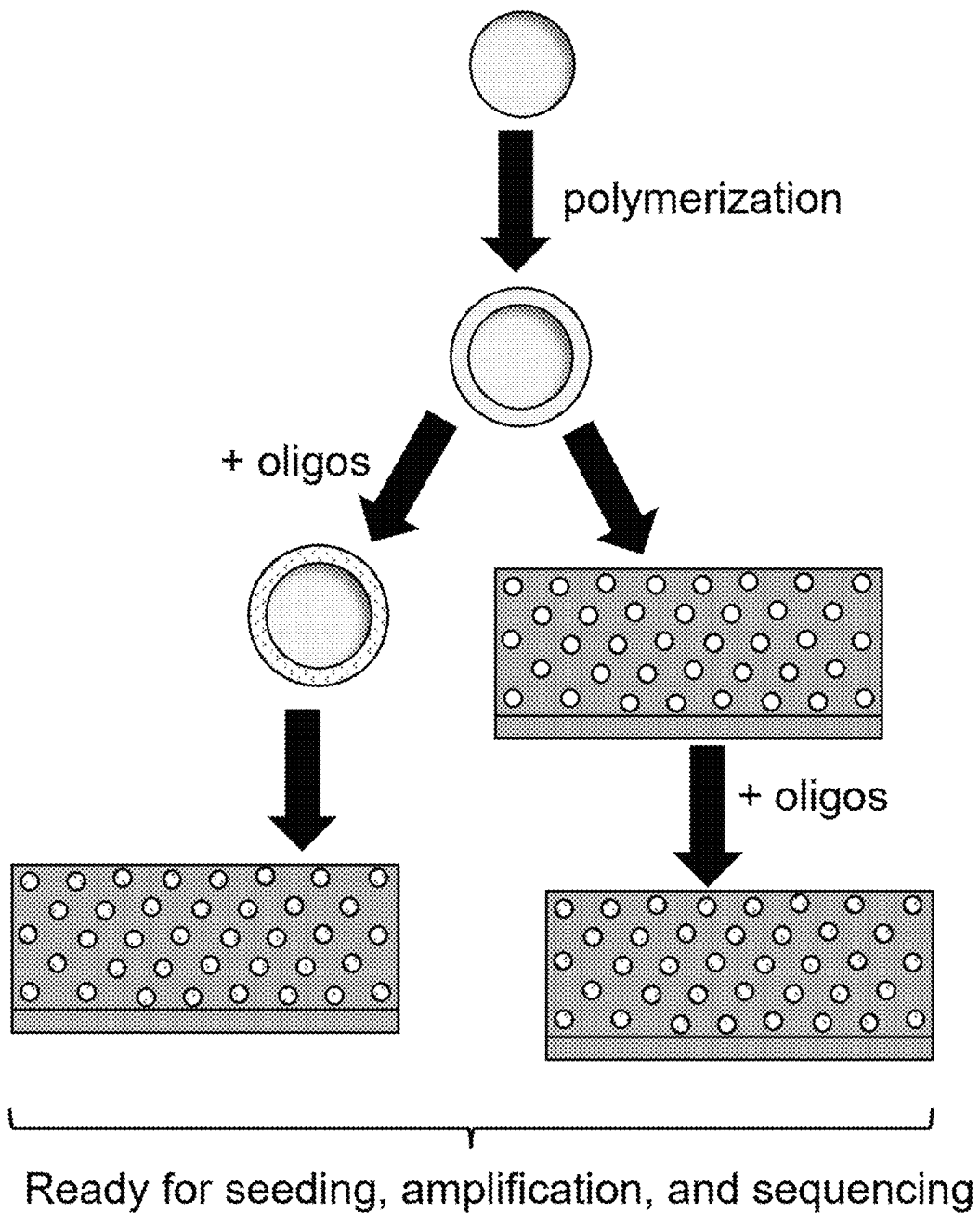
FIG. 11. An overview of the polymerization and particle loading is provided in FIG. 11. A particle core (e.g., a silica or metallic nanoparticle) is incubated with monomers under suitable polymerization conditions and particle polymers grow on the surface of the core. The functionalized particle now includes a plurality of bioconjugate reactive moieties (e.g., azido moieties). The functionalized particle may be loaded onto a patterned solid support (e.g., a multiwell container that optionally includes a passivating polymer as described herein) and arranged into the wells. Oligonucleotide moieties containing a reactive bioconjugate moiety (e.g., a DBCO moiety) are allowed to contact the particles, wherein the oligonucleotides reacts with the bioconjugate groups on the polymers and forms a bioconjugate linker, thereby covalently immobilizing the oligonucleotides to the particle. Alternatively, prior to loading into the patterned solid support, oligonucleotide moieties containing a reactive bioconjugate moiety are allowed to contact the particles and form a bioconjugate linker, thereby covalently immobilizing the oligonucleotides to the particle. The oligo-containing particles are then loaded onto the multiwell container that does not include a passivating polymer. A particle loaded patterned flow cell may include about 10,000 to about 50,000, or about 25,000 immobilized oligonucleotides per square micrometer. The pattered solid support is then ready for standard clustering (e.g., template seeding and amplification) protocols and/or subsequent detection (e.g., sequencing).

In embodiments, the particle is a functionalized particle including a particle core (e.g., a silica core) and a plurality of polymer moieties, wherein each polymer moiety includes a plurality of bioconjugate reactive moieties, a plurality of oligonucleotide moieties (e.g., oligonucleotide moieties covalently bound to the particle polymer), or a combination thereof, wherein each of the bioconjugate reactive moieties and each of the oligonucleotide moieties includes a linker binding the bioconjugate reactive moieties and oligonucleotide to the particle core. In embodiments, the particle includes a particle core and a particle polymer, wherein the bioconjugate reactive moieties and oligonucleotide moieties are covalently attached via a linker to the particle polymer. For example, FIGS. 10A-10B illustrate an embodiment of a functionalized particle as described herein. The particle polymer, as illustrated in FIGS. 10A-10B, includes a polymer (e.g., PEGMA) linked with bioconjugate reactive moieties (e.g., GMA-Az).

In some embodiments, the particle core includes glass, ceramic, metal, silica, magnetic material, or a paramagnetic material. The particle core may be an inorganic particle core. The inorganic particle core may be a metal particle core. When the particle core is a metal, the metal may be titanium, zirconium, gold, silver, platinum, cerium, arsenic, iron, aluminum or silicon. The metal particle core may be titanium, zirconium, gold, silver, or platinum and appropriate metal oxides thereof. In embodiments, the particle core is titanium oxide, zirconium oxide, cerium oxide, arsenic oxide, iron oxide, aluminum oxide, or silicon oxide. The metal oxide particle core may be titanium oxide or zirconium oxide. The particle may be titanium. The particle may be gold. The particle may be silicon dioxide. The particle may be silica. In embodiments, the particle core is in the form of a bead. For example, the core/shell layers may be formed around a supporting structure, for example, a silica, magnetic, or paramagnetic bead. In some embodiments, the composition includes a solid bead support (which itself may include a magnetic core and an encapsulating polymer layer), a functional core layer around the bead for primer attachment, and a shell polymer layer in which no amplification reactions take place. In embodiments, the particle is a silica particle includes a magnetic core, and a copolymer shell. In embodiments, the particle shell is chemically distinct from the particle core.

In embodiments, the particle core includes glass, ceramic, metal, silica, magnetic material, or a paramagnetic material. The particle core may be an inorganic particle core. The inorganic particle core may be a metal particle core. When the particle core is a metal, the metal may be titanium, zirconium, gold, silver, platinum, cerium, arsenic, iron, aluminum or silicon. The metal particle core may be titanium, zirconium, gold, silver, or platinum and appropriate metal oxides thereof. In embodiments, the particle core is titanium oxide, zirconium oxide, cerium oxide, arsenic oxide, iron oxide, aluminum oxide, or silicon oxide. The metal oxide particle core may be titanium oxide or zirconium oxide. The particle may be titanium. The particle may be gold. The particle may be silicon dioxide. The particle may be silica. In embodiments, the particle core is in the form of a bead. For example, the core/shell layers may be formed around a supporting structure, for example, a silica, magnetic, or paramagnetic bead. In embodiments, the composition includes a solid bead support (which itself may include a magnetic core and an encapsulating polymer layer), a functional core layer around the bead for primer attachment. In embodiments, the particle is a silica particle further includes a magnetic core. In embodiments, the particle polymer is chemically distinct from the particle core. In embodiments, the particle polymer is permeable to amplification and/or sequencing reagents (e.g., a polymerase, nucleotides, salts, and buffers). In embodiments, the particle includes glass or silica. In embodiments, the particle is a silica nanoparticle.

In some embodiments, the particle shell includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle shell includes polymerized units of polyacrylamide (AAm), glicydyl methacrylate (GMA), polyethylene glycol methacrylate (PEGMA), polyethylene glycol methacrylate (PEGMA), isocyanatoethyl methacrylate (IEM), or a copolymer thereof. In embodiments, the particle shell includes polymerized units of polyethylene glycol methacrylate (PEGMA) and glicydyl methacrylate (GMA). In embodiments, the particle shell includes polymerized units of polyethylene glycol methacrylate (PEGMA) and isocyanatoethyl methacrylate (IEM). In embodiments, the particle shell includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the particle shell includes polymerized units of 3-azido-2-hydroxypropyl methacrylate, 2-azido-3-hydroxypropyl methacrylate, or 2-(((2-azidoethoxy)carbonyl)amino)ethyl methacrylate. In embodiments, the particle shell includes polymerized units of 3-azido-2-hydroxypropyl methacrylate. In embodiments, the particle shell includes polymerized units of 3-azido-2-hydroxypropyl methacrylate 2-azido-3-hydroxypropyl methacrylate. In embodiments, the particle shell includes polymerized units of 3-azido-2-hydroxypropyl methacrylate 2-(((2-azidoethoxy)carbonyl)amino)ethyl methacrylate.

In some embodiments, the particle polymer includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle polymer includes polymerized units of polyethylene glycol methacrylate (PEGMA) and glicydyl methacrylate (GMA). In embodiments, the particle polymer includes polymerized units of polyethylene glycol methacrylate (PEGMA) and isocyanatoethyl methacrylate (IEM). In embodiments, the particle polymer includes polymerized units of glicydyl methacrylate azide (GMA azide) and polyethylene glycol methacrylate (PEGMA). In embodiments, the ratio of GMA azide to PEGMA is 1:1. In embodiments, the ratio of GMA azide to PEGMA is 1:2. In embodiments, the ratio of GMA azide to PEGMA is 1:3. In embodiments, the ratio of GMA azide to PEGMA is 1:4. In embodiments, the ratio of GMA azide to PEGMA is 1:5. In embodiments, the ratio of GMA azide to PEGMA is 1:6. In embodiments, the ratio of GMA azide to PEGMA is 1:7. In embodiments, the ratio of GMA azide to PEGMA is 1:8. In embodiments, the particle polymer includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the particle polymer includes polymerized units of 3-azido-2-hydroxypropyl methacrylate, 2-azido-3-hydroxypropyl methacrylate, or 2-(((2-azidoethoxy)carbonyl)amino)ethyl methacrylate. In embodiments, the particle polymer includes polymerized units of 3-azido-2-hydroxypropyl methacrylate. In embodiments, the particle polymer includes polymerized units of 3-azido-2-hydroxypropyl methacrylate 2-azido-3-hydroxypropyl methacrylate. In embodiments, the particle polymer includes polymerized units of 3-azido-2-hydroxypropyl methacrylate 2-(((2-azidoethoxy)carbonyl)amino)ethyl methacrylate. In embodiments, the particle polymer includes polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide, wherein the particle core is a silica particle. In embodiments, the particle includes a plurality of particle polymers (e.g., a plurality of polyethylene glycol methacrylate (PEGMA) and glicydyl methacrylate (GMA) azide copolymers). In embodiments, the particle includes a plurality of brush particle polymers.

In embodiments, the particle polymer is covalently bound to the particle. For example, the particle polymer is attached to the particle via a polymerization initiator, for example (3-trimethoxysilyl)propyl 2-bromo-2-methylpropionate, wherein the —Si—O— moieties are attached to a silica particle. In embodiments, the polymerization initiator has the formula:

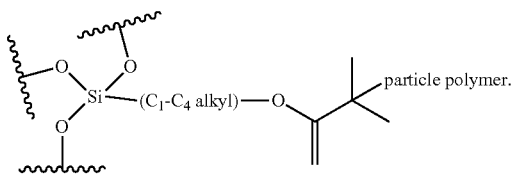

In some embodiments, the particle is a polymer particle including polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In some embodiments, the particle is a polymer particle including polymerized units of polyacrylamide (AAm), hydroxyethylmethacrylate (HEMA), hydroxyethylacrylate (HEA), hydroxypropylmethacrylate (HPMA), polyethylene glycol (PEG), isocyanatoethyl methacrylate (IEM), or a copolymer thereof. In embodiments, the particle is a polymer particle including polymerized units of polyacrylamide (AAm), glicydyl methacrylate (GMA), polyethylene glycol methacrylate (PEGMA), polyethylene glycol acrylate (PEGA), isocyanatoethyl methacrylate (IEM), or a copolymer thereof. In embodiments, the particle is a polymer particle including polymerized units of polyacrylamide (AAm) and glicydyl methacrylate (GMA). In embodiments, the particle is a polymer particle including polymerized units of polyacrylamide (AAm) and isocyanatoethyl methacrylate (IEM). In embodiments, the particle is a polymer particle including polymerized units of glicydyl methacrylate (GMA). In embodiments, the particle is a polymer particle including polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the particle is a polymer particle including polymerized units of 3-azido-2-hydroxypropyl methacrylate. In embodiments, the particle is a polymer particle including polymerized units of 2-azido-3-hydroxypropyl methacrylate. In embodiments, the particle is a polymer particle including polymerized units of 2-(((2-azidoethoxy)carbonyl)amino)ethyl methacrylate. In embodiments, the particle is a polymer particle including polymerized units of 3-azido-2-hydroxypropyl acrylate. In embodiments, the particle is a polymer particle including polymerized units of 2-azido-3-hydroxypropyl acrylate. In embodiments, the particle is a polymer particle including polymerized units of 2-(((2-azidoethoxy)carbonyl)amino) ethyl acrylate.

In embodiments, the particle is a polymeric particle including polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In some embodiments, the particle is a polymeric particle including polymerized units of polyacrylamide (AAm), hydroxyethylmethacrylate (HEMA), hydroxyethylacrylate (HEA), hydroxypropylmethacrylate (HPMA), polyethylene glycol (PEG), isocyanatoethyl methacrylate (IEM), or a copolymer thereof. In embodiments, the particle is a polymeric particle including polymerized units of polyacrylamide (AAm), glicydyl methacrylate (GMA), polyethylene glycol methacrylate (PEGMA), polyethylene glycol acrylate (PEGA), isocyanatoethyl methacrylate (IEM), or a copolymer thereof. In embodiments, the particle is a polymeric particle including polymerized units of polyacrylamide (AAm) and glicydyl methacrylate (GMA). In embodiments, the particle is a polymeric particle including polymerized units of polyacrylamide (AAm) and isocyanatoethyl methacrylate (IEM). In embodiments, the particle is a polymeric particle including polymerized units of glicydyl methacrylate (GMA). In embodiments, the particle is a polymeric particle including polymerized units of glicydyl methacrylate azide (GMA) azide. In embodiments, the particle is a polymeric particle including polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)

amino)ethyl acrylate. In embodiments, the particle is a polymeric particle including polymerized units of 3-azido-2-hydroxypropyl methacrylate. In embodiments, the particle is a polymeric particle including polymerized units of 2-azido-3-hydroxypropyl methacrylate. In embodiments, the particle is a polymeric particle including polymerized units of 2-(((2-azidoethoxy)carbonyl)amino)ethyl methacrylate. In embodiments, the particle is a polymeric particle including polymerized units of 3-azido-2-hydroxypropyl acrylate. In embodiments, the particle is a polymeric particle including polymerized units of 2-azido-3-hydroxypropyl acrylate. In embodiments, the particle is a polymeric particle including polymerized units of 2-(((2-azidoethoxy)carbonyl)amino)ethyl acrylate. In embodiments, the polymeric particle is permeable to a polymerase.

The polymer may be polymerized from a mixture of functionalized and non-functionalized monomers, such that at least some functionalized monomers that provide attachment points (e.g., azide moieties) for primers (e.g., DBCO-containing oligonucleotide primers) are spaced from one another by one or more monomers lacking such attachment points (e.g., PEG or AAm). The frequency of monomer units attached to primers within a polymer can be adjusted by changing the concentration of the corresponding functionalized monomer in the mixture of monomers. In embodiments, monomer units of the core polymer that are attached to a polynucleotide primer are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the core polymer that are attached to a polynucleotide primer (referred to herein as oligonucleotide moieties) are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the core polymer that are attached to a polynucleotide primer are separated by, on average, about or at least about 4 to 8 monomer units that are not attached to a primer. In embodiments, monomer units of the core polymer that are attached to a polynucleotide primer are separated by, on average, about 4 to 8 monomer units that are not attached to a primer. In embodiments, monomer units of the core polymer that are attached to a polynucleotide primer are separated by, on average, about or at least about 6, 7, or 8 monomer units that are not attached to a primer. In embodiments, primer-attached monomers are separated by, on average, about 1-50, 2-40, 3-30, 4-25, or 5-20 monomers not attached to primers. In embodiments, monomer units of the core polymer that are attached to a polynucleotide primer are separated by 3 monomer units that are not attached to a primer (aka 3 ng). In embodiments, monomer units of the core polymer that are attached to a polynucleotide primer are separated by 6 ng. In embodiments, monomer units the core polymer that are attached to a polynucleotide primer are separated by 9 ng. The mixture can include monomers with different functional groups (e.g., azides, alkynes, DBCO, etc.) as described herein.

In embodiments, the particles are non-covalently attached to the wells. In embodiments, the particles are physiosorbed to the wells. In embodiments, the particles are covalently attached to the wells. In embodiments, each particle attaches to the polymer layer of the surface (e.g., non-covalently attach to the polymer layer). In embodiments, the particles contact the well and remain attached without any additional means for attachment (e.g., hybridization of complementary oligonucleotides immobilized on the solid support). In embodiments, the solid support does not include immobilized oligonucleotides.

The manner in which an oligonucleotide primer is attached to the polymer will depend on the type of functional group used to form the attachment. A variety of suitable functional groups are available, examples of which are provided herein. The polymer may be polymerized from a mixture of functionalized and non-functionalized monomers, and/or a mixture of monomers with different functional groups. In embodiments, functional groups are selected that specifically react with their intended target (e.g., a paired functional group attached to a desired target, such as a primer), while also exhibiting anti-fouling characteristics that prevent, or have a reduced propensity for, non-specific binding of enzymes, dye-labeled nucleotides, and nucleic acids.

In embodiments, the particle shell is permeable to a polymerase. In embodiments, the polymer particle is permeable to a polymerase. In embodiments, the particle shell is permeable to an amplification reaction mixture and/or a sequencing reaction mixture. In embodiments, the polymer particle is permeable to an amplification reaction mixture and/or a sequencing reaction mixture. In embodiments, the particle shell is permeable to a sequencing reaction mixture. In embodiments, the polymer particle is permeable to a sequencing reaction mixture. In embodiments, the polymer particle and shell polymer are permeable to a polymerase for amplifying the target polynucleotide. In embodiments, the shell polymer has a higher permeability than the core (e.g., the particle core is substantially less permeable than the particle shell). In embodiments, the polymer shell is permeable to a polymerase for amplifying the target polynucleotide, such that the interface of the core is in contact with the polymerase. The term "sequencing reaction mixture" refers to an aqueous mixture that contains the agents and reagents necessary to allow addition of a nucleotide to a polynucleotide strand by a polymerase (e.g., addition of a dNTP or dNTP analogue to a DNA strand by a DNA polymerase). Exemplary mixtures of agents and reagents include buffers (e.g., saline-sodium citrate (SSC), tris(hydroxymethyl)aminomethane or "Tris"), salts (e.g., KCl or $(NH_4)_2SO_4$)), nucleotides (e.g., modified nucleotides), polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), detergents and/or crowding agents (e.g., PEG, Tween, BSA). In embodiments, the modified nucleotides are reversibly terminated nucleotides linked to fluorescent dyes, such that the identity of a nucleotide added in a sequencing reaction can be identified based on the fluorescent dye with which it is associated. The term "amplification reaction mixture" refers to an aqueous mixture that contains the agents and reagents necessary to make one or more copies of a nucleic acid. Exemplary components include s polymerase, a nucleic acid template, a suitable primer or set of primers, suitable nucleotides (e.g., dNTPs), and a suitable buffer.

In embodiments, the particle polymer is permeable to a polymerase. In embodiments, the polymeric particle is permeable to a polymerase. In embodiments, the particle polymer is permeable to an amplification reaction mixture and/or a sequencing reaction mixture. In embodiments, the polymeric particle is permeable to an amplification reaction mixture and/or a sequencing reaction mixture. In embodiments, the polymeric particle is permeable to a sequencing reaction mixture. The term "sequencing reaction mixture" refers to an aqueous mixture that contains the agents and reagents necessary to allow addition of a nucleotide to a polynucleotide strand by a polymerase (e.g., addition of a dNTP or dNTP analogue to a DNA strand by a DNA polymerase). Exemplary mixtures of agents and reagents include buffers (e.g., saline-sodium citrate (SSC), tris(hydroxymethyl)aminomethane or "Tris" or TE), salts (e.g., KCl or $(NH_4)_2SO_4$)), nucleotides (e.g., modified nucleotides), polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), detergents and/or crowding agents (e.g., PEG, Tween, BSA). In embodiments, the modified nucleotides are reversibly terminated nucleotides linked to fluorescent dyes, such that the identity of a nucleotide added in a sequencing reaction can be identified based on the fluorescent dye with which it is associated. The term "amplification reaction mixture" refers to an aqueous mixture that contains the agents and reagents necessary to make one or more copies of a nucleic acid. Exemplary components includes a polymerase, a nucleic acid template, a suitable primer or set of primers, suitable nucleotides (e.g., dNTPs), and a suitable buffer.

In embodiments, the solid support is subjected to lithographic patterning methods (e.g., nanolithographic to microlithographic patterning). In embodiments, prior to contacting the solid support with a plurality of particles, the solid support is subjected to lithographic patterning methods (e.g., nanolithographic to microlithographic patterning). Typically, features smaller than 10 micrometers are considered microlithographic, and features smaller than 100 nanometers are considered nanolithographic. Lithographic techniques make use of masks or templates to transfer patterns over a large area simultaneously. A powerful microfabrication technique is photolithography, i.e. the lithography using a UV light source and a photosensitive material as resist. As the name suggests, the photoresist (alternatively referred to as a resist) is an active material layer that can be patterned by selective exposure and must "resist" chemical/physical attach of the underlying substrate. In embodiments, the resist is a crosslinked polymer matrix. In embodiments, the resist includes silsesquioxane molecules. In embodiments, the resist includes polymerized epoxy-containing monomers, or polymerized poly(vinylpyrrolidone-vinyl acrylic acid) copolymers. In embodiments, the solid support includes a glass substrate having a surface coated in silsesquioxane resist (e.g., polyhedral oligosilsesquioxanemethacrylate (POSS)), an epoxy-based polymer resist (e.g., SU-8 as described in U.S. Pat. No. 4,882,245), poly(vinylpyrrolidone-vinyl acrylic acid) copolymer resist (e.g., as described in U.S. Pat. No. 7,467,632), or novolaks resist, bisazides resist, or a combination thereof (e.g., as described in U.S. Pat. No. 4,970,276). In embodiments, the resist is removed prior to loading. Alternatively, in embodiments, the resist includes the plurality of wells and remains in contact with the solid support while contacting the support with a plurality of particles.

In embodiments, the solid support includes a photoresist. A photoresist is a light-sensitive polymer material used to form a patterned coating on a surface. The process begins by coating a substrate (e.g., a glass substrate) with a light-sensitive organic material. A mask with the desired pattern is used to block light so that only unmasked regions of the material will be exposed to light. In the case of a positive photoresist, the photo-sensitive material is degraded by light and a suitable solvent will dissolve away the regions that were exposed to light, leaving behind a coating where the mask was placed. In the case of a negative photoresist, the photosensitive material is strengthened (either polymerized or cross-linked) by light, and a suitable solvent will dissolve away only the regions that were not exposed to light, leaving behind a coating in areas where the mask was not placed. In embodiments, the solid support includes an epoxy-based photoresist (e.g., SU-8, SU-8 2000, SU-8 3000, SU-8 GLM2060). In embodiments, the solid support includes a negative photoresist. Negative refers to a photoresist whereby the parts exposed to UV become cross-linked (i.e., immobilized), while the remainder of the polymer remains soluble and can be washed away during development. In embodiments, the solid support includes an Off-stoichiometry thiol-enes (OSTE) polymer (e.g., an OSTE resist). In embodiments, the solid support includes an Hydrogen Silsesquioxane (HSQ) polymer (e.g., HSQ resist). In embodiments, the solid support includes a crosslinked polymer matrix on the surface of the wells and the interstitial regions.

In embodiments, the solid support includes a nanoimprint resist. In embodiments, the solid support includes a photoresist and polymer layer, wherein the photoresist is between the solid support and the polymer layer (e.g., as depicted in FIGS. 1A-1C). In embodiments the photoresist is on the interstitial areas and not the surface of the wells. Suitable photoresist compositions are known in the art, such as, for example the compositions and resins described in U.S. Pat. Nos. 6,897,012; 6,991,888; 4,882,245; 7,467,632; 4,970,276, each of which is incorporated herein by reference in their entirety. In embodiments, the solid support includes a photoresist and polymer layer, wherein the photoresist is covalently attached to the solid support and covalently attached to the polymer layer. In embodiments, the resist is an amorphous (non-crystalline) fluoropolymer (e.g., CYTOP® from Bellex), a crystalline fluoropolymer, or a fluoropolymer having both amorphous and crystalline domains. In embodiments, the resist is a suitable polysiloxane, such as polydimethylsiloxane (PDMS).

In embodiments, the solid support includes a resist (e.g., a nanoimprint lithography (NIL) resist). Nanoimprint resists can include thermal curable materials (e.g., thermoplastic polymers), and/or UV-curable polymers. In embodiments, the solid support is generated by pressing a transparent mold possessing the pattern of interest (e.g., the pattern of wells) into photo-curable liquid film, followed by solidifying the liquid materials via a UV light irradiation. Typical UV-curable resists have low viscosity, low surface tension, and suitable adhesion to the glass substrate. For example, the solid support surface, but not the surface of the wells, is coated in an organically modified ceramic polymer (ORMOCER®, registered trademark of Fraunhofer-Gesellschaft zur Förderung der angewandten Forschung e. V. in Germany). Organically modified ceramics contain organic side chains attached to an inorganic siloxane backbone. Several ORMOCER® polymers are now provided under names such as "Ormocore", "Ormoclad" and "Ormocomp" by Micro Resist Technology GmbH. In embodiments, the solid support includes a resist as described in Haas et al Volume 351, Issues 1-2, 30 Aug. 1999, Pages 198-203, US 2015/0079351A1, US 2008/0000373, or US 2010/0160478, each of which is incorporated herein by reference. In embodiments, the solid support surface, and the surface of the wells, is coated in an organically modified ceramic polymer (ORMOCER®, registered trademark of Fraunhofer-Gesellschaft zur Förderung der angewandten Forschung e. V. in Germany). In embodiments, the resist (e.g., the organically modified ceramic polymer) is not removed prior to particle deposition. In embodiments, the wells are within the resist polymer and not the solid support.

In embodiments, the solid support includes a polymer layer (alternatively referred to as a polymer coating). In embodiments, the solid support comprises a polymer layer, wherein the polymer layer includes an amphiphilic copolymer. The term "amphiphilic copolymer" is used in accordance with its ordinary meaning and refers to a copolymer composed of polymerized hydrophilic (e.g., PEG monomers) and hydrophobic monomers (e.g., alkoxysilyl or (poly (propylene oxide) monomers). The term "amphiphilic copolymer" is used in accordance with its ordinary meaning and refers to a copolymer composed of polymerized hydrophilic (e.g., PEG monomers or HEMA monomers) and hydrophobic monomers (e.g., alkoxysilyl or (poly(propylene oxide) monomers). Amphiphilic copolymers can have both hydrophilic and hydrophobic properties. In embodiments, the polymer layer includes an amphiphilic acrylate copolymer or amphiphilic methacrylate copolymer.

In embodiments, the amphiphilic polymer includes a poloxamer. In some embodiments, the solid support includes a poloxamer layer. In some embodiments, the poloxamer is a polyoxyethylene-polyoxypropylene copolymers. In some embodiments, the poloxamer is poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, and poloxamer 407. In embodiments, the poloxamer is poloxamer 184, poloxamer 188, poloxamer 338, or poloxamer 407 (also known as F127).

Figure 7A:
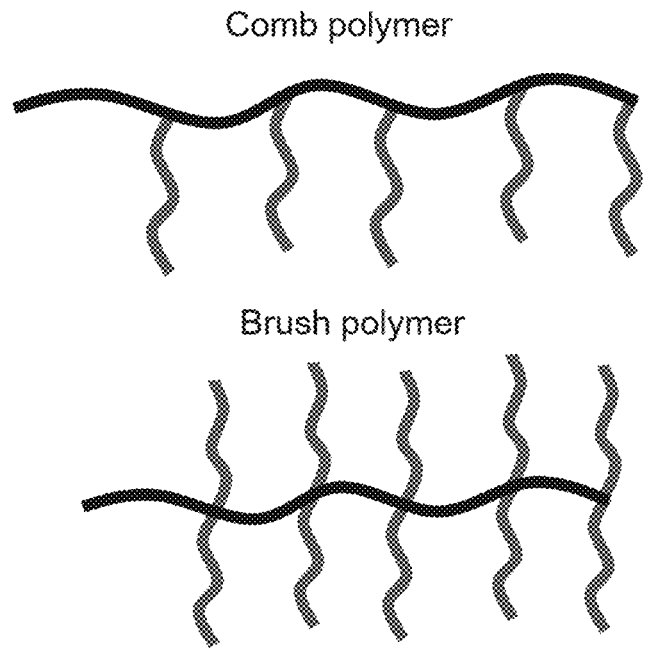
FIGS. 7A-7B.

In embodiments, the solid support includes a polymer layer, wherein the polymer layer includes a brush copolymer or a comb polymer. A comb polymer includes a main polymer chain with two or more three-way branch points and linear side chains. A brush polymer includes a main polymer chain with linear, unbranched side chains and where one or more of the branch points has four-way functionality or larger. See FIG. 7A as an example illustration of a brush and comb polymer structure. In embodiments, the polymer layer does not include oligonucleotide moieties. In embodiments, the polymer layer is substantially free of oligonucleotides. In embodiments, the polymer layer does not include oligonucleotide capture moieties. In embodiments, the polymer layer binds to the resist of the array. In embodiments, nucleic acid content is not transferred to the solid support, rather the oligonucleotide moieties are localized to the particle.

In some embodiments, the solid support includes a hydrophobic polymer layer. In embodiments, the solid support includes a perfluorinated polymer. In embodiments, the solid support includes a polyfluorinated polymer. In embodiments, the solid support includes polymerized units of a fluorine-containing methacrylate (e.g., $CH_2=C(CH_3)COOC-(CF_3)_2CF_2CF_2CF_3$). Non-limiting examples and synthetic protocols of fluorine-containing methacrylate monomers may be found in Zhang, D., (2018). Materials (Basel, Switzerland), 11(11), 2258 (2018), which is incorporated herein by reference. In embodiments, the fluorinated polymer is an amorphous (non-crystalline) fluoropolymer (e.g., CYTOP® from Bellex), a crystalline fluoropolymer, or a fluoropolymer having both amorphous and crystalline domains.

In some embodiments, the solid support includes a hydrophilic polymer layer. In some embodiments, the hydrophilic polymer is a silane functionalized polymer. In some embodiments, the silane functionalized polymer is a silane functionalized polyethylene glycol (Si-PEG) polymer or a silane functionalized poly(acrylamide) (Si-PAm). In embodiments, the polymer layer is a silane functionalized polymer. In some embodiments, the silane functionalized polymer is silane functionalized poly(acrylamide) (Si-PAm).

Figure 7B:
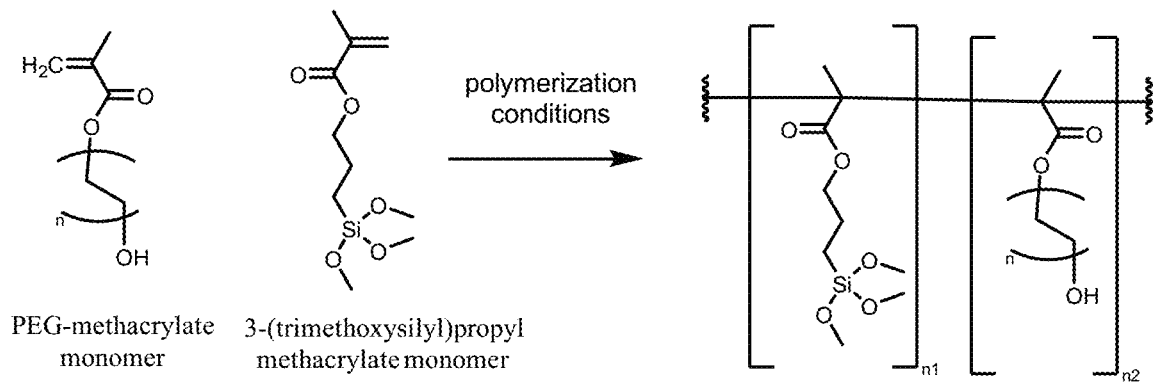

In embodiments, the polymer layer or the amphiphilic polymer includes polymerized units of alkoxysilyl polymers. In embodiments, the polymer layer includes polymerized units of alkoxysilyl polymers (e.g., TMSPM) and polymerized units of polyethylene glycol methacrylate (PEGMA); see for example an embodiment of such a copolymer in FIG. 7B. In embodiments, the amphiphilic copolymer includes polymerized units of alkoxysilyl polymers and polymerized units of polyethylene glycol methacrylate (PEGMA), or polyethylene glycol acrylate (PEGA). In embodiments, the amphiphilic copolymer includes polymerized units of 3-(trimethoxysilyl)propyl methacrylate (TMSPM), 3-(trimethoxysilyl)propyl methacrylate (TMSPA) and polymerized units of polyethylene glycol methacrylate (PEGMA), or polyethylene glycol acrylate (PEGA). In embodiments, the amphiphilic copolymer comprises polymerized units of 3-(trimethoxysilyl)propyl methacrylate (TMSPM) and polymerized units of polyethylene glycol methacrylate (PEGMA). In embodiments, the amphiphilic copolymer comprises polymerized units of 3-(trimethoxysilyl)propyl methacrylate (TMSPM), polymerized units of polyethylene glycol methacrylate (PEGMA) and polymerized units of hydroxyethylmethacrylate (HEMA). In embodiments, the amphiphilic copolymer comprises polymerized units of polyethylene glycol methacrylate (PEGMA) and polymerized units of hydroxyethylmethacrylate (HEMA).

In embodiments, the polymer layer includes polymerized units of alkoxysilyl polymers having the formula:

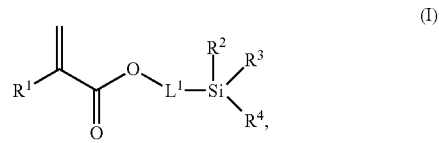

wherein $R^1$ is H or methyl; $R^2$, $R^3$, and $R^4$ are each independently substituted or unsubstituted alkyl or substituted or unsubstituted heteroalkyl, wherein at least one of $R^2$, $R^3$, and $R^4$ includes an alkoxy bond to the Si atom; and $L^1$ is substituted or unsubstituted alkylene or substituted or unsubstituted heteroalkylene. In embodiments, the polymer layer further includes polymerized units of polyethylene glycol methacrylate (PEGMA), polyethylene glycol acrylate (PEGA), sulfobetaine acrylate (SBA), carboxybetaine acrylate (CBA), phosphorylcholine acrylate (PCA), sulfobetaine methacrylate (SBMA), carboxybetaine methacrylate (CBMA), or phosphorylcholine methacrylate (PCMA). In embodiments, $R^1$ is H. In embodiments, $R^1$ is unsubstituted methyl. In embodiments, the polymer layer is an organically-modified ceramic polymer. In embodiments, the polymer includes polymerized monomers of alkoxysilyl polymers, such as

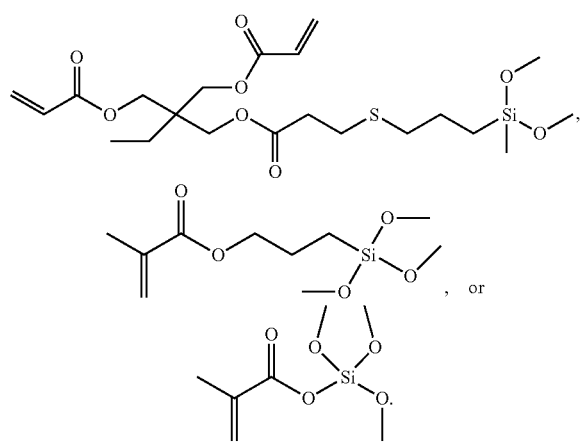

In embodiments, $R^2$ is $R^{2A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), or $R^{2A}$-substituted or unsubstituted heteroalkyl (e.g., 2 to 20, 8 to 20, 2 to 10, 2 to 8, 2 to 6, or 2 to 4 membered). In embodiments, $R^2$ is substituted or unsubstituted alkyl (e.g., $C_1$-$C_{20}$, $C_{10}$-$C_{20}$, $C_1$-$C_8$, $C_1$-$C_6$, or $C_1$-$C_4$), or substituted or unsubstituted heteroalkyl (e.g., 2 to 20, 8 to 20, 2 to 10, 2 to 8, 2 to 6, or 2 to 4 membered).

In embodiments, $R^2$ is unsubstituted —O—$C_1$-$C_6$ or —O—$C_1$-$C_4$ alkyl. In embodiments, $R^2$ is unsubstituted —O—$C_1$-$C_4$ alkyl. In embodiments, $R^2$ is unsubstituted —O—$C_1$-$C_6$ alkyl. In embodiments, $R^2$ is unsubstituted —O-methyl. In embodiments, $R^2$ is unsubstituted —O—$C_2$ alkyl. In embodiments, $R^2$ is unsubstituted —O—$C_3$ alkyl. In embodiments, $R^2$ is unsubstituted —O—$C_4$ alkyl. In embodiments, $R^2$ is unsubstituted —O—$C_5$ alkyl. In embodiments, $R^2$ is unsubstituted —O—$C_6$ alkyl. In embodiments, $R^2$ is $R^{2A}$-substituted —O—$C_1$-$C_6$ or —O—$C_1$-$C_4$ alkyl. In embodiments, $R^2$ is $R^{2A}$-substituted —O—$C_1$-$C_4$ alkyl. In embodiments, $R^2$ is $R^{2A}$-substituted —O—$C_1$-$C_6$ alkyl. In embodiments, $R^2$ is $R^{2A}$-substituted —O-methyl. In embodiments, $R^2$ is $R^{2A}$-substituted —O—$C_2$ alkyl. In embodiments, $R^2$ is $R^{2A}$-substituted —O—$C_3$ alkyl. In embodiments, $R^2$ is $R^{2A}$-substituted —O—$C_4$ alkyl. In embodiments, $R^2$ is $R^{2A}$-substituted —O—$C_5$ alkyl. In embodiments, $R^2$ is $R^{2A}$-substituted —O—$C_6$ alkyl. In embodiments, $R^2$ is $R^{2A}$-substituted 2 to 10 membered heteroalkyl. In embodiments, $R^2$ is $R^{2A}$-substituted 2 to 8 membered heteroalkyl. In embodiments, $R^2$ is $R^{2A}$-substituted 2 to 6 membered heteroalkyl. In embodiments, $R^2$ is $R^{2A}$-substituted 2 to 4 membered heteroalkyl. In embodiments, $R^2$ is an unsubstituted 2 to 10 membered heteroalkyl. In embodiments, $R^2$ is an unsubstituted 2 to 8 membered heteroalkyl. In embodiments, $R^2$ is an unsubstituted 2 to 6 membered heteroalkyl. In embodiments, $R^2$ is an unsubstituted 2 to 4 membered heteroalkyl.

$R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NH—$NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{2A}$ is —OH.

In embodiments, $R^3$ is $R^{3A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), or $R^{3A}$-substituted or unsubstituted heteroalkyl (e.g., 2 to 20, 8 to 20, 2 to 10, 2 to 8, 2 to 6, or 2 to 4 membered). In embodiments, $R^3$ is substituted or unsubstituted alkyl (e.g., $C_1$-$C_{20}$, $C_{10}$-$C_{20}$, $C_1$-$C_8$, $C_1$-$C_6$, or $C_1$-$C_4$), or substituted or unsubstituted heteroalkyl (e.g., 2 to 20, 8 to 20, 2 to 10, 2 to 8, 2 to 6, or 2 to 4 membered).

In embodiments, $R^3$ is unsubstituted —O—$C_1$-$C_6$ or —O—$C_1$-$C_4$ alkyl. In embodiments, $R^3$ is unsubstituted —O—$C_1$-$C_4$ alkyl. In embodiments, $R^3$ is unsubstituted —O—$C_1$-$C_6$ alkyl. In embodiments, $R^3$ is unsubstituted —O-methyl. In embodiments, $R^3$ is unsubstituted —O—$C_2$ alkyl. In embodiments, $R^3$ is unsubstituted —O—$C_3$ alkyl. In embodiments, $R^3$ is unsubstituted —O—$C_4$ alkyl. In embodiments, $R^3$ is unsubstituted —O—$C_5$ alkyl. In embodiments, $R^3$ is unsubstituted —O—$C_6$ alkyl. In embodiments, $R^3$ is $R^{3A}$-substituted —O—$C_1$-$C_6$ or —O—$C_1$-$C_4$ alkyl. In embodiments, $R^3$ is $R^{3A}$-substituted —O—$C_1$-$C_4$ alkyl. In embodiments, $R^3$ is $R^{3A}$-substituted —O—$C_1$-$C_6$ alkyl. In embodiments, $R^3$ is $R^{3A}$-substituted —O-methyl. In embodiments, $R^3$ is $R^{3A}$-substituted —O—$C_2$ alkyl. In embodiments, $R^3$ is $R^{3A}$-substituted —O—$C_3$ alkyl. In embodiments, $R^3$ is $R^{3A}$-substituted —O—$C_4$ alkyl. In embodiments, $R^3$ is $R^{3A}$-substituted —O—$C_5$ alkyl. In embodiments, $R^3$ is $R^{3A}$-substituted —O—$C_6$ alkyl. In embodiments, $R^3$ is $R^{3A}$-substituted 2 to 10 membered heteroalkyl. In embodiments, $R^3$ is $R^{3A}$-substituted 2 to 8 membered heteroalkyl. In embodiments, $R^3$ is $R^{3A}$-substituted 2 to 6 membered heteroalkyl. In embodiments, $R^3$ is $R^{3A}$-substituted 2 to 4 membered heteroalkyl. In embodiments, $R^3$ is an unsubstituted 2 to 10 membered heteroalkyl. In embodiments, $R^3$ is an unsubstituted 2 to 8 membered heteroalkyl. In embodiments, $R^3$ is an unsubstituted 2 to 6 membered heteroalkyl. In embodiments, $R^3$ is an unsubstituted 2 to 4 membered heteroalkyl.

$R^{3A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{3A}$ is —OH.

In embodiments, $R^4$ is $R^{4A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), or $R^{4A}$-substituted or unsubstituted heteroalkyl (e.g., 2 to 20, 8 to 20, 2 to 10, 2 to 8, 2 to 6, or 2 to 4 membered). In embodiments, $R^4$ is substituted or unsubstituted alkyl (e.g., $C_1$-$C_{20}$, $C_{10}$-$C_{20}$, $C_1$-$C_8$, $C_1$-$C_6$, or $C_1$-$C_4$), or substituted or unsubstituted heteroalkyl (e.g., 2 to 20, 8 to 20, 2 to 10, 2 to 8, 2 to 6, or 2 to 4 membered).

In embodiments, $R^4$ is unsubstituted —O—$C_1$-$C_6$ or —O—$C_1$-$C_4$ alkyl. In embodiments, $R^4$ is unsubstituted —O—$C_1$-$C_4$ alkyl. In embodiments, $R^4$ is unsubstituted —O—$C_1$-$C_6$ alkyl. In embodiments, $R^4$ is unsubstituted —O-methyl. In embodiments, $R^4$ is unsubstituted —O—$C_2$ alkyl. In embodiments, $R^4$ is unsubstituted —O—$C_3$ alkyl. In embodiments, $R^4$ is unsubstituted —O—$C_4$ alkyl. In embodiments, $R^4$ is unsubstituted —O—$C_5$ alkyl. In embodiments, $R^4$ is unsubstituted —O—$C_6$ alkyl. In embodiments, $R^4$ is $R^{4A}$-substituted —O—$C_1$-$C_6$ or —O—$C_1$-$C_4$ alkyl. In embodiments, $R^4$ is $R^{4A}$-substituted —O—$C_1$-$C_4$ alkyl. In embodiments, $R^4$ is $R^{4A}$-substituted —O—$C_1$-$C_6$ alkyl. In embodiments, $R^4$ is $R^{4A}$-substituted —O-methyl. In embodiments, $R^4$ is $R^{4A}$-substituted —O—$C_2$ alkyl. In embodiments, $R^4$ is $R^{4A}$-substituted —O—$C_3$ alkyl. In embodiments, $R^4$ is $R^{4A}$-substituted —O—$C_4$ alkyl. In embodiments, $R^4$ is $R^{4A}$-substituted —O—$C_5$ alkyl. In embodiments, $R^4$ is $R^{4A}$-substituted —O—$C_6$ alkyl. In embodiments, $R^4$ is $R^{4A}$-substituted 2 to 10 membered heteroalkyl. In embodiments, $R^4$ is $R^{4A}$-substituted 2 to 8 membered heteroalkyl. In embodiments, $R^4$ is $R^{4A}$-substituted 2 to 6 membered heteroalkyl. In embodiments, $R^4$ is $R^{4A}$-substituted 2 to 4 membered heteroalkyl. In embodiments, $R^4$ is an unsubstituted 2 to 10 membered heteroalkyl. In embodiments, $R^4$ is an unsubstituted 2 to 8 membered heteroalkyl. In embodiments, $R^4$ is an unsubstituted 2 to 6 membered heteroalkyl. In embodiments, $R^4$ is an unsubstituted 2 to 4 membered heteroalkyl.

$R^{4A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{4A}$ is —OH.

In embodiments, $L^1$ is $L^{1A}$-substituted or unsubstituted alkylene (e.g., $C_1$-$C_{20}$, $C_{10}$-$C_{20}$, $C_1$-$C_8$, $C_1$-$C_6$, or $C_1$-$C_4$), or $L^{1A}$-substituted or unsubstituted heteroalkylene (e.g., 2 to 20, 8 to 20, 2 to 10, 2 to 8, 2 to 6, or 2 to 4 membered). In embodiments, $L^1$ is substituted or unsubstituted alkylene (e.g., $C_1$-$C_{20}$, $C_{10}$-$C_{20}$, $C_1$-$C_8$, $C_1$-$C_6$, or $C_1$-$C_4$), or substituted or unsubstituted heteroalkylene (e.g., 2 to 20, 8 to 20, 2 to 10, 2 to 8, 2 to 6, or 2 to 4 membered).

In embodiments, $L^1$ is unsubstituted $C_1$-$C_6$ or $C_1$-$C_4$ alkylene. In embodiments, $L^1$ is unsubstituted $C_1$-$C_4$ alkylene. In embodiments, $L^1$ is unsubstituted $C_1$-$C_6$ alkylene. In embodiments, $L^1$ is unsubstituted methylene. In embodiments, $L^1$ is unsubstituted $C_2$ alkylene. In embodiments, $L^1$ is unsubstituted $C_3$ alkylene. In embodiments, $L^1$ is unsubstituted $C_4$ alkylene. In embodiments, $L^1$ is unsubstituted $C_5$ alkylene. In embodiments, $L^1$ is unsubstituted $C_6$ alkylene. In embodiments, $L^1$ is $L^{1A}$-substituted $C_1$-$C_6$ or $C_1$-$C_4$ alkylene. In embodiments, $L^1$ is $L^{1A}$-substituted $C_1$-$C_4$ alkylene. In embodiments, $L^1$ is $L^{1A}$-substituted $C_1$-$C_6$ alkylene. In embodiments, $L^1$ is $L^{1A}$-substituted methylene. In embodiments, $L^1$ is $L^{1A}$-substituted $C_2$ alkylene. In embodiments, $L^1$ is $L^{1A}$-substituted $C_3$ alkylene. In embodiments, $L^1$ is $L^{1A}$-substituted $C_4$ alkylene. In embodiments, $L^1$ is $L^{1A}$-substituted $C_5$ alkylene. In embodiments, $L^1$ is $L^{1A}$-substituted $C_6$ alkylene. In embodiments, $L^1$ is $L^{1A}$-substituted 2 to 10 membered heteroalkylene. In embodiments, $L^1$ is $L^{1A}$-substituted 2 to 8 membered heteroalkylene. In embodiments, $L^1$ is $L^{1A}$-substituted 2 to 6 membered heteroalkylene. In embodiments, $L^1$ is $L^{1A}$-substituted 2 to 4 membered heteroalkylene. In embodiments, $L^1$ is an unsubstituted 2 to 10 membered heteroalkylene. In embodiments, $L^1$ is an unsubstituted 2 to 8 membered heteroalkylene. In embodiments, $L^1$ is an unsubstituted 2 to 6 membered heteroalkylene. In embodiments, $L^1$ is an unsubstituted 2 to 4 membered heteroalkylene.

$L^{1A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NH—$NH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkylene (e.g., $C_1$-$C_{20}$, $C_{10}$-$C_{20}$, $C_1$-$C_8$, $C_1$-$C_6$, or $C_1$-$C_4$), unsubstituted heteroalkylene (e.g., 2 to 20, 8 to 20, 2 to 10, 2 to 8, 2 to 6, or 2 to 4 membered), unsubstituted cycloalkylene (e.g., $C_3$-$C_8$, $C_3$-$C_6$, or $C_5$-$C_6$), unsubstituted heterocycloalkylene (e.g., 3 to 8, 3 to 6, or 5 to 6 membered), unsubstituted arylene (e.g., $C_6$-$C_{10}$, $C_{10}$, or phenylene), or unsubstituted heteroarylene (e.g., 5 to 10, 5 to 9, or 5 to 6 membered). In embodiments, $L^{1A}$ is —$CH_3$.

In embodiments, $L^{1A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $L^{1A}$ is —$CH_3$.

In embodiments, the polymer coating includes polymerized units of 3-(trimethoxysilyl)propyl methacrylate (TMSPM)

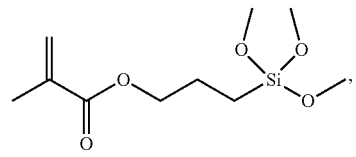 [SMILES: C=C(C)C(=O)OCCC[Si](OC)(OC)OC]

3-(trimethoxysilyl)propyl methacrylate (TMSPA)

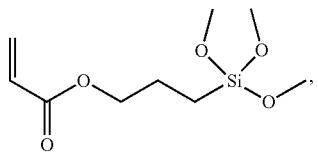

3-(triethoxysilyl)propyl methacrylate (TESPM)

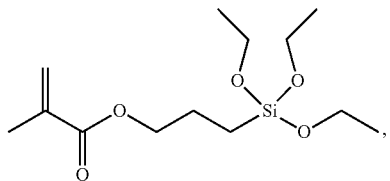 [SMILES: C=C(C)C(=O)OCCC[Si](OCC)(OCC)OCC]

3-(triethoxysilyl)propyl acrylate (TESPA)

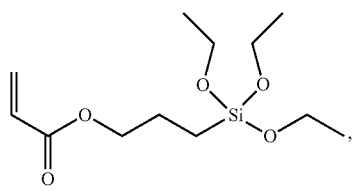 [SMILES: C=CC(=O)OCCC[Si](OCC)(OCC)OCC]

3-(dimethoxy(1-methylethoxy)silyl]propyl methacrylate

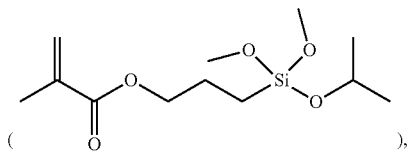 [SMILES: C=C(C)C(=O)OCCC[Si](OC)(OC)OC(C)C]

3-(ethoxydimethoxysilyl)propyl 2-methyl-2-propenoate

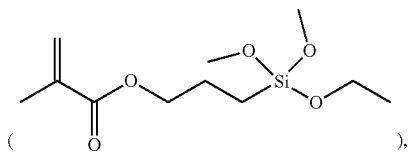 [SMILES: C=C(C)C(=O)OCCC[Si](OC)(OC)OCC]

3-(Tripropoxysilyl)propyl 2-methyl-2-propenoate

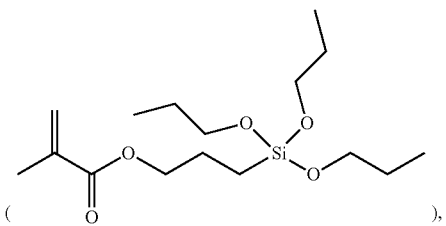 [SMILES: C=C(C)C(=O)OCCC[Si](OCCC)(OCCC)OCCC]

2-Methyl-3-(triethoxysilyl)propyl 2-methyl-2-propenoate

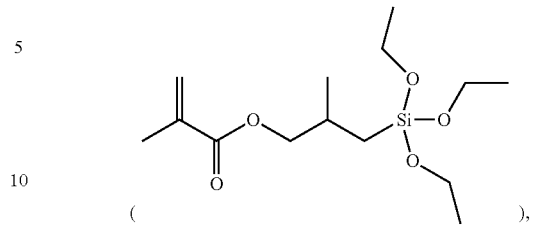

3-(Methyldipropoxysilyl)propyl 2-methyl-2-propenoate

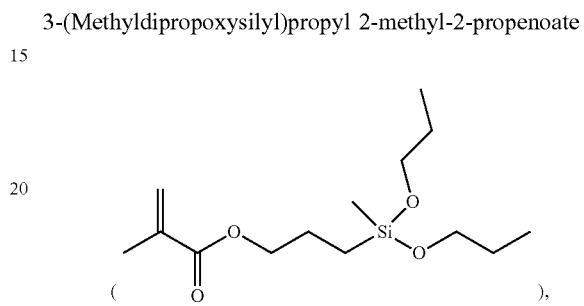

3-(Diethoxymethylsilyl)propyl 2-methyl-2-propenoate

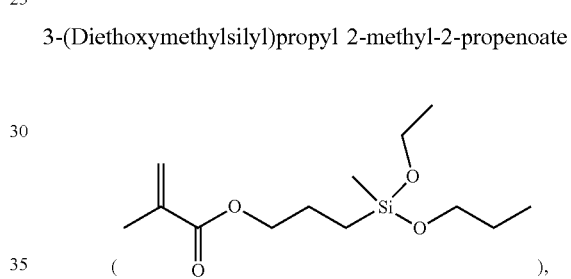

3-[Diethoxy(2-hydroxyethoxy)silyl]propyl 2-methyl-2-propenoate

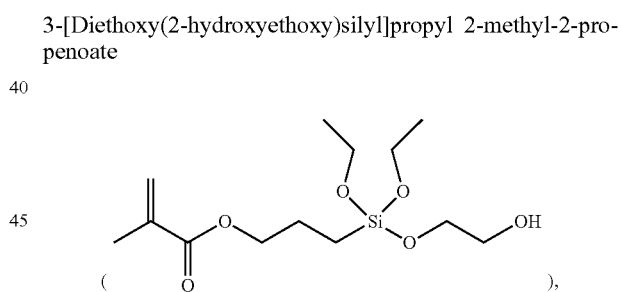

or 3-(Butyldimethoxysilyl)propyl 2-methyl-2-propenoate

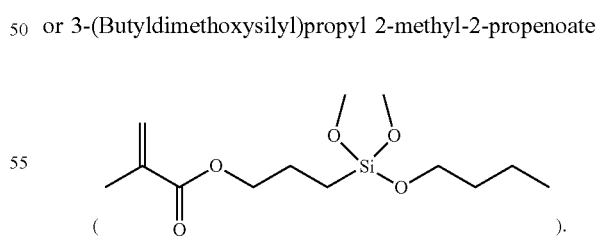

In embodiments, the polymer coating includes polymerized units of glycidyloxypropyl trimethoxysilane (GPTMS). In embodiments, the polymer coating includes polymerized units of alkoxysilyl polymers and polymerized units of polyethylene glycol methacrylate (PEGMA).

In embodiments, the average longest dimension of the nanoparticle is from about 100 nm to about 400 nm. In embodiments, the average longest dimension of the nanoparticle is about 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average longest dimension of the nanoparticle is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm. In embodiments, the average longest dimension of the nanoparticle is less than about 1000 nm. In embodiments, the average longest dimension of the nanoparticle is less than about 900 nm. In embodiments, the average longest dimension of the nanoparticle is less than about 800 nm. In embodiments, the average longest dimension of the nanoparticle is less than about 700 nm. In embodiments, the average longest dimension of the nanoparticle is less than about 600 nm. In embodiments, the average longest dimension of the nanoparticle is less than about 500 nm. In embodiments, the average longest dimension of the nanoparticle is less than about 400 nm. In embodiments, the average longest dimension of the nanoparticle is less than about 300 nm. In embodiments, the average longest dimension of the nanoparticle is less than about 200 nm. In embodiments, the average longest dimension of the nanoparticle is less than about 100 nm. In embodiments, the average longest dimension of the nanoparticle is 400 nm without the particle shell. In embodiments, the average longest dimension of the nanoparticle is about 550 to about 650 nm with the particle shell. In embodiments, the average longest dimension of the nanoparticle is about 580 to about 650 nm with the particle shell containing immobilized oligonucleotides.

In some embodiments, the average longest dimension of the particle is from about 200 nm to about 1000 nm. In embodiments, the average longest dimension of the particle is from about 150 nm to about 600 nm. In some embodiments, the average longest dimension of the particle is from about 350 nm to about 600 nm. In some embodiments, the average longest dimension of the particle is from about 400 nm to about 500 nm. In some embodiments, the average longest dimension of the particle is about 500 nm. In some embodiments, the average longest dimension of the particle is about 400 nm. In some embodiments, the average longest dimension of the particle is about 400 nm, 450 nm, 500 nm, or 550 nm. In some embodiments, the average longest dimension of the particle is about 410 nm, 420 nm, 430 nm, 440 nm or 450 nm. In some embodiments, the average longest dimension of the particle is about 460 nm, 470 nm, 480 nm, 490 nm or 500 nm. In embodiments, the average longest dimension of the particle is at least, about, or at most 100, 200, 300, 400, 500, 600, 700, 800, 900, 1000 nm, or a number or a range between any two of these values. In embodiments, the shell diameter is about 0.1-10 microns, 0.25-5 microns, 0.5-2 microns, 1 micron, or a number or a range between any two of these values. In embodiments, the particle shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm or a number or a range between any two of these values. In embodiments, the core diameter is about 150-700 nanometers, and/or the shell diameter (alternatively referred to as the particle polymer; see for example FIG. 10A) is about 0.25-5 µm (microns).

In some embodiments, the wells of the array are separated from each other by about 0.2 µm to about 2.0 µm. In some embodiments, the wells of the array are separated from each other by about 0.7 µm to about 1.5 µm. In some embodiments, the wells of the array are separated from each other by at least or at most 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm. In some embodiments, the wells of the array are from about 0.2 µm to about 2 µm in diameter, and wherein the wells of the array are about 0.5 µm to about 2 µm in depth. In some embodiments, the wells of the array are from about 0.2 µm to about 2 µm in diameter, and wherein the wells of the array are about 0.5 µm to about 1.5 µm in depth. Each well of the multiwell container is capable of retaining a volume of liquid. For example, the volume of the wells can be at least about $1\times10^{-3}$, µm³, about $1\times10^{-2}$, µm³, about 0.1 µm³, about 1 µm³, about 10 µm³, about 100 µm³, or more. In embodiments, the volume of the wells can be at most about $1\times10^4$, µm³, about $1\times10^3$, µm³, about 100 µm³, about 10 µm³, about 1 µm³, about 0.1 µm³, or less. In embodiments, the depth of the well is measured from the bottom of the well to the top of the array. In embodiments, the depth of the well is measured from the bottom of the well to the top of the interstitial region. In embodiments, the depth of the well is measured from the bottom of the well to the top of the photoresist. In embodiments, the array is a nanoarray which can have nanowells having a diameter sufficient to allow only one particle into the well. It is understood that the size of the nanowell will be dependent upon the size of the particle. In some embodiments, the diameter of the nanowells are less than 700 nm, less than 600 nm, less than 500 nm, less than 400 nm, less than 300 nm, less than 200 nm, or less than 100 nm. It is also understood that the size of the wells on the array can be of various sizes and will ultimately depend on the systems and/or apparatus used to analyze later reactions.

In some embodiments, greater than 50%, 60%, 70%, 80%, 90% or 95% of the wells include a particle. In some embodiments, greater than 50% of the wells include a particle. In some embodiments, greater than 60% of the wells include a particle. In some embodiments, greater than 70% of the wells include a particle. In some embodiments, greater than 80% of the wells include a particle. In some embodiments, greater than 90% of the wells include a particle. In some embodiments, greater than 90%, 91%, 92%, 93%, 94%, 95%, 96%, 97%, 98%, or 99% of the wells include a particle. In some embodiments, about 50%, 60%, 70%, 80%, 90% or 95% of the wells include a particle. In some embodiments, about 50% of the wells include a particle. In some embodiments, about 60% of the wells include a particle. In some embodiments, about 70% of the wells include a particle. In some embodiments, about 80% of the wells include a particle. In some embodiments, about 90% of the wells include a particle. In some embodiments, about 90%, 91%, 92%, 93%, 94%, 95%, 96%, 97%, 98%, or 99% of the wells include a particle. In embodiments, one or more wells has two or more particles in each well. In embodiments, each well has two or more particles per well. In embodiments, one or more wells has only one particle in each well. In embodiments, each well has 0 to 1 particles per well. In embodiments, each well has 0 to 3 particles per well.

In some embodiments, the interstitial regions are substantially free of oligonucleotide moieties. In some embodiments, the interstitial regions are substantially free of particles. In embodiments, the interstitial regions are substantially free of polynucleotides. In embodiments, the interstitial regions are substantially free of a polymer. In embodiments, the interstitial regions include a photoresist. In embodiments, physical removal (e.g., wiping the surface of the solid support) of any excess polymer and particles ensures the interstitial regions are substantially free of oligonucleotide moieties and/or particles. In embodiments, substantially free includes a trace amount or an undetectable amount.

In embodiments, each particle includes a plurality of oligonucleotide moieties covalently attached to said particle via a polymeric bioconjugate linker. In embodiments, the polymeric bioconjugate linker is a polymer (i.e., a molecule including structurally unique repeating units) including one or more reacted bioconjugate reactive moieties. In embodiments, the bioconjugate linker is illustrated in Scheme 1. In embodiments, the polymeric bioconjugate linker is a polymer including a subunit of formula Ia, Ib, II, or III as described in U.S. Pat. No. 11,236,387, which is incorporated herein by reference in its entirety.

In embodiments, the polymeric bioconjugate linker is polymer including a subunit having the formula:

—OCH$_2$I, —OCHCl$_2$, —OCHBr$_2$, —OCHF$_2$, —OCHI$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

$L^2$ is independently -$L^{2A}$-$L^{2B}$-$L^{2C}$-$L^{2D}$-$L^{2E}$- or a bioconjugate linker. $L^{2A}$, $L^{2B}$, $L^{2C}$, $L^{2D}$, and $L^{2E}$ are independently a bond, a bioconjugate linker, —S(O)$_2$—, —S(O)—, —S(O)$_2$NH—, —NH—, —O—, —S—, —SS—, —C(O)—, —C(O)NH—, —C(O)CH$_2$—, —NHC(O)—, —NHC(O)NH—, —C(O)O—, —OC(O)—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{10}$ or phenylene), or substituted or unsubstituted heteroarylene (e.g., 5 to 10 membered, 5 to 9 membered, or 5 to 6 membered). In embodiments, $L^2$ is a bioconjugate linker.

$L^4$ is independently -$L^{4A}$-$L^{4B}$-$L^{4C}$-$L^{4D}$-$L^{4E}$-. $L^{4A}$, $L^{4B}$, $L^{4C}$, $L^{4D}$, and $L^{4E}$ are independently a bond, —S(O)$_2$—, —S(O)—, —S(O)$_2$NH—, —NH—, —O—, —S—, —C(O)—, —C(O)NH—, —C(O)CH$_2$—, —NHC(O)—, —NHC(O)NH—, —C(O)O—, —OC(O)—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2

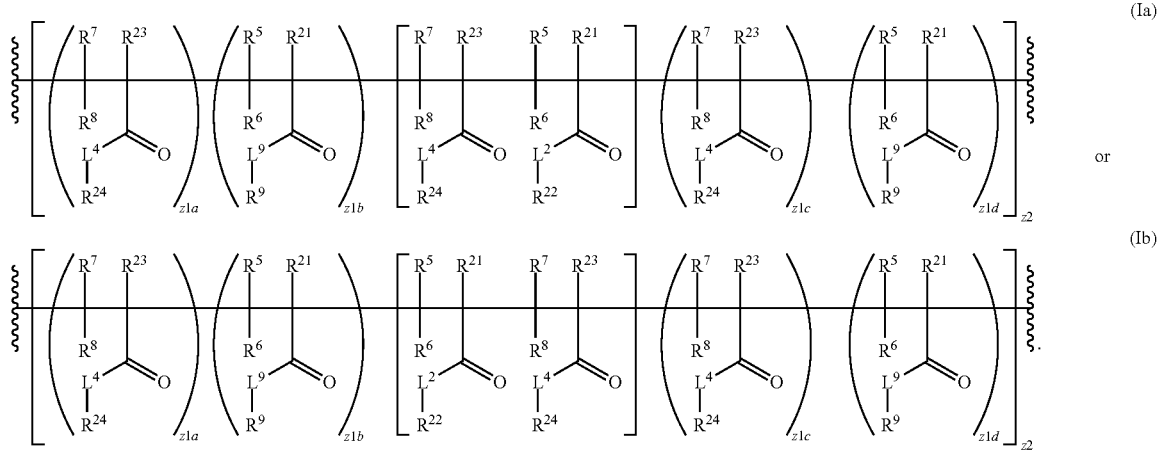

$R^{22}$ is independently an oligonucleotide moiety. $R^{21}$, $R^{23}$, $R^5$, $R^6$, $R^7$, and $R^8$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{10}$ or phenylene), or substituted or unsubstituted heteroarylene (e.g., 5 to 10 membered, 5 to 9 membered, or 5 to 6 membered).

$R^{24}$ is independently hydrogen, halogen, —$CX^{24}_3$, —$CHX^{24}_2$, —$CH_2X^{24}$, —$OCX^{24}_3$, —$OCH_2X^{24}$, —$OCHX^{24}_2$, —CN, —$SO_{n24}R^{24D}$, —$SO_{v24}NR^{24A}R^{24B}$, $NHC(O)NR^{24A}R^{24B}$, —$N(O)_{m24}$, —$NR^{24A}R^{24B}$, —C(O) $R^{24C}$, —C(O)—$OR^{24C}$, —$C(O)NR^{24A}R^{24B}$, —$OR^{24D}$, —$NR^{24A}SO_2R^{24D}$, —$NR^{24A}C(O)R^{24C}$, —$NR^{24A}C(O)$ $OR^{24C}$, —$NR^{24A}OR^{24C}$, —$OC(O)R^{24C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); wherein $R^{24}$ is a first non-reactive moiety.

$R^{24A}$, $R^{24B}$, $R^{24C}$, and $R^{24D}$ are independently hydrogen, —$CX_3$, —CN, —COOH, —$CONH_2$, —$CHX_2$, —$CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered), a protecting group, or a leaving group; $R^{24A}$ and $R^{24B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

$L^9$ is independently -$L^{9A}$-$L^{9B}$-$L^{9C}$-$L^{9D}$-$L^{9E}$-, $L^{9A}$, $L^{9B}$, $L^{9C}$, $L^{9D}$, and $L^{9E}$ are independently a bond, —$S(O)_2$—, —S(O)—, —$S(O)_2NH$—, —NH—, —O—, —S—, —SS—, —C(O)—, —C(O)NH—, —$C(O)CH_2$—, —NHC (O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

$R^9$ is independently an oligonucleotide or a second non-reactive moiety. The symbol z2 is independently an integer from 1 to 5000. The symbols z1a, z1b, z1c, and z1d are each independently an integer from 0 to 5000. X and $X^{24}$ are independently —F, —Cl, —Br, or —I. The symbol n24 is independently an integer from 0 to 4. The symbols m24 and v24 are each independently an integer from 1 to 2.

In embodiments, a substituted $R^{21}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{21}$ is substituted with a plurality of groups selected from substituent groups, size-limited substituent groups, and lower substituent groups; each substituent group, size-limited substituent group, and/or lower substituent group may optionally be different. In embodiments, when $R^{21}$ is substituted, it is substituted with at least one substituent group. In embodiments, when $R^{21}$ is substituted, it is substituted with at least one size-limited substituent group. In embodiments, when $R^{21}$ is substituted, it is substituted with at least one lower substituent group.

In embodiments, a substituted $R^{23}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{23}$ is substituted with a plurality of groups selected from substituent groups, size-limited substituent groups, and lower substituent groups; each substituent group, size-limited substituent group, and/or lower substituent group may optionally be different. In embodiments, when $R^{23}$ is substituted, it is substituted with at least one substituent group. In embodiments, when $R^{23}$ is substituted, it is substituted with at least one size-limited substituent group. In embodiments, when $R^{23}$ is substituted, it is substituted with at least one lower substituent group.

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, a substituted $R^7$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, a substituted $R^8$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^8$ is substituted with a plurality of groups selected from substituent groups, size-limited substituent groups, and lower substituent groups; each substituent group, size-limited substituent group, and/or lower substituent group may optionally be different. In embodiments, when $R^8$ is substituted, it is substituted with at least one substituent group. In embodiments, when $R^8$ is substituted, it is substituted with at least one size-limited substituent group. In embodiments, when $R^8$ is substituted, it is substituted with at least one lower substituent group.

In embodiments, a substituted $L^{2A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2A}$ is substituted with a plurality of groups selected from substituent groups, size-limited substituent groups, and lower substituent groups; each substituent group, size-limited substituent group, and/or lower substituent group may optionally be different. In embodiments, when $L^{2A}$ is substituted, it is substituted with at least one substituent group. In embodiments, when $L^{2A}$ is substituted, it is substituted with at least one size-limited substituent group. In embodiments, when $L^{2A}$ is substituted, it is substituted with at least one lower substituent group.

In embodiments, a substituted $L^{2B}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2B}$ is substituted with a plurality of groups selected from substituent groups, size-limited substituent groups, and lower substituent groups; each substituent group, size-limited substituent group, and/or lower substituent group may optionally be different. In embodiments, when $L^{2B}$ is substituted, it is substituted with at least one substituent group. In embodiments, when $L^{2B}$ is substituted, it is substituted with at least one size-limited substituent group. In embodiments, when $L^{2B}$ is substituted, it is substituted with at least one lower substituent group.

In embodiments, a substituted $L^{2C}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2C}$ is substituted with a plurality of groups selected from substituent groups, size-limited substituent groups, and lower substituent groups; each substituent group, size-limited substituent group, and/or lower substituent group may optionally be different. In embodiments, when $L^{2C}$ is substituted, it is substituted with at least one substituent group. In embodiments, when $L^{2C}$ is substituted, it is substituted with at least one size-limited substituent group. In embodiments, when $L^{2C}$ is substituted, it is substituted with at least one lower substituent group.

In embodiments, a substituted $L^{2D}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2D}$ is substituted with a plurality of groups selected from substituent groups, size-limited substituent groups, and lower substituent groups; each substituent group, size-limited substituent group, and/or lower substituent group may optionally be different. In embodiments, when $L^{2D}$ is substituted, it is substituted with at least one substituent group. In embodiments, when $L^{2D}$ is substituted, it is substituted with at least one size-limited substituent group. In embodiments, when $L^{2D}$ is substituted, it is substituted with at least one lower substituent group.

In embodiments, a substituted $L^{2E}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{2E}$ is substituted with a plurality of groups selected from substituent groups, size-limited substituent groups, and lower substituent groups; each substituent group, size-limited substituent group, and/or lower substituent group may optionally be different. In embodiments, when $L^{2E}$ is substituted, it is substituted with at least one substituent group. In embodiments, when $L^{2E}$ is substituted, it is substituted with at least one size-limited substituent group. In embodiments, when $L^{2E}$ is substituted, it is substituted with at least one lower substituent group.

In embodiments, a substituted $L^{4A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{4A}$ is substituted with a plurality of groups selected from substituent groups, size-limited substituent groups, and lower substituent groups; each substituent group, size-limited substituent group, and/or lower substituent group may optionally be different. In embodiments, when $L^{4A}$ is substituted, it is substituted with at least one substituent group. In embodiments, when $L^{4A}$ is substituted, it is substituted with at least one size-limited substituent group. In embodiments, when $L^{4A}$ is substituted, it is substituted with at least one lower substituent group.

In embodiments, a substituted $L^{4B}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{4B}$ is substituted with a plurality of groups selected from substituent groups, size-limited substituent groups, and lower substituent groups; each substituent group, size-limited substituent group, and/or lower substituent group may optionally be different. In embodiments, when $L^{4B}$ is substituted, it is substituted with at least one substituent group. In embodiments, when $L^{4B}$ is substituted, it is substituted with at least one size-limited substituent group. In embodiments, when $L^{4B}$ is substituted, it is substituted with at least one lower substituent group.

In embodiments, a substituted $L^{4C}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{4C}$ is substituted with a plurality of groups selected from substituent groups, size-limited substituent groups, and lower substituent groups; each substituent group, size-limited substituent group, and/or lower substituent group may optionally be different. In embodiments, when $L^{4C}$ is substituted, it is substituted with at least one substituent group. In embodiments, when $L^{4C}$ is substituted, it is substituted with at least one size-limited substituent group. In embodiments, when $L^{4C}$ is substituted, it is substituted with at least one lower substituent group.

In embodiments, a substituted $L^{4D}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{4D}$ is substituted with a plurality of groups selected from substituent groups, size-limited substituent groups, and lower substituent groups; each substituent group, size-limited substituent group, and/or lower substituent group may optionally be different. In embodiments, when $L^{4D}$ is substituted, it is substituted with at least one substituent group. In embodiments, when $L^{4D}$ is substituted, it is substituted with at least one size-limited substituent group. In embodiments, when $L^{4D}$ is substituted, it is substituted with at least one lower substituent group.

In embodiments, a substituted $L^{4E}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{4E}$ is substituted with a plurality of groups selected from substituent groups, size-limited substituent groups, and lower substituent groups; each substituent group, size-limited substituent group, and/or lower substituent group may optionally be different. In embodiments, when $L^{4E}$ is substituted, it is substituted with at least one substituent group. In embodiments, when $L^{4E}$ is substituted, it is substituted with at least one size-limited substituent group. In embodiments, when $L^{4E}$ is substituted, it is substituted with at least one lower substituent group.

In embodiments, a substituted $R^{24}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{24}$ is substituted with a plurality of groups selected from substituent groups, size-limited substituent groups, and lower substituent groups; each substituent group, size-limited substituent group, and/or lower substituent group may optionally be different. In embodiments, when $R^{24}$ is substituted, it is substituted with at least one substituent group. In embodiments, when $R^{24}$ is substituted, it is substituted with at least one size-limited substituent group. In embodiments, when $R^{24}$ is substituted, it is substituted with at least one lower substituent group.

In embodiments, a substituted $R^{24A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{24A}$ is substituted with a plurality of groups selected from substituent groups, size-limited substituent groups, and lower substituent groups; each substituent group, size-limited substituent group, and/or lower substituent group may optionally be different. In embodiments, when $R^{24A}$ is substituted, it is substituted with at least one substituent group. In embodiments, when $R^{24A}$ is substituted, it is substituted with at least one size-limited substituent group. In embodiments, when $R^{24A}$ is substituted, it is substituted with at least one lower substituent group.

In embodiments, a substituted $R^{24B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{24B}$ is substituted with a plurality of groups selected from substituent groups, size-limited substituent groups, and lower substituent groups; each substituent group, size-limited substituent group, and/or lower substituent group may optionally be different. In embodiments, when $R^{24B}$ is substituted, it is substituted with at least one substituent group. In embodiments, when $R^{24B}$ is substituted, it is substituted with at least one size-limited substituent group. In embodiments, when $R^{24B}$ is substituted, it is substituted with at least one lower substituent group.

In embodiments, a substituted ring formed when $R^{24A}$ and $R^{24B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{24A}$ and $R^{24B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{24A}$ and $R^{24B}$ substituents bonded to the same nitrogen atom are joined is substituted, it is substituted with at least one substituent group. In embodiments, when the substituted ring formed when $R^{24A}$ and $R^{24B}$ substituents bonded to the same nitrogen atom are joined is substituted, it is substituted with at least one size-limited substituent group. In embodiments, when the substituted ring formed when $R^{24A}$ and $R^{24B}$ substituents bonded to the same nitrogen atom are joined is substituted, it is substituted with at least one lower substituent group.

In embodiments, a substituted $R^{24C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{24C}$ is substituted with a plurality of groups selected from substituent groups, size-limited substituent groups, and lower substituent groups; each substituent group, size-limited substituent group, and/or lower substituent group may optionally be different. In embodiments, when $R^{24C}$ is substituted, it is substituted with at least one substituent group. In embodiments, when $R^{24C}$ is substituted, it is substituted with at least one size-limited substituent group. In embodiments, when $R^{24C}$ is substituted, it is substituted with at least one lower substituent group.

In embodiments, a substituted $R^{24D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{24D}$ is substituted with a plurality of groups selected from substituent groups, size-limited substituent groups, and lower substituent groups; each substituent group, size-limited substituent group, and/or lower substituent group may optionally be different. In embodiments, when $R^{24D}$ is substituted, it is substituted with at least one substituent group. In embodiments, when $R^{24D}$ is substituted, it is substituted with at least one size-limited substituent group. In embodiments, when $R^{24D}$ is substituted, it is substituted with at least one lower substituent group.

In embodiments, a substituted $L^{9A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{9A}$ is substituted with a plurality of groups selected from substituent groups, size-limited substituent groups, and lower substituent groups; each substituent group, size-limited substituent group, and/or lower substituent group may optionally be different. In embodiments, when $L^{9A}$ is substituted, it is substituted with at least one substituent group. In embodiments, when $L^{9A}$ is substituted, it is substituted with at least one size-limited substituent group. In embodiments, when $L^{9A}$ is substituted, it is substituted with at least one lower substituent group.

In embodiments, a substituted $L^{9B}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{9B}$ is substituted with a plurality of groups selected from substituent groups, size-limited substituent groups, and lower substituent groups; each substituent group, size-limited substituent group, and/or lower substituent group may optionally be different. In embodiments, when $L^{9B}$ is substituted, it is substituted with at least one substituent group. In embodiments, when $L^{9B}$ is substituted, it is substituted with at least one size-limited substituent group. In embodiments, when $L^{9B}$ is substituted, it is substituted with at least one lower substituent group.

In embodiments, a substituted $L^{9C}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{9C}$ is substituted with a plurality of groups selected from substituent groups, size-limited substituent groups, and lower substituent groups; each substituent group, size-limited substituent group, and/or lower substituent group may optionally be different. In embodiments, when $L^{9C}$ is substituted, it is substituted with at least one substituent group. In embodiments, when $L^{9C}$ is substituted, it is substituted with at least one size-limited substituent group. In embodiments, when $L^{9C}$ is substituted, it is substituted with at least one lower substituent group.

In embodiments, a substituted $L^{9D}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{9D}$ is substituted with a plurality of groups selected from substituent groups, size-limited substituent groups, and lower substituent groups; each substituent group, size-limited substituent group, and/or lower substituent group may optionally be different. In embodiments, when $L^{9D}$ is substituted, it is substituted with at least one substituent group. In embodiments, when $L^{9D}$ is substituted, it is substituted with at least one size-limited substituent group. In embodiments, when $L^{9D}$ is substituted, it is substituted with at least one lower substituent group.

In embodiments, a substituted $L^{9E}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{9E}$ is substituted with a plurality of groups selected from substituent groups, size-limited substituent groups, and lower substituent groups; each substituent group, size-limited substituent group, and/or lower substituent group may optionally be different. In embodiments, when $L^{9E}$ is substituted, it is substituted with at least one substituent group. In embodiments, when $L^{9E}$ is substituted, it is substituted with at least one size-limited substituent group. In embodiments, when $L^{9E}$ is substituted, it is substituted with at least one lower substituent group.

In embodiments, the polymeric bioconjugate linker includes a subunit having the formula:

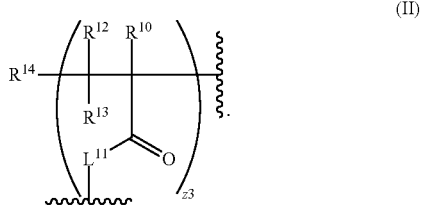

(II)

$R^{10}$, $R^{12}$, $R^{13}$, and $R^{14}$ are independently hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

$L^{11}$ is bonded to the particle. In embodiments, $L^{11}$ is covalently bonded to the solid surface of the particle. $L^{11}$ is independently -$L^{11A}$-$L^{11B}$-$L^{11C}$-$L^{11D}$-$L^{11E}$-. $L^{11A}$, $L^{11B}$, $L^{11C}$, $L^{11D}$, and $L^{11E}$ are independently a bond, —S(O)$_2$—, —S(O)—, —S(O)$_2$NH—, —NH—, —O—, —S—, —SS—, —C(O)—, —C(O)NH—, —C(O)CH$_2$—, —NHC(O)—, —NHC(O)NH—, —C(O)O—, —OC(O)—, substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered). The symbol z3 is independently an integer from 1 to 5000.

In embodiments, the polymeric bioconjugate linker is covalently bonded to the solid surface by a linker $L^{12}$, wherein $L^{12}$ is -$L^{12A}$-$L^{12B}$-$L^{12C}$-$L^{12D}$-$L^{12E}$-. $L^{12A}$, $L^{12B}$, $L^{12C}$, $L^{12D}$ and $L^{12E}$ are independently a bond, —S(O)$_2$—, —S(O)—, —S(O)$_2$NH—, —NH—, —O—, —S—, —C(O)—, —C(O)NH—, —C(O)CH$_2$—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, the polymeric bioconjugate linker does not include $L^{12}$ when the polymer includes a subunit of formula (II).

In embodiments, a substituted $R^{10}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, a substituted $R^{12}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{12}$ is substituted with a plurality of groups selected from substituent groups, size-limited substituent groups, and lower substituent groups; each substituent group, size-limited substituent group, and/or lower substituent group may optionally be different. In embodiments, when $R^{12}$ is substituted, it is substituted with at least one substituent group. In embodiments, when $R^{12}$ is substituted, it is substituted with at least one size-limited substituent group. In embodiments, when $R^{12}$ is substituted, it is substituted with at least one lower substituent group.

In embodiments, a substituted $R^{13}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{13}$ is substituted with a plurality of groups selected from substituent groups, size-limited substituent groups, and lower substituent groups; each substituent group, size-limited substituent group, and/or lower substituent group may optionally be different. In embodiments, when $R^{13}$ is substituted, it is substituted with at least one substituent group. In embodiments, when $R^{13}$ is substituted, it is substituted with at least one size-limited substituent group. In embodiments, when $R^{13}$ is substituted, it is substituted with at least one lower substituent group.

In embodiments, a substituted $R^{14}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{14}$ is substituted with a plurality of groups selected from substituent groups, size-limited substituent groups, and lower substituent groups; each substituent group, size-limited substituent group, and/or lower substituent group may optionally be different. In embodiments, when $R^{14}$ is substituted, it is substituted with at least one substituent group. In embodiments, when $R^{14}$ is substituted, it is substituted with at least one size-limited substituent group. In embodiments, when $R^{14}$ is substituted, it is substituted with at least one lower substituent group.

In embodiments, a substituted $L^{11A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{11A}$ is substituted with a plurality of groups selected from substituent groups, size-limited substituent groups, and lower substituent groups; each substituent group, size-limited substituent group, and/or lower substituent group may optionally be different. In embodiments, when $L^{11A}$ is substituted, it is substituted with at least one substituent group. In embodiments, when $L^{11A}$ is substituted, it is substituted with at least one size-limited substituent group. In embodiments, when $L^{11A}$ is substituted, it is substituted with at least one lower substituent group.

In embodiments, a substituted $L^{11B}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{11B}$ is substituted with a plurality of groups selected from substituent groups, size-limited substituent groups, and lower substituent groups; each substituent group, size-limited substituent group, and/or lower substituent group may optionally be different. In embodiments, when $L^{11B}$ is substituted, it is substituted with at least one substituent group. In embodiments, when $L^{11B}$ is substituted, it is substituted with at least one size-limited substituent group. In embodiments, when $L^{11B}$ is substituted, it is substituted with at least one lower substituent group.

In embodiments, a substituted $L^{11C}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{11C}$ is substituted with a plurality of groups selected from substituent groups, size-limited substituent groups, and lower substituent groups; each substituent group, size-limited substituent group, and/or lower substituent group may optionally be different. In embodiments, when $L^{11C}$ is substituted, it is substituted with at least one substituent group.

In embodiments, when $L^{11C}$ is substituted, it is substituted with at least one size-limited substituent group. In embodiments, when $L^{11C}$ is substituted, it is substituted with at least one lower substituent group.

In embodiments, a substituted $L^{11D}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{11D}$ is substituted with a plurality of groups selected from substituent groups, size-limited substituent groups, and lower substituent groups; each substituent group, size-limited substituent group, and/or lower substituent group may optionally be different. In embodiments, when $L^{11D}$ is substituted, it is substituted with at least one substituent group. In embodiments, when $L^{11D}$ is substituted, it is substituted with at least one size-limited substituent group. In embodiments, when $L^{11D}$ is substituted, it is substituted with at least one lower substituent group.

In embodiments, a substituted $L^{11E}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{11E}$ is substituted with a plurality of groups selected from substituent groups, size-limited substituent groups, and lower substituent groups; each substituent group, size-limited substituent group, and/or lower substituent group may optionally be different. In embodiments, when $L^{11E}$ is substituted, it is substituted with at least one substituent group. In embodiments, when $L^{11E}$ is substituted, it is substituted with at least one size-limited substituent group. In embodiments, when $L^{11E}$ is substituted, it is substituted with at least one lower substituent group.

In embodiments, a substituted $L^{12A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{12A}$ is substituted with a plurality of groups selected from substituent groups, size-limited substituent groups, and lower substituent groups; each substituent group, size-limited substituent group, and/or lower substituent group may optionally be different. In embodiments, when $L^{12A}$ is substituted, it is substituted with at least one substituent group. In embodiments, when $L^{12A}$ is substituted, it is substituted with at least one size-limited substituent group. In embodiments, when $L^{12A}$ is substituted, it is substituted with at least one lower substituent group.

In embodiments, a substituted $L^{12B}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{12B}$ is substituted with a plurality of groups selected from substituent groups, size-limited substituent groups, and lower substituent groups; each substituent group, size-limited substituent group, and/or lower substituent group may optionally be different. In embodiments, when $L^{12B}$ is substituted, it is substituted with at least one substituent group. In embodiments, when $L^{12B}$ is substituted, it is substituted with at least one size-limited substituent group. In embodiments, when $L^{12B}$ is substituted, it is substituted with at least one lower substituent group.

In embodiments, a substituted $L^{12C}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{12C}$ is substituted with a plurality of groups selected from substituent groups, size-limited substituent groups, and lower substituent groups; each substituent group, size-limited substituent group, and/or lower substituent group may optionally be different. In embodiments, when $L^{12C}$ is substituted, it is substituted with at least one substituent group. In embodiments, when $L^{12C}$ is substituted, it is substituted with at least one size-limited substituent group. In embodiments, when $L^{12C}$ is substituted, it is substituted with at least one lower substituent group.

In embodiments, a substituted $L^{12D}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{12D}$ is substituted with a plurality of groups selected from substituent groups, size-limited substituent groups, and lower substituent groups; each substituent group, size-limited substituent group, and/or lower substituent group may optionally be different. In embodiments, when $L^{12D}$ is substituted, it is substituted with at least one substituent group. In embodiments, when $L^{12D}$ is substituted, it is substituted with at least one size-limited substituent group. In embodiments, when $L^{12D}$ is substituted, it is substituted with at least one lower substituent group.

In embodiments, a substituted $L^{12E}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{12E}$ is substituted with a plurality of groups selected from substituent groups, size-limited substituent groups, and lower substituent groups; each substituent group, size-limited substituent group, and/or lower substituent group may optionally be different. In embodiments, when $L^{12E}$ is substituted, it is substituted with at least one substituent group. In embodiments, when $L^{12E}$ is substituted, it is substituted with at least one size-limited substituent group. In embodiments, when $L^{12E}$ is substituted, it is substituted with at least one lower substituent group.

In embodiments, the polymeric bioconjugate linker includes a subunit having the formula:

$$(III)$$

$R^{15}$, $R^{17}$, $R^{18}$, and $R^{19}$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

$L^{16}$ is independently -$L^{16A}$-$L^{16B}$-$L^{16C}$-$L^{16D}$-$L^{16E}$-. $L^{16A}$, $L^{16B}$, $L^{16C}$, $L^{16D}$, and $L^{16E}$ are independently a bond, —$S(O)_2$—, —S(O)—, —$S(O)_2NH$—, —NH—, —O—, —S—, —C(O)—, —C(O)NH—, —C(O)$CH_2$—, —NHC(O)—, —NHC(O)NH—, —C(O)O—, —OC(O)—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

$R^{16}$ is independently hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —CN, —$SO_{n16}R^{16D}$, —$SO_{v16}NR^{16A}R^{16B}$, —NHC(O)$NR^{16A}R^{16B}$, —N(O)$_{m16}$, —$NR^{16A}R^{16B}$, —C(O)$R^{16C}$, —C(O)—$OR^{16C}$, —C(O)$NR^{16A}R^{16B}$, —$OR^{16D}$, —$NR^{16A}SO_2R^{16D}$, —$NR^{16A}C(O)R^{16C}$, —$NR^{16A}C(O)OR^{16C}$, —$NR^{16A}OR^{16C}$, —OC(O)$R^{16C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered); wherein $R^{16}$ is a third non-reactive moiety. $R^{16A}$, $R^{16B}$, $R^{16C}$, and $R^{16D}$ are independently hydrogen, —$CX_3$, —CN, —COOH, —$CONH_2$, —$CHX_2$, —$CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered), a protecting group, or a leaving group; $R^{16A}$ and $R^{16B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

The symbol z4 is independently an integer from 1 to 5000. X and $X^{16}$ are independently —F, —Cl, —Br, or —I. The symbol n16 is independently an integer from 0 to 4. The symbols v16 and m16 are each independently 1 to 2.

In embodiments, a substituted $R^{15}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{15}$ is substituted with a plurality of groups selected from substituent groups, size-limited substituent groups, and lower substituent groups; each substituent group, size-limited substituent group, and/or lower substituent group may optionally be different. In embodiments, when $R^{15}$ is substituted, it is substituted with at least one substituent group. In embodiments, when $R^{15}$ is substituted, it is substituted with at least one size-limited substituent group. In embodiments, when $R^{15}$ is substituted, it is substituted with at least one lower substituent group.

In embodiments, a substituted $R^{17}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{17}$ is substituted with a plurality of groups selected from substituent groups, size-limited substituent groups, and lower substituent groups; each substituent group, size-limited substituent group, and/or lower substituent group may optionally be different. In embodiments, when $R^{17}$ is substituted, it is substituted with at least one substituent group. In embodiments, when $R^{17}$ is substituted, it is substituted with at least one size-limited substituent group. In embodiments, when $R^{17}$ is substituted, it is substituted with at least one lower substituent group.

In embodiments, a substituted $R^{18}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{18}$ is substituted with a plurality of groups selected from substituent groups, size-limited substituent groups, and lower substituent groups; each substituent group, size-limited substituent group, and/or lower substituent group may optionally be different. In embodiments, when $R^{18}$ is substituted, it is substituted with at least one substituent group. In embodiments, when $R^{18}$ is substituted, it is substituted with at least one size-limited substituent group. In embodiments, when $R^{18}$ is substituted, it is substituted with at least one lower substituent group.

In embodiments, a substituted $R^{19}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{19}$ is substituted with a plurality of groups selected from substituent groups, size-limited substituent groups, and lower substituent groups; each substituent group, size-limited substituent group, and/or lower substituent group may optionally be different. In embodiments, when $R^{19}$ is substituted, it is substituted with at least one substituent group. In embodiments, when $R^{19}$ is substituted, it is substituted with at least one size-limited substituent group. In embodiments, when $R^{19}$ is substituted, it is substituted with at least one lower substituent group.

In embodiments, a substituted $L^{16A}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{16A}$ is substituted with a plurality of groups selected from substituent groups, size-limited substituent groups, and lower substituent groups; each substituent group, size-limited substituent group, and/or lower substituent group may optionally be different. In embodiments, when $L^{16A}$ is substituted, it is substituted with at least one substituent group. In embodiments, when $L^{16A}$ is substituted, it is substituted with at least one size-limited substituent group. In embodiments, when $L^{16A}$ is substituted, it is substituted with at least one lower substituent group.

In embodiments, a substituted $L^{16B}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{16B}$ is substituted with a plurality of groups selected from substituent groups, size-limited substituent groups, and lower substituent groups; each substituent group, size-limited substituent group, and/or lower substituent group may optionally be different. In embodiments, when $L^{16B}$ is substituted, it is substituted with at least one substituent group. In embodiments, when $L^{16B}$ is substituted, it is substituted with at least one size-limited substituent group. In embodiments, when $L^{16B}$ is substituted, it is substituted with at least one lower substituent group.

In embodiments, a substituted $L^{16C}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{16C}$ is substituted with a plurality of groups selected from substituent groups, size-limited substituent groups, and lower substituent groups; each substituent group, size-limited substituent group, and/or lower substituent group may optionally be different. In embodiments, when $L^{16C}$ is substituted, it is substituted with at least one substituent group. In embodiments, when $L^{16C}$ is substituted, it is substituted with at least one size-limited substituent group. In embodiments, when $L^{16C}$ is substituted, it is substituted with at least one lower substituent group.

In embodiments, a substituted $L^{16D}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{16D}$ is substituted with a plurality of groups selected from substituent groups, size-limited substituent groups, and lower substituent groups; each substituent group, size-limited substituent group, and/or lower substituent group may optionally be different. In embodiments, when $L^{16D}$ is substituted, it is substituted with at least one substituent group. In embodiments, when $L^{16D}$ is substituted, it is substituted with at least one size-limited substituent group. In embodiments, when $L^{16D}$ is substituted, it is substituted with at least one lower substituent group.

In embodiments, a substituted $L^{16E}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^{16E}$ is substituted with a plurality of groups selected from substituent groups, size-limited substituent groups, and lower substituent groups; each substituent group, size-limited substituent group, and/or lower substituent group may optionally be different. In embodiments, when $L^{16E}$ is substituted, it is substituted with at least one substituent group. In embodiments, when $L^{16E}$ is substituted, it is substituted with at least one size-limited substituent group. In embodiments, when $L^{16E}$ is substituted, it is substituted with at least one lower substituent group.

In embodiments, a substituted $R^{16}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{16}$ is substituted with a plurality of groups selected from substituent groups, size-limited substituent groups, and lower substituent groups; each substituent group, size-limited substituent group, and/or lower substituent group may optionally be different. In embodiments, when $R^{16}$ is substituted, it is substituted with at least one substituent group. In embodiments, when $R^{16}$ is substituted, it is substituted with at least one size-limited substituent group. In embodiments, when $R^{16}$ is substituted, it is substituted with at least one lower substituent group.

In embodiments, a substituted $R^{16A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{16A}$ is substituted with a plurality of groups selected from substituent groups, size-limited substituent groups, and lower substituent groups; each substituent group, size-limited substituent group, and/or lower substituent group may optionally be different. In embodiments, when $R^{16A}$ is substituted, it is substituted with at least one substituent group. In embodiments, when $R^{16A}$ is substituted, it is substituted with at least one size-limited substituent group. In embodiments, when $R^{16A}$ is substituted, it is substituted with at least one lower substituent group.

In embodiments, a substituted $R^{16B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{16B}$ is substituted with a plurality of groups selected from substituent groups, size-limited substituent groups, and lower substituent groups; each substituent group, size-limited substituent group, and/or lower substituent group may optionally be different. In embodiments, when $R^{16B}$ is substituted, it is substituted with at least one substituent group. In embodiments, when $R^{16B}$ is substituted, it is substituted with at least one size-limited substituent group. In embodiments, when $R^{16B}$ is substituted, it is substituted with at least one lower substituent group.

In embodiments, a substituted ring formed when $R^{16A}$ and $R^{16B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{16A}$ and $R^{16B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{16A}$ and $R^{16B}$ substituents bonded to the same nitrogen atom are joined is substituted, it is substituted with at least one substituent group. In embodiments, when the substituted ring formed when $R^{16A}$ and $R^{16B}$ substituents bonded to the same nitrogen atom are joined is substituted, it is substituted with at least one size-limited substituent group. In embodiments, when the substituted ring formed when $R^{16A}$ and $R^{16B}$ substituents bonded to the same nitrogen atom are joined is substituted, it is substituted with at least one lower substituent group.

In embodiments, a substituted $R^{16C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{16C}$ is substituted with a plurality of groups selected from substituent groups, size-limited substituent groups, and lower substituent groups; each substituent group, size-limited substituent group, and/or lower substituent group may optionally be different. In embodiments, when $R^{16C}$ is substituted, it is substituted with at least one substituent group. In embodiments, when $R^{16C}$ is substituted, it is substituted with at least one size-limited substituent group. In embodiments, when $R^{16C}$ is substituted, it is substituted with at least one lower substituent group.

In embodiments, a substituted $R^{16D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{16D}$ is substituted with a plurality of groups selected from substituent groups, size-limited substituent groups, and lower substituent groups; each substituent group, size-limited substituent group, and/or lower substituent group may optionally be different. In embodiments, when $R^{16D}$ is substituted, it is substituted with at least one substituent group. In embodiments, when $R^{16D}$ is substituted, it is substituted with at least one size-limited substituent group. In embodiments, when $R^{16D}$ is substituted, it is substituted with at least one lower substituent group.

In embodiments, $R^{21}$ is independently —CN. In embodiments, $R^{21}$ is independently substituted or unsubstituted alkyl. In embodiments, $R^{21}$ is independently substituted or unsubstituted $C_1$-$C_4$ alkyl. In embodiments, $R^{21}$ is independently unsubstituted $C_1$-$C_4$ alkyl. In embodiments, $R^{21}$ is independently unsubstituted methyl. In embodiments, $R^{21}$ is independently unsubstituted ethyl. In embodiments, $R^{21}$ is independently unsubstituted propyl. In embodiments, $R^{21}$ is independently unsubstituted n-propyl. In embodiments, $R^{21}$ is independently unsubstituted isopropyl. In embodiments, $R^{21}$ is independently unsubstituted butyl. In embodiments, $R^{21}$ is independently unsubstituted n-butyl. In embodiments, $R^{21}$ is independently unsubstituted tert-butyl. In embodiments, $R^{21}$ is independently substituted or unsubstituted heteroalkyl. In embodiments, $R^{21}$ is independently substituted or unsubstituted 2 to 6 membered heteroalkyl. In embodiments, each $R^{21}$ is the same.

In embodiments, $L^2$ is independently a substituted or unsubstituted heteroalkylene. In embodiments, $L^{2A}$ is independently a bond. In embodiments, $L^{2B}$ and $L^{2D}$ are independently substituted or unsubstituted heteroalkylene; $L^{2C}$ is independently a substituted or unsubstituted heteroarylene; and $L^{2E}$ is independently a bond. In embodiments, $L^{2B}$ and $L^{2E}$ are independently substituted or unsubstituted heteroalkylene; $L^{2C}$ is independently a substituted or unsubstituted heteroarylene; and $L^{2D}$ is independently a substituted or unsubstituted arylene.

In embodiments, $L^{2A}$ is independently a substituted or unsubstituted heteroalkylene. In embodiments, $L^{2A}$ is independently

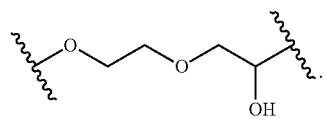 [SMILES: *OCCOCC(*)O]

In embodiments, $L^{2A}$ is independently

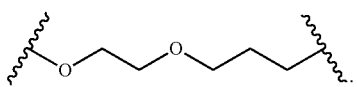 [SMILES: *CCCOCCO*]

In embodiments, $L^{2A}$ is independently

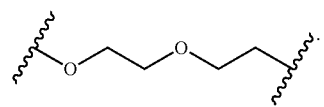 [SMILES: *CCOCCO*]

In embodiments, $L^{2A}$ is independently

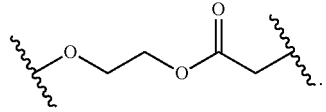 [SMILES: *CC(=O)OCCO*]

In embodiments, $L^{2A}$ is independently

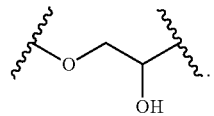

In embodiments, $L^{2A}$ is independently

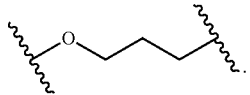 [SMILES: *CCCO*]

In embodiments, $L^{2A}$ is independently

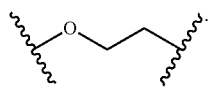 [SMILES: *CCO*]

In embodiments, $L^{2A}$ is independently

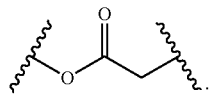 [SMILES: *CC(=O)O*]

In embodiments, $L^{2A}$ is independently

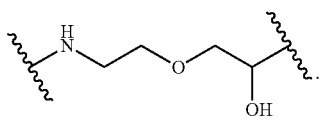 [SMILES: *NCCOCC(*)O]

In embodiments, $L^{2A}$ is independently

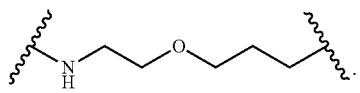 [SMILES: *CCCOCCN*]

In embodiments, $L^{2A}$ is independently

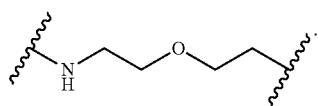 [SMILES: *CCOCCN*]

In embodiments, $L^{2A}$ is independently

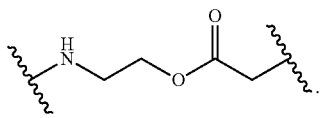 [SMILES: *CC(=O)OCCN*]

In embodiments, $L^{2A}$ is independently

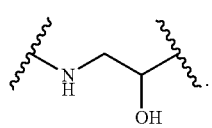 [SMILES: *NCC(*)O]

In embodiments, $L^{2A}$ is independently

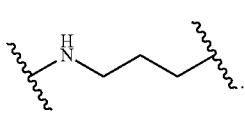 [SMILES: *CCCN*]

In embodiments, $L^{2A}$ is independently

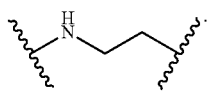 [SMILES: *CCN*]

In embodiments, $L^{2A}$ is independently

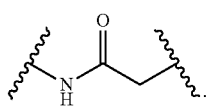 [SMILES: *CC(=O)N*]

In embodiments, $L^{2A}$ is independently a substituted or unsubstituted heteroalkylene. In embodiments, $L^{2A}$ is independently

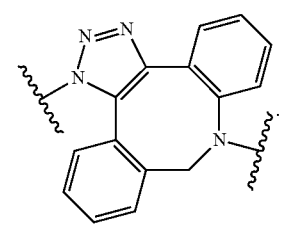 [SMILES: *N1Cc2ccccc2-c2c(nnn2*)-c2ccccc21]

In embodiments, $L^{2A}$ is independently

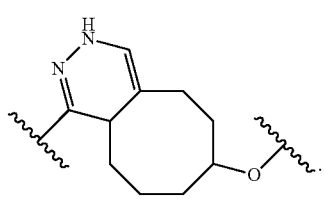 [SMILES: *OC1CCCC2C(=CNN=C2*)CC1]

In embodiments, $L^{2B}$ is independently

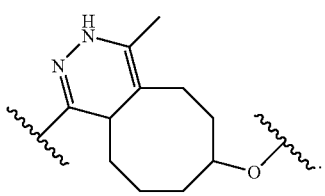 [SMILES: *OC1CCCC2C(*)=NNC(C)=C2CC1]

In embodiments, $L^{2B}$ is independently

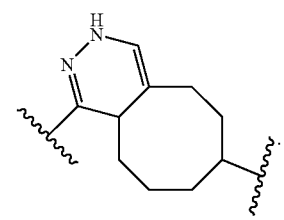 [SMILES: *C1=NNC=C2CCC(*)CCCC21]

In embodiments, $L^{2B}$ is independently

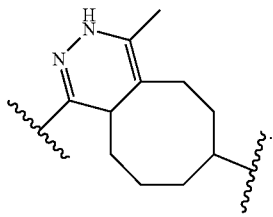 [SMILES: *C1=NNC(C)=C2CCC(*)CCCC12]

In embodiments, $L^{2B}$ is independently

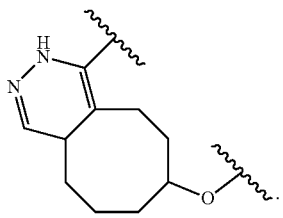 [SMILES: *OC1CCCC2C=NNC(*)=C2CC1]

In embodiments, $L^{2B}$ is independently

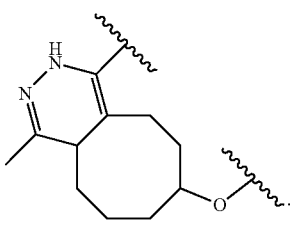 [SMILES: *OC1CCCC2C(C)=NNC(*)=C2CC1]

In embodiments, $L^{2B}$ is independently

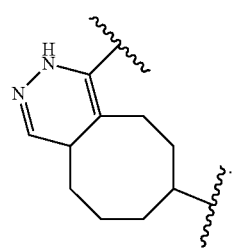 [SMILES: *C1=C2CCC(*)CCCC2C=NN1]

In embodiments, $L^{2B}$ is independently

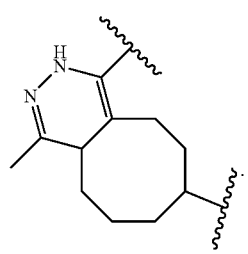 [SMILES: *C1=C2CCC(*)CCCC2C(C)=NN1]

In embodiments, $L^{2C}$ is independently a substituted or unsubstituted heteroalkylene. In embodiments, $L^{2C}$ is independently

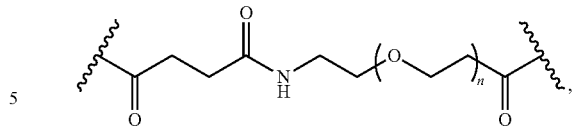

wherein n is independently an integer from 4 to 12. In embodiments, $L^{2C}$ is independently

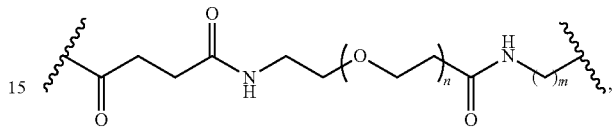

wherein n is independently an integer from 4 to 12 and m is independently an integer from 4 to 12. In embodiments, $L^{2C}$ is independently

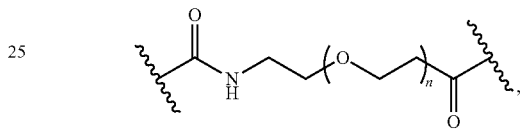

wherein n is independently an integer from 4 to 12. In embodiments, $L^{2C}$ is independently

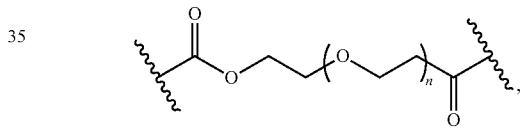

wherein n is independently an integer from 4 to 12. In embodiments, $L^{2C}$ is independently

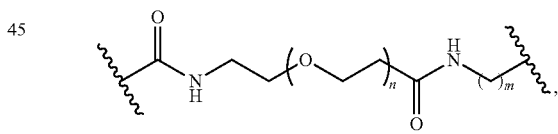

wherein n is independently an integer from 4 to 12 and m is independently an integer from 4 to 12. In embodiments, $L^{2C}$ is independently

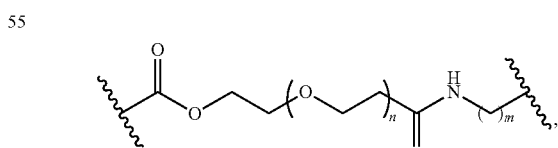

wherein n is independently an integer from 4 to 12 and m is independently an integer from 4 to 12.

In embodiments, $L^{2D}$ is independently a substituted or unsubstituted heteroalkylene. In embodiments, $L^{2D}$ is independently

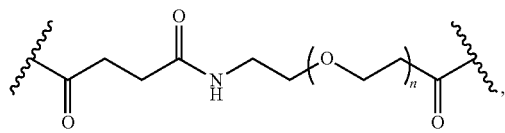

wherein n is independently an integer from 4 to 12. In embodiments, $L^{2D}$ is independently

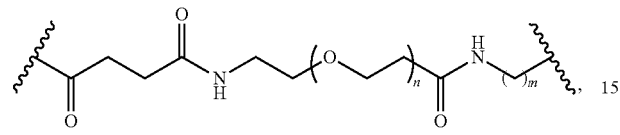

wherein n is independently an integer from 4 to 12 and m is independently an integer from 4 to 12. In embodiments, $L^{2D}$ is independently

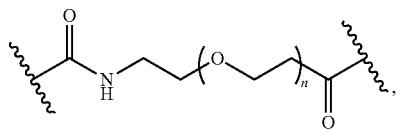

wherein n is independently an integer from 4 to 12. In embodiments, $L^{2D}$ is independently

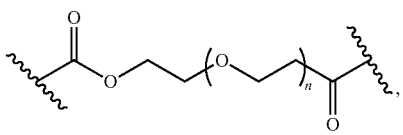

wherein n is independently an integer from 4 to 12. In embodiments, $L^{2D}$ is independently

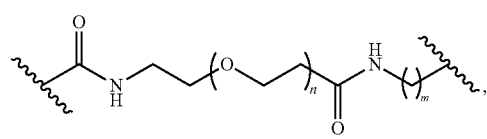

wherein n is independently an integer from 4 to 12 and m is independently an integer from 4 to 12. In embodiments, $L^{2D}$ is independently

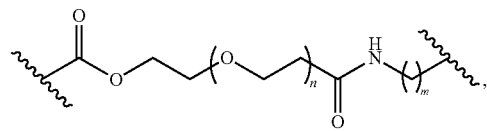

wherein n is independently an integer from 4 to 12 and m is independently an integer from 4 to 12.

In embodiments, $-L^{2C}-L^{2D}-L^{2E}-$ is independently a substituted or unsubstituted heteroalkylene. In embodiments, $-L^{2C}-L^{2D}-L^{2E}-$ is independently

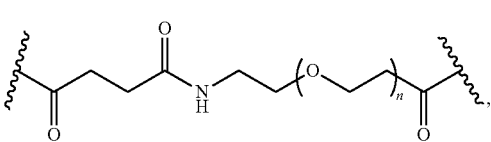

wherein n is independently an integer from 4 to 12. In embodiments, $-L^{2C}-L^{2D}-L^{2E}-$ is independently

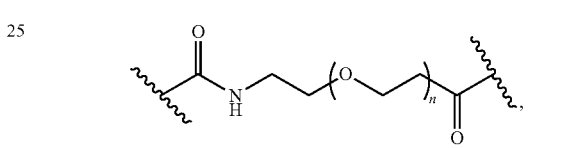

wherein n is independently an integer from 4 to 12 and m is independently an integer from 4 to 12. In embodiments, $-L^{2C}-L^{2D}-L^{2E}-$ is independently wherein n is independently an integer from 4 to 12. In embodiments, $-L^{2C}-L^{2D}-L^{2E}-$ is independently

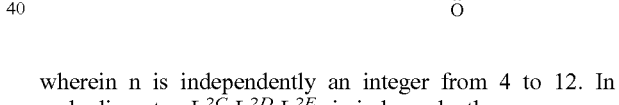

wherein n is independently an integer from 4 to 12. In embodiments, $-L^{2C}-L^{2D}-L^{2E}-$ is independently wherein n is independently an integer from 4 to 12 and m is independently an integer from 4 to 12. In embodiments, $-L^{2C}-L^{2D}-L^{2E}-$ is independently

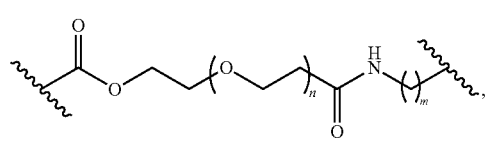

wherein n is independently an integer from 4 to 12 and m is independently an integer from 4 to 12.

In embodiments, $L^2$ is independently

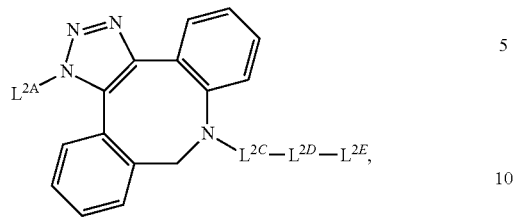

wherein $L^{2A}$, $L^{2C}$, $L^{2D}$, and $L^{2E}$ are as described herein, including in embodiments.

In embodiments, -$L^{2A}$-$L^{2B}$-$L^{2C}$- is independently

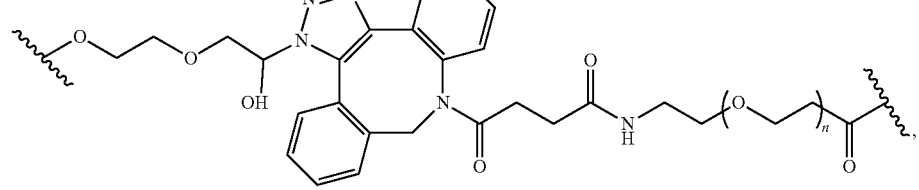

wherein n is independently an integer from 4 to 12. In embodiments, -$L^{2A}$-$L^{2B}$-$L^{2C}$- is independently

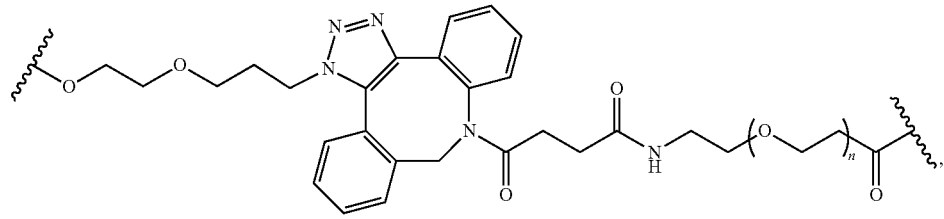

wherein n is independently an integer from 4 to 12. In embodiments, -$L^{2A}$-$L^{2B}$-$L^{2C}$- is independently

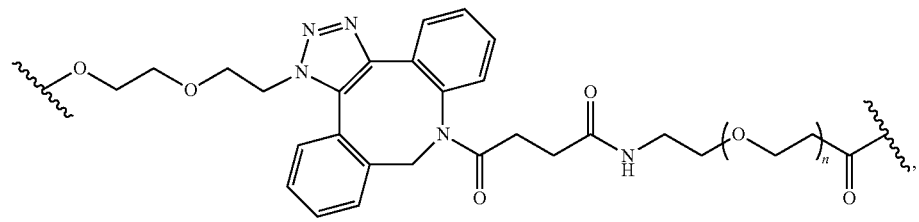

wherein n is independently an integer from 4 to 12. In embodiments, -L$^{2A}$-L$^{2B}$-L$^{2C}$- is independently

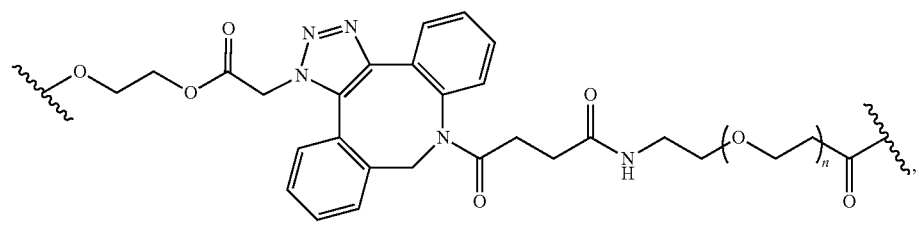

wherein n is independently an integer from 4 to 12. In embodiments, -L$^{2A}$-L$^{2B}$-L$^{2C}$- is independently

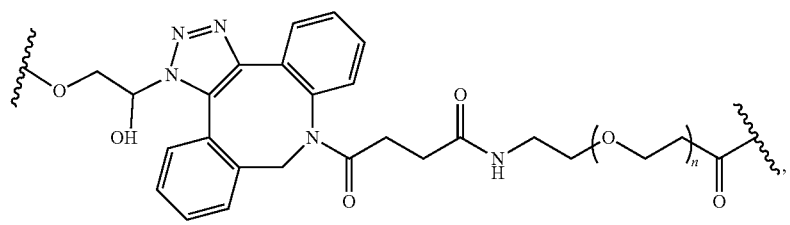

wherein n is independently an integer from 4 to 12. In embodiments, -L$^{2A}$-L$^{2B}$-L$^{2C}$- is independently

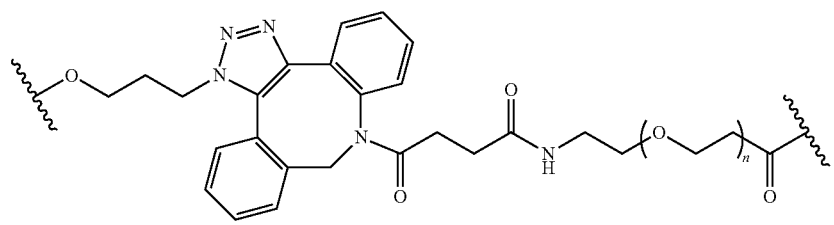

wherein n is independently an integer from 4 to 12. In embodiments, -L$^{2A}$-L$^{2B}$-L$^{2C}$- is independently

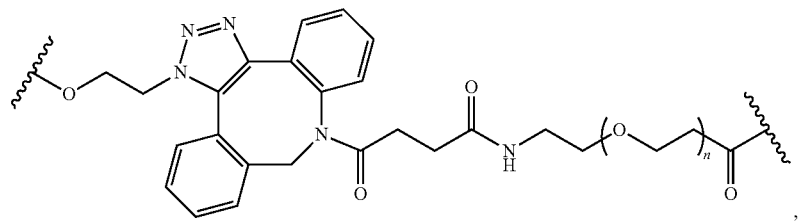

wherein n is independently an integer from 4 to 12. In embodiments, -L$^{2A}$-L$^{2B}$-L$^{2C}$- is independently

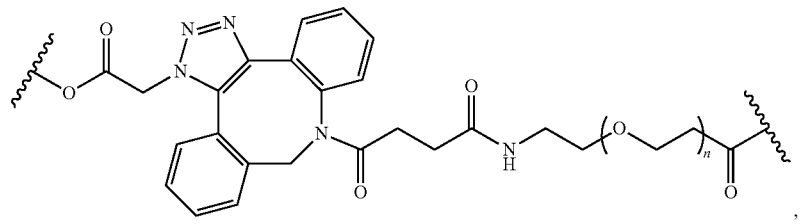

wherein n is independently an integer from 4 to 12. In embodiments, -L$^{2A}$-L$^{2B}$-L$^{2C}$- is independently

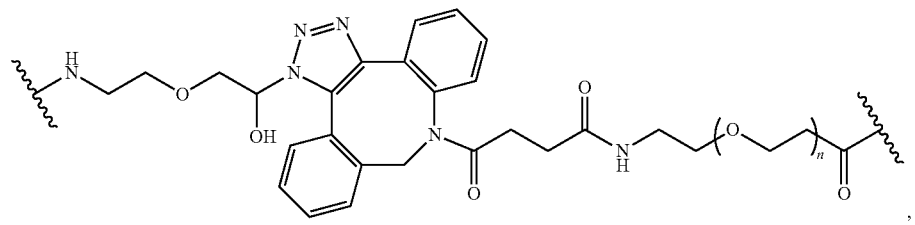

wherein n is independently an integer from 4 to 12. In embodiments, -L$^{2A}$-L$^{2B}$-L$^{2C}$- is independently

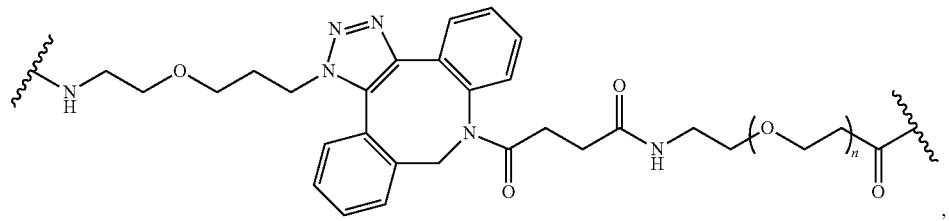

wherein n is independently an integer from 4 to 12. In embodiments, -L$^{2A}$-L$^{2B}$-L$^{2C}$- is independently

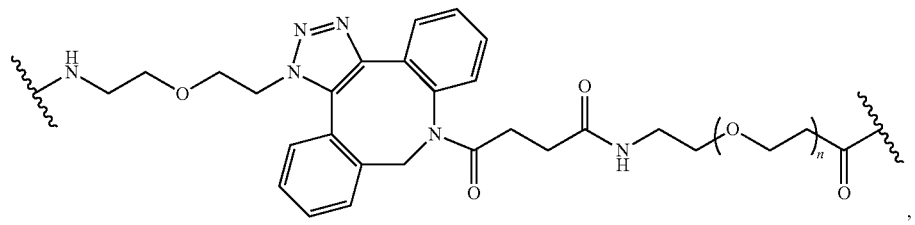

wherein n is independently an integer from 4 to 12. In embodiments, -L$^{2A}$-L$^{2B}$-L$^{2C}$- is independently

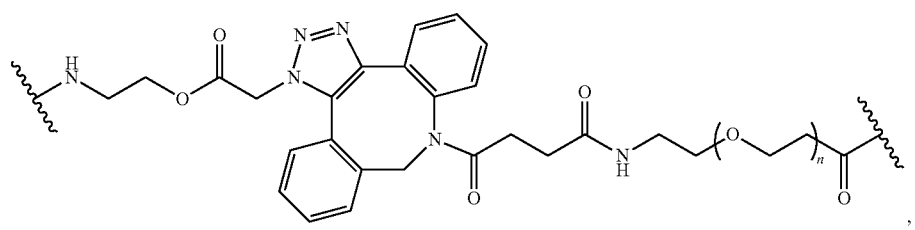

wherein n is independently an integer from 4 to 12. In embodiments, -L$^{2A}$-L$^{2B}$-L$^{2C}$- is independently

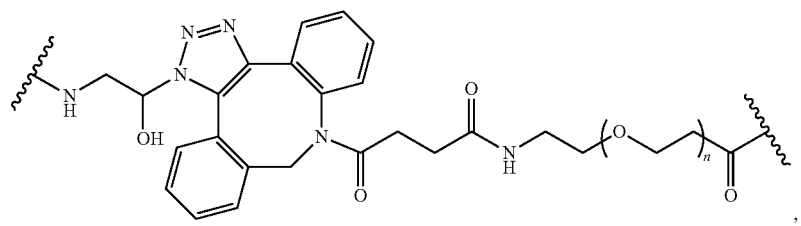

wherein n is independently an integer from 4 to 12. In embodiments, -L$^{2A}$-L$^{2B}$-L$^{2C}$- is independently

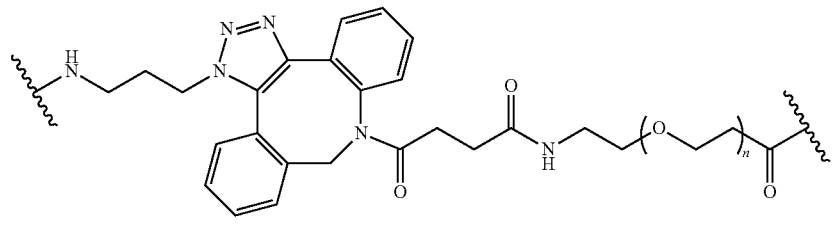

wherein n is independently an integer from 4 to 12. In embodiments, -L$^{2A}$-L$^{2B}$-L$^{2C}$- is independently

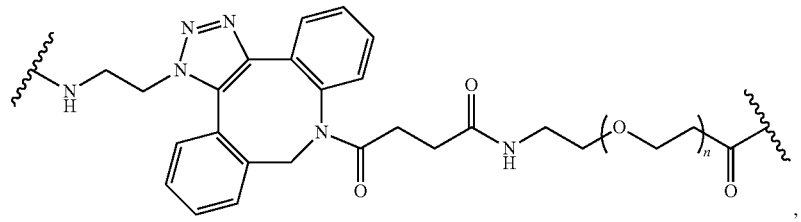

wherein n is independently an integer from 4 to 12. In embodiments, -L$^{2A}$-L$^{2B}$-L$^{2C}$- is independently

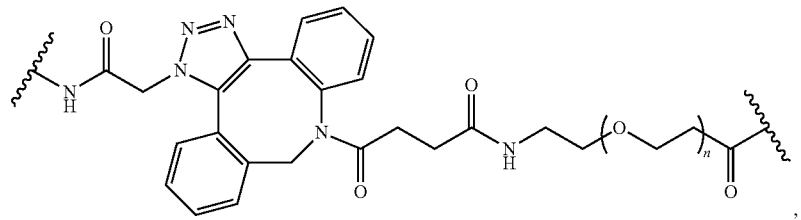

, wherein n is independently an integer from 4 to 12.

In embodiments, L$^{2D}$ is independently —S—S— and L$^{2E}$ is independently an unsubstituted C$_4$-C$_8$ alkylene. In embodiments, L$^{2D}$ is independently

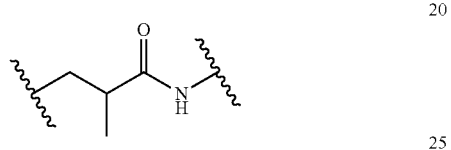

and L$^{2E}$ is independently an unsubstituted C$_4$-C$_8$ alkylene.

In embodiments, L$^2$ is independently a substituted or unsubstituted heteroalkylene. In embodiments, L$^2$ is independently

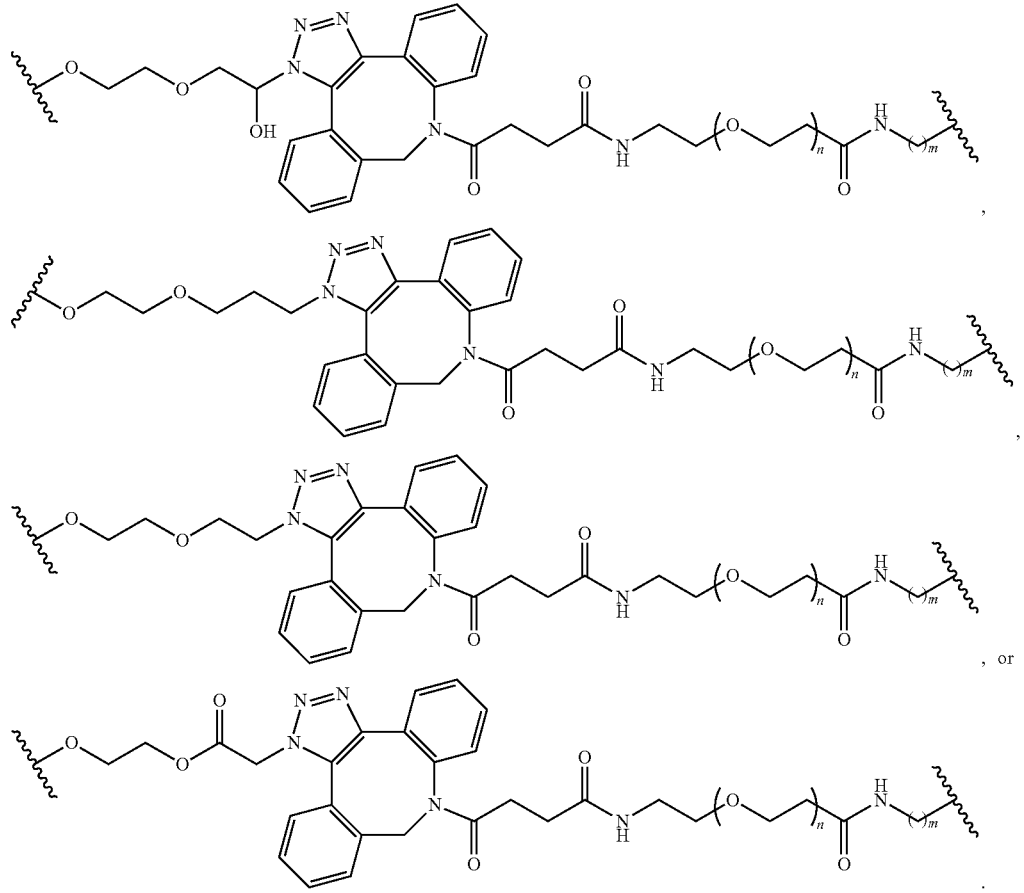

, or

The symbol n is independently an integer from 4 to 12, and the symbol m is an integer from 4 to 12. In embodiments, $L^2$ is independently
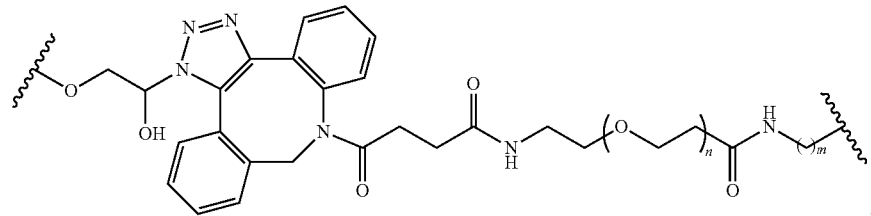
,
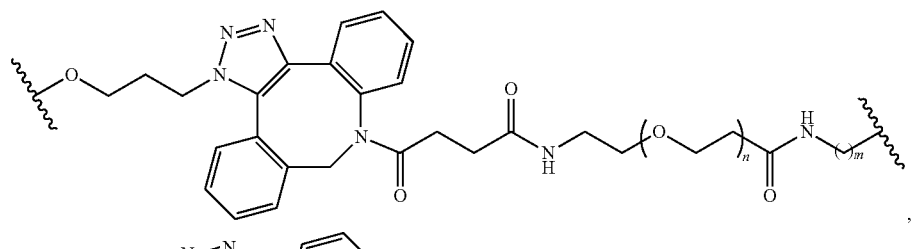
,
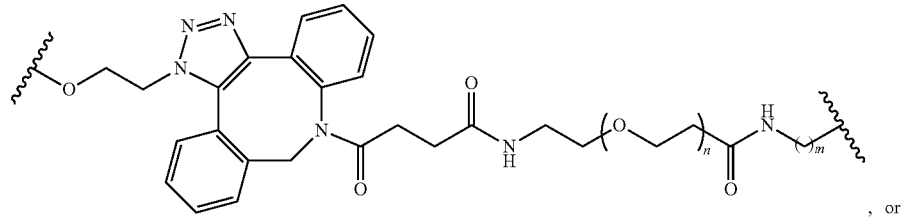
, or
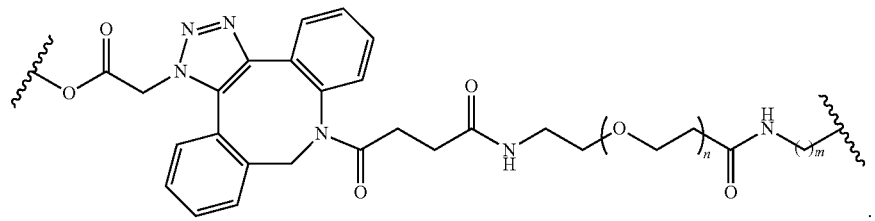
.
The symbol n is independently an integer from 4 to 12, and the symbol m is independently an integer from 4 to 12. In embodiments, $L^2$ is independently
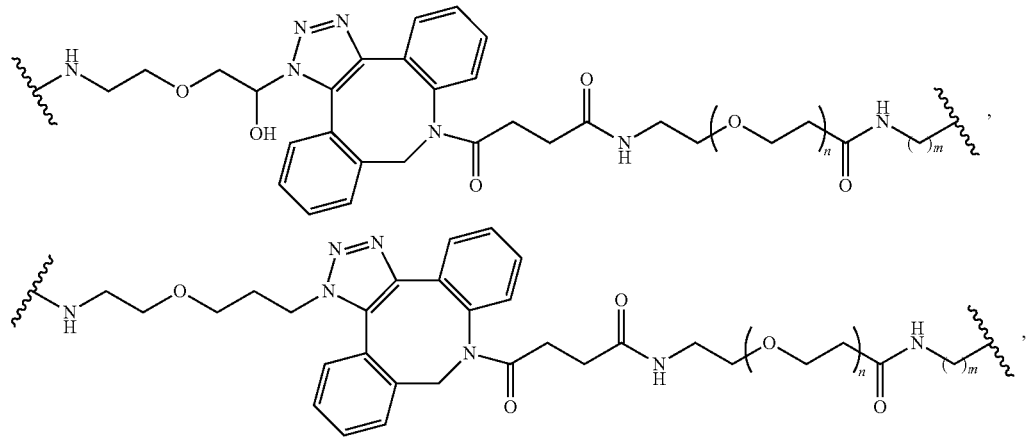

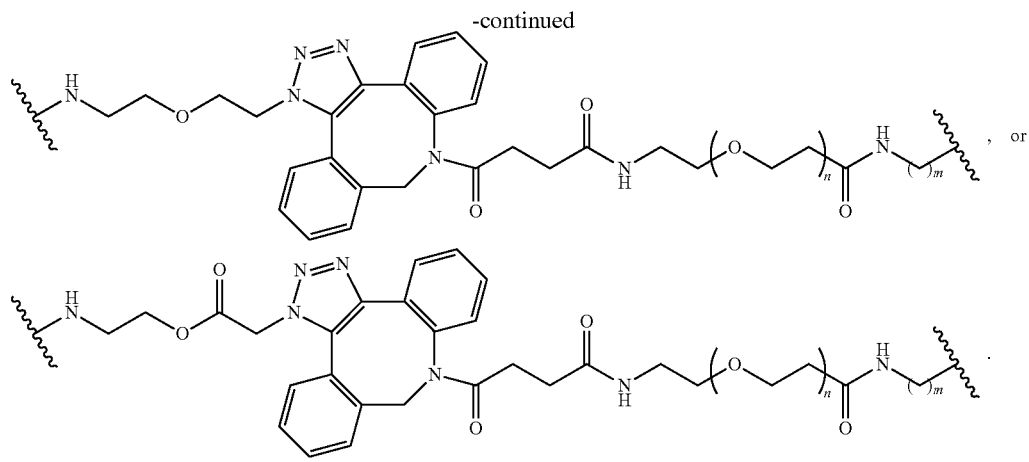

, or

The symbol n is independently an integer from 4 to 12, and the symbol m is independently an integer from 4 to 12. In embodiments, $L^2$ is independently

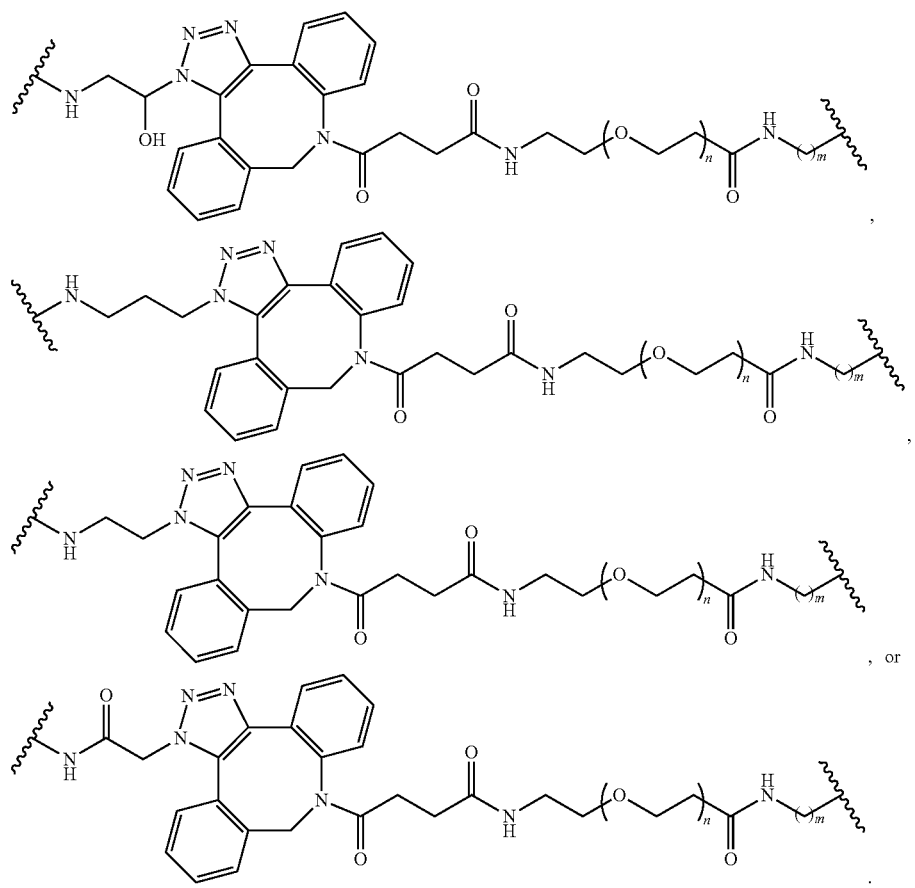

The symbol n is independently an integer from 4 to 12, and the symbol m is independently an integer from 4 to 12. In embodiments, each $L^2$ is the same.

In embodiments, $R^{23}$ is independently —CN. In embodiments, $R^{23}$ is independently substituted or unsubstituted alkyl. In embodiments, $R^{23}$ is independently substituted or unsubstituted $C_1$-$C_4$ alkyl. In embodiments, $R^{23}$ is independently unsubstituted $C_1$-$C_4$ alkyl. In embodiments, $R^{23}$ is independently unsubstituted methyl. In embodiments, $R^{23}$ is independently unsubstituted ethyl. In embodiments, $R^{23}$ is independently unsubstituted propyl. In embodiments, $R^{23}$ is independently unsubstituted n-propyl. In embodiments, $R^{23}$ is independently unsubstituted isopropyl. In embodiments, $R^{23}$ is independently unsubstituted butyl. In embodiments, $R^{23}$ is independently unsubstituted n-butyl. In embodiments, $R^{23}$ is independently unsubstituted tert-butyl. In embodiments, $R^{23}$ is independently substituted or unsubstituted heteroalkyl. In embodiments, $R^{23}$ is independently substituted or unsubstituted 2 to 6 membered heteroalkyl. In embodiments, each $R^{23}$ is the same.

In embodiments, $L^4$ is independently substituted or unsubstituted heteroalkylene. In embodiments, $L^{4B}$ and $L^{4D}$ are independently substituted or unsubstituted heteroalkylene; $L^{4C}$ is independently a substituted or unsubstituted heteroarylene; and $L^{4E}$ is independently a bond. In embodiments, $L^{4B}$ and $L^{4E}$ are independently substituted or unsubstituted heteroalkylene; $L^{4C}$ is independently a substituted or unsubstituted heteroarylene; and $L^{4D}$ is independently a substituted or unsubstituted arylene. In embodiments, $L^{4A}$ is independently a bond. In embodiments, each $L^4$ is the same.

In embodiments, $R^{24}$ is independently a non-reactive moiety selected from hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{24}$ is independently a non-reactive moiety selected from hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{24}$ is independently hydrogen, —$OCH_2CH_2$—($OCH_2CH_2$)$_p$—$OCH_3$ or —$N(CH_3)_2$; and p is an integer from 0 to 10. In embodiments, each $R^{24}$ is the same. In embodiments, -$L^4$-$R^{24}$ is independently —$OCH_2CH_2$—($OCH_2CH_2$)$_p$—$OCH_3$ or —$N(CH_3)_2$; and p is an integer from 4 to 10.

In embodiments, $R^5$ and $R^6$ are independently hydrogen. In embodiments, $R^5$ is independently hydrogen. In embodiments, $R^5$ is independently substituted or unsubstituted $C_1$-$C_4$ alkyl. In embodiments, $R^5$ is independently unsubstituted $C_1$-$C_4$ alkyl. In embodiments, $R^5$ is independently unsubstituted methyl. In embodiments, $R^5$ is independently unsubstituted ethyl. In embodiments, $R^5$ is independently unsubstituted propyl. In embodiments, $R^5$ is independently unsubstituted n-propyl. In embodiments, $R^5$ is independently unsubstituted isopropyl. In embodiments, $R^5$ is independently unsubstituted butyl. In embodiments, $R^5$ is independently unsubstituted n-butyl. In embodiments, $R^5$ is independently unsubstituted tert-butyl. In embodiments, each $R^5$ is the same.

In embodiments, $R^6$ is independently hydrogen. In embodiments, $R^6$ is independently substituted or unsubstituted $C_1$-$C_4$ alkyl. In embodiments, $R^6$ is independently unsubstituted $C_1$-$C_4$ alkyl. In embodiments, $R^6$ is independently unsubstituted methyl. In embodiments, $R^6$ is independently unsubstituted ethyl. In embodiments, $R^6$ is independently unsubstituted propyl. In embodiments, $R^6$ is independently unsubstituted n-propyl. In embodiments, $R^6$ is independently unsubstituted isopropyl. In embodiments, $R^6$ is independently unsubstituted butyl. In embodiments, $R^6$ is independently unsubstituted n-butyl. In embodiments, $R^6$ is independently unsubstituted tert-butyl. In embodiments, each $R^6$ is the same.

In embodiments, $R^7$ and $R^8$ are independently hydrogen. In embodiments, $R^7$ is independently hydrogen. In embodiments, $R^7$ is independently substituted or unsubstituted $C_1$-$C_4$ alkyl. In embodiments, $R^7$ is independently unsubstituted $C_1$-$C_4$ alkyl. In embodiments, $R^7$ is independently unsubstituted methyl. In embodiments, $R^7$ is independently unsubstituted ethyl. In embodiments, $R^7$ is independently unsubstituted propyl. In embodiments, $R^7$ is independently unsubstituted n-propyl. In embodiments, $R^7$ is independently unsubstituted isopropyl. In embodiments, $R^7$ is independently unsubstituted butyl. In embodiments, $R^7$ is independently unsubstituted n-butyl. In embodiments, $R^7$ is independently unsubstituted tert-butyl. In embodiments, each $R^7$ is the same.

In embodiments, $R^8$ is independently hydrogen. In embodiments, $R^8$ is independently substituted or unsubstituted $C_1$-$C_4$ alkyl. In embodiments, $R^8$ is independently unsubstituted $C_1$-$C_4$ alkyl. In embodiments, $R^8$ is independently unsubstituted methyl. In embodiments, $R^8$ is independently unsubstituted ethyl. In embodiments, $R^8$ is independently unsubstituted propyl. In embodiments, $R^8$ is independently unsubstituted n-propyl. In embodiments, $R^8$ is independently unsubstituted isopropyl. In embodiments, $R^8$ is independently unsubstituted butyl. In embodiments, $R^8$ is independently unsubstituted n-butyl. In embodiments, $R^8$ is independently unsubstituted tert-butyl. In embodiments, each $R^8$ is the same.

In embodiments, $L^{9A}$ is independently a bond. In embodiments, $L^{9B}$ and $L^{9D}$ are independently substituted or unsubstituted heteroalkylene; $L^{9C}$ is independently a substituted or unsubstituted heteroarylene; and $L^{9E}$ is independently a bond. In embodiments, $L^{9B}$ and $L^{9E}$ are independently substituted or unsubstituted heteroalkylene; $L^{9C}$ is independently a substituted or unsubstituted heteroarylene; and $L^{9D}$ is independently a substituted or unsubstituted arylene.

In embodiments, $L^{9A}$ is independently a substituted or unsubstituted heteroalkylene. In embodiments, $L^{9A}$ is independently

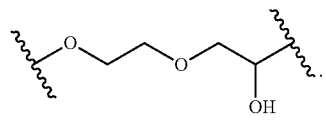 [SMILES: *OCCOCC(*)O]

In embodiments, $L^{9A}$ is independently

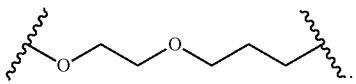

In embodiments, $L^{9A}$ is independently

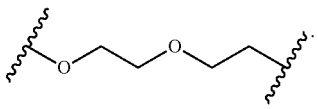 [SMILES: *CCOCCO*]

In embodiments $L^{9A}$ is independently

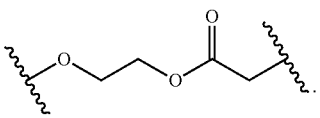 [SMILES: *CC(=O)OCCO*]

In embodiments, $L^{9A}$ is independently

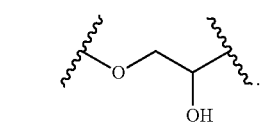 [SMILES: *OCC(*)O]

In embodiments, $L^{9A}$ is independently

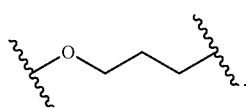 [SMILES: *CCCO*]

In embodiments, $L^{9A}$ is independently

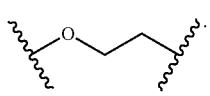

In embodiments, $L^{9A}$ is independently

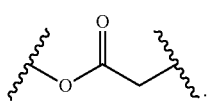

In embodiments, $L^{9A}$ is independently

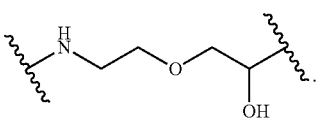

In embodiments, $L^{9A}$ is independently

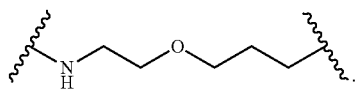 [SMILES: *CCCOCCN*]

In embodiments, $L^{9A}$ is independently

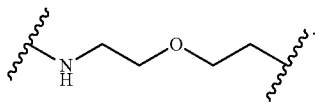 [SMILES: *CCOCCN*]

In embodiments, $L^{9A}$ is independently

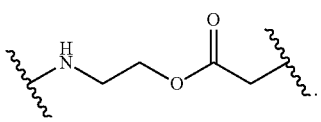 [SMILES: *CC(=O)OCCN*]

In embodiments, $L^{9A}$ is independently

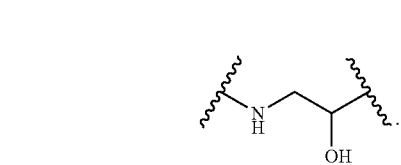

In embodiments, $L^{9A}$ is independently

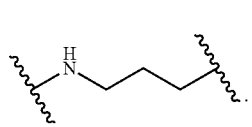

In embodiments, $L^{9A}$ is independently

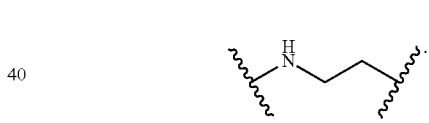

In embodiments, $L^{9A}$ is independently

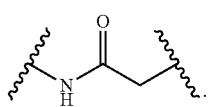 [SMILES: *CC(=O)N*]

In embodiments, $L^{9B}$ is independently a substituted or unsubstituted heteroarylene. In embodiments, $L^{9B}$ is independently

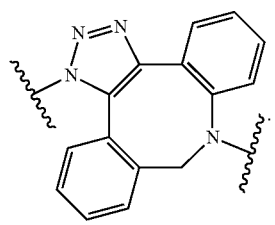 [SMILES: *N1Cc2ccccc2-c2c(nnn2*)-c2ccccc21]

In embodiments, $L^{9B}$ is independently

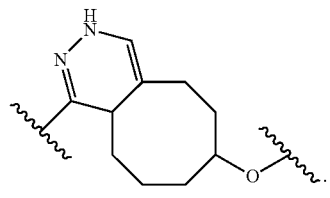 [SMILES: *OC1CCCC2C(=CNN=C2*)CC1]

In embodiments, $L^{9B}$ is independently

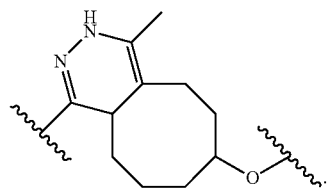 [SMILES: *OC1CCCC2C(*)=NNC(C)=C2CC1]

In embodiments, $L^{9B}$ is independently

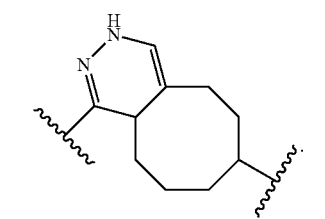 [SMILES: *C1=NNC=C2CCC(*)CCCC21]

In embodiments, $L^{9B}$ is independently

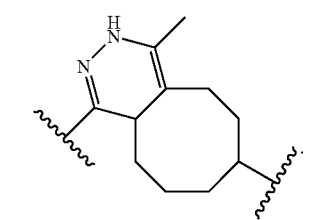 [SMILES: *C1=NNC(C)=C2CCC(*)CCCC12]

In embodiments, $L^{9B}$ is independently

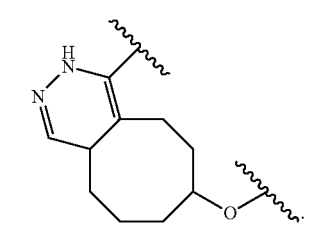 [SMILES: *OC1CCCC2C=NNC(*)=C2CC1]

In embodiments, $L^{9B}$ is independently

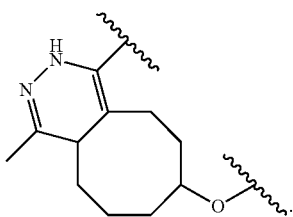 [SMILES: *OC1CCCC2C(C)=NNC(*)=C2CC1]

In embodiments, $L^{9B}$ is independently

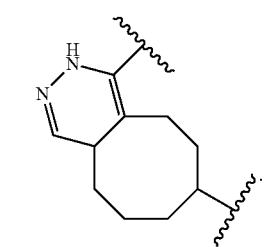 [SMILES: *C1=C2CCC(*)CCCC2C=NN1]

In embodiments, $L^{9B}$ is independently

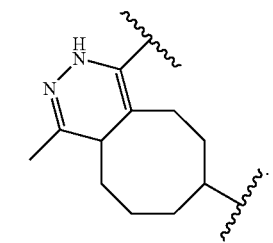 [SMILES: *C1=C2CCC(*)CCCC2C(C)=NN1]

In embodiments, $L^{9C}$ is independently a substituted or unsubstituted heteroalkylene. In embodiments, $L^{9C}$ is independently

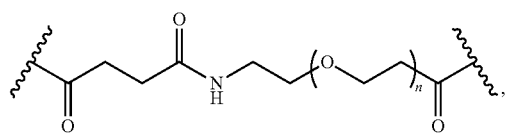

wherein n is independently an integer from 4 to 12. In embodiments, $L^{9C}$ is independently

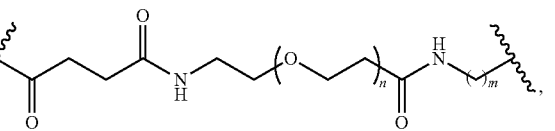

wherein n is independently an integer from 4 to 12 and m is independently an integer from 4 to 12. In embodiments, $L^{9C}$ is independently

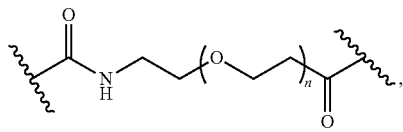

wherein n is independently an integer from 4 to 12. In embodiments, $L^{9C}$ is independently

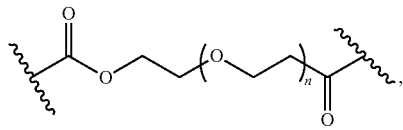

wherein n is independently an integer from 4 to 12. In embodiments, $L^{9C}$ is independently

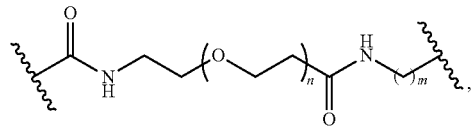

wherein n is independently an integer from 4 to 12 and m is independently an integer from 4 to 12. In embodiments, $L^{9C}$ is independently

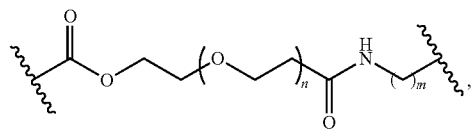

wherein n is independently an integer from 4 to 12 and m is independently an integer from 4 to 12.

In embodiments, $L^{9D}$ is independently a substituted or unsubstituted heteroalkylene. In embodiments, $L^{9D}$ is independently

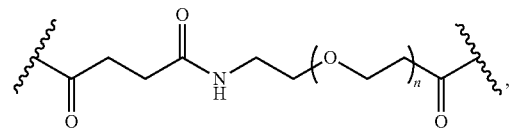

wherein n is independently an integer from 4 to 12. In embodiments, $L^{9D}$ is independently wherein n is independently an integer from 4 to 12 and m is independently an integer from 4 to 12. In embodiments, $L^{9D}$ is independently

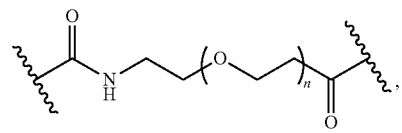

wherein n is independently an integer from 4 to 12. In embodiments, $L^{9D}$ is independently

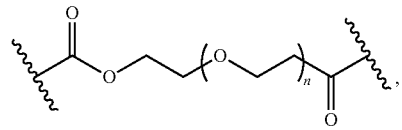

wherein n is independently an integer from 4 to 12. In embodiments, $L^{9D}$ is independently

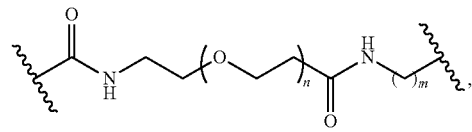

wherein n is independently an integer from 4 to 12 and m is independently an integer from 4 to 12. In embodiments, $L^{9D}$ is independently

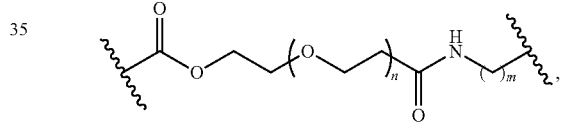

wherein n is independently an integer from 4 to 12 and m is independently an integer from 4 to 12.

In embodiments, $-L^{9C}-L^{9D}-L^{9E}-$ is independently a substituted or unsubstituted heteroalkylene. In embodiments, $-L^{9C}-L^{9D}-L^{9E}-$ is independently

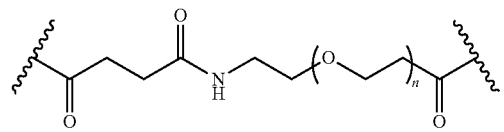

wherein n is independently an integer from 4 to 12. In embodiments, $-L^{9C}-L^{9D}-L^{9E}-$ is independently wherein n is independently an integer from 4 to 12 and m is independently an integer from 4 to 12. In embodiments, $-L^{9C}-L^{9D}-L^{9E}-$ is independently

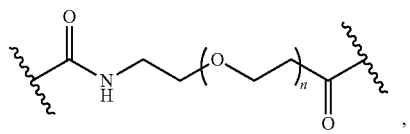

wherein n is independently an integer from 4 to 12. In embodiments, -L$^{9C}$-L$^{9D}$-L$^{9E}$- is independently

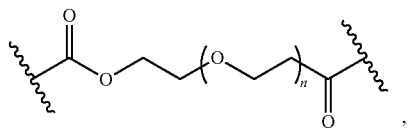

wherein n is independently an integer from 4 to 12. In embodiments, -L$^{9C}$-L$^{9D}$-L$^{9E}$- is independently

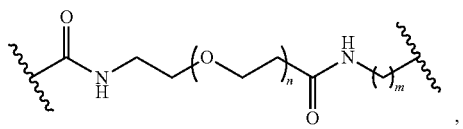

wherein n is independently an integer from 4 to 12 and m is independently an integer from 4 to 12. In embodiments, -L$^{9C}$-L$^{9D}$-L$^{9E}$- is independently

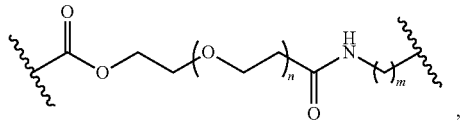

wherein n is independently an integer from 4 to 12 and m is independently an integer from 4 to 12.

In embodiments, L$^9$ is independently

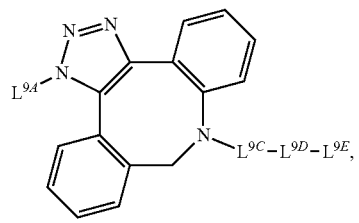

wherein L$^{9A}$, L$^{9C}$, L$^{9D}$, and L$^{9E}$ are as described herein, including in embodiments.

In embodiments, -L$^{9A}$-L$^{9B}$-L$^{9C}$- is independently

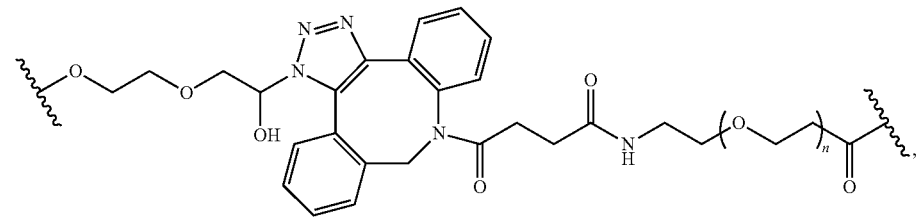

wherein n is independently an integer from 4 to 12. In embodiments, -L$^{9A}$-L$^{9B}$-L$^{9C}$- is independently

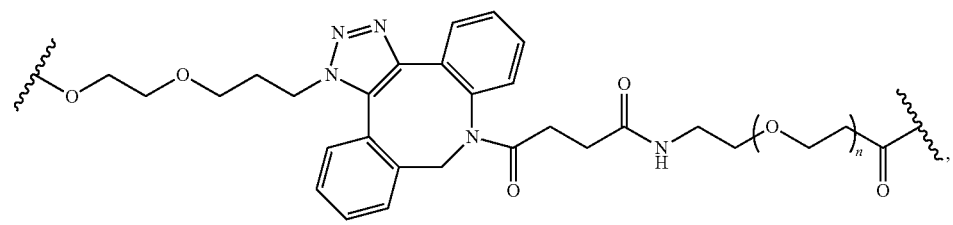

wherein n is independently an integer from 4 to 12. In embodiments, -L$^{9A}$-L$^{9B}$-L$^{9C}$- is independently

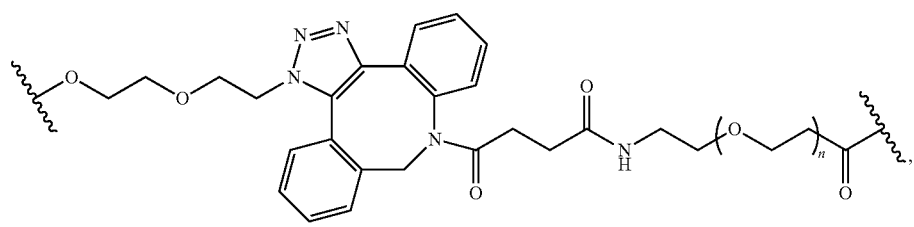

wherein n is independently an integer from 4 to 12. In embodiments, -L$^{9A}$-L$^{9B}$-L$^{9C}$- is independently

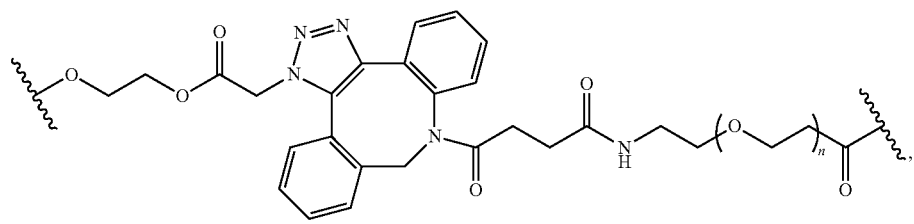

wherein n is independently an integer from 4 to 12. In embodiments, -L$^{9A}$-L$^{9B}$-L$^{9C}$- is independently

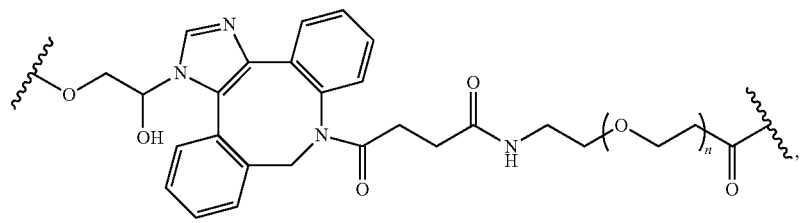

wherein n is independently an integer from 4 to 12. In embodiments, -L$^{9A}$-L$^{9B}$-L$^{9C}$- is independently

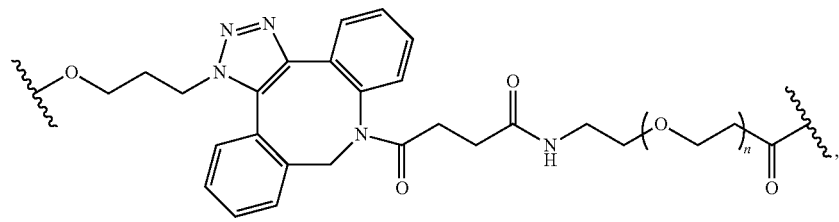

wherein n is independently an integer from 4 to 12. In embodiments, -L$^{9A}$-L$^{9B}$-L$^{9C}$- is independently

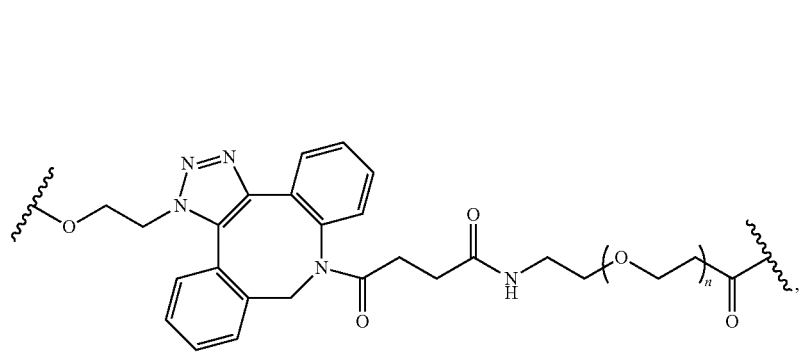

wherein n is independently an integer from 4 to 12. In embodiments, -L$^{9A}$-L$^{9B}$-L$^{9C}$- is independently

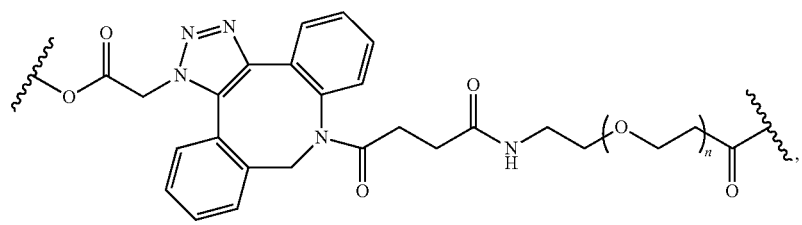

wherein n is independently an integer from 4 to 12. In embodiments, -L$^{9A}$-L$^{9B}$-L$^{9C}$- is independently

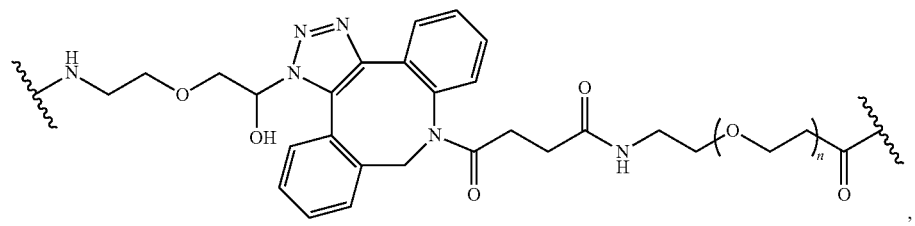

wherein n is independently an integer from 4 to 12. In embodiments, -L$^{9A}$-L$^{9B}$-L$^{9C}$- is independently

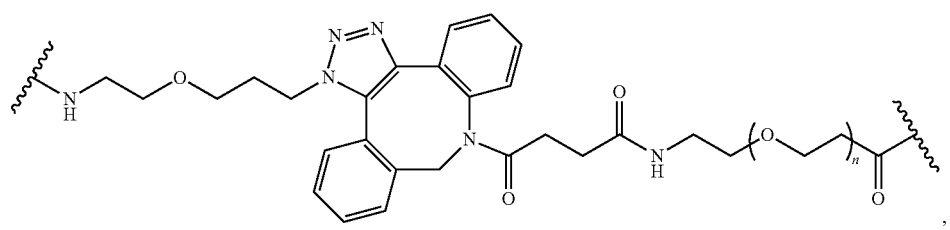

wherein n is independently an integer from 4 to 12. In embodiments, -L$^{9A}$-L$^{9B}$-L$^{9C}$- is independently

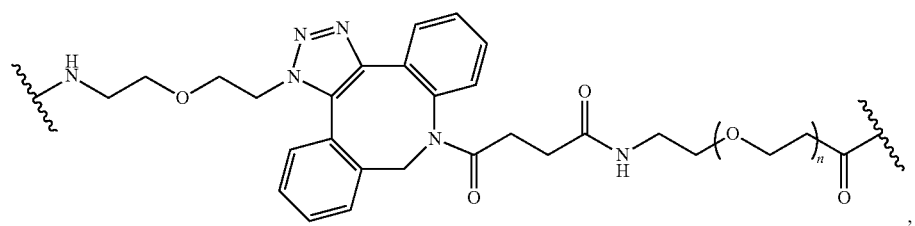

, wherein n is independently an integer from 4 to 12. In embodiments, -L$^{9A}$-L$^{9B}$-L$^{9C}$- is independently

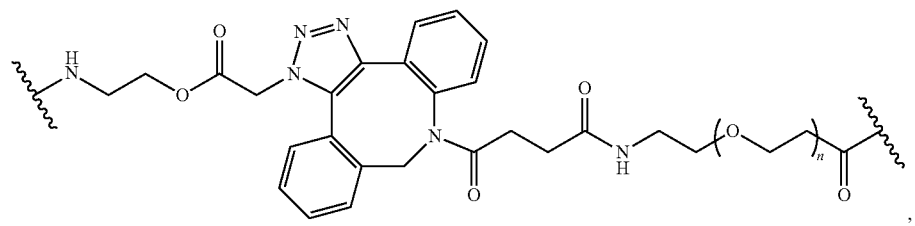

, wherein n is independently an integer from 4 to 12. In embodiments, -L$^{9A}$-L$^{9B}$-L$^{9C}$- is independently

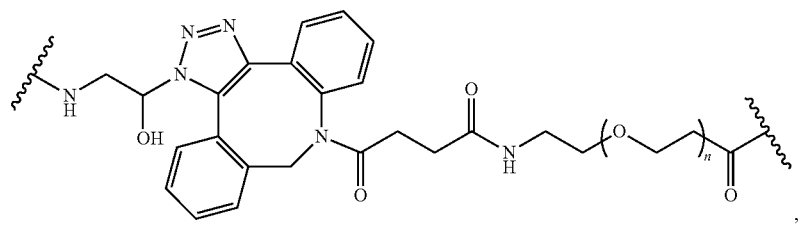

, wherein n is independently an integer from 4 to 12. In embodiments, -L$^{9A}$-L$^{9B}$-L$^{9C}$- is independently

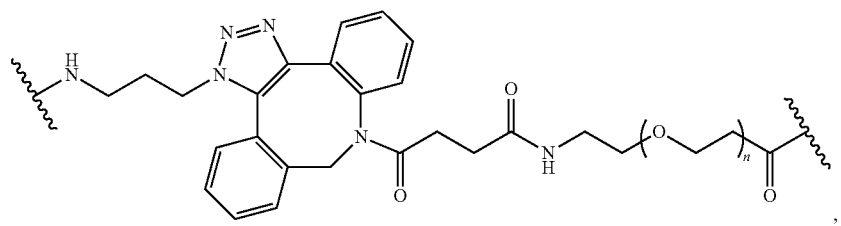

, wherein n is independently an integer from 4 to 12. In embodiments, -L$^{9A}$-L$^{9B}$-L$^{9C}$- is independently

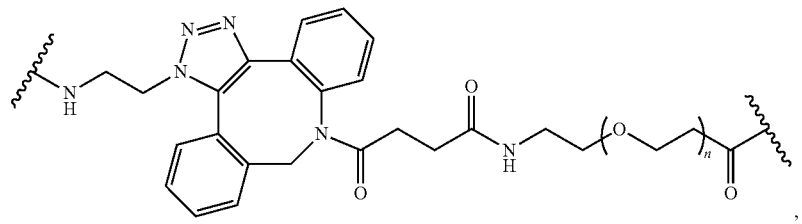

wherein n is independently an integer from 4 to 12. In embodiments, -L$^{9A}$-L$^{9B}$-L$^{9C}$- is independently

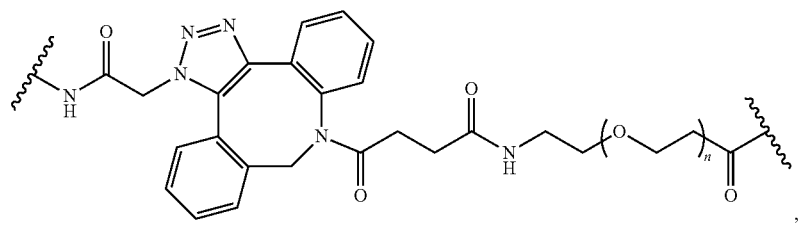

wherein n is independently an integer from 4 to 12.

In embodiments, L$^{9D}$ is independently —S—S— and L$^{9E}$ is independently an unsubstituted C$_4$-C$_8$ alkylene. In embodiments, L$^{9D}$ is independently

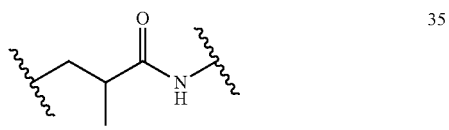

and L$^{9E}$ is independently an unsubstituted C$_4$-C$_8$ alkylene.

In embodiments, L$^9$ is independently

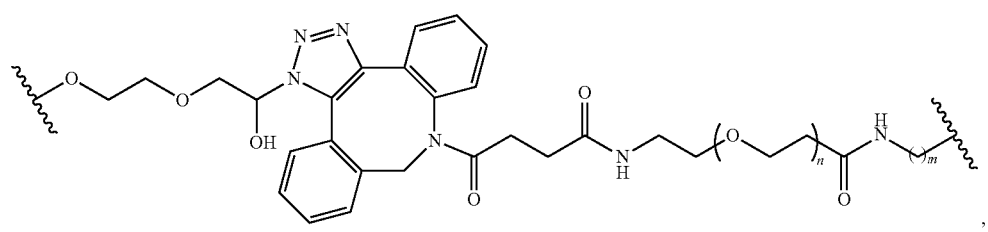

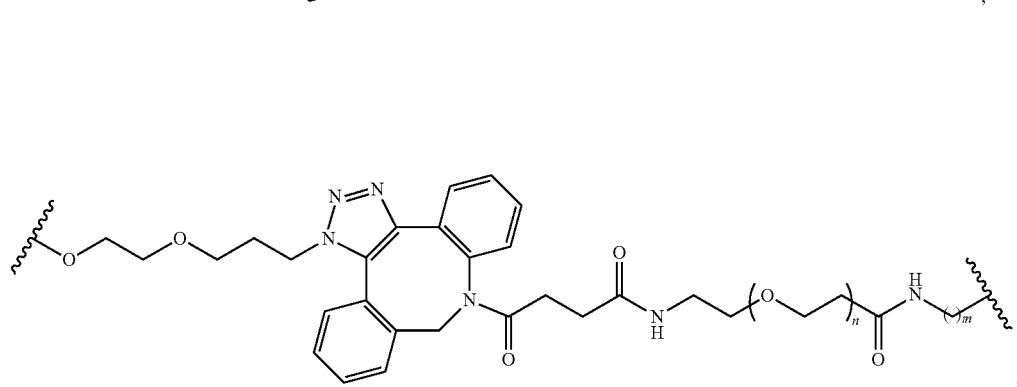

-continued
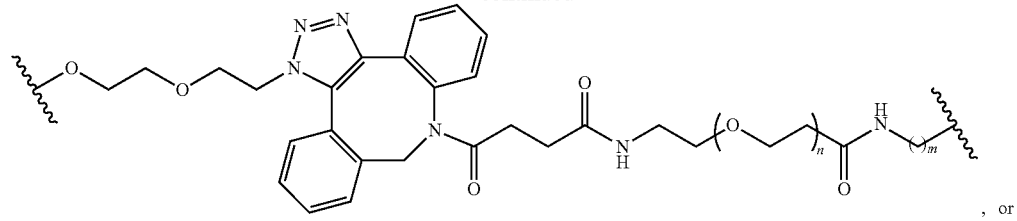
, or
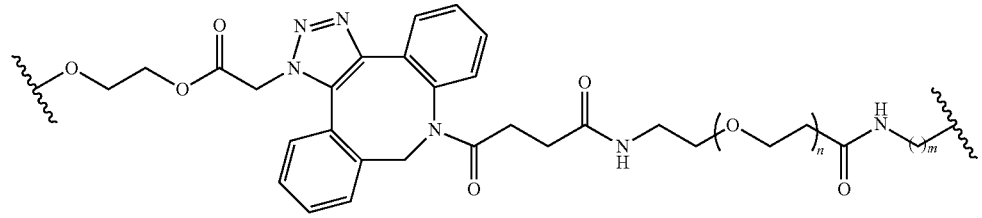
.
In embodiments, $L^9$ is independently
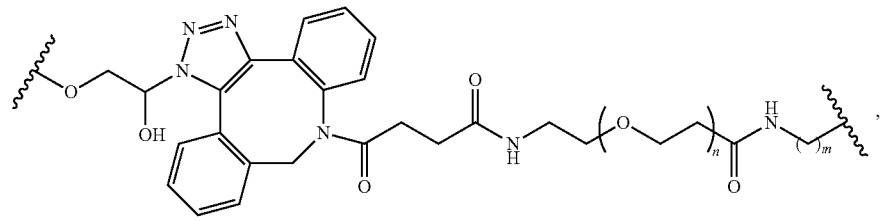
,
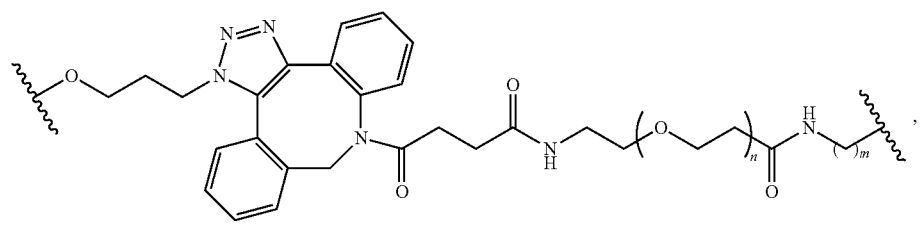
,
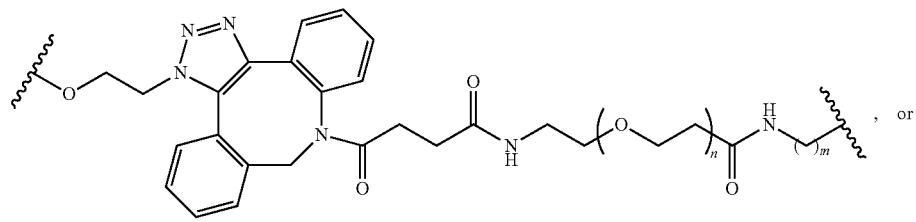
, or
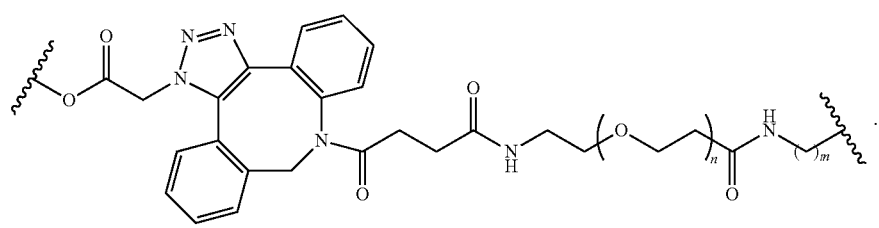
.

In embodiments, L⁹ is independently
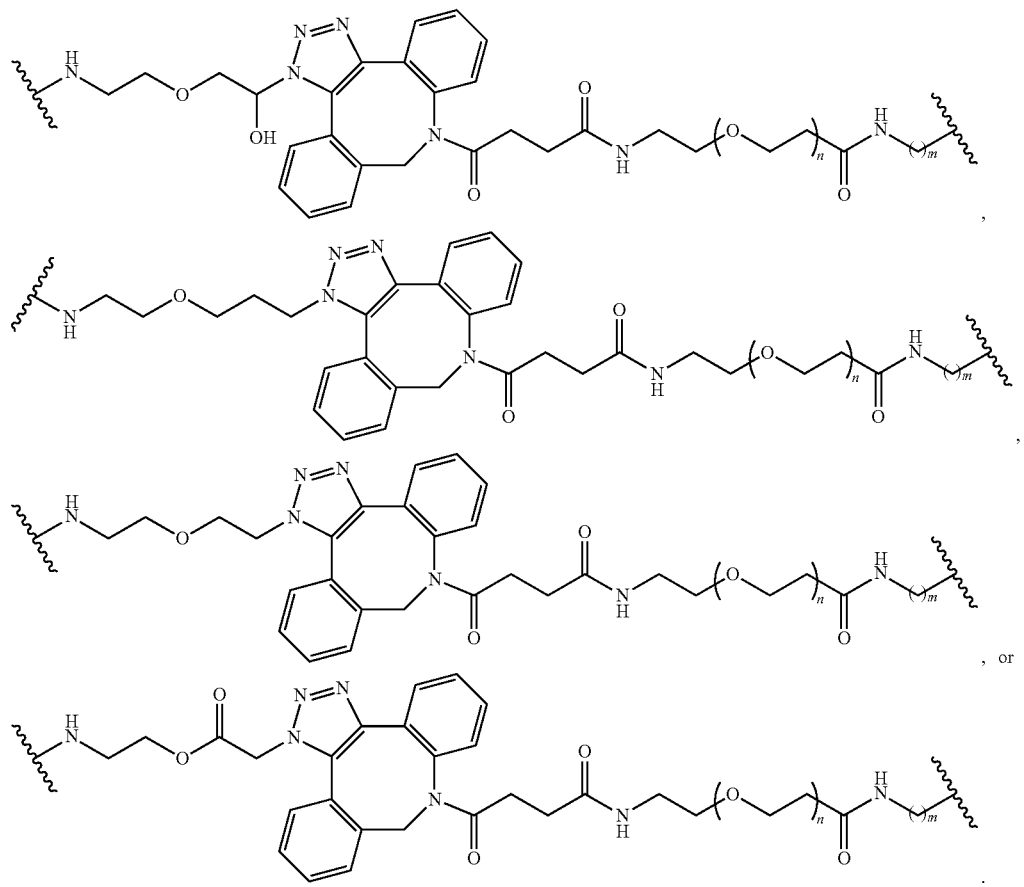
In embodiments, L⁹ is independently
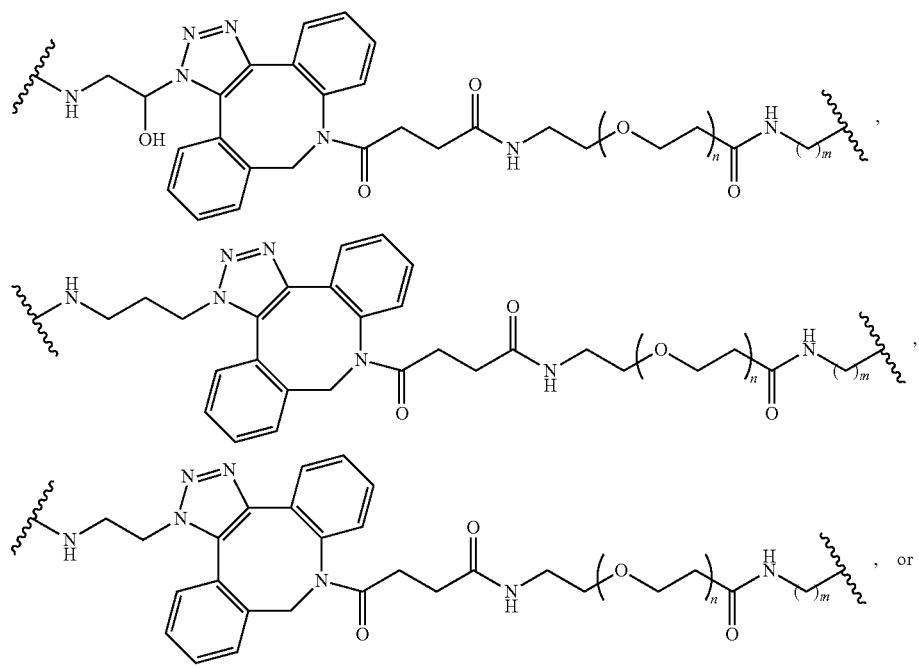

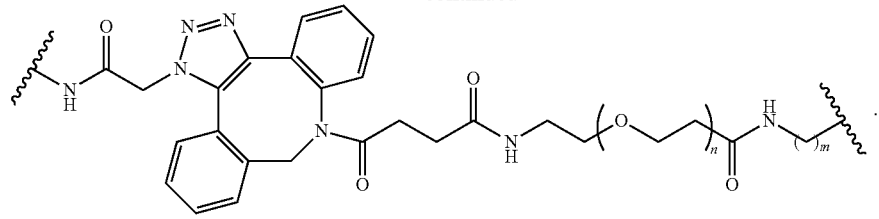

The symbol n is independently an integer from 4 to 12, and the symbol m is independently an integer from 4 to 12. In embodiments, each $L^9$ is the same.

In embodiments, $R^9$ is independently 1) an oligonucleotide moiety; or 2) a second non-reactive moiety selected from hydrogen, halogen, $-CX^9{}_3$, $-CHX^9{}_2$, $-CH_2X^9$, $-OCX^9{}_3$, $-OCH_2X^9$, $-OCHX^9{}_2$, $-CN$, $-SO_{n9}R^{9D}$, $SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, $-C(O)NR^{9A}R^{9B}$, $-OR^{9D}$, $-NR^{9A}SO_2R^{9D}$, $-NR^{9A}C(O)R^{9C}$, $-NR^{9A}C(O)OR^{9C}$, $-NR^{9A}OR^{9C}$, $-OC(O)R^{9C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). $R^{9A}$, $R^{9B}$, $R^{9C}$, and $R^{9D}$ are independently hydrogen, $-CX_3$, $-CN$, $-COOH$, $-CONH_2$, $-CHX_2$, $-CH_2X$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), substituted or unsubstituted heteroaryl (e.g., 5 to 10 membered, 5 to 9 membered, or 5 to 6 membered), a protecting group, or a leaving group; $R^{9A}$ and $R^{9B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered). X and $X^9$ are independently $-F$, $-Cl$, $-Br$, or $-I$. The symbol n9 is independently an integer from 0 to 4. The symbols m9 and v9 are each independently an integer from 1 to 2. In embodiments, $R^9$ is independently an oligonucleotide moiety. In embodiments, when $R^{22}$ and $R^9$ are each independently an oligonucleotide moiety, the $R^{22}$ and $R^9$ oligonucleotide moieties are the same. In embodiments, when $R^{22}$ and $R^9$ are each independently an oligonucleotide moiety, the $R^{22}$ and $R^9$ oligonucleotide moieties are different. In embodiments, when $R^{24}$ is a first non-reactive moiety and $R^9$ is a second non-reactive moiety, $R^{24}$ and $R^9$ are different. In embodiments, when $R^{24}$ is a first non-reactive moiety and $R^9$ is a second non-reactive moiety, $R^{24}$ and $R^9$ are the same.

In embodiments, a substituted $R^9$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group.

In embodiments, a substituted $R^{9A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9A}$ is substituted with a plurality of groups selected from substituent groups, size-limited substituent groups, and lower substituent groups; each substituent group, size-limited substituent group, and/or lower substituent group may optionally be different. In embodiments, when $R^{9A}$ is substituted, it is substituted with at least one substituent group. In embodiments, when $R^{9A}$ is substituted, it is substituted with at least one size-limited substituent group. In embodiments, when $R^{9A}$ is substituted, it is substituted with at least one lower substituent group.

In embodiments, a substituted $R^{9B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9B}$ is substituted with a plurality of groups selected from substituent groups, size-limited substituent groups, and lower substituent groups; each substituent group, size-limited substituent group, and/or lower substituent group may optionally be different. In embodiments, when $R^{9B}$ is substituted, it is substituted with at least one substituent group. In embodiments, when $R^{9B}$ is substituted, it is substituted with at least one size-limited substituent group. In embodiments, when $R^{9B}$ is substituted, it is substituted with at least one lower substituent group.

In embodiments, a substituted ring formed when $R^{9A}$ and $R^{9B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{9A}$ and $R^{9B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{9A}$ and $R^{9B}$ substituents bonded to the same nitrogen atom are joined is substituted, it is substituted with at least one substituent group. In embodiments, when the substituted ring formed when $R^{9A}$ and $R^{9B}$ substituents bonded to the same nitrogen atom are joined is substituted, it is substituted with at least one size-limited substituent group. In embodiments, when the substituted ring formed when $R^{9A}$ and $R^{9B}$ substituents bonded to the same nitrogen atom are joined is substituted, it is substituted with at least one lower substituent group.

In embodiments, a substituted $R^{9C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9C}$ is substituted with a plurality of groups selected from substituent groups, size-limited substituent groups, and lower substituent groups; each substituent group, size-limited substituent group, and/or lower substituent group may optionally be different. In embodiments, when $R^{9C}$ is substituted, it is substituted with at least one substituent group. In embodiments, when $R^{9C}$ is substituted, it is substituted with at least one size-limited substituent group. In embodiments, when $R^{9C}$ is substituted, it is substituted with at least one lower substituent group.

In embodiments, a substituted $R^{9D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{9D}$ is substituted with a plurality of groups selected from substituent groups, size-limited substituent groups, and lower substituent groups; each substituent group, size-limited substituent group, and/or lower substituent group may optionally be different. In embodiments, when $R^{9D}$ is substituted, it is substituted with at least one substituent group. In embodiments, when $R^{9D}$ is substituted, it is substituted with at least one size-limited substituent group. In embodiments, when $R^{9D}$ is substituted, it is substituted with at least one lower substituent group.

In embodiments, $R^9$ is independently a non-reactive moiety selected from halogen, $-CX^9_3$, $-CHX^9_2$, $-CH_2X^9$, $-OCX^9_3$, $-OCH_2X^9$, $-OCHX^9_2$, $-CN$, $-SO_{n9}R^{9D}$, $-SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, $-C(O)NR^{9A}R^{9B}$, $-OR^{9D}$, $-NR^{9A}SO_2R^{9D}$, $-NR^{9A}C(O)R^{9C}$, $-NR^{9A}C(O)OR^{9C}$, $-NR^{9A}OR^{9C}$, $-OC(O)R^{9C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^9$ is independently a non-reactive moiety selected from halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^9$ is independently hydrogen, $-OCH_2CH_2-(OCH_2CH_2)_p-OCH_3$ or $-N(CH_3)_2$; and p is independently an integer from 0 to 10. In embodiments, each $R^9$ is the same.

In embodiments, $-L^9-R^9$ is independently $-OCH_2CH_2-(OCH_2CH_2)_p-OCH_3$ or $-N(CH_3)_2$; and p is independently an integer from 4 to 10.

In embodiments, $R^{10}$ is independently $-CN$. In embodiments, $R^{10}$ is independently substituted or unsubstituted alkyl. In embodiments, $R^{10}$ is independently substituted or unsubstituted $C_1$-$C_4$ alkyl. In embodiments, $R^{10}$ is independently unsubstituted $C_1$-$C_4$ alkyl. In embodiments, $R^{10}$ is independently unsubstituted methyl. In embodiments, $R^{10}$ is independently unsubstituted ethyl. In embodiments, $R^{10}$ is independently unsubstituted propyl. In embodiments, $R^{10}$ is independently unsubstituted n-propyl. In embodiments, $R^{10}$ is independently unsubstituted isopropyl. In embodiments, $R^{10}$ is independently unsubstituted butyl. In embodiments, $R^{10}$ is independently unsubstituted n-butyl. In embodiments, $R^{10}$ is independently unsubstituted tert-butyl. In embodiments, $R^{10}$ is independently substituted or unsubstituted heteroalkyl. In embodiments, $R^{10}$ is independently substituted or unsubstituted 2 to 6 membered heteroalkyl. In embodiments, each $R^{10}$ is the same.

In embodiments, $L^{11}$ is independently a substituted or unsubstituted heteroalkylene. In embodiments, $L^{11A}$ is independently a bond. In embodiments, $L^{11B}$ and $L^{11D}$ are independently substituted or unsubstituted heteroalkylene; $L^{11C}$ is independently a substituted or unsubstituted heteroarylene; and $L^{11E}$ is independently a bond. In embodiments, $L^{11B}$ and $L^{11E}$ are independently substituted or unsubstituted heteroalkylene; $L^{11C}$ is independently a substituted or unsubstituted heteroarylene; and $L^{11D}$ is independently a substituted or unsubstituted arylene. In embodiments, $L^{11A}$ is independently a substituted or unsubstituted heteroalkylene.

In embodiments, $L^{11}$ is independently

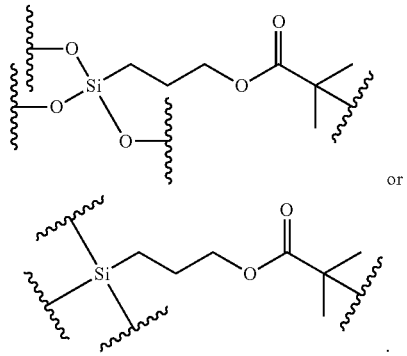

In embodiments, $L^{12}$ is independently a substituted or unsubstituted heteroalkylene. In embodiments, $L^{12B}$ and $L^{12D}$ are independently substituted or unsubstituted heteroalkylene; $L^{12D}$ is independently a substituted or unsubstituted heteroarylene; and $L^{12E}$ is independently a bond. In embodiments, $L^{2B}$ and $L^{12E}$ are independently substituted or unsubstituted heteroalkylene; $L^{12C}$ is independently a substituted or unsubstituted heteroarylene; and $L^{12D}$ is independently a substituted or unsubstituted arylene. In embodiments, $L^{12A}$ is independently a bond.

In embodiments, $L^{12}$ is independently

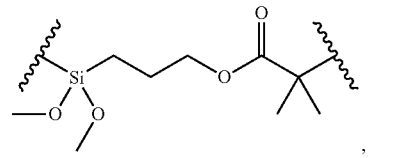

,

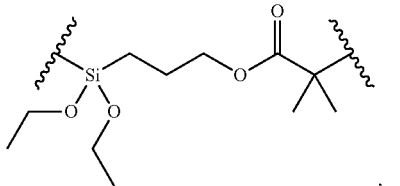

,

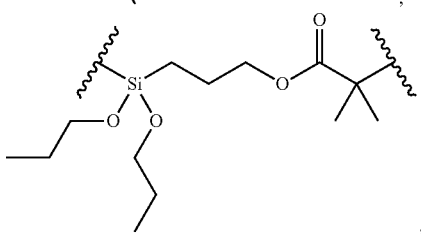

,

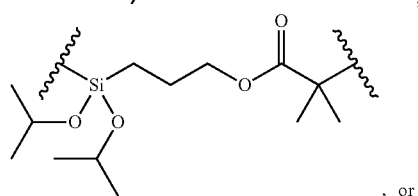

, or

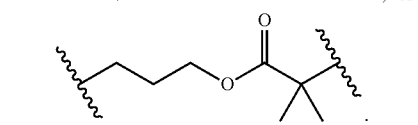

.

In embodiments, $L^{12}$ is independently

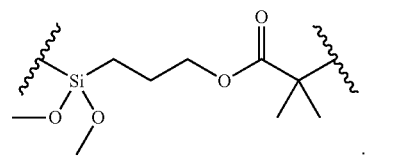 [SMILES: *C(C)(C)C(=O)OCCC[Si](*)(OC)OC]

.

In embodiments, $L^{12}$ is independently

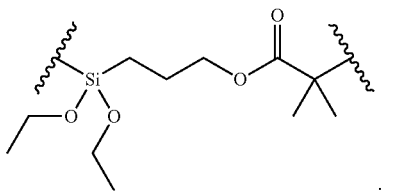 [SMILES: *C(C)(C)C(=O)OCCC[Si](*)(OCC)OCC]

.

In embodiments, $L^{12}$ is independently

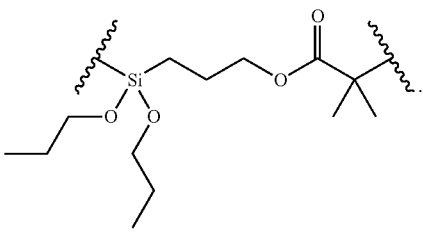 [SMILES: *C(C)(C)C(=O)OCCC[Si](*)(OCCC)OCCC]

.

In embodiments, $L^{12}$ is independently

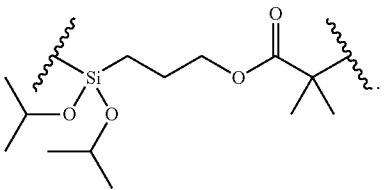 [SMILES: *C(C)(C)C(=O)OCCC[Si](*)(OC(C)C)OC(C)C]

.

In embodiments, $L^{12}$ is independently

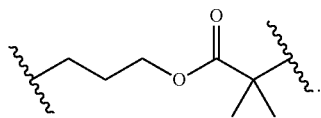 [SMILES: *CCCOC(=O)C(*)(C)C]

.

In embodiments, $L^{12}$ is independently

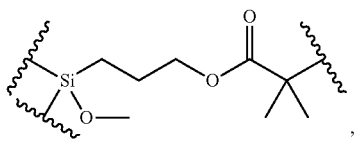

,

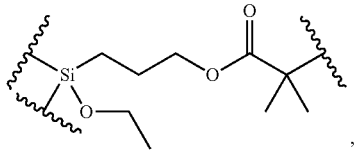

,

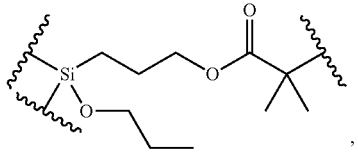

,

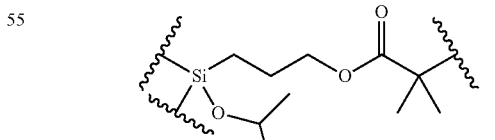

, or

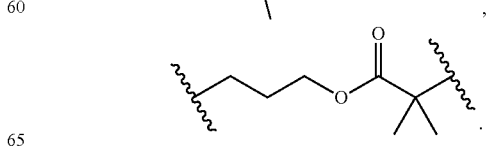

.

In embodiments, $L^{12}$ is independently

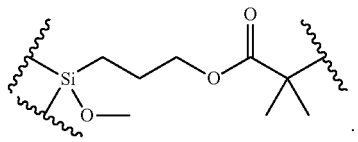 [SMILES: *C(C)(C)C(=O)OCCC[Si](*)(*)OC]

In embodiments, $L^{12}$ is independently

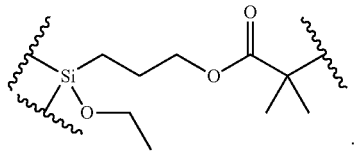 [SMILES: *C(C)(C)C(=O)OCCC[Si](*)(*)OCC]

In embodiments, $L^{12}$ is independently

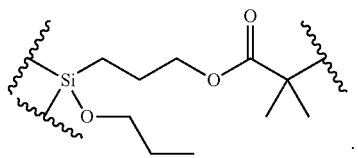 [SMILES: *C(C)(C)C(=O)OCCC[Si](*)(*)OCCC]

In embodiments, $L^{12}$ is independently

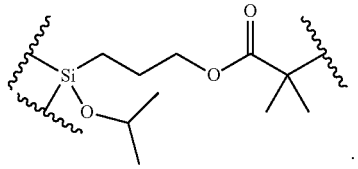 [SMILES: *C(C)(C)C(=O)OCCC[Si](*)(*)OC(C)C]

In embodiments, $L^{12}$ is independently

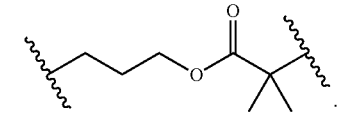 [SMILES: *CCCOC(=O)C(*)(C)C]

In embodiments, $L^{12}$ is independently

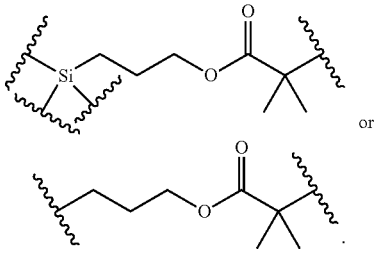

or

In embodiments, $L^{12}$ is independently

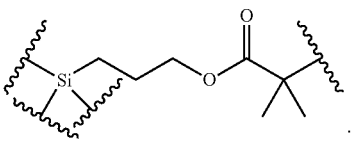 [SMILES: *C(C)(C)C(=O)OCCC[Si](*)(*)*]

In embodiments, $L^{12}$ is independently

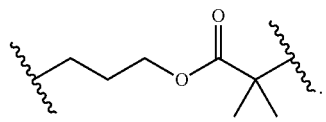 [SMILES: *CCCOC(=O)C(*)(C)C]

In embodiments, $L^{12}$ is the same.

In embodiments, $R^{12}$ and $R^{13}$ are independently hydrogen. In embodiments, $R^{12}$ is independently hydrogen. In embodiments, $R^{12}$ is independently substituted or unsubstituted $C_1$-$C_4$ alkyl. In embodiments, $R^{12}$ is independently unsubstituted $C_1$-$C_4$ alkyl. In embodiments, $R^{12}$ is independently unsubstituted methyl. In embodiments, $R^{12}$ is independently unsubstituted ethyl. In embodiments, $R^{12}$ is independently unsubstituted propyl. In embodiments, $R^{12}$ is independently unsubstituted n-propyl. In embodiments, $R^{12}$ is independently unsubstituted isopropyl. In embodiments, $R^{12}$ is independently unsubstituted butyl. In embodiments, $R^{12}$ is independently unsubstituted n-butyl. In embodiments, $R^{12}$ is independently unsubstituted tert-butyl. In embodiments, each $R^{12}$ is the same. In embodiments, $R^{13}$ is independently hydrogen. In embodiments, $R^{13}$ is independently substituted or unsubstituted $C_1$-$C_4$ alkyl. In embodiments, $R^{13}$ is independently unsubstituted $C_1$-$C_4$ alkyl. In embodiments, $R^{13}$ is independently unsubstituted methyl. In embodiments, $R^{13}$ is independently unsubstituted ethyl. In embodiments, $R^{13}$ is independently unsubstituted propyl. In embodiments, $R^{13}$ is independently unsubstituted n-propyl. In embodiments, $R^{13}$ is independently unsubstituted isopropyl. In embodiments, $R^{13}$ is independently unsubstituted butyl. In embodiments, $R^{13}$ is independently unsubstituted n-butyl. In embodiments, $R^{13}$ is independently unsubstituted tert-butyl. In embodiments, each $R^{13}$ is the same.

In embodiments, $R^{14}$ is independently halogen. In embodiments, $R^{14}$ is independently —Br. In embodiments, $R^{14}$ is independently —OH. In embodiments, $R^{14}$ is independently substituted or unsubstituted alkyl. In embodiments, $R^{14}$ is independently substituted or unsubstituted $C_1$-$C_4$ alkyl. In embodiments, $R^{14}$ is independently unsubstituted $C_1$-$C_4$ alkyl. In embodiments, $R^{14}$ is independently unsubstituted methyl. In embodiments, $R^{14}$ is independently unsubstituted ethyl. In embodiments, $R^{14}$ is independently unsubstituted propyl. In embodiments, $R^{14}$ is independently unsubstituted n-propyl. In embodiments, $R^{14}$ is independently unsubstituted isopropyl. In embodiments, $R^{14}$ is independently unsubstituted butyl. In embodiments, $R^{14}$ is independently unsubstituted n-butyl. In embodiments, $R^{14}$ is independently unsubstituted tert-butyl. In embodiments, $R^{14}$ is independently substituted or unsubstituted heteroalkyl. In embodiments, $R^{14}$ is independently substituted or unsubstituted 2 to 6 membered heteroalkyl. In embodiments, $R^{14}$ is independently substituted or unsubstituted $C_1$-$C_4$ alkyl. In embodiments, $R^{14}$ is independently —O-(unsubstituted $C_1$-$C_4$ alkyl). In embodiments, $R^{14}$ is independently unsubstituted methoxy. In embodiments, $R^{14}$ is independently unsubstituted ethoxy. In embodiments, $R^{14}$ is independently unsubstituted propoxy. In embodiments, $R^{14}$ is independently unsubstituted n-propoxy. In embodiments, $R^{14}$ is independently unsubstituted isopropoxy. In embodiments, $R^{14}$ is independently unsubstituted butoxy. In embodiments, $R^{14}$ is independently unsubstituted n-butoxy. In embodiments, $R^{14}$ is independently unsubstituted tert-butoxy. In embodiments, $R^{14}$ is independently —C(CH$_3$)$_2$CN. In embodiments, $R^{14}$ is independently —CH$_2$CN. In embodiments, $R^{14}$ is independently —CH$_2$Ph. In embodiments, $R^{14}$ is independently

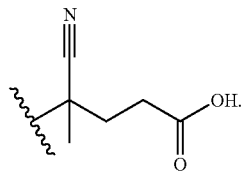 [SMILES: *C(C)(C#N)CCC(=O)O]

In embodiments, $R^{14}$ is independently

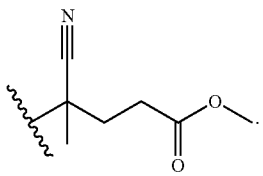 [SMILES: *C(C)(C#N)CCC(=O)OC]

In embodiments, $R^{14}$ is independently

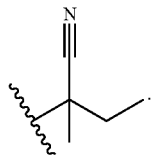

In embodiments, $R^{14}$ is independently

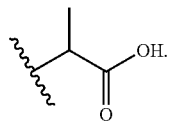 [SMILES: *C(C)C(=O)O]

In embodiments, $R^{14}$ is independently

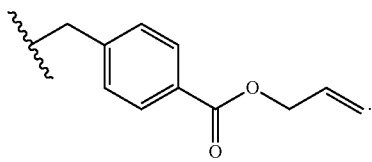 [SMILES: *Cc1ccc(C(=O)OCC=C)cc1]

In embodiments, $R^{14}$ is independently

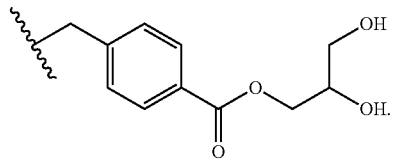 [SMILES: *Cc1ccc(C(=O)OCC(O)CO)cc1]

In embodiments, $R^{14}$ is independently

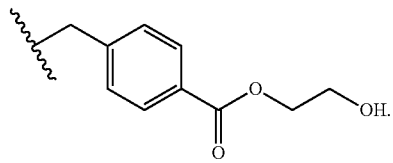 [SMILES: *Cc1ccc(C(=O)OCCO)cc1]

In embodiments, each $R^{14}$ is the same.

In embodiments, $R^{15}$ is independently —CN. In embodiments, $R^{15}$ is independently substituted or unsubstituted alkyl. In embodiments, $R^{15}$ is independently substituted or unsubstituted $C_1$-$C_4$ alkyl. In embodiments, $R^{15}$ is independently unsubstituted $C_1$-$C_4$ alkyl. In embodiments, $R^{15}$ is independently unsubstituted methyl. In embodiments, $R^{15}$ is independently unsubstituted ethyl. In embodiments, $R^{15}$ is independently unsubstituted propyl. In embodiments, $R^{15}$ is independently unsubstituted n-propyl. In embodiments, $R^{15}$ is independently unsubstituted isopropyl. In embodiments, $R^{15}$ is independently unsubstituted butyl. In embodiments, $R^{15}$ is independently unsubstituted n-butyl. In embodiments, $R^{15}$ is independently unsubstituted tert-butyl. In embodiments, $R^{15}$ is independently substituted or unsubstituted heteroalkyl. In embodiments, $R^{15}$ is independently substituted or unsubstituted 2 to 6 membered heteroalkyl. In embodiments, each $R^{15}$ is the same.

In embodiments, $L^{16}$ is independently substituted or unsubstituted heteroalkylene. In embodiments, $L^{16B}$ and $L^{16D}$ are independently substituted or unsubstituted heteroalkylene; $L^{16C}$ is independently a substituted or unsubstituted heteroarylene; and $L^{16E}$ is independently a bond. In embodiments, $L^{16B}$ and $L^{16E}$ are independently substituted or unsubstituted heteroalkylene; $L^{16C}$ is independently a substituted or unsubstituted heteroarylene; and $L^{16D}$ is independently a substituted or unsubstituted arylene. In embodiments, $L^{16A}$ is independently a bond. In embodiments, each $L^{16}$ is the same.

In embodiments, $R^{16}$ is independently a non-reactive moiety selected from hydrogen, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{16}$ is independently a non-reactive moiety selected from hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{16}$ is independently hydrogen, —OCH$_2$CH$_2$—(OCH$_2$CH$_2$)$_p$—OCH$_3$ or —N(CH$_3$)$_2$; and p is an integer from 0 to 10. In embodiments, p is an integer from 1 to 10. In embodiments, each $R^{16}$ is the same.

In embodiments, when $R^{24}$ is a first non-reactive moiety, $R^9$ is a second non-reactive moiety, and $R^{16}$ is a third non-reactive moiety, $R^{24}$, $R^9$, and $R^{16}$ are different. In embodiments, when $R^{24}$ is a first non-reactive moiety, $R^9$ is a second non-reactive moiety, and $R^{16}$ is a third non-reactive moiety, $R^{24}$, $R^9$, and $R^{16}$ are the same. In embodiments, when $R^{24}$ is a non-reactive moiety and $R^{16}$ is a non-reactive moiety, $R^{24}$ and $R^{16}$ are different. In embodiments, when $R^{24}$ is a non-reactive moiety and $R^{16}$ is a non-reactive moiety, $R^{24}$ and $R^{16}$ are the same.

In embodiments, -L$^{16}$-R$^{16}$ is independently —OCH$_2$CH$_2$—(OCH$_2$CH$_2$)$_p$—OCH$_3$ or —N(CH$_3$)$_2$; and p is an integer from 4 to 10. In embodiments, $R^{17}$ and $R^{18}$ are independently hydrogen.

In embodiments, $R^{17}$ is independently hydrogen. In embodiments, $R^{17}$ is independently substituted or unsubstituted $C_1$-$C_4$ alkyl. In embodiments, $R^{17}$ is independently unsubstituted $C_1$-$C_4$ alkyl. In embodiments, $R^{17}$ is independently unsubstituted methyl. In embodiments, $R^{17}$ is independently unsubstituted ethyl. In embodiments, $R^{17}$ is independently unsubstituted propyl. In embodiments, $R^{17}$ is independently unsubstituted n-propyl. In embodiments, $R^{17}$ is independently unsubstituted isopropyl. In embodiments, $R^{17}$ is independently unsubstituted butyl. In embodiments, $R^{17}$ is independently unsubstituted n-butyl. In embodiments, $R^{17}$ is independently unsubstituted tert-butyl. In embodiments, each $R^{17}$ is the same. In embodiments, $R^{18}$ is independently hydrogen. In embodiments, $R^{18}$ is independently substituted or unsubstituted $C_1$-$C_4$ alkyl. In embodiments, $R^{18}$ is independently unsubstituted $C_1$-$C_4$ alkyl. In embodiments, $R^{18}$ is independently unsubstituted methyl. In embodiments, $R^{18}$ is independently unsubstituted ethyl. In embodiments, $R^{18}$ is independently unsubstituted propyl. In embodiments, $R^{18}$ is independently unsubstituted n-propyl. In embodiments, $R^{18}$ is independently unsubstituted isopropyl. In embodiments, $R^{18}$ is independently unsubstituted butyl. In embodiments, $R^{18}$ is independently unsubstituted n-butyl. In embodiments, $R^{18}$ is independently unsubstituted tert-butyl. In embodiments, each $R^{18}$ is the same. In embodiments, $R^{19}$ is independently halogen. In embodiments, $R^{19}$ is independently —Br. In embodiments, $R^{19}$ is independently —OH. In embodiments, $R^{19}$ is independently substituted or unsubstituted alkyl. In embodiments, $R^{19}$ is independently substituted or unsubstituted $C_1$-$C_4$ alkyl. In embodiments, $R^{19}$ is independently unsubstituted $C_1$-$C_4$ alkyl. In embodiments, $R^{19}$ is independently unsubstituted methyl. In embodiments, $R^{19}$ is independently unsubstituted ethyl. In embodiments, $R^{19}$ is independently unsubstituted propyl. In embodiments, $R^{19}$ is independently unsubstituted n-propyl. In embodiments, $R^{19}$ is independently unsubstituted isopropyl. In embodiments, $R^{19}$ is independently unsubstituted butyl. In embodiments, $R^{19}$ is independently unsubstituted n-butyl. In embodiments, $R^{19}$ is independently unsubstituted tert-butyl. In embodiments, $R^{19}$ is independently substituted or unsubstituted heteroalkyl. In embodiments, $R^{19}$ is independently substituted or unsubstituted 2 to 6 membered heteroalkyl. In embodiments, $R^{19}$ is independently substituted or unsubstituted $C_1$-$C_4$ alkyl. In embodiments, $R^{19}$ is independently —O-(unsubstituted $C_1$-$C_4$ alkyl). In embodiments, $R^{19}$ is independently unsubstituted methoxy. In embodiments, $R^{19}$ is independently unsubstituted ethoxy. In embodiments, $R^{19}$ is independently unsubstituted propoxy. In embodiments, $R^{19}$ is independently unsubstituted n-propoxy. In embodiments, $R^{19}$ is independently unsubstituted isopropoxy. In embodiments, $R^{19}$ is independently unsubstituted butoxy. In embodiments, $R^{19}$ is independently unsubstituted n-butoxy. In embodiments, $R^{19}$ is independently unsubstituted tert-butoxy. In embodiments, $R^{19}$ is independently —C(CH$_3$)$_2$CN. In embodiments, $R^{19}$ is independently —CH$_2$CN. In embodiments, $R^{19}$ is independently —CH$_2$Ph. In embodiments, $R^{19}$ is independently

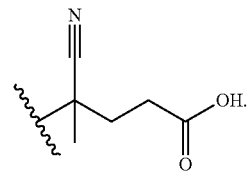 [SMILES: *C(C)(C#N)CCC(=O)O]

In embodiments, $R^{19}$ is independently

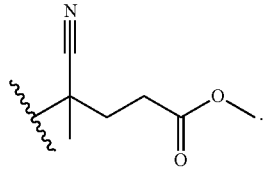 [SMILES: *C(C)(C#N)CCC(=O)OC]

In embodiments, $R^{19}$ is independently

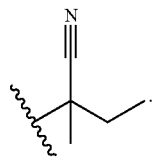 [SMILES: *C(C)(C#N)CC]

In embodiments, $R^{19}$ is independently

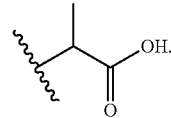 [SMILES: *C(C)C(=O)O]

In embodiments, R$^{19}$ is independently

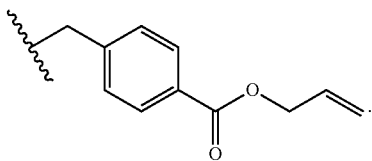 [SMILES: *Cc1ccc(C(=O)OCC=C)cc1]

In embodiments, R$^{19}$ is independently

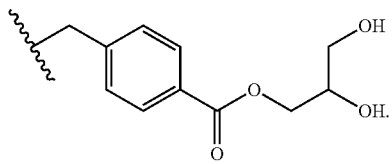 [SMILES: *Cc1ccc(C(=O)OCC(O)CO)cc1]

In embodiments, R$^{19}$ is independently

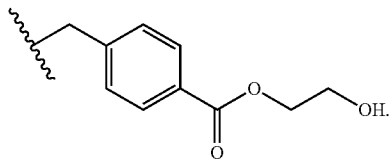 [SMILES: *Cc1ccc(C(=O)OCCO)cc1]

In embodiments, each R$^{19}$ is the same.

In embodiments, z1a is independently an integer from 0 to 10. In embodiments, z1a is independently an integer from 0 to 20. In embodiments, z1a is independently an integer from 0 to 30. In embodiments, z1a is independently an integer from 0 to 40. In embodiments, z1a is independently an integer from 0 to 50. In embodiments, z1a is independently an integer from 0 to 60. In embodiments, z1a is independently an integer from 0 to 70. In embodiments, z1a is independently an integer from 0 to 80. In embodiments, z1a is independently an integer from 0 to 90. In embodiments, z1a is independently an integer from 0 to 100. In embodiments, z1a is independently an integer from 0 to 150. In embodiments, z1a is independently an integer from 0 to 200. In embodiments, z1a is independently an integer from 0 to 250. In embodiments, z1a is independently an integer from 0 to 300. In embodiments, z1a is independently an integer from 0 to 350. In embodiments, z1a is independently an integer from 0 to 400. In embodiments, z1a is independently an integer from 0 to 450. In embodiments, z1a is independently an integer from 0 to 500. In embodiments, z1a is independently an integer from 0 to 550. In embodiments, z1a is independently an integer from 0 to 600. In embodiments, z1a is independently an integer from 0 to 650. In embodiments, z1a is independently an integer from 0 to 700. In embodiments, z1a is independently an integer from 0 to 750. In embodiments, z1a is independently an integer from 0 to 800. In embodiments, z1a is independently an integer from 0 to 850. In embodiments, z1a is independently an integer from 0 to 900. In embodiments, z1a is independently an integer from 0 to 950. In embodiments, z1a is independently an integer from 0 to 1000. In embodiments, z1a is independently an integer from 0 to 1500. In embodiments, z1a is independently an integer from 0 to 2000. In embodiments, z1a is independently an integer from 0 to 2500. In embodiments, z1a is independently an integer from 0 to 3000. In embodiments, z1a is independently an integer from 0 to 3500. In embodiments, z1a is independently an integer from 0 to 4000. In embodiments, z1a is independently an integer from 0 to 4500. In embodiments, z1a is independently an integer from 0 to 5000. In embodiments, z1a is independently an integer from 1 to 10. In embodiments, z1a is independently an integer from 1 to 20. In embodiments, z1a is independently an integer from 1 to 30. In embodiments, z1a is independently an integer from 1 to 40. In embodiments, z1a is independently an integer from 1 to 50. In embodiments, z1a is independently an integer from 1 to 60. In embodiments, z1a is independently an integer from 1 to 70. In embodiments, z1a is independently an integer from 1 to 80. In embodiments, z1a is independently an integer from 1 to 90. In embodiments, z1a is independently an integer from 1 to 100. In embodiments, z1a is independently an integer from 1 to 150. In embodiments, z1a is independently an integer from 1 to 200. In embodiments, z1a is independently an integer from 1 to 250. In embodiments, z1a is independently an integer from 1 to 300. In embodiments, z1a is independently an integer from 1 to 350. In embodiments, z1a is independently an integer from 1 to 400. In embodiments, z1a is independently an integer from 1 to 450. In embodiments, z1a is independently an integer from 1 to 500. In embodiments, z1a is independently an integer from 1 to 550. In embodiments, z1a is independently an integer from 1 to 600. In embodiments, z1a is independently an integer from 1 to 650. In embodiments, z1a is independently an integer from 1 to 700. In embodiments, z1a is independently an integer from 1 to 750. In embodiments, z1a is independently an integer from 1 to 800. In embodiments, z1a is independently an integer from 1 to 850. In embodiments, z1a is independently an integer from 1 to 900. In embodiments, z1a is independently an integer from 1 to 950. In embodiments, z1a is independently an integer from 1 to 1000. In embodiments, z1a is independently an integer from 1 to 1500. In embodiments, z1a is independently an integer from 1 to 2000. In embodiments, z1a is independently an integer from 1 to 2500. In embodiments, z1a is independently an integer from 1 to 3000. In embodiments, z1a is independently an integer from 1 to 3500. In embodiments, z1a is independently an integer from 1 to 4000. In embodiments, z1a is independently an integer from 1 to 4500. In embodiments, z1a is independently an integer from 1 to 5000. In embodiments, z1b is independently an integer from 0 to 10. In embodiments, z1b is independently an integer from 0 to 20. In embodiments, z1b is independently an integer from 0 to 30. In embodiments, z1b is independently an integer from 0 to 40. In embodiments, z1b is independently an integer from 0 to 50. In embodiments, z1b is independently an integer from 0 to 60. In embodiments, z1b is independently an integer from 0 to 70. In embodiments, z1b is independently an integer from 0 to 80. In embodiments, z1b is independently an integer from 0 to 90. In embodiments, z1b is independently an integer from 0 to 100. In embodiments, z1b is independently an integer from 0 to 150. In embodiments, z1b is independently an integer from 0 to 200. In embodiments, z1b is independently an integer from 0 to 250. In embodiments, z1b is independently an integer from 0 to 300. In embodiments, z1b is independently an integer from 0 to 350. In embodiments, z1b is independently an integer from 0 to 400. In embodiments, z1b is independently an integer from 0 to 450. In embodiments, z1b is independently an integer from 0 to 500. In embodiments, z1b is independently an integer from 0 to 550. In embodiments, z1b is independently an integer from 0 to 600. In embodiments, $z1b$ is independently an integer from 0 to 650. In embodiments, $z1b$ is independently an integer from 0 to 700. In embodiments, $z1b$ is independently an integer from 0 to 750. In embodiments, $z1b$ is independently an integer from 0 to 800. In embodiments, $z1b$ is independently an integer from 0 to 850. In embodiments, $z1b$ is independently an integer from 0 to 900. In embodiments, $z1b$ is independently an integer from 0 to 950. In embodiments, $z1b$ is independently an integer from 0 to 1000. In embodiments, $z1b$ is independently an integer from 0 to 1500. In embodiments, $z1b$ is independently an integer from 0 to 2000. In embodiments, $z1b$ is independently an integer from 0 to 2500. In embodiments, $z1b$ is independently an integer from 0 to 3000. In embodiments, $z1b$ is independently an integer from 0 to 3500. In embodiments, $z1b$ is independently an integer from 0 to 4000. In embodiments, $z1b$ is independently an integer from 0 to 4500. In embodiments, $z1b$ is independently an integer from 0 to 5000. In embodiments, $z1b$ is independently an integer from 1 to 10. In embodiments, $z1b$ is independently an integer from 1 to 20. In embodiments, $z1b$ is independently an integer from 1 to 30. In embodiments, $z1b$ is independently an integer from 1 to 40. In embodiments, $z1b$ is independently an integer from 1 to 50. In embodiments, $z1b$ is independently an integer from 1 to 60. In embodiments, $z1b$ is independently an integer from 1 to 70. In embodiments, $z1b$ is independently an integer from 1 to 80. In embodiments, $z1b$ is independently an integer from 1 to 90. In embodiments, $z1b$ is independently an integer from 1 to 100. In embodiments, $z1b$ is independently an integer from 1 to 150. In embodiments, $z1b$ is independently an integer from 1 to 200. In embodiments, $z1b$ is independently an integer from 1 to 250. In embodiments, $z1b$ is independently an integer from 1 to 300. In embodiments, $z1b$ is independently an integer from 1 to 350. In embodiments, $z1b$ is independently an integer from 1 to 400. In embodiments, $z1b$ is independently an integer from 1 to 450. In embodiments, $z1b$ is independently an integer from 1 to 500. In embodiments, $z1b$ is independently an integer from 1 to 550. In embodiments, $z1b$ is independently an integer from 1 to 600. In embodiments, $z1b$ is independently an integer from 1 to 650. In embodiments, $z1b$ is independently an integer from 1 to 700. In embodiments, $z1b$ is independently an integer from 1 to 750. In embodiments, $z1b$ is independently an integer from 1 to 800. In embodiments, $z1b$ is independently an integer from 1 to 850. In embodiments, $z1b$ is independently an integer from 1 to 900. In embodiments, $z1b$ is independently an integer from 1 to 950. In embodiments, $z1b$ is independently an integer from 1 to 1000. In embodiments, $z1b$ is independently an integer from 1 to 1500. In embodiments, $z1b$ is independently an integer from 1 to 2000. In embodiments, $z1b$ is independently an integer from 1 to 2500. In embodiments, $z1b$ is independently an integer from 1 to 3000. In embodiments, $z1b$ is independently an integer from 1 to 3500. In embodiments, $z1b$ is independently an integer from 1 to 4000. In embodiments, $z1b$ is independently an integer from 1 to 4500. In embodiments, $z1b$ is independently an integer from 1 to 5000. In embodiments, $z1c$ is independently an integer from 0 to 10. In embodiments, $z1c$ is independently an integer from 0 to 20. In embodiments, $z1c$ is independently an integer from 0 to 30. In embodiments, $z1c$ is independently an integer from 0 to 40. In embodiments, $z1c$ is independently an integer from 0 to 50. In embodiments, $z1c$ is independently an integer from 0 to 60. In embodiments, $z1c$ is independently an integer from 0 to 70. In embodiments, $z1c$ is independently an integer from 0 to 80. In embodiments, $z1c$ is independently an integer from 0 to 90. In embodiments, $z1c$ is independently an integer from 0 to 100. In embodiments, $z1c$ is independently an integer from 0 to 150. In embodiments, $z1c$ is independently an integer from 0 to 200. In embodiments, $z1c$ is independently an integer from 0 to 250. In embodiments, $z1c$ is independently an integer from 0 to 300. In embodiments, $z1c$ is independently an integer from 0 to 350. In embodiments, $z1c$ is independently an integer from 0 to 400. In embodiments, $z1c$ is independently an integer from 0 to 450. In embodiments, $z1c$ is independently an integer from 0 to 500. In embodiments, $z1c$ is independently an integer from 0 to 550. In embodiments, $z1c$ is independently an integer from 0 to 600. In embodiments, $z1c$ is independently an integer from 0 to 650. In embodiments, $z1c$ is independently an integer from 0 to 700. In embodiments, $z1c$ is independently an integer from 0 to 750. In embodiments, $z1c$ is independently an integer from 0 to 800. In embodiments, $z1c$ is independently an integer from 0 to 850. In embodiments, $z1c$ is independently an integer from 0 to 900. In embodiments, $z1c$ is independently an integer from 0 to 950. In embodiments, $z1c$ is independently an integer from 0 to 1000. In embodiments, $z1c$ is independently an integer from 0 to 1500. In embodiments, $z1c$ is independently an integer from 0 to 2000. In embodiments, $z1c$ is independently an integer from 0 to 2500. In embodiments, $z1c$ is independently an integer from 0 to 3000. In embodiments, $z1c$ is independently an integer from 0 to 3500. In embodiments, $z1c$ is independently an integer from 0 to 4000. In embodiments, $z1c$ is independently an integer from 0 to 4500. In embodiments, $z1c$ is independently an integer from 0 to 5000. In embodiments, $z1c$ is independently an integer from 1 to 10. In embodiments, $z1c$ is independently an integer from 1 to 20. In embodiments, $z1c$ is independently an integer from 1 to 30. In embodiments, $z1c$ is independently an integer from 1 to 40. In embodiments, $z1c$ is independently an integer from 1 to 50. In embodiments, $z1c$ is independently an integer from 1 to 60. In embodiments, $z1c$ is independently an integer from 1 to 70. In embodiments, $z1c$ is independently an integer from 1 to 80. In embodiments, $z1c$ is independently an integer from 1 to 90. In embodiments, $z1c$ is independently an integer from 1 to 100. In embodiments, $z1c$ is independently an integer from 1 to 150. In embodiments, $z1c$ is independently an integer from 1 to 200. In embodiments, $z1c$ is independently an integer from 1 to 250. In embodiments, $z1c$ is independently an integer from 1 to 300. In embodiments, $z1c$ is independently an integer from 1 to 350. In embodiments, $z1c$ is independently an integer from 1 to 400. In embodiments, $z1c$ is independently an integer from 1 to 450. In embodiments, $z1c$ is independently an integer from 1 to 500. In embodiments, $z1c$ is independently an integer from 1 to 550. In embodiments, $z1c$ is independently an integer from 1 to 600. In embodiments, $z1c$ is independently an integer from 1 to 650. In embodiments, $z1c$ is independently an integer from 1 to 700. In embodiments, $z1c$ is independently an integer from 1 to 750. In embodiments, $z1c$ is independently an integer from 1 to 800. In embodiments, $z1c$ is independently an integer from 1 to 850. In embodiments, $z1c$ is independently an integer from 1 to 900. In embodiments, $z1c$ is independently an integer from 1 to 950. In embodiments, $z1c$ is independently an integer from 1 to 1000. In embodiments, $z1c$ is independently an integer from 1 to 1500. In embodiments, $z1c$ is independently an integer from 1 to 2000. In embodiments, $z1c$ is independently an integer from 1 to 2500. In embodiments, $z1c$ is independently an integer from 1 to 3000. In embodiments, $z1c$ is independently an integer from 1 to 3500. In embodiments, z1c is independently an integer from 1 to 4000. In embodiments, z1c is independently an integer from 1 to 4500. In embodiments, z1c is independently an integer from 1 to 5000. In embodiments, z1d is independently an integer from 0 to 10. In embodiments, z1d is independently an integer from 0 to 20. In embodiments, z1d is independently an integer from 0 to 30. In embodiments, z1d is independently an integer from 0 to 40. In embodiments, z1d is independently an integer from 0 to 50. In embodiments, z1d is independently an integer from 0 to 60. In embodiments, z1d is independently an integer from 0 to 70. In embodiments, z1d is independently an integer from 0 to 80. In embodiments, z1d is independently an integer from 0 to 90. In embodiments, z1d is independently an integer from 0 to 100. In embodiments, z1d is independently an integer from 0 to 150. In embodiments, z1d is independently an integer from 0 to 200. In embodiments, z1d is independently an integer from 0 to 250. In embodiments, z1d is independently an integer from 0 to 300. In embodiments, z1d is independently an integer from 0 to 350. In embodiments, z1d is independently an integer from 0 to 400. In embodiments, z1d is independently an integer from 0 to 450. In embodiments, z1d is independently an integer from 0 to 500. In embodiments, z1d is independently an integer from 0 to 550. In embodiments, z1d is independently an integer from 0 to 600. In embodiments, z1d is independently an integer from 0 to 650. In embodiments, z1d is independently an integer from 0 to 700. In embodiments, z1d is independently an integer from 0 to 750. In embodiments, z1d is independently an integer from 0 to 800. In embodiments, z1d is independently an integer from 0 to 850. In embodiments, z1d is independently an integer from 0 to 900. In embodiments, z1d is independently an integer from 0 to 950. In embodiments, z1d is independently an integer from 0 to 1000. In embodiments, z1d is independently an integer from 0 to 1500. In embodiments, z1d is independently an integer from 0 to 2000. In embodiments, z1d is independently an integer from 0 to 2500. In embodiments, z1d is independently an integer from 0 to 3000. In embodiments, z1d is independently an integer from 0 to 3500. In embodiments, z1d is independently an integer from 0 to 4000. In embodiments, z1d is independently an integer from 0 to 4500. In embodiments, z1d is independently an integer from 0 to 5000. In embodiments, z1d is independently an integer from 1 to 10. In embodiments, z1d is independently an integer from 1 to 20. In embodiments, z1d is independently an integer from 1 to 30. In embodiments, z1d is independently an integer from 1 to 40. In embodiments, z1d is independently an integer from 1 to 50. In embodiments, z1d is independently an integer from 1 to 60. In embodiments, z1d is independently an integer from 1 to 70. In embodiments, z1d is independently an integer from 1 to 80. In embodiments, z1d is independently an integer from 1 to 90. In embodiments, z1d is independently an integer from 1 to 100. In embodiments, z1d is independently an integer from 1 to 150. In embodiments, z1d is independently an integer from 1 to 200. In embodiments, z1d is independently an integer from 1 to 250. In embodiments, z1d is independently an integer from 1 to 300. In embodiments, z1d is independently an integer from 1 to 350. In embodiments, z1d is independently an integer from 1 to 400. In embodiments, z1d is independently an integer from 1 to 450. In embodiments, z1d is independently an integer from 1 to 500. In embodiments, z1d is independently an integer from 1 to 550. In embodiments, z1d is independently an integer from 1 to 600. In embodiments, z1d is independently an integer from 1 to 650. In embodiments, z1d is independently an integer from 1 to 700. In embodiments, z1d is independently an integer from 1 to 750. In embodiments, z1d is independently an integer from 1 to 800. In embodiments, z1d is independently an integer from 1 to 850. In embodiments, z1d is independently an integer from 1 to 900. In embodiments, z1d is independently an integer from 1 to 950. In embodiments, z1d is independently an integer from 1 to 1000. In embodiments, z1d is independently an integer from 1 to 1500. In embodiments, z1d is independently an integer from 1 to 2000. In embodiments, z1d is independently an integer from 1 to 2500. In embodiments, z1d is independently an integer from 1 to 3000. In embodiments, z1d is independently an integer from 1 to 3500. In embodiments, z1d is independently an integer from 1 to 4000. In embodiments, z1d is independently an integer from 1 to 4500. In embodiments, z1d is independently an integer from 1 to 5000. In embodiments, z2 is independently an integer from 0 to 10. In embodiments, z2 is independently an integer from 0 to 20. In embodiments, z2 is independently an integer from 0 to 30. In embodiments, z2 is independently an integer from 0 to 40. In embodiments, z2 is independently an integer from 0 to 50. In embodiments, z2 is independently an integer from 0 to 60. In embodiments, z2 is independently an integer from 0 to 70. In embodiments, z2 is independently an integer from 0 to 80. In embodiments, z2 is independently an integer from 0 to 90. In embodiments, z2 is independently an integer from 0 to 100. In embodiments, z2 is independently an integer from 0 to 150. In embodiments, z2 is independently an integer from 0 to 200. In embodiments, z2 is independently an integer from 0 to 250. In embodiments, z2 is independently an integer from 0 to 300. In embodiments, z2 is independently an integer from 0 to 350. In embodiments, z2 is independently an integer from 0 to 400. In embodiments, z2 is independently an integer from 0 to 450. In embodiments, z2 is independently an integer from 0 to 500. In embodiments, z2 is independently an integer from 0 to 550. In embodiments, z2 is independently an integer from 0 to 600. In embodiments, z2 is independently an integer from 0 to 650. In embodiments, z2 is independently an integer from 0 to 700. In embodiments, z2 is independently an integer from 0 to 750. In embodiments, z2 is independently an integer from 0 to 800. In embodiments, z2 is independently an integer from 0 to 850. In embodiments, z2 is independently an integer from 0 to 900. In embodiments, z2 is independently an integer from 0 to 950. In embodiments, z2 is independently an integer from 0 to 1000. In embodiments, z2 is independently an integer from 0 to 1500. In embodiments, z2 is independently an integer from 0 to 2000. In embodiments, z2 is independently an integer from 0 to 2500. In embodiments, z2 is independently an integer from 0 to 3000. In embodiments, z2 is independently an integer from 0 to 3500. In embodiments, z2 is independently an integer from 0 to 4000. In embodiments, z2 is independently an integer from 0 to 4500. In embodiments, z2 is independently an integer from 0 to 5000. In embodiments, z2 is independently an integer from 1 to 10. In embodiments, z2 is independently an integer from 1 to 20. In embodiments, z2 is independently an integer from 1 to 30. In embodiments, z2 is independently an integer from 1 to 40. In embodiments, z2 is independently an integer from 1 to 50. In embodiments, z2 is independently an integer from 1 to 60. In embodiments, z2 is independently an integer from 1 to 70. In embodiments, z2 is independently an integer from 1 to 80. In embodiments, z2 is independently an integer from 1 to 90. In embodiments, z2 is independently an integer from 1 to 100. In embodiments, z2 is independently an integer from 1 to 150. In embodiments, z2 is independently an integer from 1 to 200. In embodiments, z2 is independently an integer from 1 to 250. In embodiments, $z2$ is independently an integer from 1 to 300. In embodiments, $z2$ is independently an integer from 1 to 350. In embodiments, $z2$ is independently an integer from 1 to 400. In embodiments, $z2$ is independently an integer from 1 to 450. In embodiments, $z2$ is independently an integer from 1 to 500. In embodiments, $z2$ is independently an integer from 1 to 550. In embodiments, $z2$ is independently an integer from 1 to 600. In embodiments, $z2$ is independently an integer from 1 to 650. In embodiments, $z2$ is independently an integer from 1 to 700. In embodiments, $z2$ is independently an integer from 1 to 750. In embodiments, $z2$ is independently an integer from 1 to 800. In embodiments, $z2$ is independently an integer from 1 to 850. In embodiments, $z2$ is independently an integer from 1 to 900. In embodiments, $z2$ is independently an integer from 1 to 950. In embodiments, $z2$ is independently an integer from 1 to 1000. In embodiments, $z2$ is independently an integer from 1 to 1500. In embodiments, $z2$ is independently an integer from 1 to 2000. In embodiments, $z2$ is independently an integer from 1 to 2500. In embodiments, $z2$ is independently an integer from 1 to 3000. In embodiments, $z2$ is independently an integer from 1 to 3500. In embodiments, $z2$ is independently an integer from 1 to 4000. In embodiments, $z2$ is independently an integer from 1 to 4500. In embodiments, $z2$ is independently an integer from 1 to 5000. In embodiments, $z3$ is independently an integer from 0 to 10. In embodiments, $z3$ is independently an integer from 0 to 20. In embodiments, $z3$ is independently an integer from 0 to 30. In embodiments, $z3$ is independently an integer from 0 to 40. In embodiments, $z3$ is independently an integer from 0 to 50. In embodiments, $z3$ is independently an integer from 0 to 60. In embodiments, $z3$ is independently an integer from 0 to 70. In embodiments, $z3$ is independently an integer from 0 to 80. In embodiments, $z3$ is independently an integer from 0 to 90. In embodiments, $z3$ is independently an integer from 0 to 100. In embodiments, $z3$ is independently an integer from 0 to 150. In embodiments, $z3$ is independently an integer from 0 to 200. In embodiments, $z3$ is independently an integer from 0 to 250. In embodiments, $z3$ is independently an integer from 0 to 300. In embodiments, $z3$ is independently an integer from 0 to 350. In embodiments, $z3$ is independently an integer from 0 to 400. In embodiments, $z3$ is independently an integer from 0 to 450. In embodiments, $z3$ is independently an integer from 0 to 500. In embodiments, $z3$ is independently an integer from 0 to 550. In embodiments, $z3$ is independently an integer from 0 to 600. In embodiments, $z3$ is independently an integer from 0 to 650. In embodiments, $z3$ is independently an integer from 0 to 700. In embodiments, $z3$ is independently an integer from 0 to 750. In embodiments, $z3$ is independently an integer from 0 to 800. In embodiments, $z3$ is independently an integer from 0 to 850. In embodiments, $z3$ is independently an integer from 0 to 900. In embodiments, $z3$ is independently an integer from 0 to 950. In embodiments, $z3$ is independently an integer from 0 to 1000. In embodiments, $z3$ is independently an integer from 0 to 1500. In embodiments, $z3$ is independently an integer from 0 to 2000. In embodiments, $z3$ is independently an integer from 0 to 2500. In embodiments, $z3$ is independently an integer from 0 to 3000. In embodiments, $z3$ is independently an integer from 0 to 3500. In embodiments, $z3$ is independently an integer from 0 to 4000. In embodiments, $z3$ is independently an integer from 0 to 4500. In embodiments, $z3$ is independently an integer from 0 to 5000. In embodiments, $z3$ is independently an integer from 1 to 10. In embodiments, $z3$ is independently an integer from 1 to 20. In embodiments, $z3$ is independently an integer from 1 to 30. In embodiments, $z3$ is independently an integer from 1 to 40. In embodiments, $z3$ is independently an integer from 1 to 50. In embodiments, $z3$ is independently an integer from 1 to 60. In embodiments, $z3$ is independently an integer from 1 to 70. In embodiments, $z3$ is independently an integer from 1 to 80. In embodiments, $z3$ is independently an integer from 1 to 90. In embodiments, $z3$ is independently an integer from 1 to 100. In embodiments, $z3$ is independently an integer from 1 to 150. In embodiments, $z3$ is independently an integer from 1 to 200. In embodiments, $z3$ is independently an integer from 1 to 250. In embodiments, $z3$ is independently an integer from 1 to 300. In embodiments, $z3$ is independently an integer from 1 to 350. In embodiments, $z3$ is independently an integer from 1 to 400. In embodiments, $z3$ is independently an integer from 1 to 450. In embodiments, $z3$ is independently an integer from 1 to 500. In embodiments, $z3$ is independently an integer from 1 to 550. In embodiments, $z3$ is independently an integer from 1 to 600. In embodiments, $z3$ is independently an integer from 1 to 650. In embodiments, $z3$ is independently an integer from 1 to 700. In embodiments, $z3$ is independently an integer from 1 to 750. In embodiments, $z3$ is independently an integer from 1 to 800. In embodiments, $z3$ is independently an integer from 1 to 850. In embodiments, $z3$ is independently an integer from 1 to 900. In embodiments, $z3$ is independently an integer from 1 to 950. In embodiments, $z3$ is independently an integer from 1 to 1000. In embodiments, $z3$ is independently an integer from 1 to 1500. In embodiments, $z3$ is independently an integer from 1 to 2000. In embodiments, $z3$ is independently an integer from 1 to 2500. In embodiments, $z3$ is independently an integer from 1 to 3000. In embodiments, $z3$ is independently an integer from 1 to 3500. In embodiments, $z3$ is independently an integer from 1 to 4000. In embodiments, $z3$ is independently an integer from 1 to 4500. In embodiments, $z3$ is independently an integer from 1 to 5000. In embodiments, $z4$ is independently an integer from 0 to 10. In embodiments, $z4$ is independently an integer from 0 to 20. In embodiments, $z4$ is independently an integer from 0 to 30. In embodiments, $z4$ is independently an integer from 0 to 40. In embodiments, $z4$ is independently an integer from 0 to 50. In embodiments, $z4$ is independently an integer from 0 to 60. In embodiments, $z4$ is independently an integer from 0 to 70. In embodiments, $z4$ is independently an integer from 0 to 80. In embodiments, $z4$ is independently an integer from 0 to 90. In embodiments, $z4$ is independently an integer from 0 to 100. In embodiments, $z4$ is independently an integer from 0 to 150. In embodiments, $z4$ is independently an integer from 0 to 200. In embodiments, $z4$ is independently an integer from 0 to 250. In embodiments, $z4$ is independently an integer from 0 to 300. In embodiments, $z4$ is independently an integer from 0 to 350. In embodiments, $z4$ is independently an integer from 0 to 400. In embodiments, $z4$ is independently an integer from 0 to 450. In embodiments, $z4$ is independently an integer from 0 to 500. In embodiments, $z4$ is independently an integer from 0 to 550. In embodiments, $z4$ is independently an integer from 0 to 600. In embodiments, $z4$ is independently an integer from 0 to 650. In embodiments, $z4$ is independently an integer from 0 to 700. In embodiments, $z4$ is independently an integer from 0 to 750. In embodiments, $z4$ is independently an integer from 0 to 800. In embodiments, $z4$ is independently an integer from 0 to 850. In embodiments, $z4$ is independently an integer from 0 to 900. In embodiments, $z4$ is independently an integer from 0 to 950. In embodiments, $z4$ is independently an integer from 0 to 1000. In embodiments, $z4$ is independently an integer from 0 to 1500. In embodiments, $z4$ is independently an integer from 0 to 2000. In embodiments, z4 is independently an integer from 0 to 2500. In embodiments, z4 is independently an integer from 0 to 3000. In embodiments, z4 is independently an integer from 0 to 3500. In embodiments, z4 is independently an integer from 0 to 4000. In embodiments, z4 is independently an integer from 0 to 4500. In embodiments, z4 is independently an integer from 0 to 5000. In embodiments, z4 is independently an integer from 1 to 10. In embodiments, z4 is independently an integer from 1 to 20. In embodiments, z4 is independently an integer from 1 to 30. In embodiments, z4 is independently an integer from 1 to 40. In embodiments, z4 is independently an integer from 1 to 50. In embodiments, z4 is independently an integer from 1 to 60. In embodiments, z4 is independently an integer from 1 to 70. In embodiments, z4 is independently an integer from 1 to 80. In embodiments, z4 is independently an integer from 1 to 90. In embodiments, z4 is independently an integer from 1 to 100. In embodiments, z4 is independently an integer from 1 to 150. In embodiments, z4 is independently an integer from 1 to 200. In embodiments, z4 is independently an integer from 1 to 250. In embodiments, z4 is independently an integer from 1 to 300. In embodiments, z4 is independently an integer from 1 to 350. In embodiments, z4 is independently an integer from 1 to 400. In embodiments, z4 is independently an integer from 1 to 450. In embodiments, z4 is independently an integer from 1 to 500. In embodiments, z4 is independently an integer from 1 to 550. In embodiments, z4 is independently an integer from 1 to 600. In embodiments, z4 is independently an integer from 1 to 650. In embodiments, z4 is independently an integer from 1 to 700. In embodiments, z4 is independently an integer from 1 to 750. In embodiments, z4 is independently an integer from 1 to 800. In embodiments, z4 is independently an integer from 1 to 850. In embodiments, z4 is independently an integer from 1 to 900. In embodiments, z4 is independently an integer from 1 to 950. In embodiments, z4 is independently an integer from 1 to 1000. In embodiments, z4 is independently an integer from 1 to 1500. In embodiments, z4 is independently an integer from 1 to 2000. In embodiments, z4 is independently an integer from 1 to 2500. In embodiments, z4 is independently an integer from 1 to 3000. In embodiments, z4 is independently an integer from 1 to 3500. In embodiments, z4 is independently an integer from 1 to 4000. In embodiments, z4 is independently an integer from 1 to 4500. In embodiments, z4 is independently an integer from 1 to 5000.

In some embodiments, each of the plurality of bioconjugate reactive moieties include an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In some embodiments, each of the plurality of bioconjugate reactive moieties include an amine moiety, azide moiety, dibenzocyclooctyne (DBCO) moiety, epoxy moiety, or isocyanate moiety. In embodiments, each of the plurality of bioconjugate reactive moieties include an amine moiety, azide moiety, alkyne moiety, dibenzocyclooctyne (DBCO) moiety, epoxy moiety, or isocyanate moiety. In embodiments, the bioconjugate reactive moiety is an azido moiety. In embodiments, the first bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the second bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the first and the second bioconjugate reactive moieties are different. In embodiments, the first and the second bioconjugate reactive moieties are reactive with each other (e.g., an azide moiety and an DBCO moiety) to form a bioconjugate linker.

In embodiments, the particle polymer includes a copolymer of two or more of the following polymerizable monomers, wherein at least one of the polymerizable monomers includes a bioconjugate reactive moiety: polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), and/or isocyanatoethyl methacrylate (IEM).

In embodiments, the oligonucleotide moiety (alternatively referred to herein as primer or polynucleotide primer) is covalently attached to the polymer. In embodiments, the 5' end of the oligonucleotide moiety contains a functional group that is tethered to the polymer (i.e., the particle shell polymer or the polymeric particle). Non-limiting examples of covalent attachment include amine-modified oligonucleotide moieties reacting with epoxy or isothiocyanate groups on the polymer, succinylated oligonucleotide moieties reacting with aminophenyl or aminopropyl functional groups on the polymer, dibenzocycloctyne-modified oligonucleotide moieties reacting with azide functional groups on the particle polymer (or vice versa), trans-cyclooctyne-modified oligonucleotide moieties reacting with tetrazine or methyl tetrazine groups on the polymer (or vice versa), disulfide modified oligonucleotide moieties reacting with mercaptofunctional groups on the polymer, amine-functionalized oligonucleotide moieties reacting with carboxylic acid groups on the polymer via 1-ethyl-3-(3-dimethylaminopropyl)-carbodiimide hydrochloride (EDC) chemistry, thiol-modified oligonucleotide moieties attaching to a polymer via a disulfide bond or maleimide linkage, alkyne-modified oligonucleotide moieties attaching to a polymer via copper-catalyzed click reactions to azide functional groups on the polymer, and acrydite-modified oligonucleotide moieties polymerizing with free acrylic acid monomers on the polymer to form polyacrylamide or reacting with thiol groups on the polymer. In embodiments, the oligonucleotide moiety is attached to the polymer through electrostatic binding. For example, the negatively charged phosphate backbone of the primer may be bound electrostatically to positively charged monomers in the polymer.

In embodiments, each particle includes multiple copies of one or more oligonucleotide moieties. In embodiments, each particle includes multiple copies oligonucleotide moieties having the same sequence. In embodiments, the one or more oligonucleotide moieties include at least two different primers attached to the polymer (e.g., a forward and a reverse primer), each of which may be present in multiple copies. In embodiments, about or at most at most about 50%, 40%, 30%, 25%, 20%, 15%, 10%, 5%, or less of the monomers in the polymer of each particle are attached to a copy of the oligonucleotide moiety. In embodiments, about 1-25%, about 2-20%, about 3-15%, about 4-14%, or about 5-12% of the monomers in the polymer of each particle are attached to a copy of the oligonucleotide moiety, or a number or a range between any two of these values. In embodiments, about 5-10% of the monomers in the polymer of each particle are attached to a copy of the oligonucleotide moiety. In embodiments, two different oligonucleotide moieties are attached to the particle (e.g., a forward and a reverse primer), which facilitates generating multiple amplification products from the first extension product or a complement thereof.

In embodiments, each of the particles include oligonucleotide moieties substantially identical to all the particles in the array. In embodiments, each of the particles include at least two species of oligonucleotide moieties that are substantially identical to all the particles in the array. In embodiments, each of the particles comprise substantially the same oligonucleotide moieties (e.g., a first population of oligonucleotide moieties and a second population of oligonucleotide moieties). In embodiments, each of the particles comprise at least two species of substantially the same oligonucleotide moieties (i.e., the same sequences). In embodiments, each particle includes a plurality of P7 or P5 nucleic acid sequences or complementary sequences thereof (i.e., P5' or P7'). The P5 and P7 adapter sequences are described in U.S. Patent Publication No. 2011/0059865 A1, which is incorporated herein by reference in its entirety. The terms P5 and P7 may be used when referring to amplification primers, e.g., universal primers. The terms P5' (P5 prime) and P7' (P7 prime) refer to the complement of P5 and P7, respectively. In embodiments, each particle includes a first plurality of a platform primer sequence and a second plurality of a differing platform primer sequence. In embodiments, the platform primer sequence is used during amplification reactions (e.g., solid phase amplification). In embodiments, each particle includes oligonucleotide moieties capable of annealing to an adapter of a library nucleic acid molecule. The term "library" merely refers to a collection or plurality of template nucleic acid molecules which share common sequences at their 5' ends (e.g., the first end) and common sequences at their 3' ends (e.g., the second end). The term "adapter" as used herein refers to any linear oligonucleotide that can be ligated to a nucleic acid molecule, thereby generating nucleic acid products that can be sequenced on a sequencing platform (e.g., an Illumina or Singular Genomics' G4™ sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In embodiments, each of the particles include at least two populations of substantially the same oligonucleotide moieties.

In some embodiments, the oligonucleotide moiety is about 5 to about 50 nucleotides in length. In some embodiments, the oligonucleotide moiety is about 5 to about 40 nucleotides in length. In some embodiments, the oligonucleotide moiety is about 10 to about 45 nucleotides in length. In some embodiments, the oligonucleotide moiety is about 15 to about 40 nucleotides in length. In some embodiments, the oligonucleotide moiety is about 20 to about 35 nucleotides in length. In some embodiments, the oligonucleotide moiety is about 20 to about 30 nucleotides in length. In some embodiments, the oligonucleotide moiety is about 25 to about 30 nucleotides in length. In embodiments, the oligonucleotide moiety is about 25 to about 35 nucleotides in length. In embodiments, the oligonucleotide moiety is about 30 to about 50 nucleotides in length. In embodiments, the oligonucleotide moiety is about 30 to about 75 nucleotides in length. In embodiments, the oligonucleotide moiety is about 50 to about 150 nucleotides in length. In embodiments, the oligonucleotide moiety is about 75 to about 200 nucleotides in length. In embodiments, the oligonucleotide moiety is a capture oligonucleotide, wherein the oligonucleotide is capable of hybridizing to a common sequence in a library of nucleic acid molecules. In embodiments, the oligonucleotide is capable of hybridizing to a common sequence (e.g., a sequence described in U.S. Patent Publication 2016/0256846, which is incorporated herein by reference, for example SEQ ID NO: 3, SEQ ID NO: 4, SEQ ID NO: 5, or SEQ ID NO: 11 of U.S. Patent Publication 2016/0256846).

In embodiments, the oligonucleotide moiety includes spacer nucleotides. Including spacer nucleotides in the linker puts the target polynucleotide in an environment having a greater resemblance to free solution. This can be beneficial, for example, in enzyme-mediated reactions such as sequencing-by-synthesis. It is believed that such reactions suffer less steric hindrance issues that can occur when the polynucleotide is directly attached to the particle or is attached through a very short linker (e.g., a linker comprising about 1 to 3 carbon atoms). Spacer nucleotides form part of the oligonucleotide moiety but do not participate in any reaction carried out on or with the oligonucleotide (e.g., a hybridization or amplification reaction). In embodiments, the spacer nucleotides include 1 to 20 nucleotides. In embodiments, the linker includes 10 spacer nucleotides. In embodiments, the linker includes 12 spacer nucleotides. In embodiments, the linker includes 15 spacer nucleotides. It is preferred to use polyT spacers, although other nucleotides and combinations thereof can be used. In embodiments, the linker includes 10, 11, 12, 13, 14, or 15 T spacer nucleotides.

In embodiments, the linker includes 12 T spacer nucleotides. Spacer nucleotides are typically included at the 5' ends of oligonucleotide which are attached to the particle. Attachment can be achieved via a phosphorothioate present at the 5' end of the oligonucleotide, an azide moiety, a dibenzocyclooctyne (DBCO) moiety, or any other bioconjugate reactive moiety (e.g., a bioconjugate moiety as described herein). The linker may be a carbon-containing chain such as those of formula —$(CH_2)n$- wherein "n" is from 1 to about 1000. However, a variety of other linkers may be used so long as the linkers are stable under conditions used in DNA sequencing. In embodiments, the linker includes polyethylene glycol (PEG) having a general formula of —$(CH_2$—$CH_2$—$O)m$-, wherein m is from about 1 to 500.

In embodiments, the linker, or the oligonucleotides (e.g., primers) include a cleavable site. A cleavage site is a site which allows controlled cleavage of the immobilized polynucleotide strand (e.g., the linker, the primer, or the polynucleotide) by chemical, enzymatic or photochemical means. Any suitable enzymatic, chemical, or photochemical cleavage reaction may be used to cleave the cleavage site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage; generation of an abasic site and subsequent hydrolysis, etc. In embodiments, the cleavage site is included in the oligonucleotide (e.g., within the oligonucleotide sequence of the primer). In embodiments, the linker or the oligonucleotide includes a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Oligonucleotide nucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, each of the particle-immobilized oligonucleotides (e.g., immobilized primers) is about 5 to about 25 nucleotides in length. In embodiments, each of the particle-immobilized oligonucleotides (e.g., immobilized primers) is about 10 to about 40 nucleotides in length. In embodiments, each of the particle-immobilized oligonucleotides (e.g., immobilized primers) is about 5 to about 100 nucleotides in length. In embodiments, each of the particle-immobilized oligonucleotides (e.g., immobilized primers) is about 20 to 200 nucleotides in length. In embodiments, each of the particle-immobilized oligonucleotides (e.g., immobilized primers) about or at least about 5, 6, 7, 8, 9, 10, 12, 15, 18, 20, 25, 30, 35, 40, 50 or more nucleotides in length. In embodiments, one or more particle-immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the 3' modification is a 3'-phosphate modification includes a 3' phosphate moiety, which is removed by a PNK enzyme.

In embodiments, the oligonucleotide moiety includes one or more phosphorothioate nucleotides. In embodiments, the oligonucleotide moiety includes a plurality of phosphorothioate nucleotides. In embodiments, about or at least about 20%, 30%, 40%, 50%, 60%, 70%, 80%, 90%, or about 100% of the nucleotides in the oligonucleotide moiety are phosphorothioate nucleotides. In embodiments, most of the nucleotides in the oligonucleotide moiety are phosphorothioate nucleotides. In embodiments, all of the nucleotides in the oligonucleotide moiety are phosphorothioate nucleotides. In embodiments, none of the nucleotides in the oligonucleotide moiety are phosphorothioate nucleotides.

In some embodiments, the oligonucleotide moiety is capable of hybridizing to a complementary sequence of a template nucleic acid. In embodiments, the oligonucleotide moiety includes DNA. In embodiments, the oligonucleotide moiety includes RNA. In embodiments, the oligonucleotide moiety is DNA. In embodiments, the oligonucleotide moiety is RNA. In embodiments, the oligonucleotide moiety includes a single-stranded DNA. In embodiments, the oligonucleotide moiety includes a single-stranded RNA. In embodiments, the oligonucleotide moiety is a single-stranded DNA. In embodiments, the oligonucleotide moiety is a single-stranded RNA. In embodiments, the oligonucleotide moiety is a nucleic acid sequence complementary to a target polynucleotide (e.g., complementary to a common adapter sequence of the target polynucleotide).

In some embodiments, the particle includes a plurality of bioconjugate reactive moieties. In embodiments, the particle includes a plurality of azide moieties, alkyne moieties, dibenzocyclooctyne (DBCO) moieties, epoxy moieties, or isocyanate moieties. In some embodiments, the particle includes a plurality of oligonucleotide moieties (e.g., ssDNA moieties).

In embodiments, the compositions described herein (e.g., the solid support and/or the particle) do not include poly(N-(5-azidoacetamidylpentyl)acrylamide-co-acrylamide (PAZAM).

In an aspect is provided a nucleic acid sequencing device, including: a stage configured to hold an array as described herein; an array as described herein, including embodiments; and a detector for obtaining sequencing data. In some embodiments, the detector is an imaging detector, such as a CCD, EMCCD, or s-CMOS detector.

In an aspect is provided a nucleic acid sequencing device, including: a stage configured to hold an array or solid support as described herein, including embodiments; an array or solid support as described herein, including embodiments; and a detector for obtaining sequencing data. In some embodiments, the detector is an imaging detector, such as a CCD, EMCCD, or s-CMOS detector.

The term "nucleic acid sequencing device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, for the purpose of determining the nucleic acid sequence of a template polynucleotide. Nucleic acid sequencing devices may further include valves, pumps, and specialized functional coatings on interior walls. Nucleic acid sequencing devices may include a receiving unit, or platen, that orients the flow cell such that a maximal surface area of the flow cell is available to be exposed to an optical lens. Other nucleic acid sequencing devices include those provided by Singular Genomics™ such as the G4™ sequencing platform, Illumina™, Inc. (e.g., HiSeq™, MiSeq™, NextSeq™, or NovaSeq™ systems), Life Technologies™ (e.g., ABI PRISM™, or SOLiD™ systems), Pacific Biosciences (e.g., systems using SMRT™ Technology such as the Sequel™ or RS II™ systems), or Qiagen (e.g., Genereader™ system). Nucleic acid sequencing devices may further include fluidic reservoirs (e.g., bottles), valves, pressure sources, pumps, sensors, control systems, valves, pumps, and specialized functional coatings on interior walls. In embodiments, the device includes a plurality of a sequencing reagent reservoirs and a plurality of clustering reagent reservoirs. In embodiments, the clustering reagent reservoir includes amplification reagents (e.g., an aqueous buffer containing enzymes, salts, and nucleotides, denaturants, crowding agents, etc.) In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of each of the reservoirs can vary. The fluid can be, for example, an aqueous solution which may contain buffers (e.g., saline-sodium citrate (SSC), ascorbic acid, tris(hydroxymethyl)aminomethane or "Tris"), aqueous salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes. In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). In embodiments, the nucleic acid sequencing device includes an imaging system (e.g., an imaging system as described herein). The imaging system capable of exciting one or more of the identifiable labels (e.g., a fluorescent label) linked to a nucleotide and thereafter obtain image data for the identifiable labels. The image data (e.g., detection data) may be analyzed by another component within the device. The imaging system may include a system described herein and may include a fluorescence spectrophotometer including an objective lens and/or a solid-state imaging device. The solid-state imaging device may include a charge coupled device (CCD) and/or a complementary metal oxide semiconductor (CMOS). The system may also include circuitry and processors, including systems using microcontrollers, reduced instruction set computers (RISC), application specific integrated circuits (ASICs), field programmable gate array (FPGAs), logic circuits, and any other circuit or processor capable of executing functions described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. In embodiments, the device includes a thermal control assembly useful to control the temperature of the reagents.

In an aspect is provided a flow cell including a particle as described herein, wherein the particle is within a well of the flow cell.

In an aspect is provided a kit, including the array as described herein. In an aspect is provided a kit, including the solid support as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, particles, labeled nucleotides, and/or modified nucleotides), buffers, salts, and/or labels (e.g., fluorophores). In embodiments, the kit includes an array with particles already loaded into the wells. In embodiments, the particles are in a container. In embodiments, the particles are in aqueous suspension or as a powder within the container. The container may be a storage device or other readily usable vessel capable of storing and protecting the particles. The kit may also include a flow cell. In embodiments, kit includes the solid support and a flow cell carrier (e.g., a flow cell carrier as described in US 2021/0190668, which is incorporated herein by reference for all purposes).

In an aspect is provided a kit, including the plurality of particles as described herein. Generally, the kit includes one or more containers providing a composition and one or more additional reagents (e.g., a buffer suitable for polynucleotide extension).

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant $P.$ $abyssi$ polymerase (e.g., such as a mutant $P.$ $abyssi$ polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

III. Methods

In an aspect is provided a method of amplifying a target polynucleotide, the method including contacting an array as described herein, including embodiments, with a plurality of oligonucleotide moieties. In embodiments, the array includes a solid support including a surface, the surface comprising a plurality of wells separated from each other by interstitial regions on the surface, wherein one or more wells includes a particle, wherein the particle includes a plurality of bioconjugate reactive moieties; and wherein there is at least one particle per well. In embodiments, each oligonucleotide moiety includes a bioconjugate reactive moiety that reacts and forms a bioconjugate linker that covalently links the oligonucleotide moiety to the particle. In embodiments, the method includes contacting the array with a sample including a target polynucleotide; and amplifying the target polynucleotide to produce an amplification product (e.g., an amplicon), wherein amplifying includes extension of the oligonucleotide moiety hybridized to the target polynucleotide.

In an aspect is provided a method of amplifying a target polynucleotide, the method including contacting an array, alternatively referred to as a multiwell container and/or solid support as described herein, including embodiments, with a plurality of oligonucleotide moieties, and amplifying the target polynucleotide hybridized to the oligonucleotides.

In an aspect is provided a method of amplifying a target polynucleotide, the method including contacting an array or solid support as described herein, including embodiments, with a plurality of oligonucleotide moieties. In embodiments, the array includes a solid support including a surface, the surface comprising a plurality of wells separated from each other by interstitial regions on the surface, wherein one or more wells includes a particle, wherein the particle includes a plurality of bioconjugate reactive moieties; and wherein there is at least one particle per well. In embodiments, each oligonucleotide moiety includes a bioconjugate reactive moiety that reacts and forms a bioconjugate linker that covalently links the oligonucleotide moiety to the particle. In embodiments, the method includes contacting the array with a sample including a target polynucleotide; and amplifying the target polynucleotide to produce an amplification product (e.g., an amplicon), wherein amplifying includes extension of the oligonucleotide moiety hybridized to the target polynucleotide.

In embodiments, the oligonucleotide moiety includes a DBCO bioconjugate reactive moiety that reacts with an azide bioconjugate reactive moiety on the particle and forms a bioconjugate linker that covalently links the oligonucleotide moiety to the particle, for example according to the following scheme:

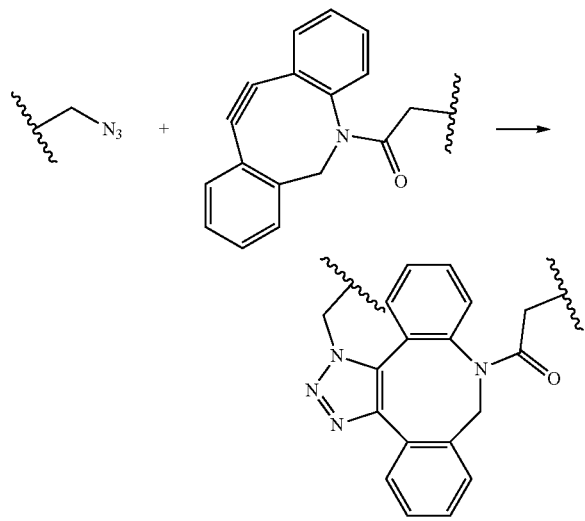

Scheme 1. An example mechanism of the bioconjugate covalent linker formed by reacting a DBCO containing oligonucleotide with a particle containing an azide moiety.

The symbol "⁂" refers to the attachment point to the oligonucleotide moiety and the particle polymer, respectively.

In an aspect is provided a method of amplifying a target polynucleotide, the method including contacting an array with a sample including a target polynucleotide. In embodiments, the array includes a solid support including a surface, the surface comprising a plurality of wells separated from each other by interstitial regions on the surface, wherein one or more wells includes a particle, wherein the particle includes a plurality of oligonucleotide moieties; and wherein there is at least one particle per well. In embodiments, the array includes a solid support as described herein. In embodiments the solid support includes a surface, the surface comprising a plurality of wells separated from each other by interstitial regions on the surface, wherein one or more wells includes a particle, wherein the particle includes a plurality of oligonucleotide moieties; and wherein there is at least one particle per well. In embodiments, the method includes amplifying the target polynucleotide to produce an amplification product, wherein amplifying includes extension of the oligonucleotide moiety hybridized to the target polynucleotide. In embodiments, amplifying includes a plurality of cycles of strand denaturation, primer hybridization, and primer extension.

In an aspect is provided a method of amplifying a target polynucleotide. In embodiments, the method includes contacting the solid support as described herein with a sample including a target polynucleotide; and amplifying the target polynucleotide to produce an amplification product, wherein amplifying includes extension of the oligonucleotide moiety hybridized to the target polynucleotide. In embodiments, the target polynucleotide includes a complementary sequence to the oligonucleotide covalently attached to the particle.

In embodiments, the method includes contacting a particle as described herein with a sample including a target polynucleotide; and amplifying the target polynucleotide to produce an amplification product immobilized to the particle, wherein amplifying includes extension of the oligonucleotide moiety hybridized to the target polynucleotide, and contacting the solid support with the amplified product immobilized to the particle. In embodiments, the target polynucleotide includes a complementary sequence to the oligonucleotide covalently attached to the particle. In embodiments, the method further includes detecting the amplification product (e.g., sequencing the amplification product).

In embodiments, amplifying includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of the methods. In embodiments, amplifying includes a bridge polymerase chain reaction amplification. In embodiments, amplifying includes a thermal bridge polymerase chain reaction (t-bPCR) amplification. In embodiments, amplifying includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions. In embodiments, amplifying includes generating a double-stranded amplification product.

A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can comprise nucleic acids obtained from one or more subjects. In some embodiments, a sample comprises nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments, a subject is suspected of having a genetic variation or a disease or condition associated with a genetic variation.

It will be appreciated that any of the amplification methodologies described herein or known in the art can be utilized with universal or target-specific primers to amplify the target polynucleotide. Suitable methods for amplification include, but are not limited to, the polymerase chain reaction (PCR), strand displacement amplification (SDA), transcription mediated amplification (TMA) and nucleic acid sequence-based amplification (NASBA), for example, as described in U.S. Pat. No. 8,003,354, which is incorporated herein by reference in its entirety. The above amplification methods can be employed to amplify one or more nucleic acids of interest. Additional examples of amplification processes include, but are not limited to, bridge-PCR, recombinase polymerase amplification (RPA), loop-mediated isothermal amplification (LAMP), rolling circle amplification (RCA), strand displacement amplification, RCA with exponential strand displacement amplification. In embodiments, amplification comprises an isothermal amplification reaction. In embodiments, amplification comprises bridge amplification. In general, bridge amplification uses repeated steps of annealing of primers to templates, primer extension, and separation of extended primers from templates. Because primers are attached within the core polymer, the extension products released upon separation from an initial template is also attached within the core. The 3' end of an amplification product is then permitted to anneal to a nearby reverse primer that is also attached within the core, forming a "bridge" structure. The reverse primer is then extended to produce a further template molecule that can form another bridge. In embodiments, forward and reverse primers hybridize to primer binding sites that are specific to a particular target nucleic acid. In embodiments, forward and reverse primers hybridize to primer binding sites that have been added to, and are common among, target polynucleotides. Adding a primer binding site to target nucleic acids can be accomplished by any suitable method, examples of which include the use of random primers having common 5' sequences and ligating adapter nucleotides that include the primer binding site. Examples of additional clonal amplification techniques include, but are not limited to, bridge PCR, solid-phase rolling circle amplification (RCA), solid-phase exponential rolling circle amplification, solid-phase recombinase polymerase amplification (RPA), solid-phase helicase dependent amplification (HDA), template walking amplification, emulsion PCR on particles (beads), or combinations of the aforementioned methods. Optionally, during clonal amplification, additional solution-phase primers can be supplemented in the flow cell for enabling or accelerating amplification.

In embodiments, amplifying includes contacting the plurality of particles with one or more reagents for amplifying the target polynucleotide. Examples of reagents include but are not limited to polymerase, buffer, and nucleotides (e.g., an amplification reaction mixture). In certain embodiments, the term "amplifying" refers to a method that includes a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In embodiments, amplifying generates an amplicon. In embodiments, an amplicon contains multiple, tandem copies of the circularized nucleic acid molecule of the corresponding sample nucleic acid. The number of copies can be varied by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. Generally, the number of copies of a nucleic acid in an amplicon is at least 100, 200, 500, 1000, 2000, 3000, 4000, 5000, 6000, 7000, 8000, 9000 and 10,000 copies, and can be varied depending on the application. As disclosed herein, one form of an amplicon is as a nucleic acid "ball" localized to the particle and/or well of the array. The number of copies of the nucleic acid can therefore provide a desired size of a nucleic acid "ball" or a sufficient number of copies for subsequent analysis of the amplicon, e.g., sequencing.

In embodiments, the sample includes a plurality of target polynucleotides at a concentration selected such that a majority of the particles in which the amplification occurs includes amplicons of only one original target polynucleotide. In embodiments, about or at least about 60%, 70%, 80%, 90%, 95%, or more of the particles in which amplification occurs contains amplicons of only one original target polynucleotide.

In embodiments, the methods further include a step of separating particles that include amplicons (e.g., amplification product(s)) from particles that do not include amplicons. For example, particles that do not include amplicon, also referred to as "blank" particles, can be separated from particles with amplicon by charge-based separation. Since DNA carries a negative charge, the particles that contain amplified products will be significantly charged compared to the "blank" particles. The particles containing amplicons can be separated from the "blank" particles by an electric field. By choosing a relatively low seeding ratio, e.g. <20%, or <10%, or <5%, the probability of having more than 1 template per particle (multiple seeding) can be greatly reduced. The large fraction of unseeded "blank" particles can then be removed by charge-based separation, resulting in nearly pure population of single-seeded particles for monoclonal amplification. In embodiments, the methods comprise amplifying a target polynucleotide in solution, separating particles containing amplicons from "blank" particles, and depositing the particles containing amplicons in a container (e.g., a flow cell) for sequencing. Alternatively, the particles may contain a magnetic core and may be separated by applying a magnetic field.

In embodiments, the methods further include repeating the contacting and amplifying steps using the separated particles that do not include an amplicon. In embodiments, the contacting is repeated with an aliquot of the same sample as in the original contacting, and particles from the repeated steps are pooled (e.g., in a container, such as a flow cell) prior to sequencing. In embodiments, repeating the contacting and amplifying steps does not involve separating particles that do not include an amplicon from those that do contain an amplicon.

In embodiments of the methods provided herein, arraying the particles occurs prior to contacting the particles with a sample that includes a target polynucleotide. In other embodiments, arraying the particles occurs after contacting the particles with a sample that includes a target polynucleotide. In other embodiments, arraying the particles occurs after amplifying the target polynucleotide.

In an aspect is provided a method of making an array of nucleic acids on a surface, the method including: a) providing a solid support including a surface, the surface including a plurality of wells wherein the wells are separated from each other by interstitial regions on the surface; b) providing a plurality of particles, wherein each particle includes a plurality of bioconjugate reactive moieties; c) arraying the particles onto the surface; d) contacting the particles with a plurality of oligonucleotide moieties, wherein each oligonucleotide moiety includes a bioconjugate reactive moiety that reacts and forms a bioconjugate linker that covalently links the oligonucleotide moiety to the particle.

In an aspect is a method of making an array of nucleic acids on a surface, the method including: a) providing a solid support including a surface, the surface including a plurality of wells wherein the wells are separated from each other by interstitial regions on the surface; b) providing a plurality of particles, wherein each particle includes a plurality of oligonucleotide moieties; c) arraying the particles onto the surface; d) contacting the particles with a plurality of template nucleic acid moieties, wherein a complementary sequence of the template nucleic acid moieties hybridizes to the oligonucleotide moiety of the particle. In embodiments, the average longest dimension of the particle is from about 150 nm to about 1,000 nm.

In an aspect is provided a method of making an array of nucleic acids on a surface, the method including: a) providing a solid support including a surface, the surface including a plurality of wells wherein the wells are separated from each other by interstitial regions on the surface and wherein the surface comprises a polymer layer and is substantially free of oligonucleotide moieties; b) providing a plurality of particles; c) arraying the particles onto the surface; d) contacting the particles with a plurality of template nucleic acid moieties, wherein a complementary sequence of the template nucleic acid moieties hybridizes to the oligonucleotide moiety of the particle. In embodiments, the average longest dimension of the particle is from about 150 nm to about 1,000 nm.

In another aspect is provided a method of making an array of template nucleic acids, the method including: contacting a solid support including two or more wells with a plurality of particles, wherein each particle includes a plurality of oligonucleotide moieties attached to the particle via a bioconjugate linker; wherein the average longest dimension of the particle is from about 150 nm to about 1,000 nm; and contacting the particles with a plurality of template nucleic acid moieties, wherein a complementary sequence of the template nucleic acid moieties hybridizes to the oligonucleotide moiety of the particle and is extended with a polymerase to form an array of template nucleic acids.

In embodiments of the methods provided herein, the contacting step is performed under non-hybridizing conditions. In embodiments of the methods provided herein, the contacting step is performed under non-hybridizing conditions initially, then the conditions are changed to hybridizing conditions. In embodiments of the methods provided herein, the contacting step is performed under hybridizing conditions initially, then the conditions are changed to non-hybridizing conditions. In general, contacting the sample under non-hybridizing conditions can facilitate distribution of target polynucleotides within a polymeric particle prior to subsequent steps (e.g., amplification). Examples of non-hybridizing conditions include but are not limited to low salt, high temperature, and/or presence of additives such as formamide. The precise nature of non-hybridizing conditions (e.g., the temperature, or the amounts of salt or formamide) will vary with factors such as the length, GC-content, or melting temperature (Tm) of primers (or the target-hybridizing portion thereof) present in the reaction. In embodiments, primers are designed to have Tm's within 15, 10, 5, 3 or fewer degrees of one another. In embodiments, non-hybridizing conditions comprises a temperature that is about or at least about 5, 10, 15, 20, or more degrees above the average Tm of primers in the reaction.

In embodiments, the method includes determining the nucleic acid sequence of the target polynucleotide. In embodiments, the method further includes detecting the oligonucleotides, or extension products or complements thereof. In embodiments, the method includes detecting the template nucleic acid and/or determining the nucleic acid sequence of the target polynucleotide. In embodiments, the molecule further includes quantifying the target nucleic acid molecule or amplicons. Methods for quantifying a target polynucleotide or amplicon are well known to one of skilled in the art. For example, during amplification of the target nucleic acid, quantitative techniques such as real-time polymerase chain reaction (RT-PCR) can be used to quantify the copy number of target nucleic acid molecules present in the clonal object as discussed in Logan et al. Real-Time PCR: Current Technology and Applications, Caister Academic Press. (2009). RT-PCR follows the general principle of polymerase chain reaction, however inclusion of detection molecules, such as non-specific fluorescent dyes that intercalate with any double-stranded DNA, or sequence-specific DNA probes consisting of oligonucleotides that are labeled with a fluorescent reporter, which permits detection only after hybridization of the probe with its complementary DNA target, allows for the detection of nucleic acid formed during amplification. The rate of detectable molecules is proportional to the copy number of target nucleic acid molecules present in the clonal object. Furthermore, quantifying the target nucleic acid molecule or amplicons can be done following amplification using standard gel electrophoresis and/or Southern blot techniques, which are well known in the art.

In embodiments, the method further includes sequencing the amplification product(s). Sequencing includes, for example, detecting a sequence of signals within the particle. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the readout is accomplished by epifluorescence imaging. A variety of sequencing chemistries are available, non-limiting examples of which are described herein.

In an aspect is provided a method of sequencing a target polynucleotide, the method including contacting an array as described herein, including embodiments, with a plurality of oligonucleotide moieties. In embodiments, the array includes a solid support including a surface, the surface comprising a plurality of wells separated from each other by interstitial regions on the surface, wherein one or more wells includes a particle, wherein the particle includes a plurality of bioconjugate reactive moieties; and wherein there is at least one particle per well. In embodiments, each oligonucleotide moiety includes a bioconjugate reactive moiety that reacts and forms a bioconjugate linker that covalently links the oligonucleotide moiety to the particle. In embodiments, the method includes contacting the array with a sample including a target polynucleotide; and amplifying the target polynucleotide to produce an amplification product, wherein amplifying includes extension of the oligonucleotide moiety hybridized to the target polynucleotide. In embodiments, the method includes sequencing the amplification product. The initiation point for a sequencing reaction may be provided by annealing of a sequencing primer to a target polynucleotide present at a feature of the array. In embodiments, a known adapter sequence region that is present on a target nucleic acid, for example, as a result of an amplification reaction described previously herein, can be used as a priming site for annealing of a sequencing primer. In embodiments, a sequencing reaction includes steps of hybridizing a sequencing primer to a single-stranded region of a linearized amplification product, sequentially incorporating one or more nucleotides into a nucleic acid strand complementary to the region of amplified template strand to be sequenced, identifying the base present in one or more of the incorporated nucleotide(s) and thereby determining the sequence of a region of the template strand.

In an aspect is provided a method of sequencing a target polynucleotide, the method including contacting an array with a sample including a target polynucleotide. In embodiments, the array is as described herein. In embodiments the array includes a solid support including a surface, the surface including a plurality of wells separated from each other by interstitial regions on the surface, wherein one or more wells includes a particle, wherein the particle includes a plurality of oligonucleotide moieties; and wherein there is at least one particle per well. In embodiments, the method includes amplifying the target polynucleotide to produce an amplification product, wherein amplifying includes extension of the oligonucleotide moiety hybridized to the target polynucleotide. In embodiments, the method includes sequencing the amplification product.

In an aspect is provided a method of sequencing a template polynucleotide. In embodiments, the method includes contacting a solid support (e.g., a solid support as described herein) with a sample including a template polynucleotide. In embodiments, the method include hybridizing the template polynucleotide to the oligonucleotide moiety. In embodiments, the method includes extending the oligonucleotide moiety to generate a complement of the template polynucleotide immobilized to the particle. In embodiments, the method includes forming a plurality of amplification products by subjecting the solid support to suitable amplification conditions (e.g., as described herein). In embodiments, the method includes contacting the immobilized template polynucleotide, or complement thereof, with a sequencing primer, and with a polymerase, incorporating one or more nucleotides into an extension strand. In embodiments, the method includes detecting the one or more nucleotides incorporated into the extension strand.

In embodiments, sequencing includes extending a sequencing primer to incorporate a nucleotide containing a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product of a target nucleic acid). In embodiments, the sequencing includes sequencing-by-synthesis, sequencing by ligation, or pyrosequencing, and generates a sequencing read. In embodiments, the sequencing includes sequencing-by-binding and generates one or more sequencing reads.

In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated.

In embodiments, the method includes sequencing the first and/or the second strand of a amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. In embodiments, sequencing includes detecting a sequence of signals and generating one or more sequencing reads. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US Patent Publication 2018/0274024, WO 2017/205336, US Patent Publication 2018/0258472, each of which are incorporated herein in their entirety for all purposes.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, each particle core includes a silica, magnetic, or paramagnetic material, such as in the form of a bead or particle. For example, the particle shell layers may be formed around and encapsulating a supporting bead, for example, a silica, magnetic, or paramagnetic bead.

In embodiments, the particle is a functionalized particle including a particle core and a particle shell, wherein said particle shell includes the plurality of bioconjugate reactive moieties, the plurality of oligonucleotide moieties, or a combination thereof, wherein each of the bioconjugate reactive moieties and each of the oligonucleotide moieties comprise a linker binding said bioconjugate reactive moieties and oligonucleotide to the particle core. In embodiments, the functionalized particle is a silica particle.

In embodiments, the particle is a functionalized particle including a particle core and a plurality of particle polymers. In embodiments, each particle polymer includes a plurality of bioconjugate reactive moieties, a plurality of oligonucleotide moieties, or a combination thereof. In embodiments, the functionalized particle is a silica particle. In embodiments of the methods provided herein, the particle is a polymeric particle.

In embodiments, arraying the particles includes contacting the surface with a first solution comprising the plurality of particles in an anti-solvent. In embodiments, the particle includes acrylamide and the anti-solvent is an aqueous ethanol solution. In embodiments, the particle includes sulfobetaine acrylate (SBA), carboxybetaine acrylate (CBA), phosphorylcholine acrylate (PCA), sulfobetaine methacrylate (SBMA), carboxybetaine methacrylate (CBMA), or phosphorylcholine methacrylate (PCMA) and the anti-solvent is an aqueous acetone solution. In embodiments, arraying the particles further includes removing the first solution and contacting the surface with a second solution, wherein the second solution is an aqueous solution capable of expanding the volume of the particle. In embodiments, the second solution includes water. In embodiments of the methods provided herein, the second solution expands the volume of the particles by up to 10%, up to 20%, up to 30%, up to 40%, up to 50%, up to 60%, up to 70%, up to 80%, up to 100%, up to 150%, up to 200%, or more relative to particle in an anti-solvent. In embodiments of the methods provided herein, the solvent expands the volume of the particles by 10-200%, 30-150%, or 50-100%, relative to particle in an anti-solvent. In embodiments of the methods provided herein, the presence of the solvent expands the volume of the particles by up to 90% relative to particle in an anti-solvent.

In embodiments, the polymers of the present disclosure (e.g., polymer particles) swell with a solvent in which they are suspended, and the refractive index of the suspension is about the same as the solvent. In embodiments of the methods provided herein, the polymer particle or the shell polymer, have a refractive index of about 1.2-1.6, 1.25-1.5, or 1.3-1.4 when hydrated. In embodiments, the polymer particle or the shell polymer have a refractive index of about 1.3 when hydrated.

In embodiments, the polymers of the present disclosure (e.g., polymeric particles) swell with a solvent in which they are suspended, and the refractive index of the suspension is about the same as the solvent. In embodiments of the methods provided herein, the polymeric particle or the shell polymer, have a refractive index of about 1.2-1.6, 1.25-1.5, or 1.3-1.4 when hydrated. In embodiments, the polymeric particle or the shell polymer have a refractive index of about 1.3 when hydrated.

In an aspect, provided herein are methods of sequencing target polynucleotides, the methods including contacting a polymer particle with a sample that includes target polynucleotides, amplifying the target polynucleotides to produce discrete amplicon clusters, and sequencing the amplicon clusters. In embodiments, the polymer particle includes a polymer covalently attached to polynucleotide primers. In embodiments, amplifying the target includes extension of primers along the target polynucleotides within the polymer particle. In embodiments, each amplicon cluster originates from amplification of a single target polynucleotide. In embodiments, sequencing comprises detecting sequences of signals within the polymer particle.

In an aspect, provided herein are methods of sequencing target polynucleotides, the methods including contacting a polymeric particle with a sample that includes target polynucleotides, amplifying the target polynucleotides to produce discrete amplicon clusters, and sequencing the amplicon clusters. In embodiments, the polymeric particle includes a polymer covalently attached to polynucleotide primers. In embodiments, amplifying the target includes extension of primers along the target polynucleotides within the polymeric particle. In embodiments, each amplicon cluster originates from amplification of a single target polynucleotide. In embodiments, sequencing comprises detecting sequences of signals within the polymeric particle.

In embodiments of the methods provided herein, the target polynucleotides are at a concentration in the sample selected to produce amplicon clusters having a desired density. For example, the concentration of target polynucleotides is selected based on a calculation of (a) the average size of a cluster of amplicons that will result from amplification under selected conditions (e.g. a selected duration and number of extension steps), and (b) a desired separation between adjacent amplicon clusters in the array.

In embodiments of the methods provided herein, the amplicon clusters have a mean or median separation from one another of about 0.5-5 µm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm or a number or a range between any two of these values. The mean or median separation may be measured center-to-center (i.e., the center of one amplicon cluster to the center of a second amplicon cluster). In embodiments of the methods provided herein, the amplicon clusters have a mean or median separation (measured center-to-center) from one another of about 0.5-5 µm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 µm.

Neighboring features of an array can be discrete one from the other in that they do not overlap. Accordingly, the features can be adjacent to each other or separated by a gap (e.g., an interstitial space). In embodiments where features are spaced apart, neighboring sites can be separated, for example, by a distance of less than 10 µm, 5 µm, 1 µm, 0.9 µm, 0.8 µm, 0.7 µm, 0.6 µm, 0.5 µm, or less. The layout of features on an array can also be understood in terms of center-to-center distances between neighboring features. An array useful in the invention can have neighboring features with center-to-center spacing of less than about 10 µm, 5 µm, 1 µm, 0.9 µm, 0.8 µm, 0.7 µm, 0.6 µm, 0.5 µm or less. Furthermore, it will be understood that the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array.

In embodiments, each feature generated on the surface of an array can be of similar or smaller size than the area of the surface occupied by the particle from which the feature was produced, and all the features will typically be of similar size and intensity to each other. The uniform size, uniform intensity, and lack of overlap provides a convenient density of features per unit area. Detection of tightly packed non-overlapping arrays with features of uniform size and intensity are typically easier to analyze than images where a subset of the features overlap with each other.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000 nanometers or a number or a range between any two of these values.

In embodiments, the arrays include about 10,000,000 features/cm$^2$ to about 5,000,000,000 features/cm$^2$. In embodiments, the arrays include about 100,000,000 features/cm$^2$ to about 1,000,000,000 features/cm$^2$. In embodiments, the arrays include about 100,000 features/cm$^2$ to about 100,000,000 features/cm$^2$. In embodiments, the arrays include about or about 10,000,000 features/cm$^2$ to about 50,000,000 features/cm$^2$.

In embodiments of the methods provided herein, the contacting step is performed under non-hybridizing conditions. Examples of non-hybridizing conditions are described above, and include but are not limited to low salt, high temperature, or presence of additives such as formamide.

EXAMPLES

Example 1. Superior Coverage of Nucleic Acid Templates within Nanoarrays

Patterned arrays are an important tool in biomedical research, providing a two-dimensional platform that arranges biological samples and enables high-throughput analyses. Delivering breakthroughs in proteomics, multiplexed immunoassays, and complex genomic analyses, microarrays can be designed to host thousands, or even ten-thousands, of features that can be subjected to simultaneous reaction conditions. Microarrays are typically fabricated by spotting, imprinting, or directly synthesizing biomolecules on solid supports such as glasses, silicon wafers, and other functionalized substrates. In general terms, a target of interest (e.g., a protein or gene sequence) is immobilized as discrete features, or spots, on a substrate. Each feature may contain one to thousands of identical targets if subjected to an amplification technique. A successful detection event occurs when a labeled probe is brought into contact with the array, and if the probe interacts with the target, an increase of fluorescence intensity over a background level is produced, which can be measured using an appropriate detector.

Array techniques that rely on the random distribution of features typically suffer from a low ratio of incorporation event/pixel, due to a high number of dark pixels with no features (for example, if the density of features is too diffuse), or a high number of pixels that carry multiple overlapping features of different sequence (if the density of features is too concentrated) or both (due to the random nature of feature placement). An ideal and more efficient use of the imaging pixels occurs when the features on the surface are tightly packed, non-overlapping, and of similar size and intensity to each other. The present invention provides compositions and methods of manufacturing arrays of features that avoid low ratios of bases/pixels associated with typical commercial array fabrication methods, while exploiting advantages of random feature fabrication. Maximizing the number of target polynucleotides per surface area will enable scientists to analyze a complex genome on one small glass chip, about 1 cm$^2$ in size.

Although the microarray has become a mainstay for parallel screening of several nucleic acids and proteins, it has several disadvantages. For example, microarray applications require large sample volumes and long incubation times because of the larger spot size (e.g., 1-150 μm). Bead-based microarrays were developed by David Walt at Tufts University and subsequently commercialized by Bead-Chip products (Walt, D. R. Science 2000, 287(5452), 451-452) and others (Brenner et al. Nat. Biotechnol. 2000, 18, 630-634), however, the large diameter of the beads (e.g., 3 μm to 40 μm) limit the theoretical maximum density and practical use of the underlying array. A significant reduction in particle size is necessary to achieve higher throughput, less reagent consumption, and faster data acquisitions. For context, the average diameter of a grain of sand is 60 to 2,000 μm ("Relationship of Transported Particle Size to Water Velocity." 1994 Earth Science Reference Tables. Albany, NY: University of the State of New York, 1994), and manipulating nanoparticles is challenging. Particles suspended in liquids are prone to form aggregates, and given the unique properties pertinent to nanoparticles, such as shape, size, surface characteristics, composition, and electronic structures, nanoparticle aggregation is more problematic than their bulk counterparts (i.e., microparticles). Further reducing the bead size to submicron dimensions, while not aggregating and retaining the necessary functional properties to form highly dense arrays, withstand repeated cycles of complex biochemical processes that result in signal generation and detection, has until now, remained elusive.

In embodiments, the array and associated particles as described herein address the problem of achieving a high array density with complete to near-complete loading of particles into wells of an array, enabling greater coverage of monoclonal templates per cm$^2$. Highly efficient loading is achieved with a pattern of high-density particle-occupancy sites separated by a non-binding surface (e.g., interstitial space), wherein the particle type and size, preparation methods, and areas of discrete spaced apart regions are selected so that substantially all such regions contain at most only one single particle. An array that achieves high coverage of monoclonal templates is advantageous for detection and data analysis of signals collected from the arrays during sequencing analysis. Tuning the particle size allows for additional control of the quantity of particles per well (e.g., 2 or more particles per well).

Polynucleotides on particles of the invention herein, confined to the restricted area of discrete, punctate clusters provide a more concentrated or intense signal, particularly when fluorescent probes are used in analytical operations, thereby providing higher signal-to-noise values and greater confidence in detection. By generating punctate clusters in an array that will provide a signal, data collection is simplified and less sophisticated image analysis systems are needed to detect fewer pixels compared to traditional systems. As described supra, a benefit provided by embodiments of the array may include an increased signal intensity during sequencing-by-synthesis. The increase in signal intensity may reduce an error rate by reducing the number of clusters, for example, that emit a low intensity of light. Maintaining the interstitial spaces of the array free from non-specifically bound oligonucleotides, and subsequently amplified clusters, would help quarantine signal production to regions that have a potential broader dynamic range of signal emittance.

A benefit of the invention described herein may include a decrease in signal to noise ratio that enables faster scan speeds and reduces overall time for conducting a protocol. For instance, with respect to sequencing-by-synthesis technology, faster scan speeds on sequencing instruments are desired, but faster scan speeds result in fewer photons being collected per cluster on the imaging camera. With fewer photons captured, the signal to noise ratio typically decreases and it becomes more difficult to confidently assign a base. Furthermore, on some sequencing instruments, low NA optics result in signals that are inherently larger and dimmer, potentially yielding higher error rates. Embodiments set forth herein may increase the number of photons that are captured by eliminating regions of non-specific binding. The increase in signal intensity may improve overall sequencing performance by reducing sequencing error arising from low intensity clusters (e.g., those found in interstitial spaces) and cluster dropouts during long sequencing runs.

The array of the invention described herein may include particles of various compositions. In some embodiments, the particles may include solid core particles (e.g., a core made of glass, ceramic, metal, silica, magnetic material, or a paramagnetic material) with a plurality of particle polymers (e.g., a particle polymer moieties including polyacrylamide (Aam), poly-N-isopropylacrylamide, polyethylene glycol acrylate, methacrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof). In embodiments, the solid core particle is a silica particle. In embodiments, the particle polymer includes PEGMA and GMA azide copolymers. In other embodiments, the array includes particles made up entirely of a polymeric scaffold (e.g., including a copolymer described supra). The polymeric particle is permeable to sequencing reaction mixtures and amplification reaction mixtures, including reagents, oligonucleotides, and polymerases. The polymer compositions provided herein prevent nanoparticle aggregation.

Figure 4:
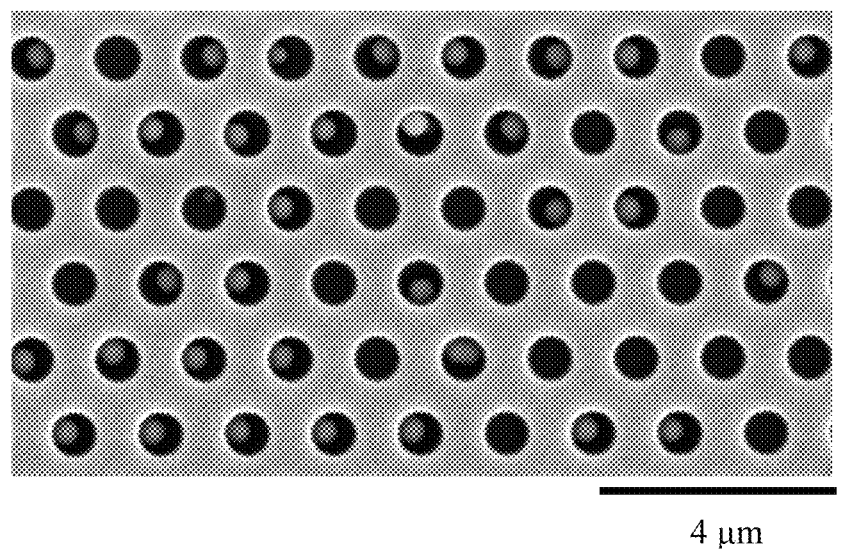
FIG. 4 is a scanning electron micrograph of a subsection of the array with particles arrayed in each well. Magnification of image is 10,000×. The scale bar denotes 4 μm. The center-to-center distance of each well is approximately 1 μm.
Figure 8:
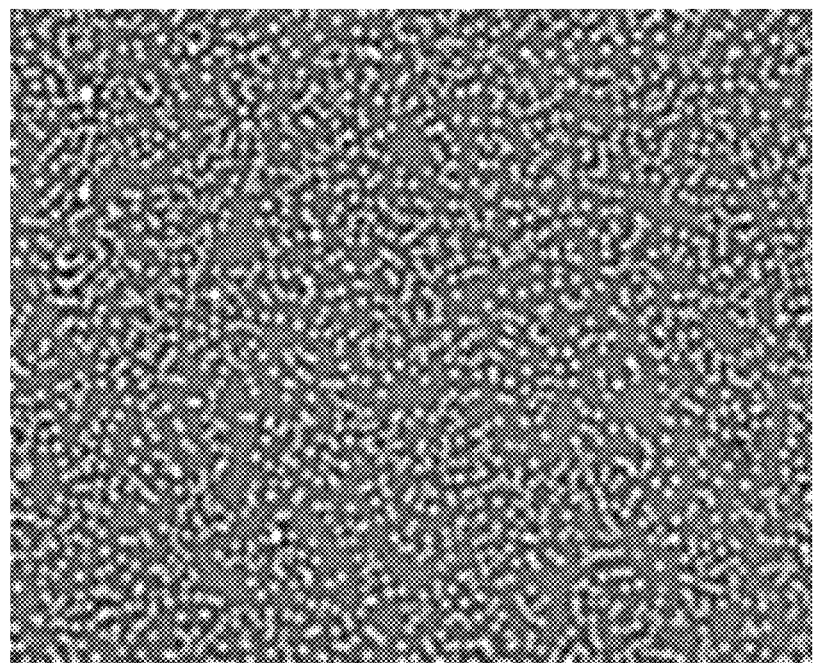
FIG. 8 is a brightfield image of pure polymeric particles (i.e., particles not containing a solid particle core) synthesized as described herein having an average diameter of about 550 nm. Exemplary particles of the invention have a diameter of less than 1000 nm.

One feature of the invention described herein includes an array with wells containing particles dispersed into the array, wherein the particles are in the sub-micron diameter (i.e., the diameter of the particle is less than or equal to about 1 μm) range. As shown in FIG. 8, pure particles below 1000 nm in diameter may be utilized in combination with an array of the invention. Particles with smaller diameters, for example, diameters of about 500 nm to 400 nm or smaller, may be implemented to increase the array loading efficiency and high coverage. We have validated the ability to deposit such sub-micron particles in an array with high coverage (see, FIG. 4, for example). In embodiments, the particle has a diameter of about 400 nm. In embodiments, the particle has a diameter of about 450 nm. In embodiments, the thickness of the surrounding particle polymers (also referred to herein as the particle shell) is about 50 to about 200 nm (see FIG. 10A). In embodiments, the thickness of the copolymeric shell is about 50 nm. In embodiments, the thickness of the copolymeric shell is about 100 nm. In embodiments, the thickness of the copolymeric shell is about 150 nm. In embodiments, the thickness of the copolymeric shell is about 200 nm.

Particles of the invention may be loaded into wells through several methods known in the art. For example, particles loading may simply be gravity driven. Gravity driven loading may also be accelerated by subsequently spinning down the array in a centrifuge, or with an orbital mixer to increase the particle settling rate. Such combinations are optimized so that no more than one particle is loaded into a given well, while achieve near complete coverage of the array with high uniformity. Additional particle loading techniques may involve agitating (e.g., vortexing), capillary assisted wetting, and/or centrifugation. In other embodiments, sonication and/or physical wiping with a flat tool may be used as a post-loading cleaning technique to reduce doubly-loaded wells and clear interstitial regions of particles. Post-cleaning may also simply consist of rinsing with a solvent, shaking, sonicating, wiping, or a combination thereof to remove non-specifically bound particles.

Figure 3:
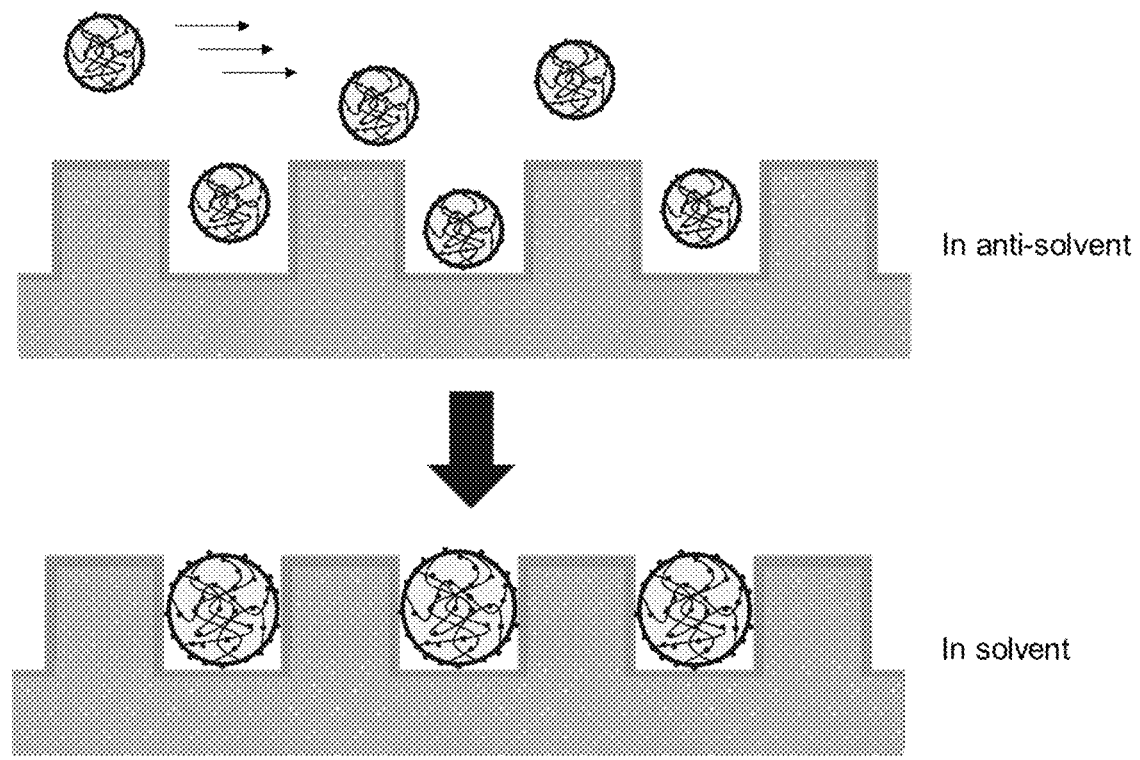
FIG. 3 illustrates one embodiment wherein polymeric particles as described herein are introduced in an anti-solvent (e.g., ethanol) to a patterned substrate. In the presence of anti-solvent the volume of the particles is reduced relative to the volume of the particles in water. Subsequently, the reaction conditions are changed such that an aqueous solvent (e.g., water) is present, which swells the particles, causing them to remain trapped in the wells. The particles may include oligonucleotide moieties, or the oligonucleotide moieties may be added following deposition of the particles.

An alternative approach to arraying particles into wells is illustrated in FIG. 3. In this approach, oligonucleotide primer-coated particles are introduced in an anti-solvent (e.g., ethanol). In the presence of anti-solvent the volume of the primer-coated particles is reduced relative to the volume of the primer-coated particles in solvent. Subsequently, the reaction conditions are changed such that a solvent (e.g., water) is present, which swells the particles, causing them to remain trapped in the wells.

Figure 2A:
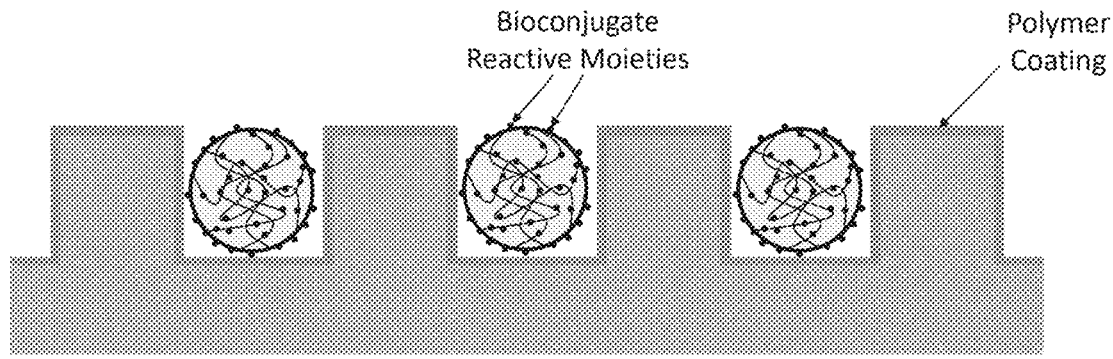
FIGS. 2A-2B are illustrations of particles in wells of an array as described herein.
Figure 2B:
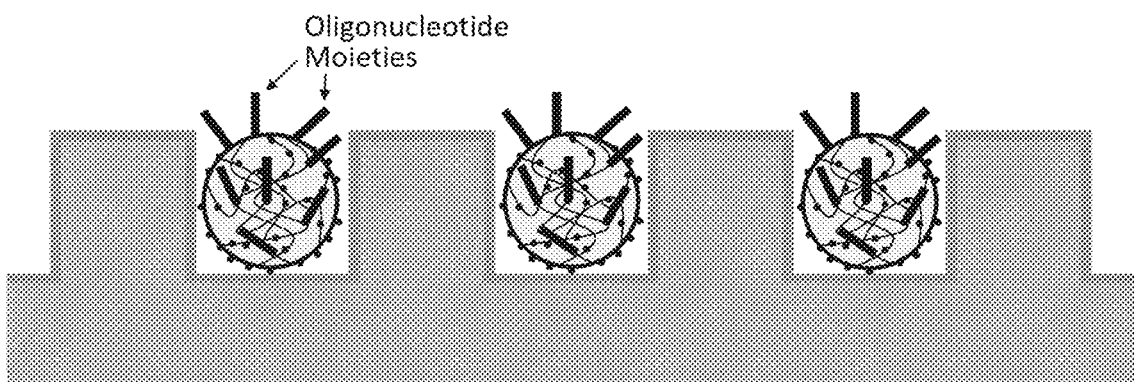
Figure 5A:
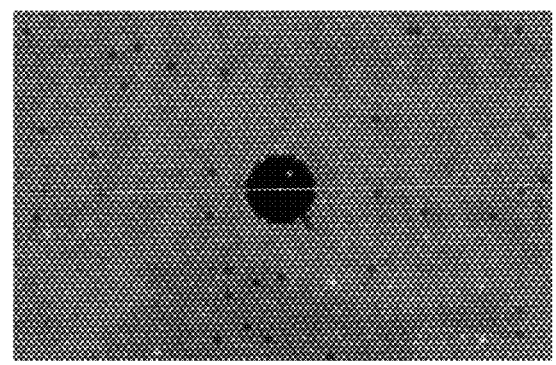
FIGS. 5A-5B are fluorescent images of an array of the invention showing particles loaded in wells, the particles decorated with oligonucleotide primers that have been labeled with FAM-labeled complementary oligonucleotides. The wells have a 1 μm center-to-center distance (FIG. 5A) and a 1.4 μm center-to-center distance (FIG. 5B). The center circle is a reference fiducial marker useful in alignment for detection apparatus.
Figure 5B:
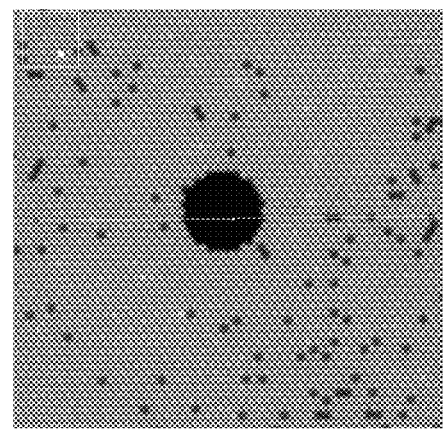

The particles are decorated with bioconjugate reactive moieties (e.g., a plurality of bioconjugate reactive moieties, depicted as small dots in FIG. 2A), such that either before, or after, loading the particles into a well, one or more oligonucleotide moieties may be bound to the particles, as depicted in FIG. 2B and imaged in FIGS. 5A-5B. In some embodiments, the oligonucleotides moiety is about 5 to about 45 nucleotides in length and is capable of hybridizing to a library nucleic acid molecule. In embodiments, the oligonucleotide moiety is capable of hybridizing to a complementary sequence of a template nucleic acid.

In order to obtain high-density particle loading with minimal background, the solid support of the array may be coated with a passivating polymer (e.g., a copolymer such as a silane functionalized polyethylene glycol (Si-PEG) copolymer or a silane functionalized poly(acrylamide) (Si-Pam)). The passivating polymer may be hydrophilic or hydrophobic (e.g., polyfluorinated polymer) and may be a comb polymer or brush polymer that is useful at preventing non-specific binding of additional agents to the array (e.g., oligonucleotides in solution). Illustrations of the different well shapes of the array are depicted in FIGS. 1A-1C. Using known nanolithographic fabrication techniques, a glass substrate may be etched such that the well is anisotropic (FIG. 1A), partially anisotropic (FIG. 1B), or isotropic (FIG. 1C). The array may include a photoresist (e.g., a fluorinated polymer later) prior to receiving an additional polymer coating (e.g., a poloxamer or alkoxysilyl polymer). The photoresist may be removed prior to the addition of the additional polymer using known techniques in the art (e.g., solvent removal). In embodiments, the additional polymer coating reduces the non-specific binding of oligonucleotide moieties. In embodiments, the particles are physiosorbed to the surface of the wells. Surprisingly, no covalent linkage between the particle and the array, nor hybridization of particles bearing an oligonucleotide sequence that is complementary to an immobilized primer on the array, is needed to retain the particles in the well. The interaction between the particle and the passivating polymer is sufficient to retain the particles in the well during amplification and sequencing.

Figure 1D:
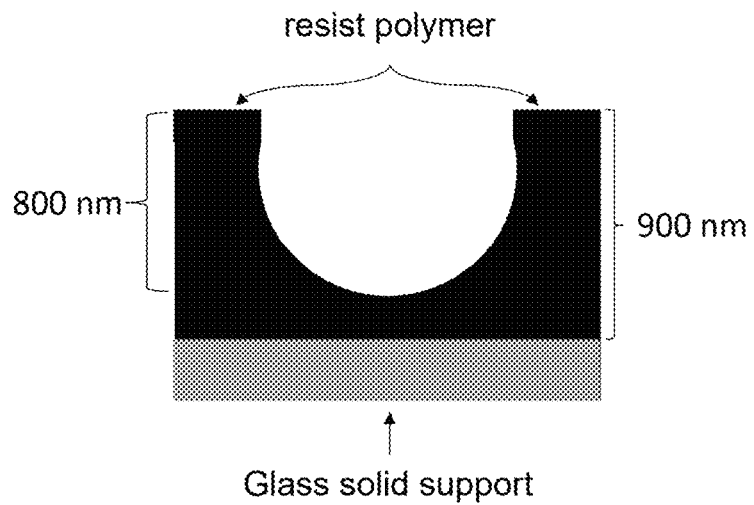

The array may include a nanoimprint resist (e.g., organically-modified ceramic polymers, such as OrmoComp® from micro resist technology GmbH), which contains the plurality of wells (e.g., see FIG. 1D). Organically-modified ceramics are hybrid polymers with inorganic and organic moieties linked by stable covalent bonds and based on organically modified alkoxysilanes, functionalized organic polymers or both. See K. H. Haas, H. Wolter, "Synthesis, properties and applications of inorganic-organic copolymers (ORMOCER®s)," Current Opinions in Solid State and Materials Science, vol. 4, pp. 571-580, 1999, which is incorporated herein by reference. In nanolithography technologies, organically-modified ceramic polymers behave similarly to negative-tone photoresists, such as SU-8, and provide glass-like material properties after UV curing. Typical organically-modified ceramic polymers include oxides (e.g., $SiO_2$, $ZrO$, $MgO$, $Al_2O_3$, $TiO_2$ or $Ta_2O_5$), silicon oxide (—Si—O—) groups, polymerizable monomers (e.g., acryl or methacrylate monomers), and one or more alkyl moieties. In embodiments, the organically-modified ceramic polymer includes alkoxysilane and/or polymerized units of alkoxysilyl monomers. In embodiments, the organically-modified ceramic polymer includes polymerized monomers of

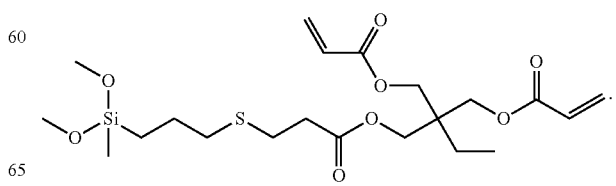

In embodiments, the organically-modified ceramic polymer is stable (i.e., does not measurably degrade) up to about 300° C.

Figure 6A:
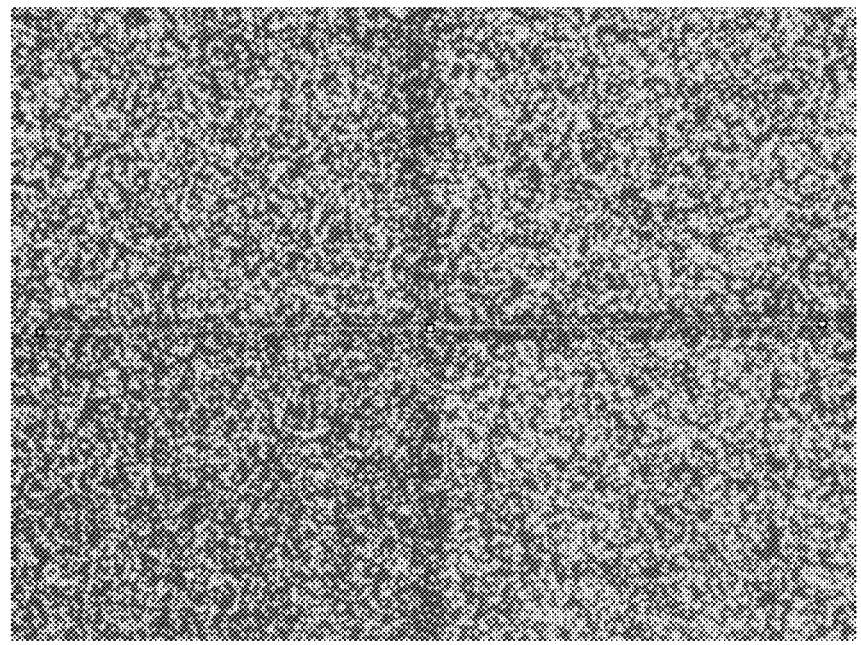
FIGS. 6A-6B are fluorescent images of FAM-labeled clusters generated from oligonucleotide primer-coated particles that were hybridized to template nucleic acids and amplified to generate an amplification product on the particle. To quantify the amount of non-specific binding in the interstitial space, the array contains a reference interstitial channel in the form of a cross, i.e., a region of interstitial space that does not include any particles.
Figure 6B:
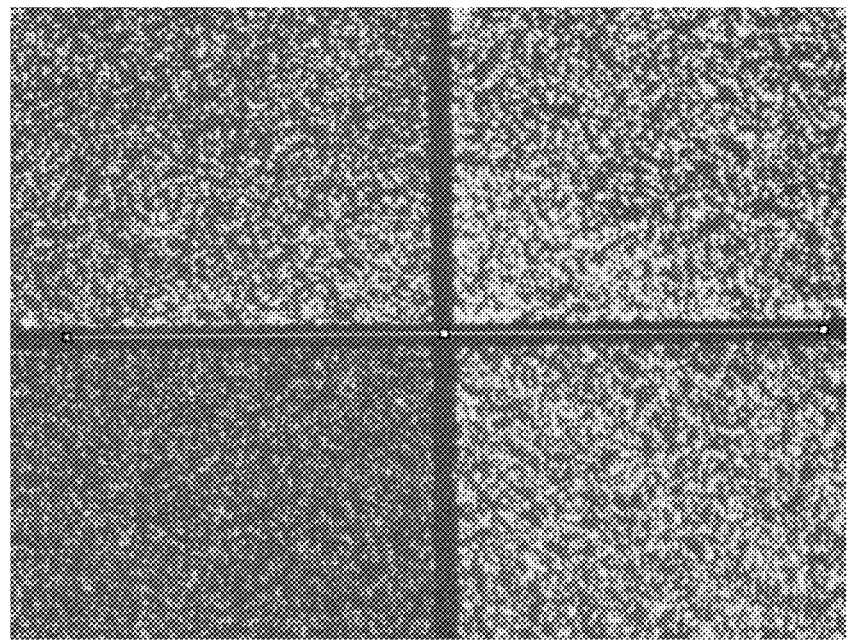
Figure 9A:
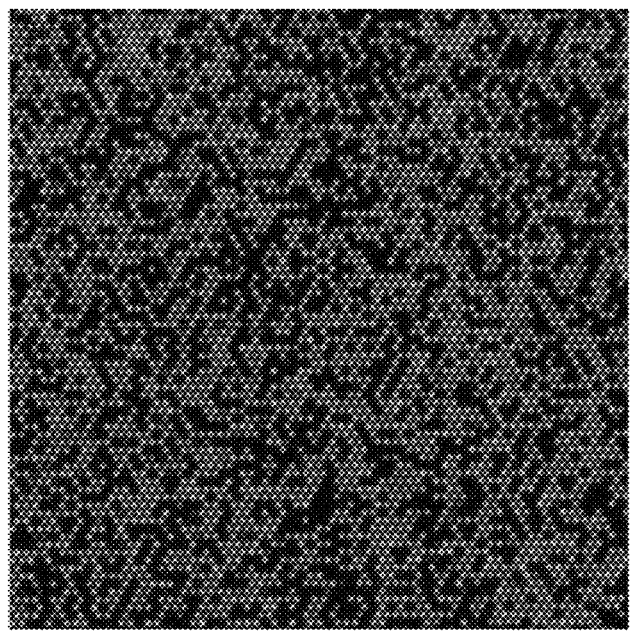
FIGS. 9A-9D depict images of a patterned solid support that includes wells separated by 1.4 um (center to center) filled with particles that include a plurality of oligonucleotide moieties. The diameter of the particle core was varied, from 400 nm (FIG. 9A), 450 nm (FIG. 9B), and 500 nm (FIG. 9C) and a fluorescently labeled complementary probe hybridized to the immobilized oligonucleotide was detected. Particle cores with an average diameter of about 400 nm provided uniform coverage. Optimizing the loading conditions and particle concentrations provided a surface with approximately 92% coverage (e.g., over 92% of the wells have a particle), as shown in FIG. 9D. Each discrete spot represents a feature available for sequencing, as confirmed by the fluorescent probe.
Figure 9B:
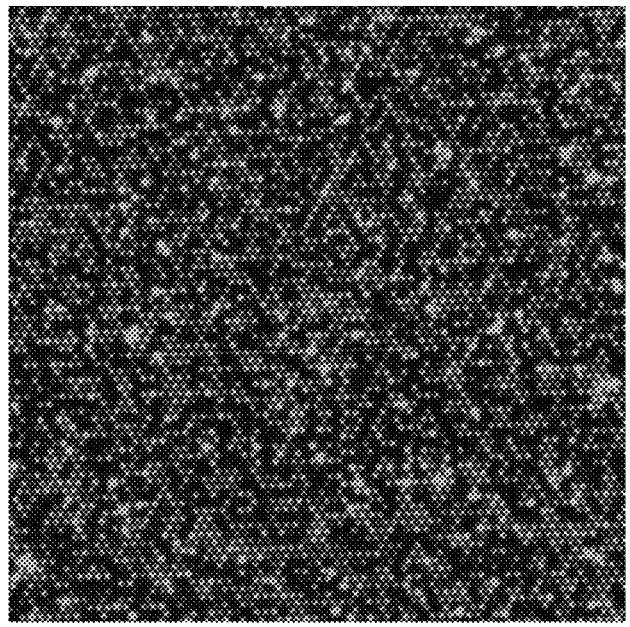
Figure 9C:
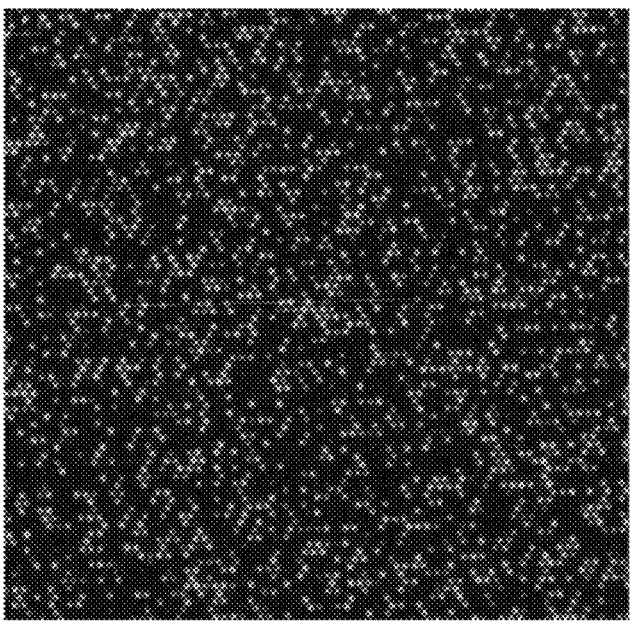
Figure 9D:
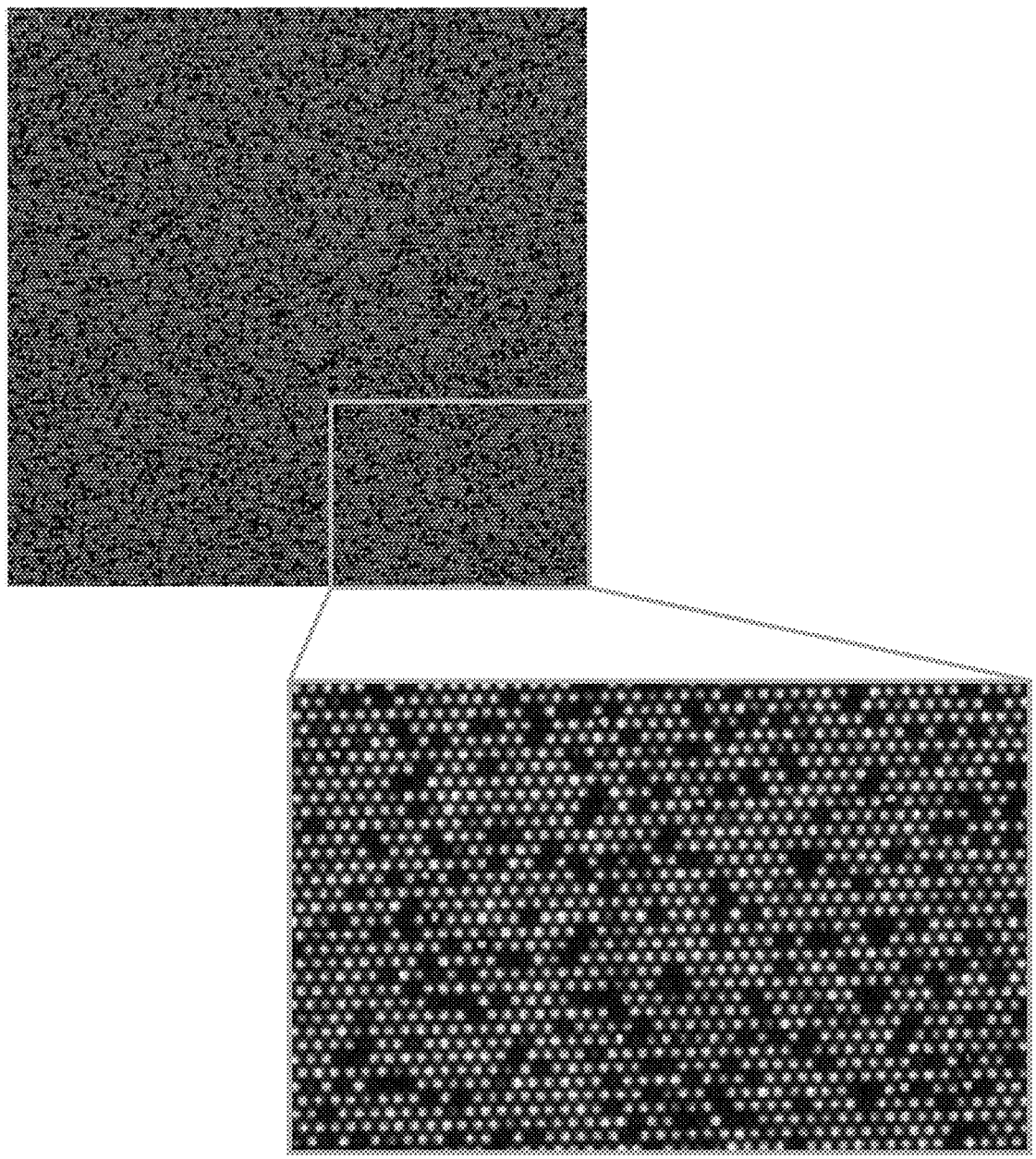

For example, by coating the array with a brush hydrophilic polymer (e.g., a random copolymer of p[PEGMA-co-TESPM]), significantly less detectable oligonucleotides in the interstitial regions following cluster amplification of hybridized template nucleic acids, compared to a control particle-loaded array lacking a hydrophilic polymer coating (see, FIGS. 6A-6B) is observed. The array may also be coated with a polymer (e.g., a random copolymer of p[PEGMA-co-HEMA-co-TMSPM] or p[PEGMA-co-HEMA] to provide surfaces with a visible nanopattern (see FIGS. 9A-9C). The arrayed particles may then be subjected to seeding with template polynucleotides. Additionally, following seeding, the arrayed particles may then be subjected to amplification and sequencing (e.g., sequencing-by-synthesis) to determine the identity of the polynucleotide template(s) attached to each discrete particle in the array.

Example 2. Synthetic Materials and Methods

Synthesis of polymeric particles useful for the methods and compositions described herein may be synthesized as follows. Synthesis of polymeric cores were performed by dispersion polymerization in water/alcohol mixtures in which monomer(s) are soluble. AAm and azide functionalized monomers were added to the reactor along with a stabilizer, FRP initiator and solvent and mixed. The reaction vessel was sealed and bubbled with inert gas in the ice bath. A crosslinker (e.g., bis-AAm) was dissolved in water/alcohol mixture in another tube and bubbled with inert gas, simultaneously. After around 30 min, main reaction vessel was heated to above 50° C. and mixed via stirrer bar in the constant rate. The crosslinker solution was added slowly. Other functional monomer(s) can be added during or after the crosslinker addition to the main reactor. For example, 25 mg Ammonium persulfate (APS), 0.5 g AAm, 130 mg of GMA-$N_3$, 1 g of PVP (average mol wt 40,000), 16 g ethanol and 4 g water added to the first reaction vessel along with magnetic stirrer bar. The reaction vessel was sealed and purged with inert gas for at least 30 min and cooled. In another container, 8 g of ethanol, 2 g water and 24 mg N,N'-Methylenebis(acrylamide) mixed and bubbled with inert gas (solution 2). After around 30 min, main reaction vessel was heated to above 50° C. and mixed via stirrer bar in the constant rate. The crosslinker solution was added slowly, followed by addition of 11 ul of glycidyl methacrylate (GMA). The particles may further be modified by converting the epoxy to azide using known techniques in the art (e.g., aqueous sodium azide). In another example, 25 mg Ammonium persulfate (APS), 0.5 g AAm, 75 mg of HEMA-N3, 0.4 g of PVP (average mol wt 40,000), 17 g ethanol and 3 g water were added to the reactor (solution 1) along with a magnetic stirrer bar. The reactor was sealed and purged with an inert gas for at least 30 minutes, in an ice bath. To form the crosslinker solution, in another container, 8.5 g of ethanol, 1.5 g water and 24 mg N,N'-Methylenebis(acrylamide) was mixed and bubbled with inert gas (solution 2). The reactor is immersed in an oil bath (60° C.) to start the reaction while mixed at a 120 rpm stirring rate. After 20 minutes, solution 2 is added to the reactor with a syringe pump (at a rate of 6 ml/h). At the end of crosslinker solution addition, 11 ul of glycidyl methacrylate (GMA) was added to remaining solution. It was bubbled and then continued to be added to the main reactor to achieve epoxy decorated functionalized particles.

Surface Initiated ATRP Particle Polymerization General Methods. The substrate particle (e.g., silica particle or metal particle) containing a polymerization initiator is immersed in polymerization reaction mixture as described above. This mixture depends on the type of monomers, and can include (i) solvent(s), monomer(s), initiator, and ligand or (ii) solvent(s), monomer(s) and initiator. Monomer ratios were adjusted to create polymers brushed with different spacers between neighboring side chains (ng) (i.e., determining the ratio of monomers with functional groups, e.g., azide or alkyne moieties, to monomers with non-functional groups, e.g., PEG). In embodiments, the ratio of functional groups to non-functional groups is 1:1. In embodiments, the ratio of functional groups to non-functional groups is 1:2. In embodiments, the ratio of functional groups to non-functional groups is 1:3. In embodiments, the ratio of functional groups to non-functional groups is 1:4. In embodiments, the ratio of functional groups to non-functional groups is 1:5. In embodiments, the ratio of functional groups to non-functional groups is 1:6. In embodiments, the ratio of functional groups to non-functional groups is 1:7. In embodiments, the ratio of functional groups to non-functional groups is 1:8. Modulating the ng (i.e., the ratio of functional groups to non-functional groups of the copolymer allows for control of the density of oligonucleotides.

In embodiments, the polymer does not include N-(5-bromoacetamidylpentyl) acrylamide (BRAPA). The polymers and copolymers described herein have increased solubility in water and have a greater density of functional groups (e.g., a ratio of non-reactive groups such as PEG to reactive groups such as azide, is 3:1) as compared to acrylamide-based copolymers (e.g., N-(5-bromoacetamidyl-pentyl) acrylamide (BRAPA)). Typical acrylamide based polymers and copolymers need to increase the ratio of functional groups to non-functional groups (NR:R) around 8:1 to 20:1 to maintain solubility, which ultimately limits the density of oligonucleotides.

Synthesis of GMA-azide. Starting with sodium azide ($NaN_3$), it was dissolved in deionized water and the pH was reduced by dropwise addition of HCl to achieve a pH of 5.0. Approximately 30 mL of glycidyl methacrylate (GMA) was added to the sodium azide mixture via a syringe and stirred overnight to generate a mixture GMA-azides having the major and minor structures

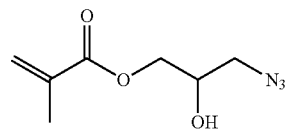

3-azido-2-hydroxypropyl methacrylate and

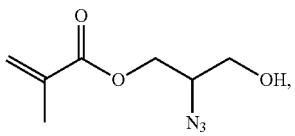

2-azido-3-hydroxypropyl methacrylate confirmed via NMR. The GMA-azide was then purified.

Synthesis of 2-(((2-azidoethoxy)carbonyl)amino)ethyl methacrylate. Starting with sodium azide (NaN₃), it was dissolved in deionized water and 30 mL of 2-bromoethanol was added via syringe. The reaction was maintained at 55° C. and stirred overnight. Approximately 25 g of 2-Isocyanatoethyl methacrylate (IEM) was added to the azidoethanol (N₃EtOH) mixture and stirred at room temperature for 2-3 hours. A solution of dibutyltin dilaurate (DBTDL) and dichloromethane (DCM) was transferred to the IEM mixture and stirred overnight at room temperature to generate IEM-azide. The IEM-azide was then purified and confirmed via NMR to have the structure

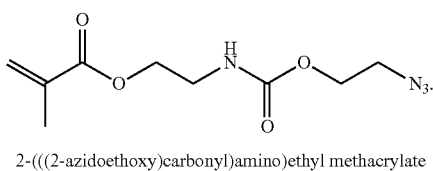 [SMILES: C=C(C)C(=O)OCCNC(=O)OCCN=[N+]=[N-]]

2-(((2-azidoethoxy)carbonyl)amino)ethyl methacrylate

Example 3. Preparation of Silica Particles

Functionalization of Silica Particles. Silica and deionized (DI) water are mixed in a vessel and sonicated at room temperature. Once the particles are dispersed, tetrabutylammonium hydroxide (55% TBAH in solution) was mixed with the solution and placed into a closed system, stirred under ventilation for 24 hours at 60° C. The solution is centrifuged, and the liquid is discarded. The remaining particles are mixed with DI water then sonicated at room temperature. The particles are washed with DI water until the pH of the solution is 7. The particles are centrifuged, and the supernatant is discarded. A polymerization initiator compound (i.e., an ATRP initiator), (3-trimethoxysilyl)propyl 2-bromo-2-methylpropionate is added dropwise to the particles in solution and mixed for 24 hours at room temperature. The particles are then washed and redispersed by sonication to give particles modified with ATRP polymerization initiator.

Polymerization of Silica Particles. Through a column of basic alumina, PEGMA$_{500}$, Mn=500 was passed through to remove BHT inhibitor. The purified PEGMA$_{500}$ was added to ATRP-initiator functionalized silica particles in ethanol in a flask and sonicated until the particles are dispersed. GMA-Azide, 2-hydroxyethyl 2-bromoisobutyrate (OH-EBiB), CuBr$_2$, 1,1,4,7,10,10-Hexamethyltriethylenetramine (HMTETA) was then added to the reaction flask. Copper(I) bromide (CuBr) is added to the reaction flask and the flask was heated to 60° C. The reaction mixture was rinsed, centrifuged, and the supernatant is removed. Fresh ethanol was added to the particles, and this solution is vortex and sonicated several times. The supernatant was removed to provide polymerized silica particles that were examined under microscope.

Addition of Oligonucleotide Primers to Polymerized Silica Particles. In a reactor containing ethanol/buffer solution oligonucleotide primers were added. To this same reactor, polymerized silica particles are added and the mixture was sonicated and stirred overnight. The resulting polymerized silica particles with oligonucleotide primers are spun down and washed before being dispersed in an ethanol/salt solution. Following sonication, the particles were stored in solution.

Example 4. Preparation of Polymerized Surface Slides

Into an air free reaction vessel, azobisisobutyronitrile (AIBN) is added followed by 4-cyano-4-(phenylcarbonothioylthio)pentanoic acid (CTA), purified PEGMA, Mn=500 and purified TMSPM. Anhydrous toluene and anhydrous acetone are added to the reaction vessel, and everything is mixed under N$_2$ for 1 hr in ice then stirred at an increased temperature (e.g., 50° C. to 70° C.) overnight.

A solution of polymer in toluene is poured into a glass reaction vessel and glass slides (e.g., patterned slides) are then added to this vessel. The reaction vessel is placed in a desiccator and sealed for 15-18 hrs. The slides were placed into another container containing toluene, sonicated, and then placed into a container containing ethanol and sonicated again.

Example 5. Particle Loading

The following are examples of general particle loading techniques which may be applied in carrying out the invention. To a patterned glass slide containing a photoresist with wells spaced 1.0 μm apart (center-to-center), a copolymer of PEGMA-co-TMSPM is applied to the surface. The ratio of alkoxysilyl groups to PEG groups was 1:8. Approximately 4 mL of a colloidal solution containing approximately 10$^{10}$ silica core particles (400 nm diameter) having a PEGMA-co-GMA azide shell were incubated with the array and allowed to settle into the wells. The ratio of azide functional groups to PEG functional groups was 1:4. The colloidal solution included ethanol, isopropyl alcohol, and water. The incubated array may be subjected to centrifugation (e.g., 2000 RPM for 12 minutes) or vortexed (e.g., 300 RPM for 12 minutes) to accelerate particle loading. Following loading, the array was washed 3× with water or ethanol and sonicated for 3 minutes. An additional wash step is performed with an ethanol, isopropyl alcohol, and water solution. The particle loaded array is allowed to dry or may be wiped down to accelerate surface drying. The array may be stored in an aqueous solution until ready to use.

To a patterned glass slide containing a photoresist with wells spaced 1.4 μm apart (center-to-center), a copolymer of PEGMA-co-TMSPM is applied to the surface. The ratio of alkoxysilyl groups to PEG groups was 1:8. Approximately 4 mL of a colloidal solution containing approximately 10$^{10}$ silica core particles (500 nm diameter) having a PEGMA-co-GMA azide shell were incubated with the array and allowed to settle into the wells. The ratio of azide functional groups to PEG functional groups was 1:4. The colloidal solution included ethanol, isopropyl alcohol, and water. The incubated array was subjected to centrifugation (e.g., 2000 RPM for 12 minutes) to accelerate particle loading. Following loading, the array was washed 3× with water or ethanol and sonicated for 3 minutes and allowed to dry. An additional wash step is performed with an ethanol, isopropyl alcohol, and water solution. The particle loaded array is allowed to dry or may be wiped down to accelerate surface drying. The array may be stored in an aqueous solution until ready to use.

Quality control experiments were performed on the particle loaded arrays. Approximately 95% of the available wells had a single particle. Following primer deposition, i.e., the oligonucleotide moieties covalently attached to the reactive moieties on the particles, a FAM-labeled complement was incubated in the array and imaged. As shown in FIGS. 5A-5B, the fluorescent intensity of the discrete particles is observed and is in contrast to the reference fiducial (i.e., the center circle in FIGS. 5A-5B) and the interstitial regions which do not contain any FAM-labeled complements, and thus do not include any oligonucleotide primers.

The particles were physiosorbed in the wells. Surprisingly, no covalent linkage nor tethering to immobilized oligonucleotides between the particle to the well was used. Efforts to remove the particles from wells included inverting the array, wiping, rinsing, and sonicating overnight in ethanol and toluene. Quality control experiments comparing the FAM-labeled probe intensity before and after sonicating were indistinguishable, indicating the particles remain in the wells, despite the aggressive treatments.

Polymerized silica particles are added to a mixture of ethanol, isopropyl alcohol and water and sonicated. Into this solution was added a polymerized surface slide (i.e., a passivated slide). The slide and particle solution are shaken and incubated for 1 to 8 hours. Following this incubation period, the slides are shaken in an ethanol solution several times. To check the quantity of synthesized particles deposited onto the polymerized surface slides, phase contrast microscopy was performed on the slides.

Polymerized silica particles with oligonucleotide primers in loading solution (TE buffer with NaCl which may optionally contain ethanol) is sonicated. Following sonication, the particles in solution was added to a tray containing patterned glass slide(s) that contain a resist, for example SU-8 and/or Ormocomp®, and shaken for 10 min. Following shaking, the tray is placed at 4° C. The slides are dried, washed and dried again. The slides were examined under microscope to check the quantity of polymerized silica particles with oligonucleotide primers particles deposited on the slides.

Embodiments

The present disclosure provides the following additional illustrative embodiments.

Embodiment P-1. An array, comprising: a solid support comprising a surface, the surface comprising a plurality of wells separated from each other by interstitial regions on the surface, wherein the surface comprises a polymer layer and is substantially free of oligonucleotide moieties, wherein one or more wells contains a particle, wherein the particle comprises a plurality of bioconjugate reactive moieties, a plurality of oligonucleotide moieties, or a combination thereof.

Embodiment P-2. An array, comprising: a solid support comprising a surface, the surface comprising a plurality of wells separated from each other by interstitial regions on the surface, wherein one or more wells contains a particle, wherein the particle comprises a plurality of bioconjugate reactive moieties, a plurality of oligonucleotide moieties, or a combination thereof; and the average longest dimension of the particle is from about 100 nm to about 1000 nm.

Embodiment P-3. The array of Embodiment P-1 or P-2, wherein there is at least one particle per well.

Embodiment P-4. The array of Embodiment P-1 or P-2, wherein there is one particle per well.

Embodiment P-5. The array of any one of Embodiments P-1 to P-4, wherein the particle is a functionalized particle comprising a particle core and a particle shell, wherein said particle shell comprises the plurality of bioconjugate reactive moieties, the plurality of oligonucleotide moieties, or a combination thereof, wherein each of said bioconjugate reactive moieties and each of said oligonucleotide moieties comprise a linker binding said bioconjugate reactive moieties and oligonucleotide to said particle core.

Embodiment P-6. The array of Embodiment P-5, wherein the particle core comprises glass, ceramic, metal, silica, magnetic material, or a paramagnetic material.

Embodiment P-7. The array of Embodiment P-5, wherein the particle shell comprises polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

Embodiment P-8. The array of Embodiment P-5, wherein the particle shell comprises polymerized units of polyacrylamide (AAm), glicydyl methacrylate (GMA), polyethylene glycol methacrylate (PEGMA), polyethylene glycol methacrylate (PEGMA), isocyanatoethyl methacrylate (IEM), or a copolymer thereof.

Embodiment P-9. The array of Embodiment P-5, wherein the particle shell comprises polymerized units of a) polyethylene glycol methacrylate (PEGMA) and glicydyl methacrylate (GMA) or b) polyethylene glycol methacrylate (PEGMA) and isocyanatoethyl methacrylate (IEM).

Embodiment P-10. The array of any one of Embodiments P-5 to P-9, wherein the particle shell is permeable to a polymerase.

Embodiment P-11. The array of any one of Embodiments P-1 to P-4, wherein the particle is a polymer particle comprising polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

Embodiment P-12. The array of any one of Embodiments P-1 to P-4, wherein the particle is a polymer particle comprising polyacrylamide (AAm), glicydyl methacrylate (GMA), polyethylene glycol methacrylate (PEGMA), polyethylene glycol acrylate (PEGA), isocyanatoethyl methacrylate (IEM), or a copolymer thereof.

Embodiment P-13. The array of any one of Embodiments P-1 to P-4, wherein the particle is a polymer particle comprising polymerized units of polyacrylamide (AAm) and glicydyl methacrylate (GMA); polyacrylamide (AAm) and isocyanatoethyl methacrylate (IEM); or glicydyl methacrylate (GMA).

Embodiment P-14. The array of any one of Embodiments P-11 to P-13, wherein the polymer particle is permeable to a polymerase.

Embodiment P-15. The array of any one of Embodiments P-1 to P-14, wherein the solid support comprises a polymer layer, wherein the polymer layer comprises an amphiphilic copolymer.

Embodiment P-16. The array of any one of Embodiments P-1 to P-14, wherein the solid support comprises a polymer layer, wherein the polymer layer comprises an amphiphilic acrylate copolymer or amphiphilic methacrylate copolymer.

Embodiment P-17. The array of any one of Embodiments P-1 to P-16, wherein the solid support comprises a photoresist and polymer layer, wherein the photoresist is between the solid support and the polymer layer.

Embodiment P-18. The array of any one of Embodiments P-1 to P-17, wherein the amphiphilic copolymer comprises a poloxamer.

Embodiment P-19. The array of any one of Embodiments P-1 to P-17, wherein the amphiphilic copolymer comprises a brush copolymer or a comb polymer.

Embodiment P-20. The array of any one of Embodiments P-1 to P-17, wherein the amphiphilic copolymer comprises polymerized units of alkoxysilyl polymers.

Embodiment P-21. The array of any one of Embodiments P-15 to P-20, wherein amphiphilic copolymer comprises polymerized units of 3-(trimethoxysilyl)propyl methacrylate (TMSPM), 3-(trimethoxysilyl)propyl methacrylate (TMSPA), 3-(triethoxysilyl)propyl methacrylate (TESPM), 3-(triethoxysilyl)propyl acrylate (TESPA), 3-(dimethoxy(1-methylethoxy)silyl]propyl methacrylate, 3-(ethoxydimethoxysilyl)propyl 2-methyl-2-propenoate, 3-(Tripropoxysilyl)propyl 2-methyl-2-propenoate, 2-Methyl-3-(triethoxysilyl)propyl 2-methyl-2-propenoate, 3-(Methyldipropoxysilyl)propyl 2-methyl-2-propenoate, 3-(Diethoxymethylsilyl)propyl 2-methyl-2-propenoate, 3-[Diethoxy(2-hydroxyethoxy)silyl]propyl 2-methyl-2-propenoate, 3-(Butyldimethoxysilyl)propyl 2-methyl-2-propenoate.

Embodiment P-22. The array of Embodiment P-20 or P-21, further comprising polymerized units of polyethylene glycol methacrylate (PEGMA), polyethylene glycol acrylate (PEGA), sulfobetaine acrylate (SBA), carboxybetaine acrylate (CBA), phosphorylcholine acrylate (PCA), sulfobetaine methacrylate (SBMA), carboxybetaine methacrylate (CBMA), or phosphorylcholine methacrylate (PCMA).

Embodiment P-23. The array of any one of Embodiments P-15 to P-20, wherein amphiphilic copolymer comprises polymerized units of alkoxysilyl polymers and polymerized units of polyethylene glycol methacrylate (PEGMA), or polyethylene glycol acrylate (PEGA).

Embodiment P-24. The array of any one of Embodiments P-15 to P-20, wherein amphiphilic copolymer comprises polymerized units of 3-(trimethoxysilyl)propyl methacrylate (TMSPM), 3-(trimethoxysilyl)propyl methacrylate (TMSPA) and polymerized units of polyethylene glycol methacrylate (PEGMA), or polyethylene glycol acrylate (PEGA).

Embodiment P-25. The array of any one of Embodiments P-1 to P-22, wherein the average longest dimension of the particle is from about 150 nm to about 600 nm.

Embodiment P-26. The array of any one of Embodiments P-1 to P-22, wherein the average longest dimension of the particle is from about 350 nm to about 600 nm.

Embodiment P-27. The array of any one of Embodiments P-1 to P-22, wherein the average longest dimension of the particle is from about 400 nm to about 500 nm.

Embodiment P-28. The array of any one of Embodiments P-1 to P-27, wherein the wells are separated from each other by about 0.2 µm to about 2.0 µm.

Embodiment P-29. The array of any one of Embodiments P-1 to P-27, wherein the wells are separated from each other by about 0.7 µm to about 1.5 µm.

Embodiment P-30. The array of any one of Embodiments P-1 to P-29, wherein the wells are from about 0.2 µm to about 2 µm in diameter, and wherein the wells are about 0.5 µm to about 2 µm in depth.

Embodiment P-31. The array of any one of Embodiments P-1 to P-30, wherein greater than 50%, 60%, 70%, 80%, 90% or 95% of the wells comprise a particle.

Embodiment P-32. The array of any one of Embodiments P-1 to P-30, wherein greater than 90% of the wells contain a particle.

Embodiment P-33. The array of any one of Embodiments P-1 to P-30, wherein greater than 90%, 91%, 92%, 93%, 94%, 95%, 96%, 97%, 98%, or 99% of the wells comprise a particle.

Embodiment P-34. The array of any one of Embodiments P-31 to P-33, wherein each of the particles comprise oligonucleotide moieties substantially identical to all the particles in the array.

Embodiment P-35. The array of any one of Embodiments P-31 to P-33, wherein each of the particles comprise at least two species of oligonucleotide moieties that are substantially identical to all the particles in the array.

Embodiment P-36. The array of any one of Embodiments P-1 to P-34, wherein the interstitial regions are substantially free of oligonucleotide moieties.

Embodiment P-37. The array of any one of Embodiments P-1 to P-36, wherein each of the plurality of bioconjugate reactive moieties comprise an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety.

Embodiment P-38. The array of any one of Embodiments P-1 to P-36, wherein each of the plurality of bioconjugate reactive moieties comprise an amine moiety, azide moiety, alkyne moiety, dibenzocyclooctyne (DBCO) moiety, epoxy moiety, or isocyanate moiety.

Embodiment P-39. The array of any one of Embodiments P-1 to P-38, wherein the oligonucleotide moiety is about 5 to about 40 nucleotides in length.

Embodiment P-40. The array of any one of Embodiments P-1 to P-38, wherein the oligonucleotide moiety is about 20 to about 30 nucleotides in length.

Embodiment P-41. The array of any one of Embodiments P-1 to P-39, wherein the oligonucleotide moiety is capable of hybridizing to a complementary sequence of a template nucleic acid.

Embodiment P-42. The array of any one of Embodiments P-1 to P-41, wherein the particle comprises a plurality of azide moieties, alkyne moieties, dibenzocyclooctyne (DBCO) moieties, epoxy moieties, or isocyanate moieties.

Embodiment P-43. The array of any one of Embodiments P-1 to P-41, wherein the particle comprises a plurality of oligonucleotide moieties.

Embodiment P-44. A method of amplifying a target polynucleotide, the method comprising: contacting the array of any one of Embodiments P-1 to P-43 with a plurality of oligonucleotide moieties, each oligonucleotide moiety comprising a bioconjugate reactive moiety that reacts and forms a bioconjugate linker that covalently links the oligonucleotide moiety to the particle, contacting the array with a sample comprising a target polynucleotide; and amplifying the target polynucleotide to produce an amplification product, wherein amplifying comprises extension of the oligonucleotide moiety hybridized to the target polynucleotide.

Embodiment P-45. A method of amplifying a target polynucleotide, the method comprising: contacting the array of Embodiment P-43 with a sample comprising a target polynucleotide; and amplifying the target polynucleotide to produce an amplification product, wherein amplifying comprises extension of the oligonucleotide moiety hybridized to the target polynucleotide.

Embodiment P-46. A method of making an array of nucleic acids on a surface, the method comprising: a) providing a solid support comprising a surface, the surface comprising a plurality of wells wherein the wells are separated from each other by interstitial regions on the surface; b) providing a plurality of particles, wherein each particle comprises a plurality of bioconjugate reactive moieties; c) arraying the particles onto the surface; d) contacting the particles with a plurality of oligonucleotide moieties, wherein each oligonucleotide moiety comprises a bioconjugate reactive moiety that reacts and forms a bioconjugate linker that covalently links the oligonucleotide moiety to the particle.

Embodiment P-47. A method of making an array of template nucleic acids on a surface, the method comprising: a) providing a solid support comprising a surface, the surface comprising a plurality of wells wherein the wells are separated from each other by interstitial regions on the surface; b) providing a plurality of particles, wherein each particle comprises a plurality of oligonucleotide moieties; wherein the average longest dimension of the particle is from about 150 nm to about 1,000 nm; c) arraying the particles onto the surface; d) contacting the particles with a plurality of template nucleic acid moieties, wherein a complementary sequence of the template nucleic acid moieties hybridizes to the oligonucleotide moiety of the particle.

Embodiment P-48. The method of Embodiment P-46 or P-47, wherein the particle is a functionalized particle comprising a particle core and a particle shell, wherein said particle shell comprises the plurality of bioconjugate reactive moieties, the plurality of oligonucleotide moieties, or a combination thereof, wherein each of said bioconjugate reactive moieties and each of said oligonucleotide moieties comprise a linker binding said bioconjugate reactive moieties and oligonucleotide to said particle core.

Embodiment P-49. The method of Embodiment P-46 or P-47, wherein the particle is a polymer particle.

Embodiment P-50. The method of Embodiment P-49, wherein arraying the particles comprises contacting the surface with a first solution comprising the plurality of particles in an anti-solvent.

Embodiment P-51. The method of Embodiment P-50, wherein the particle comprises acrylamide and the anti-solvent is an aqueous ethanol solution.

Embodiment P-52. The method of Embodiment P-50, wherein the particle comprises sulfobetaine acrylate (SBA), carboxybetaine acrylate (CBA), phosphorylcholine acrylate (PCA), sulfobetaine methacrylate (SBMA), carboxybetaine methacrylate (CBMA), or phosphorylcholine methacrylate (PCMA) and the anti-solvent is an aqueous acetone solution.

Embodiment P-53. The method of Embodiment P-50, further comprising removing the first solution and contacting the surface with a second solution, wherein the second solution is an aqueous solution capable of expanding the volume of the particle.

Embodiment P-54. A nucleic acid sequencing device, comprising: a stage configured to hold an array of any one of Embodiments P-1 to P-43; an array of any one of Embodiments P-1 to P-43; and a detector for obtaining sequencing data.

Additional Embodiments

Embodiment 1. A solid support comprising two or more wells, wherein each well is separated by about 0.2 μm to about 2.0 μm and each well comprises at least one particle, said particle comprising a plurality of oligonucleotide moieties covalently attached to said particle via a bioconjugate linker, wherein the bioconjugate linker is formed via a reaction between a particle polymer comprising a first bioconjugate reactive moiety and an oligonucleotide comprising a second bioconjugate reactive moiety, and wherein the average longest dimension of the particle is from about 100 nm to about 1000 nm.

Embodiment 2. The solid support of Embodiment 1, wherein the solid support comprises a polymer layer.

Embodiment 3. The solid support of Embodiment 2, wherein the polymer layer comprises polymerized units of alkoxysilyl methacrylate, alkoxysilyl acrylate, alkoxysilyl methylacrylamide, alkoxysilyl methylacrylamide, or a copolymer thereof.

Embodiment 4. The solid support of Embodiment 1, wherein the solid support comprises a photoresist, wherein the photoresist is a silsesquioxane resist, an epoxy-based polymer resist, poly(vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist.

Embodiment 5. The solid support of any one of Embodiments 1 to 4, wherein the particle comprises silica, glass, ceramic, metal, magnetic material, or a paramagnetic material.

Embodiment 6. The solid support of any one of Embodiments 1 to 5, wherein the particle polymer comprises polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis (acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

Embodiment 7. The solid support of any one of Embodiments 1 to 4, wherein the particle polymer comprises polymerized units of polyacrylamide (AAm), glicydyl methacrylate (GMA), glicydyl methacrylate (GMA) azide, polyethylene glycol methacrylate (PEGMA), polyethylene glycol methacrylate (PEGMA), isocyanatoethyl methacrylate (IEM), or a copolymer thereof.

Embodiment 8. The solid support of any one of Embodiments 1 to 4, wherein the particle polymer comprises polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide.

Embodiment 9. The solid support of any one of Embodiments 1 to 4, wherein the particle is a polymeric particle comprising polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

Embodiment 10. The solid support of any one of Embodiments 1 to 4, wherein the particle is a polymeric particle comprising polyacrylamide (AAm), glicydyl methacrylate (GMA), polyethylene glycol methacrylate (PEGMA), polyethylene glycol acrylate (PEGA), isocyanatoethyl methacrylate (IEM), or a copolymer thereof.

Embodiment 11. The solid support of any one of Embodiments 1 to 4, wherein the particle is a polymeric particle comprising polymerized units of polyacrylamide (AAm) and glicydyl methacrylate (GMA); polyacrylamide (AAm) and isocyanatoethyl methacrylate (IEM); or glicydyl methacrylate (GMA).

Embodiment 12. The solid support of any one of Embodiments 9 to 11, wherein the polymeric particle is permeable to a polymerase.

Embodiment 13. The solid support of any one of Embodiments 1 to 12, wherein the solid support further comprises an amphiphilic copolymer layer.

Embodiment 14. The solid support of Embodiment 13, wherein the amphiphilic copolymer comprises a poloxamer.

Embodiment 15. The solid support of Embodiment 1, wherein the amphiphilic copolymer comprises a brush copolymer or a comb polymer.

Embodiment 16. The solid support of Embodiment 13, wherein the amphiphilic copolymer comprises polymerized units of alkoxysilyl polymers.

Embodiment 17. The solid support of Embodiment 13, wherein amphiphilic copolymer comprises polymerized units of 3-(trimethoxysilyl)propyl methacrylate (TMSPM), 3-(trimethoxysilyl)propyl methacrylate (TMSPA), 3-(triethoxysilyl)propyl methacrylate (TESPM), 3-(triethoxysilyl)propyl acrylate (TESPA), hydroxyethylmethacrylate (HEMA), 3-(dimethoxy(1-methylethoxy)silyl]propyl methacrylate, 3-(ethoxydimethoxysilyl)propyl 2-methyl-2-propenoate, 3-(Tripropoxysilyl)propyl 2-methyl-2-propenoate, 2-Methyl-3-(triethoxysilyl)propyl 2-methyl-2-propenoate, 3-(Methyldipropoxysilyl)propyl 2-methyl-2-propenoate, 3-(Diethoxymethylsilyl)propyl 2-methyl-2-propenoate, 3-[Diethoxy(2-hydroxyethoxy)silyl]propyl 2-methyl-2-propenoate, 3-(Butyldimethoxysilyl)propyl 2-methyl-2-propenoate.

Embodiment 18. The solid support of Embodiment 16 or 17, further comprising polymerized units of polyethylene glycol methacrylate (PEGMA), polyethylene glycol acrylate (PEGA), sulfobetaine acrylate (SBA), carboxybetaine acrylate (CBA), phosphorylcholine acrylate (PCA), sulfobetaine methacrylate (SBMA), carboxybetaine methacrylate (CBMA), or phosphorylcholine methacrylate (PCMA).

Embodiment 19. The solid support of Embodiment 13, wherein amphiphilic copolymer comprises polymerized units of alkoxysilyl polymers and polymerized units of polyethylene glycol methacrylate (PEGMA), or polyethylene glycol acrylate (PEGA).

Embodiment 20. The solid support of Embodiment 13, wherein amphiphilic copolymer comprises polymerized units of 3-(trimethoxysilyl)propyl methacrylate (TMSPM), 3-(trimethoxysilyl)propyl methacrylate (TMSPA) and polymerized units of polyethylene glycol methacrylate (PEGMA), or polyethylene glycol acrylate (PEGA).

Embodiment 21. The solid support of any one of Embodiments 1 to 20, wherein the average longest dimension of the particle is from about 150 nm to about 600 nm.

Embodiment 22. The solid support of any one of Embodiments 1 to 20, wherein the average longest dimension of the particle is from about 350 nm to about 600 nm.

Embodiment 23. The solid support of any one of Embodiments 1 to 20, wherein the average longest dimension of the particle is from about 400 nm to about 500 nm.

Embodiment 24. The solid support of any one of Embodiments 1 to 20, wherein the average longest dimension of the particle is about 450 nm.

Embodiment 25. The solid support of any one of Embodiments 1 to 24, wherein the solid support comprises about $1 \times 10^6$ to about $5 \times 10^{10}$ wells.

Embodiment 26. The solid support of any one of Embodiments 1 to 25, wherein the wells are separated from each other by about 0.5 µm to about 2.0 µm.

Embodiment 27. The solid support of any one of Embodiments 1 to 25, wherein the wells are separated from each other by about 0.7 µm to about 1.5 µm.

Embodiment 28. The solid support of any one of Embodiments 1 to 25, wherein the wells are from about 0.2 µm to about 2 µm in diameter, and wherein the wells are about 0.5 µm to about 2 µm in depth.

Embodiment 29. The solid support of any one of Embodiments 25 to 28, wherein greater than 50%, 60%, 70%, 80%, 90% or 95% of the wells comprise a particle.

Embodiment 30. The solid support of any one of Embodiments 25 to 28, wherein greater than 90% of the wells contain a particle.

Embodiment 31. The solid support of any one of Embodiments 25 to 28, wherein greater than 90%, 91%, 92%, 93%, 94%, 95%, 96%, 97%, 98%, or 99% of the wells comprise a particle.

Embodiment 32. The solid support of any one of Embodiments 1 to 31, wherein each particle comprises substantially the same oligonucleotide moieties.

Embodiment 33. The solid support of any one of Embodiments 1 to 31, wherein each of the particles comprise at least two populations of substantially the same oligonucleotide moieties.

Embodiment 34. The solid support of any one of Embodiments 1 to 33, wherein the first bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety.

Embodiment 35. The solid support of any one of Embodiments 1 to 33, wherein the first bioconjugate reactive moiety is an amine moiety, azide moiety, alkyne moiety, dibenzocyclooctyne (DBCO) moiety, epoxy moiety, or isocyanate moiety.

Embodiment 36. The solid support of any one of Embodiments 1 to 35, wherein the oligonucleotide moiety is about 5 to about 40 nucleotides in length.

Embodiment 37. The solid support of any one of Embodiments 1 to 35, wherein the oligonucleotide moiety is about 20 to about 35 nucleotides in length.

Embodiment 38. The solid support of any one of Embodiments 1 to 37, wherein the oligonucleotide moiety is capable of hybridizing to a complementary sequence of a template nucleic acid.

Embodiment 39. The solid support of any one of Embodiments 1 to 37, wherein the oligonucleotide moiety is capable of hybridizing to a common sequence in a library of nucleic acid molecules.

Embodiment 40. A method of amplifying a target polynucleotide, the method comprising: contacting the solid support of any one of Embodiments 1 to 39 with a sample comprising a target polynucleotide; and amplifying the target polynucleotide to produce an amplification product, wherein amplifying comprises extension of the oligonucleotide moiety hybridized to the target polynucleotide.

Embodiment 41. A method of making an array of template nucleic acids, the method comprising: contacting a solid support comprising two or more wells with a plurality of particles, wherein each particle comprises a plurality of oligonucleotide moieties attached to said particle via a bioconjugate linker; wherein the average longest dimension of the particle is from about 150 nm to about 1,000 nm; and contacting said particles with a plurality of template nucleic acid moieties, wherein a complementary sequence of the template nucleic acid moieties hybridizes to the oligonucleotide moiety of the particle and is extended with a polymerase to form an array of template nucleic acids.

What is claimed is:

1. A method of forming an array of oligonucleotides, said method comprising:
contacting a solid support comprising a plurality of wells with a plurality of particles and binding one or more particles in a well, wherein each well is separated by about 0.2 µm to about 2.0 µm from any adjacent well, and wherein said solid support comprises an organically modified ceramic polymer resist; and
contacting the particles with a plurality of oligonucleotide moieties to form particle-immobilized oligonucleotide moieties, wherein each particle-immobilized oligonucleotide comprises an oligonucleotide moiety covalently attached to said particle via a bioconjugate linker, wherein the bioconjugate linker is formed via a reaction between a particle polymer comprising a first bioconjugate reactive moiety and an oligonucleotide comprising a second bioconjugate reactive moiety.

2. The method of claim 1, wherein said solid support comprises polymerized units of alkoxysilyl methacrylate, alkoxysilyl acrylate, alkoxysilyl methylacrylamide, alkoxysilyl acrylamide, or a copolymer thereof.

3. The method of claim 1, wherein binding one or more particles in a well comprises non-covalently binding said particles in the wells.

4. The method of 1, wherein the particle polymer is covalently bound to the particle.

5. The method of claim 1, wherein the particle polymer comprises polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

6. The method of claim 1, wherein the particle polymer comprises polyacrylamide (AAm), poly-N-isopropylacrylamide, poly N-isopropylpolyacrylamide, polyethylene glycol acrylate, methacrylate, polyacrylic acid, poly(hydroxyethyl methacrylate) (PHEMA), poly(methyl methacrylate) (PMMA), poly(N-isopropylacrylamide) (PNIPAAm), glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

7. The method of claim 1, wherein the particle polymer comprises poly(hydroxyethyl methacrylate) (PHEMA), poly(methyl methacrylate) (PMMA), poly(N-isopropylacrylamide) (PNIPAAm), glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof.

8. The method of claim 1, wherein the particle polymer comprises polymerized units of a) polyethylene glycol methacrylate (PEGMA) and glicydyl methacrylate (GMA),
b) polyethylene glycol methacrylate (PEGMA) and isocyanatoethyl methacrylate (IEM), or
c) polyethylene glycol methacrylate (PEGMA) and glicydyl methacrylate (GMA) azide.

9. The method of claim 1, wherein the first bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety.

10. The method of claim 1, wherein each particle comprises a plurality of bioconjugate reactive moieties selected from the following: a plurality of amine moieties, a plurality of aldehyde moieties, a plurality of alkyne moieties, a plurality of azide moieties, a plurality of carboxylic acid moieties, a plurality of dibenzocyclooctyne (DBCO) moieties, a plurality of tetrazine moieties, a plurality of epoxy moieties, a plurality of isocyanate moieties, a plurality of furan moieties, a plurality of maleimide moieties, a plurality of thiol moieties, or a plurality of transcyclooctene (TCO) moieties.

11. The method of claim 1, wherein each particle comprises a plurality of bioconjugate reactive moieties selected from the following: a plurality of azide moieties or a plurality of dibenzocyclooctyne (DBCO) moieties.

12. The method of claim 1, further comprising contacting said particle-immobilized oligonucleotides with a plurality of template nucleic acid moieties, wherein a complementary sequence of the template nucleic acid moieties hybridizes to the oligonucleotide moiety of the particle and is extended with a polymerase.

13. The method of claim 12, wherein the template nucleic acid moieties comprise single-stranded DNA or single-stranded RNA.

14. The method of claim 1, wherein the plurality of oligonucleotide moieties comprises a first population of oligonucleotide moieties and a second population of oligonucleotide moieties, and wherein a particle comprises an oligonucleotide moiety from the first population of oligonucleotide moieties covalently attached to said particle and an oligonucleotide moiety from the second population of oligonucleotide moieties covalently attached to said particle.

15. The method of claim 1, wherein the oligonucleotide moiety is about 5 to about 100 nucleotides in length.

16. The method of claim 1, wherein the oligonucleotide moiety comprises, from 5' to 3', a spacer sequence and a primer binding sequence, wherein said spacer sequence comprises 1 to 20 nucleotides.

17. The method of claim 1, wherein the oligonucleotide moiety comprises a cleavable site.

18. The method of claim 1, wherein the solid support comprises about $1 \times 10^5$ to about $5 \times 10^{10}$ wells.

19. The method of claim 1, wherein the solid support comprises about 0.5 million wells per $mm^2$, about 1 million wells per $mm^2$, or about 2 million wells per $mm^2$.

20. The method of claim 1, wherein the wells of the solid support are about 0.2 µm to about 2.0 µm in diameter, and wherein the wells are about 0.5 µm to about 2.0 µm in depth.

21. The method of claim 1, wherein the average longest dimension of the particle is from about 150 nm to about 1,000 nm.

22. The method of claim 1, wherein the particle polymer comprises polymerized units of polyethylene glycol methacrylate (PEGMA).

23. The method of claim 1, wherein the particle is a silica particle.

24. The method of claim 1, wherein the organically modified ceramic polymer resist comprises polymerized alkoxysilyl methacrylate polymers and metal oxides.

25. The method of claim 1, wherein the organically modified ceramic polymer resist comprises polymerized alkoxysilyl acrylate polymers and metal oxides.

26. The method of claim 1, wherein the plurality of wells are in said organically modified ceramic polymer resist.

* * * * *